(12) United States Patent
Eckelman et al.

(10) Patent No.: US 12,331,132 B2
(45) Date of Patent: *Jun. 17, 2025

(54) MULTISPECIFIC POLYPEPTIDE CONSTRUCTS HAVING CONSTRAINED CD3 BINDING AND RELATED METHODS AND USES

(71) Applicant: Inhibrx Biosciences, Inc., La Jolla, CA (US)

(72) Inventors: Brendan P. Eckelman, La Jolla, CA (US); Michael D. Kaplan, La Jolla, CA (US); Katelyn M. Willis, La Jolla, CA (US); John C. Timmer, La Jolla, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,354

(22) Filed: Jun. 6, 2023

(65) Prior Publication Data

US 2023/0295336 A1    Sep. 21, 2023

Related U.S. Application Data

(63) Continuation of application No. 16/380,963, filed on Apr. 10, 2019, now abandoned.

(60) Provisional application No. 62/656,331, filed on Apr. 11, 2018.

(51) Int. Cl.
| | | |
|---|---|---|
| *C07K 16/30* | (2006.01) | |
| *A61P 35/00* | (2006.01) | |
| *C07K 1/14* | (2006.01) | |

(52) U.S. Cl.
CPC .............. *C07K 16/30* (2013.01); *A61P 35/00* (2018.01); *C07K 1/14* (2013.01); *C07K 2317/31* (2013.01); *C07K 2317/522* (2013.01); *C07K 2317/55* (2013.01); *C07K 2317/569* (2013.01); *C07K 2317/622* (2013.01); *C07K 2317/624* (2013.01); *C07K 2317/64* (2013.01); *C07K 2317/66* (2013.01); *C07K 2317/732* (2013.01); *C07K 2317/734* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,522,811 | A | 6/1985 | Eppstein et al. |
| 5,151,510 | A | 9/1992 | Stec et al. |
| 5,223,409 | A | 6/1993 | Ladner et al. |
| 5,258,498 | A | 11/1993 | Huston et al. |
| 5,500,362 | A | 3/1996 | Robinson et al. |
| 5,525,491 | A | 6/1996 | Huston et al. |
| 5,571,698 | A | 11/1996 | Ladner et al. |
| 5,624,821 | A | 4/1997 | Winter et al. |
| 5,648,260 | A | 7/1997 | Winter et al. |
| 5,731,168 | A | 3/1998 | Carter et al. |
| 5,733,743 | A | 3/1998 | Ladner et al. |
| 5,750,373 | A | 5/1998 | Garrard et al. |
| 5,821,047 | A | 10/1998 | Garrard et al. |
| 5,821,337 | A | 10/1998 | Carter et al. |
| 5,837,500 | A | 11/1998 | Ladner et al. |
| 5,871,907 | A | 2/1999 | Winter et al. |
| 5,969,108 | A | 10/1999 | McCafferty et al. |
| 6,040,136 | A | 3/2000 | Garrard et al. |
| 6,132,992 | A | 10/2000 | Ledbetter et al. |
| 6,172,197 | B1 | 1/2001 | McCafferty et al. |
| 6,194,551 | B1 | 2/2001 | Idusogie et al. |
| 6,291,159 | B1 | 9/2001 | Winter et al. |
| 6,737,056 | B1 | 5/2004 | Presta |
| 6,831,161 | B1 | 12/2004 | Uhlen et al. |
| 6,955,877 | B1 | 10/2005 | Nygren et al. |
| 6,979,538 | B2 | 12/2005 | Ladner et al. |
| 7,025,962 | B1 | 4/2006 | Gorman et al. |
| 7,063,943 | B1 | 6/2006 | McCafferty et al. |
| 7,118,879 | B2 | 10/2006 | Ladner et al. |
| 7,183,076 | B2 | 2/2007 | Arathoon et al. |
| 7,208,293 | B2 | 4/2007 | Ladner et al. |
| 7,332,571 | B2 | 2/2008 | Miao et al. |
| 7,332,581 | B2 | 2/2008 | Presta |
| 7,385,028 | B2 | 6/2008 | Miao et al. |
| 7,638,299 | B2 | 12/2009 | Cho et al. |
| 7,642,044 | B2 | 1/2010 | Thogersen et al. |

(Continued)

FOREIGN PATENT DOCUMENTS

| | | |
|---|---|---|
| AU | 2013/202755 | 5/2013 |
| AU | 2015/202560 | 6/2015 |

(Continued)

OTHER PUBLICATIONS

Alegre et al., "Effect of a single amino acid mutation on the activating and immunosuppressive properties of a "humanized" OKT3 monoclonal antibody," J Immunol (1992) 148(11):3461-3468.

(Continued)

*Primary Examiner* — Anand U Desai
*Assistant Examiner* — Cheom-Gil Cheong
(74) *Attorney, Agent, or Firm* — Morrison & Foerster LLP

(57) ABSTRACT

The invention relates generally to multispecific polypeptides having constrained CD3 binding. In some embodiments, components of the multispecific polypeptides are connected by a non-cleavable linker. Also provided are methods of making and using these multispecific polypeptides in a variety of therapeutic, diagnostic and prophylactic indications.

21 Claims, 36 Drawing Sheets
Specification includes a Sequence Listing.

(56) References Cited

U.S. PATENT DOCUMENTS

| | | | |
|---|---|---|---|
| 7,696,312 B2 | 4/2010 | Miao et al. |
| 7,888,533 B2 | 2/2011 | Tian et al. |
| 8,044,178 B2 | 10/2011 | Boghaert et al. |
| 8,669,350 B2 | 3/2014 | Chou et al. |
| 9,346,884 B2 | 5/2016 | Beste et al. |
| 9,605,084 B2 | 3/2017 | Moore et al. |
| 9,644,016 B2 | 5/2017 | Stagliano et al. |
| 9,650,446 B2 | 5/2017 | Moore et al. |
| 9,701,759 B2 | 7/2017 | Desjarlais et al. |
| 10,010,626 B2 | 7/2018 | Chang et al. |
| 10,066,015 B2 | 9/2018 | Zhukovsky et al. |
| 10,087,250 B2 | 10/2018 | Bruenker et al. |
| 10,093,742 B2 | 10/2018 | Timmer et al. |
| 10,131,710 B2 | 11/2018 | Moore et al. |
| 10,501,551 B2 | 12/2019 | Eckelman et al. |
| 10,858,417 B2 | 12/2020 | Moore et al. |
| 11,866,507 B2 | 1/2024 | Eckelman et al. |
| 2004/0220388 A1 | 11/2004 | Mertens et al. |
| 2005/0014934 A1 | 1/2005 | Hinton et al. |
| 2005/0123546 A1 | 6/2005 | Umana et al. |
| 2007/0004909 A1 | 1/2007 | Johnson et al. |
| 2007/0009523 A1 | 1/2007 | Presta |
| 2008/0113412 A1 | 5/2008 | Sheffer et al. |
| 2008/0279851 A1 | 11/2008 | Coyle et al. |
| 2008/0300163 A1 | 12/2008 | Cho et al. |
| 2009/0155843 A1 | 6/2009 | Ottow et al. |
| 2009/0162380 A1 | 6/2009 | Glaser et al. |
| 2009/0208454 A1 | 8/2009 | Kraynov et al. |
| 2010/0035812 A1 | 2/2010 | Hays Putnam et al. |
| 2010/0093608 A1 | 4/2010 | Tian et al. |
| 2010/0254998 A1 | 10/2010 | Bossenmaier et al. |
| 2011/0015345 A1 | 1/2011 | Pinkstaff et al. |
| 2011/0097339 A1 | 4/2011 | Holmes et al. |
| 2011/0189203 A1 | 8/2011 | Hermans et al. |
| 2012/0149876 A1 | 6/2012 | Von Kreudenstein et al. |
| 2013/0224188 A1 | 8/2013 | Eckelman et al. |
| 2013/0273054 A1 | 10/2013 | Bossenmaier et al. |
| 2014/0072581 A1 | 3/2014 | Dixit et al. |
| 2014/0140989 A1 | 5/2014 | Eckelman et al. |
| 2014/0154253 A1 | 6/2014 | Ng et al. |
| 2014/0288275 A1 | 9/2014 | Moore et al. |
| 2014/0294823 A1 | 10/2014 | Moore et al. |
| 2014/0363426 A1 | 12/2014 | Moore et al. |
| 2014/0377253 A1 | 12/2014 | Harding et al. |
| 2015/0079088 A1 | 3/2015 | Lowman et al. |
| 2015/0087810 A1 | 3/2015 | Moore et al. |
| 2015/0239991 A1 | 8/2015 | Blein et al. |
| 2015/0307628 A1 | 10/2015 | Kim et al. |
| 2015/0322119 A1 | 11/2015 | Engelhardt et al. |
| 2016/0039942 A1 | 2/2016 | Cobbold et al. |
| 2016/0122425 A1 | 5/2016 | Daugherty et al. |
| 2016/0194399 A1 | 7/2016 | Irving et al. |
| 2016/0207981 A1 | 7/2016 | Eckelman et al. |
| 2016/0289324 A1 | 10/2016 | Moore et al. |
| 2017/0015753 A1 | 1/2017 | Timmer et al. |
| 2017/0022284 A1 | 1/2017 | Timmer et al. |
| 2017/0037130 A1 | 2/2017 | Raum et al. |
| 2017/0081397 A1 | 3/2017 | Stagliano et al. |
| 2017/0114141 A1 | 4/2017 | Amann et al. |
| 2017/0137517 A1 | 5/2017 | Bowman et al. |
| 2017/0198050 A1 | 7/2017 | Eckelman et al. |
| 2017/0198051 A1 | 7/2017 | Eckelman et al. |
| 2017/0204139 A1 | 7/2017 | Moore et al. |
| 2017/0209492 A1 | 7/2017 | June et al. |
| 2017/0320958 A1 | 11/2017 | Timmer et al. |
| 2018/0011883 A1 | 1/2018 | Goldbrenner et al. |
| 2018/0016354 A1 | 1/2018 | Wozniak-Knopp et al. |
| 2018/0230225 A1 | 8/2018 | Fan et al. |
| 2019/0010242 A1 | 1/2019 | Eckelman et al. |
| 2019/0100594 A1 | 4/2019 | Timmer et al. |
| 2019/0218515 A1 | 7/2019 | Ballesteros Nobell et al. |
| 2019/0330366 A1 | 10/2019 | Eckelman et al. |
| 2020/0048350 A1 | 2/2020 | Eckelman et al. |
| 2020/0190193 A1 | 6/2020 | Pandit et al. |
| 2021/0340273 A1 | 11/2021 | Timmer et al. |
| 2021/0380679 A1 | 12/2021 | Eckelman et al. |
| 2023/0124851 A1 | 4/2023 | Eckelman et al. |
| 2023/0348600 A1 | 11/2023 | Timmer et al. |
| 2024/0101704 A1 | 3/2024 | Eckelman et al. |

FOREIGN PATENT DOCUMENTS

| | | |
|---|---|---|
| AU | 2016/213702 | 8/2016 |
| CA | 2477192 | 11/2001 |
| CA | 2441653 | 3/2005 |
| CN | 101583376 | 11/2009 |
| CN | 108084265 | 5/2018 |
| EP | 1 378 520 | 1/2004 |
| EP | 1 736 484 | 12/2006 |
| EP | 2920209 | 9/2015 |
| EP | 2914634 | 12/2017 |
| EP | 3502140 | 6/2019 |
| WO | WO-1998/050431 | 11/1998 |
| WO | WO-2000/024884 | 5/2000 |
| WO | WO-2001/077342 | 10/2001 |
| WO | WO 2002/059264 | 8/2002 |
| WO | WO-2005/063816 | 7/2005 |
| WO | WO-2005/100402 | 10/2005 |
| WO | WO-2006/029879 | 3/2006 |
| WO | WO 2009/018386 | 2/2009 |
| WO | WO-2009/068649 | 6/2009 |
| WO | WO-2009/089004 | 7/2009 |
| WO | WO-2009/124931 | 10/2009 |
| WO | WO 2010/009391 | 1/2010 |
| WO | WO 2010/037836 | 4/2010 |
| WO | WO-2010/151792 | 12/2010 |
| WO | WO-2011/143545 | 11/2011 |
| WO | WO 2012/025525 | 3/2012 |
| WO | WO-2012/058768 | 5/2012 |
| WO | WO-2012/162067 | 11/2012 |
| WO | WO-2012/162583 | 11/2012 |
| WO | WO 2013/041687 | 3/2013 |
| WO | WO-2013/101909 | 7/2013 |
| WO | WO 2013/128194 | 9/2013 |
| WO | WO-2014/067011 | 5/2014 |
| WO | WO-2014/089113 | 6/2014 |
| WO | WO-2014/099997 | 6/2014 |
| WO | WO-2014/125273 | 8/2014 |
| WO | WO-2014/144960 | 9/2014 |
| WO | WO-2014/145806 | 9/2014 |
| WO | WO 2015/026894 | 2/2015 |
| WO | WO 2015/168469 | 11/2015 |
| WO | WO 2015/187793 | 12/2015 |
| WO | WO 2015/197598 | 12/2015 |
| WO | WO-2015/197789 | 12/2015 |
| WO | WO-2016/020309 | 2/2016 |
| WO | WO-2016/033225 | 3/2016 |
| WO | WO-2016/034666 | 3/2016 |
| WO | WO 2016/046778 | 3/2016 |
| WO | WO-2016/055593 | 4/2016 |
| WO | WO-2016/086189 | 6/2016 |
| WO | WO-2016/087416 | 6/2016 |
| WO | WO-2016/097408 | 6/2016 |
| WO | WO-2016/105450 | 6/2016 |
| WO | WO-2016/138038 | 9/2016 |
| WO | WO-2016/180982 | 11/2016 |
| WO | WO-2016/192613 | 12/2016 |
| WO | WO-2017/021349 | 2/2017 |
| WO | WO-2017/030926 | 2/2017 |
| WO | WO-2017/055398 | 4/2017 |
| WO | WO-2017/060144 | 4/2017 |
| WO | WO-2017/134140 | 8/2017 |
| WO | WO-2017/134440 | 8/2017 |
| WO | WO-2017/172981 | 10/2017 |
| WO | WO-2017/182672 | 10/2017 |
| WO | WO-2018/014260 | 1/2018 |
| WO | WO-2018/027025 | 2/2018 |
| WO | WO-2018/127473 | 7/2018 |
| WO | WO-2018/167486 | 9/2018 |
| WO | WO-2018/185045 | 10/2018 |
| WO | WO-2018/191438 | 10/2018 |
| WO | WO 2019/200022 | 10/2019 |
| WO | WO-2019/201866 | 10/2019 |
| WO | WO-2020/023553 | 1/2020 |

(56) References Cited

FOREIGN PATENT DOCUMENTS

| WO | WO-2020/076970 | 4/2020 |
|----|----------------|--------|
| WO | WO-2020/076977 | 4/2020 |
| WO | WO-2020/076992 | 4/2020 |
| WO | WO-2020/077257 | 4/2020 |
| WO | WO-2021/155071 | 8/2021 |

OTHER PUBLICATIONS

Asano et al. "Domain order of a bispecific diabody dramatically enhances its antitumor activity beyond structural format conversion: the case of the hEx3 diabody." *Protein Engineering, Design & Selection* 26.5 (2013): 359-367.
Bacac et al., "CD20 Tcb (RG6026), a Novel "2:1" T Cell Bispecific Antibody for the Treatment of B Cell Malignancies," Blood (2016) 128:1836.
Baldrick, "Pharmaceutical Excipient Development: The Need for Preclinical Guidance," Regul Toxicol Pharm (2000) 32(2):210-218.
Barre et al., "Cleavage Specificity Analysis of Six Type II Transmembrane Serine Proteases (TTSPs) Using PICS with Proteome-Derived Peptide Libraries," PLOS One (2014) 9(9):e105984.
Barthelemy et al. "Comprehensive analysis of the factors contributing to the stability and solubility of autonomous human VH domains." *Journal of Biological Chemistry* 283.6 (2008): 3639-3654.
Beiboer et al. "Guided selection of a pan carcinoma specific antibody reveals similar binding characteristics yet structural divergence between the original murine antibody and its human equivalent." *Journal of Molecular Biology* 296.3 (2000): 833-849.
Beliveau et al., "Probing the substrate specificities of matriptase, matriptase-2, hepsin and DESC1 with internally quenched fluorescent peptides," FEBS J (2009) 276(8):2213-2226.
Beranger et al., "Correspondence between the IMGT unique numbering for C-Domain, the IMGT exon numbering, the Eu and Kabat numberings: Human IGHG," IMGT Scientific chart. Published on May 17, 2016. Retrieved on Jul. 19, 2018. Retrieved from http://www.imgt.org/IMGTScientificChart/Numbering/Hu_IGHGnber.html.
Bowie et al., "A method to identify protein sequences that fold into a known three-dimensional structure," Science (1991) 253(5016):164-170.
Brinkmann et al., "The making of bispecific antibodies," MABS (2017) 9(2):182-212.
Bruggemann et al., "Comparison of the effector functions of human immunoglobulins using a matched set of chimeric antibodies," J Exp Med (1987) 166(5):1351-1361.
Bulliard et al., "Activating $Fc_\gamma$ receptors contribute to the antitumor activities of immunoregulatory receptor-targeting antibodies," J Exp Med (2013) 210(9): 1685-1693.
Carter et al., "Bispecific human IgG by design," J Immunol Methods (2001) 248(1-2):7-15.
Charman, "Lipids, lipophilic drugs, and oral drug delivery-some emerging concepts," J Pharm Sci (2000) 89(8):967-978.
Chen et al., "A Unique Substrate Recognition Profile for Matrix Metalloproteinase-2." J Biol Chem (2002) 277(6):4485-4491.
Chen et al., "Fusion protein linkers: property, design and functionality," Adv Drug Deliv Rev (2013) 65(10):1357-1369.
Cheng et al., "Construction and expression of a reshaped VH domain against human CD28 molecules," Preparative Biochemistry and Biotechnology (2002) 32(3):239-251.
Choi et al. "Predicting antibody complementarity determining region structures without classification." *Molecular BioSystems* 7.12 (2011): 3327-3334.
Chothia et al., "Canonical structures for the hypervariable regions of immunoglobulins," J Mol Biol (1987) 196(4):901-917.
Chothia et al., "Conformations of immunoglobulin hypervariable regions," Nature (1989) 342(6252):877-883.
Clynes et al., "Fc receptors are required in passive and active immunity to melanoma," Proc Natl Acad Sci USA (1998) 95(2):652-656.
Cragg et al., "Antibody specificity controls in vivo effector mechanisms of anti-CD20 reagents," Blood (2004) 103:2738-2743.
Cragg et al., "Complement-mediated lysis by anti-CD20 mAb correlates with segregation into lipid rafts," Blood (2003) 101(3):1045-1052.
Dall'Acqua et al., "Properties of Human IgG1s Engineered for Enhanced Binding to the Neonatal Fc Receptor (FcRn)*," J Biol Chem (2006) 281(33):23514-23524.
Davies et al., "Antibody-Antigen Complexes," Annu Rev Biochem (1990) 59:439-473.
Davis et al., "SEEDbodies: fusion proteins based on strand-exchange engineered domain (Seed) CH3 heterodimers in an Fc analogue platform for asymmetric binders or immunofusions and bispecific antibodies," Protein Eng Des Sel (2010) 23(4):195-202.
Deisenhofer, "Crystallographic refinement and atomic models of a human Fc fragment and its complex with fragment B of protein A from *Staphylococcus aureus* at 2.9- and 2.8-.ANG. resolution," Biochemistry (1981) 20(9):2361-2370.
De Genst et al. "Antibody repertoire development in camelids." *Developmental & Comparative Immunology* 30.1-2 (2006): 187-198.
Driessens et al. "Costimulatory and coinhibitory receptors in anti-tumor immunity." *Immunological reviews* (2009) 229.1: 126-144.
Gazzano-Santoro et al., "A non-radioactive complement-dependent cytotoxicity assay for anti-CD20 monoclonal antibody," J Immunol Methods (1997) 202(2):163-171.
Griffiths et al. "Human anti-self antibodies with high specificity from phage display libraries." *The EMBO journal* 12.2 (1993): 725-734.
Gunasekaran et al., "Enhancing antibody Fc heterodimer formation through electrostatic steering effects: applications to bispecific molecules and monovalent IgG," J Biol Chem (2010) 285(25):19637-19646.
Ha et al., "Immunoglobulin Fc Heterodimer Platform Technology: From Design to Applications in Therapeutic Antibodies and Proteins," Front Immunol (2016) 7:394.
Harris et al., "Definition and Redesign of the Extended Substrate Specificity of Granzyme B*," J Biol Chem (1998) 273(42):27364-27373.
Harwood et al., "Attack, a novel bispecific T cell-recruiting antibody with trivalent EGFR binding and monovalent CD3 binding for cancer immunotherapy," Oncoimmunology (2018) 7(1):e1377874.
Hellstrom et al., "Antitumor effects of L6, an IgG2a antibody that reacts with most human carcinomas," Proc Natl Acad Sci USA (1986) 83(18):7059-7063.
Hellstrom et al., "Strong antitumor activities of IgG3 antibodies to a human melanoma-associated ganglioside," Proc Natl Acad Sci USA (1985) 82(5):1499-1502.
Henry et al., "Stability-Diversity tradeoffs impose fundamental constraints on selection of synthetic human VH/VL single-domain antibodies from in vitro display libraries," Frontiers in Immunology (2017) 8:1-15.
Hernandez-Hoyos et al., "MOR209/ES414, a Novel Bispecific Antibody Targeting PSMA for the Treatment of Metastatic Castration-Resistant Prostate Cancer," Mol Cancer Ther (2016) 15(9):2155-2165.
Huet et al., "Multivalent nanobodies targeting death receptor 5 elicit superior tumor killing through efficient caspase induction," MABS (2014) 6(6):1560-70.
Husain et al., "Expanding the boundaries of biotherapeutics with bispecific antibodies," Biodrugs (2018) 32(5):441-64.
Idusogie et al., "Engineered antibodies with increased activity to recruit complement," J Immunol (2001) 166(4):2571-2575.
Jendeberg et al., "Engineering of Fc(1) and Fc(3) from human immunoglobulin G to analyse subclass specificity for staphylococcal protein A," J Immnuol Methods (1997) 201(1):25-34.
Kaneko et al., "Optimizing Therapeutic Antibody Function," Biodrugs (2011) 25(1):1-11.
Kim et al., "Mutational approaches to improve the biophysical properties of human single-domain antibodies," Biochimica et Biophysica Acta (2014) 1844:1983-2001.

(56) References Cited

OTHER PUBLICATIONS

Klimka et al., "Human Anti-CD30 Recombinant Antibodies by Guided Phage Antibody Selection Using Cell Panning," Br. J. Cancer (2000) 83(2):252-260.

Kumar et al., "Molecular cloning and expression of the Fabs of human autoantibodies in *Escherichia coli*," J. Biol. Chem. (2000) 275:35129-36.

Kuo et al., "Engineering a CD123×CD3 bispecific scFv immunofusion for the treatment of leukemia and elimination of leukemia stem cells," Protein Eng Des Sel. (2012) 25(10): 561-9.

La Rocca et al., "Zymographic detection and clinical correlations of MMP-2 and MMP-9 in breast cancer sera," British Journal of Cancer (2004) 90:1414-1421.

Laplanche et al., "Phosphorothioate-modified oligodeoxyribonucleotides. III. NMR and UV spectroscopic studies of the Rp-Rp, Sp-Sp, and Rp-Sp duplexes, [d(GGSAATTCC) ]2, derived from diastereomeric O-ethyl phosphorothioates," Nucleic Acids Res (1986) 14(22):9081-9093.

Lazar et al., "Engineered antibody Fc variants with enhanced effector function," Proc Natl Acad Sci USA (2006) 103(11):4005-4010.

Leaver-Fay et al., "Computationally Designed Bispecific Antibodies using Negative State Repertoires," Structure (2016) 24(4):641-651.

Ma et al., "Targeting immunotherapy for bladder cancer using anti-CD3x B7-H3 bispecific antibody," Cancer Med (2018) 7(10):5167-5177.

Maeda et al., "Engineering of functional chimeric protein G-Vargula luciferase," Anal Biochem. (1997) 249(2):147-52.

Malia et al. "Epitope mapping and structural basis for the recognition of phosphorylated tau by the anti-tau antibody AT8." *Proteins: Structure, Function, and Bioinformatics* 84.4 (2016): 427-434.

Malmqvist, "Biospecific interaction analysis using biosensor technology," Nature (1993) 361:186-187.

Marasco et al., "Design, intracellular expression, and activity of a human antihuman immunodeficiency virus type 1 gp120 single-chain antibody," Proc Natl Acad Sci USA (1993) 90(16):7889-7893.

Merchant et al., "An efficient route to human bispecific IgG," Nat Biotechnol (1998) 16(7):677-681.

Miller, "Protein-protein recognition and the association of immunoglobulin constant domains," JMB (1990) 216(4):965-973.

Moore et al., "A novel bispecific antibody format enables simultaneous bivalent and monovalent co-engagement of distinct target antigens," MAbs (2011) 3(6):546-557.

Moore et al., "Engineered Fc variant antibodies with enhanced ability to recruit complement and mediate effector functions," MAbs (2010) 2(2):181-189.

Nagorsen et al., "Immunomodulatory therapy of cancer with T cell-engaging BiTE antibody blinatumomab," Exp Cell Res. (2011) 317(9): 1255-60.

Natsume et al., "Engineered Antibodies of IgG1/IgG3 Mixed Isotype with Enhanced Cytotoxic Activities," Cancer Res (2008) 68(10):3863-3872.

Nyman et al., "Structural characterisation of N-linked and O-linked oligosaccharides derived from interferon-alpha2b and interferon-alpha14c produced by Sendai-virus-induced human peripheral blood leukocytes," Eur J Biochem. (1998) 253(2): 485-93.

Ohannesian et al., "Carcinoembryonic antigen and other glycoconjugates act as ligands for galectin-3 in human colon carcinoma cells," Cancer Res. (1995) 55(10): 2191-2199.

Osbourn, et al., "From Rodent Regents to Human Therapeutics Using Antibody Guided Selection," Methods. (2005) 36:61-68.

Padlan, "A possible procedure for reducing the immunogenicity of antibody variable domains while preserving their ligand-binding properties," Mol Immunol (1991) 28(4-5): 489-498.

Pan et al., "Structural characterization of human interferon gamma. Heterogeneity of the carboxyl terminus," Eur J Biochem. (1987) 166(1): 145-149.

Pan et al., "Site-specific PEGylation of an anti-CEA/CD3 bispecific antibody improves its antitumor efficacy," Int J Nanomedicine. (2018)13: 3189-3201.

Pedroza-Gonzalez et al., "GITR engagement in combination with CTLA-4 blockade completely abrogates immunosuppression mediated by human liver tumor-derived regulatory T cells ex vivo," Oncoimmunology (2015) 4(12):e1051297.

Pessano, S. et al., "The T3/T Cell Receptor Complex: Antigenic Distinction Between the Two 20-kd T3 (T3-δand T3-Eε) Subunits," The EMBO Journal (1985) 4(2):337-344.

Pestka et al., The human interferons—from protein purification and sequence to cloning and expression in bacteria: before, between, and beyond, Arch Biochem Biophys. (1983) 221(1): 1-37.

Pestka, vol. 119. Interferons (Part C) (1986) Meth. Enzymol, 199: 3-4.

Petkova et al., "Enhanced half-life of genetically engineered human IgG1 antibodies in a humanized FcRn mouse model: potential application in humorally mediated autoimmune disease," Int Immunol (2006) 18(12):1759-1769.

Poe et al., "Human cytotoxic lymphocyte granzyme B. Its purification from granules and the characterization of substrate and inhibitor specificity," J Biol Chem (1991) 266(1):98-103.

Pollard et al., "Fixation, processing, and immunochemical reagent effects on preservation of T-lymphocyte surface membrane antigens in paraffin-embedded tissue," J Histochem Cytochem. (1987)35(11): 1329-38.

Portolano et al., "Lack of promiscuity in autoantigen-specific H and L chain combinations as revealed by human H and L chain "roulette"," J. Immunol. (1993) 150:880-887.

Powell et al., "Compendium of excipients for parenteral formulations," PDA J Pharm Sci Technol (1998) 52(5):238-311.

Presta et al., "Humanization of an Antibody Directed Against IgE," J. Immunol. (1993) 151(2): 2623-2632.

Queen et al., "A humanized antibody that binds to the interleukin 2 receptor," Proc Natl Acad Sci USA (1989) 86:10029-10033.

Ravetch et al., "Fc receptors," Annu Rev Immunol. (1991) 9:457-92.

Reusch et al., "A Novel Tetravalent Bispecific T and Ab (CD30/CD16A) Efficiently Recruits NK Cells for the Lysis of CD30+ Tumor Cells," mABs (2014) 6(Suppl 3): 727-738.

Ridgway et al., "'Knobs-into-holes' engineering of antibody CH3 domains for heavy chain heterodimerization," Protein engineering (1996) 9(7):617-621.

Riechmann et al., "Reshaping Human Antibodies for Therapy," Nature (1988) 332: 323-327.

Rodrigues et al., "Engineering a humanized bispecific F(ab')2 fragment for improved binding to T cells," Int J Cancer Suppl. (1992) 7:45-50.

Rosenberg et al., "Use of Tumor-Infiltrating Lymphocytes and Interleukin-2 in the Immunotherapy of Patients With Metastatic Melanoma. A Preliminary Report," N Engl J Med. (1988) 319(25): 1676-1680.

Rosok et al., "A Combinatorial Library Strategy for the Rapid Humanization of Anticarcinoma BR96 Fab," J. Biol. Chem. (1996) 271(37): 22611-22618.

Rowland et al., "Drug Localisation and Growth Inhibition Studies of Vindesine-Monoclonal Anti-CEA Conjugates in a Human Tumour Xenograft," Cancer Immunol. Immunother. (1986) 21:183-187.

Sadelain et al., "The basic principles of chimeric antigen receptor design," Cancer Discov. (2013) 3(4): 388-398.

Sadelain et al., "The promise and potential pitfalls of chimeric antigen receptors," Curr Opin Immunol. (2009) 21(2): 215-23.

Schmiedel e tal. "Expression of a bispecific dsFv-dsFv' antibody fragment in *Escherichia coli*." Protein Engineering 13.10 (2000): 725-734.

Seimetz et al., "Development and approval of the trifunctional antibody catumaxomab (anti-EpCAM x anti-CD3) as a targeted cancer immunotherapy," Cancer Treat Rev (2010) 36:458-467.

Shields et al., "High Resolution Mapping of the Binding Site on Human IgG1 for FcγRI, FcγRII, FcγRIII, and FcRn and Design of IgG1 Variants with Improved Binding to the FcγR*," JBC (2001) 276(9):6591-6604.

(56) References Cited

OTHER PUBLICATIONS

Sims et al., "A Humanized CD18 Antibody Can Block Function Without Cell Destruction," J. Immunol. (1993) 151(4): 2296-2308.
Sitaraman et al., "High-throughput protein expression using cell-free system," Methods Mol. Biol. (2009) 498: 229-44.
Smith-Gill et al., "Contributions of immunoglobulin heavy and light chains to antibody specificity for lysozyme and two haptens," J. Immunol. (1987) 139:4135-44.
Song et al., "Light chain of natural antibody plays a dominant role in protein antigen binding," Biochem. Biophys. Res. Comm. (2000) 268:390-94.
Southall et al., "Immunohistological distribution of 5T4 antigen in normal and malignant tissues," Br J Cancer. (1990) 61(1): 89-95.
Southgate et al., "CXCR4 mediated chemotaxis is regulated by 5T4 oncofetal glycoprotein in mouse embryonic cells," PLoS One. (2010) 5(4): e9982.
Spirin, "High-Throughput Cell-Free Systems for Synthesis of Functionally Active Proteins," Trends Biotechnol. (2004) 22(10): 538-545.
Starzynska et al., "The expression of 5T4 antigen in colorectal and gastric carcinoma," Br J Cancer. (1992) 66(5): 867-869.
Starzynska et al., "5T4 oncofetal antigen in gastric carcinoma and its clinical significance," Eur J Gastroenterol Hepatol. (1998) 10(6): 479-484.
Stavenhagen et al., "Enhancing the potency of therapeutic monoclonal antibodies via Fc optimization," Adv Enzyme Regul (2008) 48:152-164.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res (2007) 67(18):8882-8890.
Stec et al., Automated solid-phase synthesis, separation, and stereochemistry of phosphorothioate analogs of oligodeoxyribonucleotides, J Am Chem Soc (1984) 106(20):6077-6079.
Stein et al. "Physicochemical properties of phosphorothioate oligodeoxynucleotides," Nucleic Acids Res (1988) 16(8):3209-3221.
Streit et al., "Angiogenesis, lymphangiogenesis, and melanoma metastasis," Oncogene (2003) 22(20):3172-3179.
Taylor et al., "Nanocell targeting using engineered bispecific antibodies," Mabs (2015) 7(1):53-65.
Thornberry et al., "A combinatorial approach defines specificities of members of the caspase family and granzyme B. Functional relationships established for key mediators of apoptosis," J Biol Chem (1997) 272(29):17907-17911.
Thornton et al., "Prediction of progress at last," Nature (1991) 354:105-106.
Tonini et al., "Molecular basis of angiogenesis and cancer," Oncogene (2003) 22(42):6549-6556.
Uhlmann et al., "Antisense oligonucleotides: a new therapeutic principle," Chem Rev (1990) 90(4):543-584.
Valedkarimi et al., "Antibody-cytokine fusion proteins for improving efficacy and safety of cancer therapy," Biomed Pharmacother. (2017) 95: 731-742.
Van De Winkel et al., "Human IgG Fc receptor heterogeneity: molecular aspects and clinical implications," Immunol Today. (1993) 14(5): 215-21.
Vivier et al., "Structure and function of the CD16:zeta:gamma complex expressed on human natural-killer cells," Int J Cancer. Suppl. 7 (1992) 7:11-14.
Von Kreudenstein et al., "Improving biophysical properties of a bispecific antibody scaffold to aid developability: quality by molecular design," MAbs (2013) 5(5):646-654.
Wang, "Lyophilization and development of solid protein pharmaceuticals," Int J Pharm (2000) 203(1-2):1-60.
Ward et al., "Binding activities of a repertoire of single immunoglobulin variable domains secreted from *Escherichia coli*," Nature (1989) 341:544-56.
Weidle et al. "The intriguing options of multispecific antibody formats for treatment of cancer." *Cancer genomics & proteomics* 10.1 (2013): 1-18.
Wirthmueller et al., "Signal transduction by Fc gamma RIII (CD16) is mediated through the gamma chain," J Exp Med. (1992) 175(5):1381-90.
Wrigley et al., "5T4 oncofetal antigen expression in ovarian carcinoma.," Int J Gynecol Cancer. (1995) 5(4): 269-274.
Xing et al., "BiHC, a T-Cell-Engaging Bispecific Recombinant Antibody, Has Potent Cytotoxic Activity Against Her2 Tumor Cells," Transl Oncol (2017) 10(5):780-785.
Yada et al., "A novel humanized anti-human death receptor 5 antibody CS-1008 induces apoptosis in tumor cells without toxicity in hepatocytes," Ann Oncol (2008) 19(6):1060-1067.
Yamamoto et al., "Creation of interferon-alpha8 mutants with amino acid substitutions against interferon-alpha receptor-2 binding sites using phage display system and evaluation of their biologic properties," J Interferon Cytokine Res. (2009) 29(3): 161-70.
Yang et al., "A Common Pathway for T Lymphocyte Activation Involving Both The CD3-Ti Complex and CD2 Sheep Erythrocyte Receptor Determinants," J. Immunol. (1986) 137(4): 1097-1100.
Yao et al., "Advances in targeting cell surface signalling molecules for immune modulation," Nat Rev Drug Discov (2013) 12(2):130-146.
Young et al., "Antibody-Cytokine Fusion Proteins for Treatment of Cancer: Engineering Cytokines For Improved Efficacy and Safety," Seminars in Oncology. (2014) 41(5):623-636, 19 pages.
Zalevsky et al., "Enhanced antibody half-life improves in vivo activity," Nat Biotechnol (2010) 28(2):157-159.
Zhang et al., "Lexatumumab (TRAIL-receptor 2 mAb) induces expression of DR5 and promotes apoptosis in primary and metastatic renal cell carcinoma in a mouse orthotopic model," Cancer Lett (2007) 251(1):146-157.
Zon et al., "Phosphorothioate oligonucleotides: chemistry, purification, analysis, scale-up and future directions," Anticancer Drug Res (1991) 6(6):539-568.
Miyazaki, "Studies on Alpaca VHH antibodies for industrial applications," Kagoshima University Repository, Jun. 1, 2015, 102 pages. https://ir.kagoshima-u.ac.jp/records/9025 (Machine translation provided).
Zhang et al., "Amplification Ex Vivo and Cytocidal Activity of Leukemia Tumor-Associated Antigen-Specific Cytotoic T Lympohcytes," Chinese Journal of Experimental Hematology, (2015) 23(3); 814-820; (Article in Chinese; English abstract provided).
Bork et al., "Powers and pitfalls in sequence analysis: the 70% hurdle," Genome Res. (2000) 10(4):398-400.
Brown et al., "Tolerance of single, but not multiple, amino acid replacements in antibody VH CDR 2: a means of minimizing B cell wastage from somatic hypermutation?," J Immunol. May 1, 1996;156(9):3285-91.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol. (1990) 111(5 Pt 1):2129- 38.
Goel et al., "Plasticity within the antigen-combining site may manifest as molecular mimicry in the humoral immune response," J Immunol. Dec. 15, 2004;173(12):7358-67.
Khan et al., "Adjustable locks and flexible keys: plasticity of epitope-paratope interactions in germline antibodies," J Immunol. (2014) 192(11):5398-405.
Kulmanov et al., "DeepGO: predicting protein functions from sequence and interactions using a deep ontology-aware classifier," Bioinformatics. Feb. 15, 2018;34(4):660-668.
Lloyd et al., "Modelling the human immune response: performance of a 1011 human antibody repertoire against a broad panel of therapeutically relevant antigens," Protein Eng Des Sel. Mar. 22, 2009(3):159-68.
Miosge et al., "Comparison of predicted and actual consequences of missense mutations," Proc Natl Acad Sci USA. (2015) 112(37):E5189-98.
Poosarla et al., "Computational de novo design of antibodies binding to a peptide with high affinity," Biotechnol Bioeng. (2017) 114(6):1331-1342.

(56) References Cited

OTHER PUBLICATIONS

Rabia et al., "Understanding and overcoming trade-offs between antibody affinity, specificity, stability and solubility," Biochem Eng J. Sep. 15, 2018:137:365-374.
Skolnick et al., "From genes to protein structure and function: novel applications of computational approaches in the genomic era," Trends Biotechnol. (2000) 18(1):34-9.
Vajdos et al., "Comprehensive functional maps of the antigen-binding site of an anti-ErbB2 antibody obtained with shotgun scanning mutagenesis," J Mol Biol. Jul. 5, 2002;320(2):415-28.
Vattekatte et al., "Discrete analysis of camelid variable domains: sequences, structures, and in-silico structure prediction," PeerJ. Mar. 6, 2020:8:e8408. doi: 10.7717/peerj.8408. eCollection 2020.

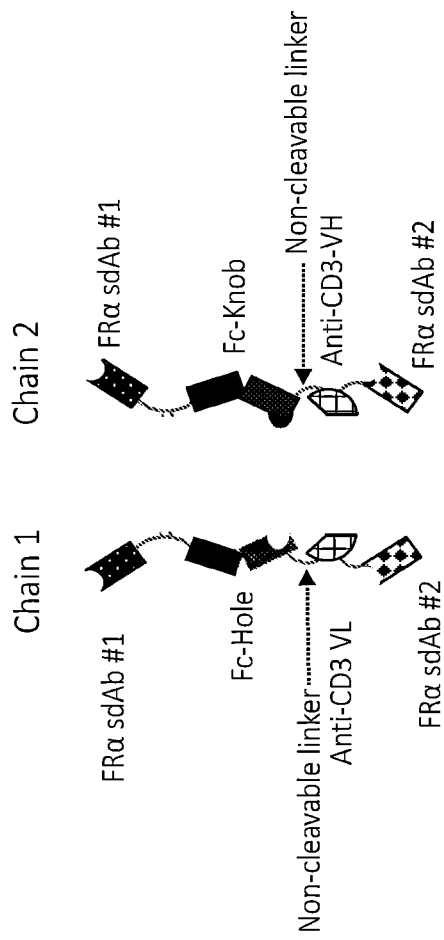
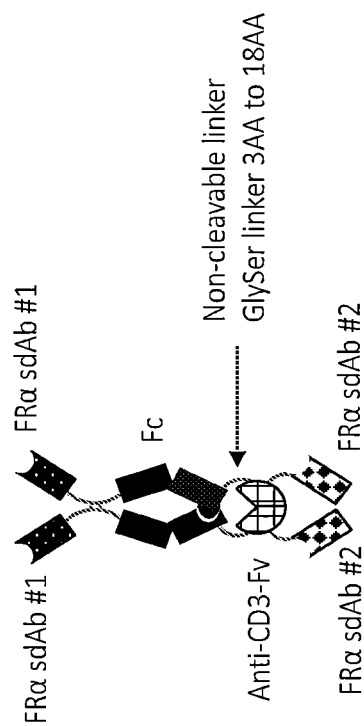
FIG. 2A
FIG. 2B

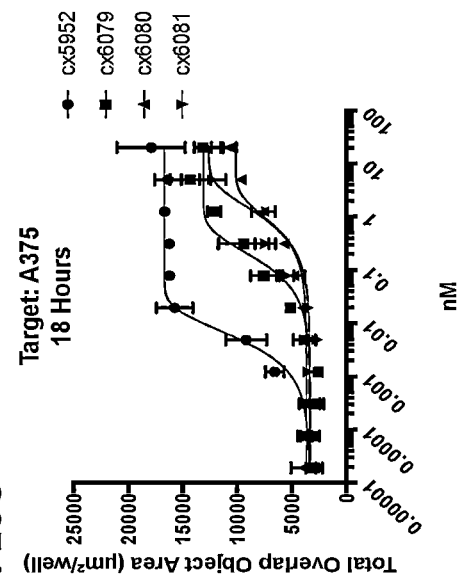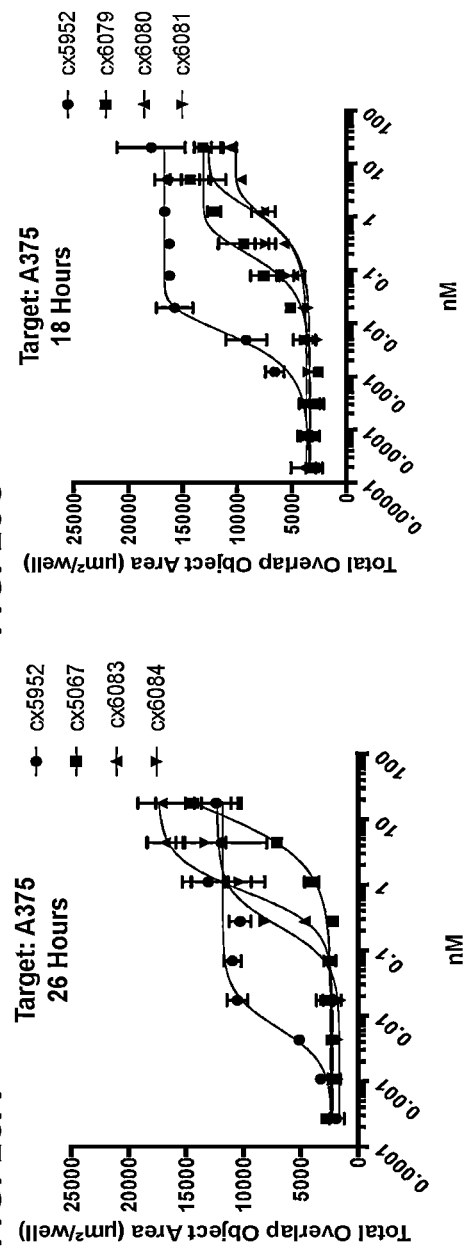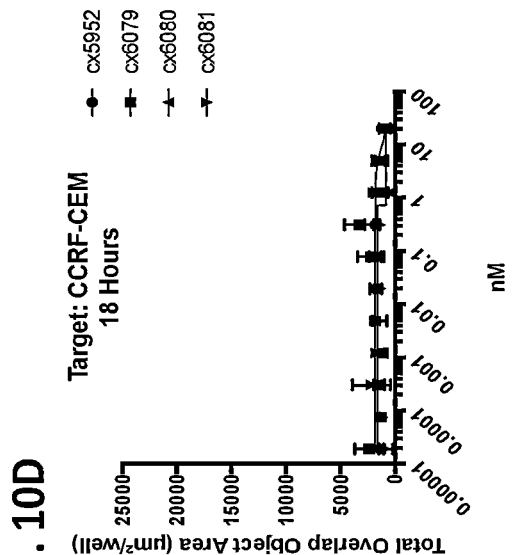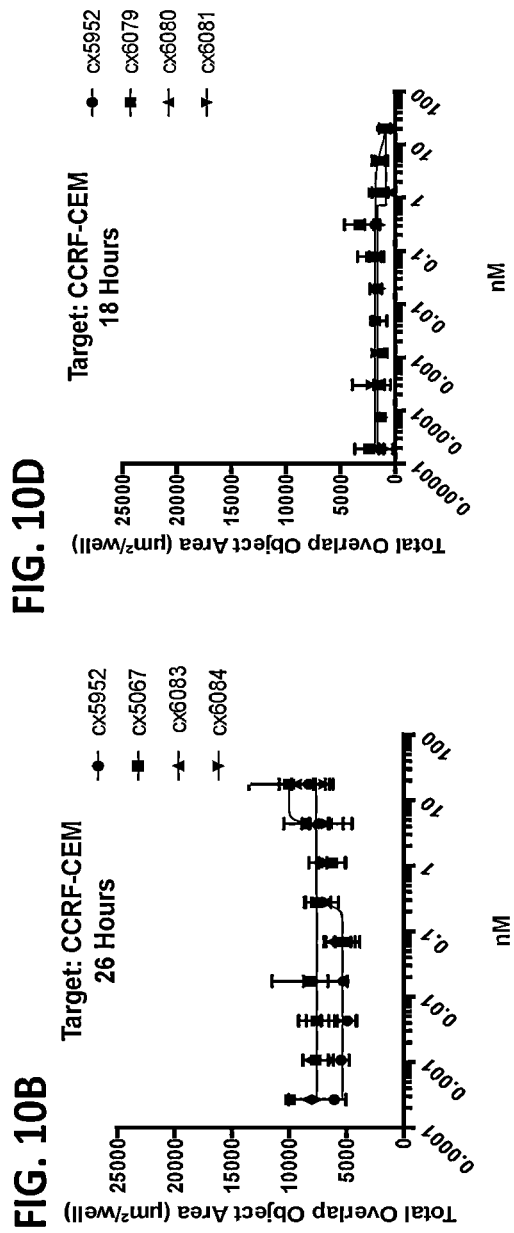
FIG. 10A  FIG. 10C
FIG. 10B  FIG. 10D

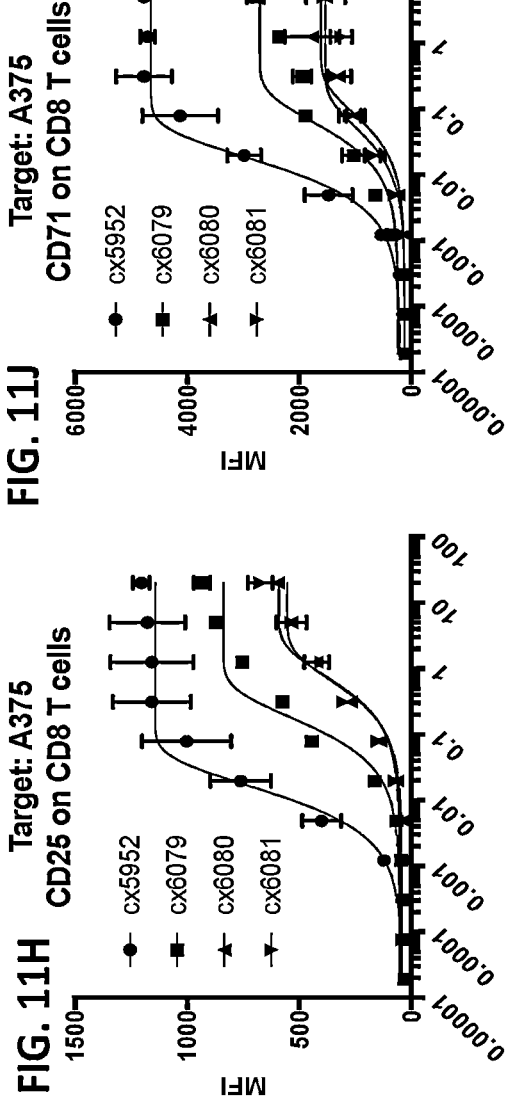
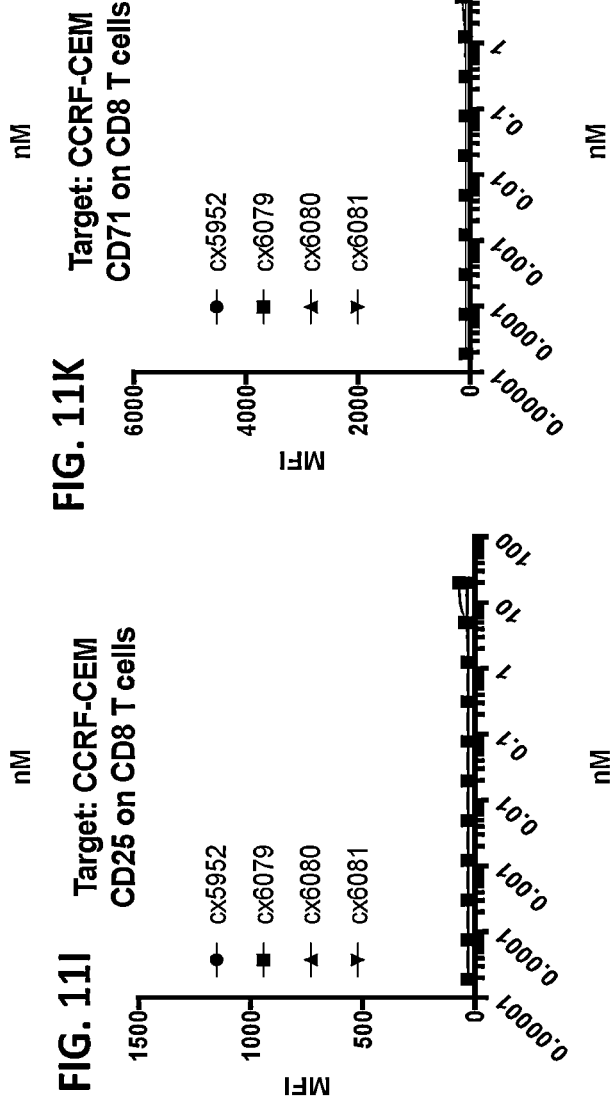

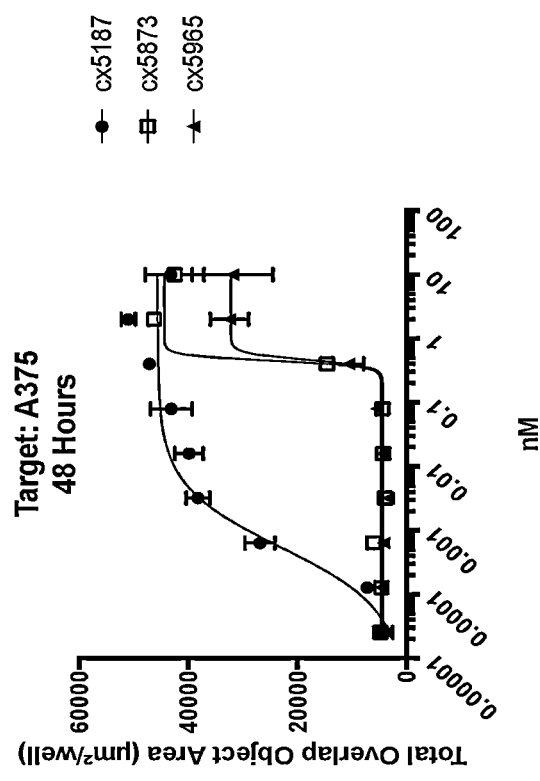
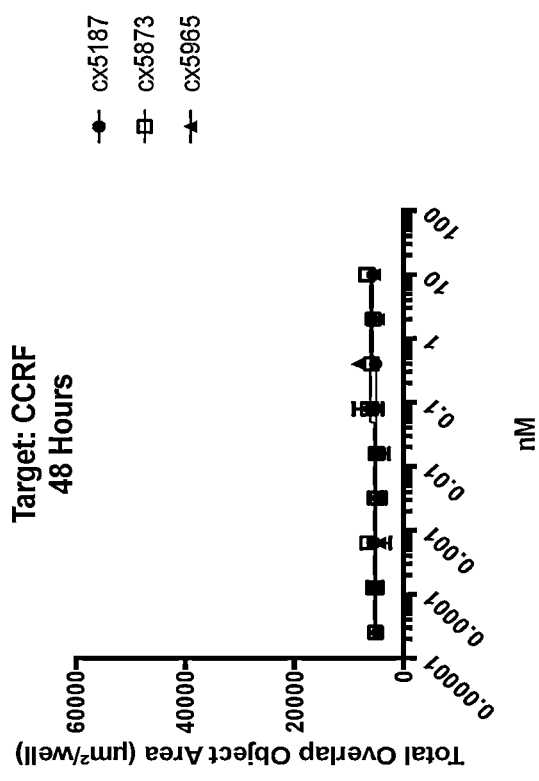
FIG. 14A
FIG. 14B

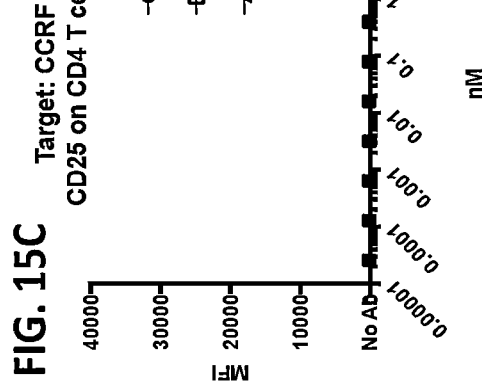
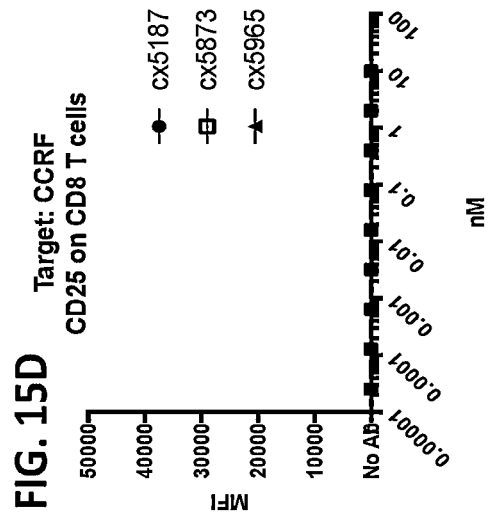
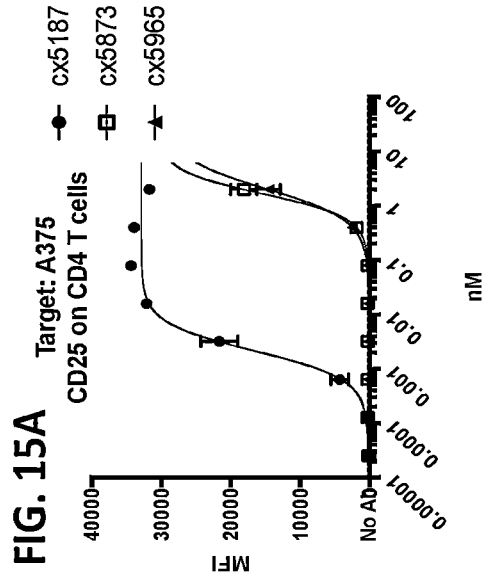
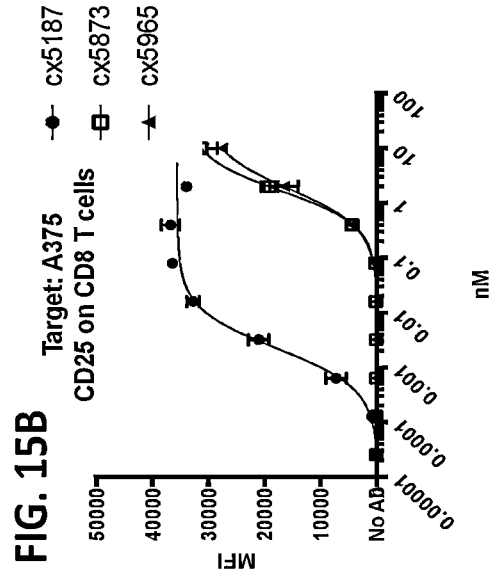

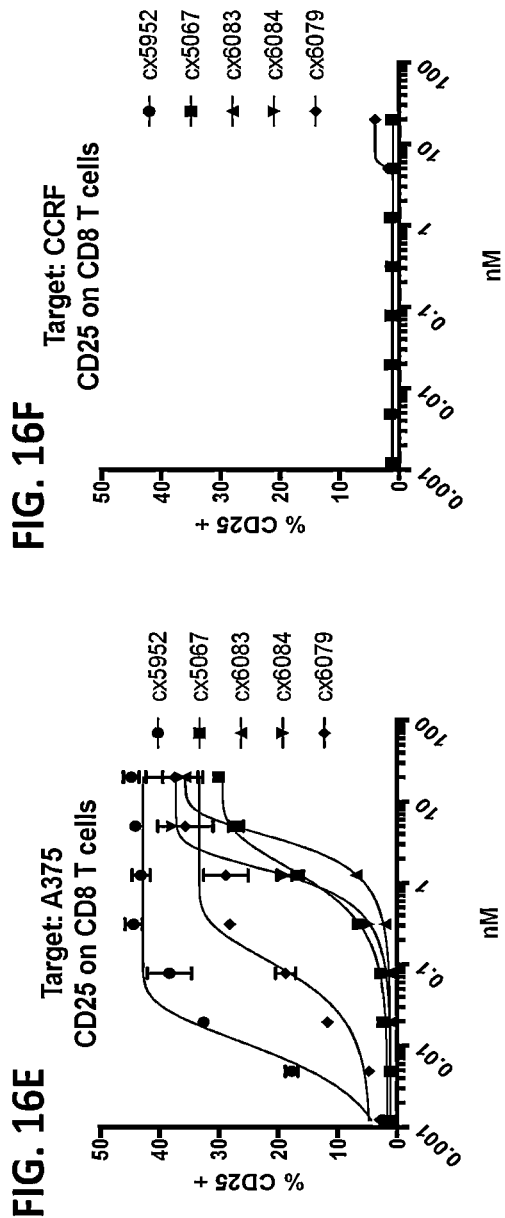
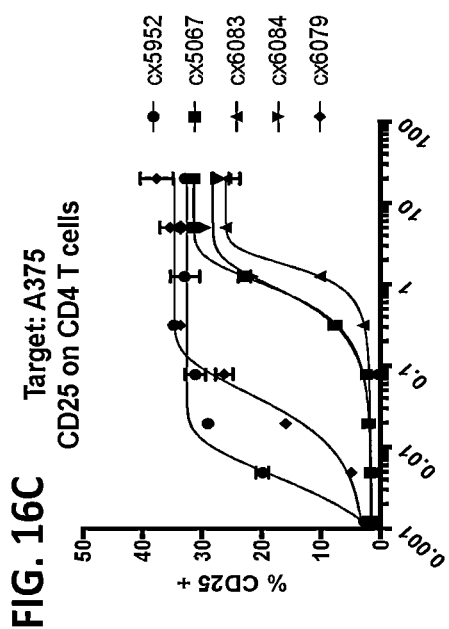

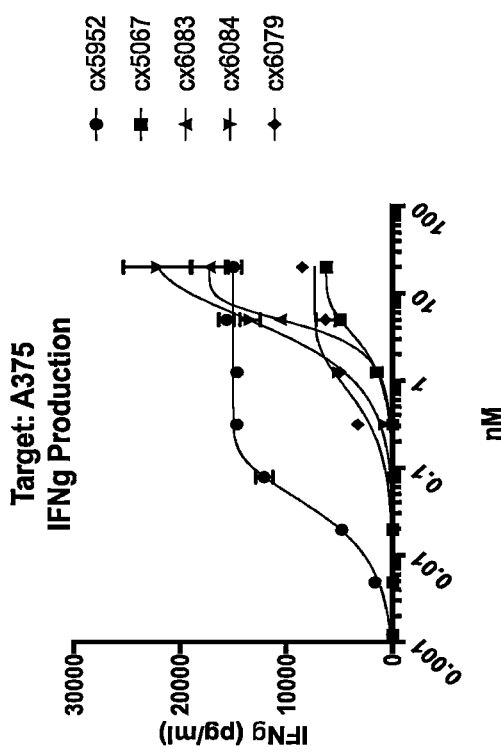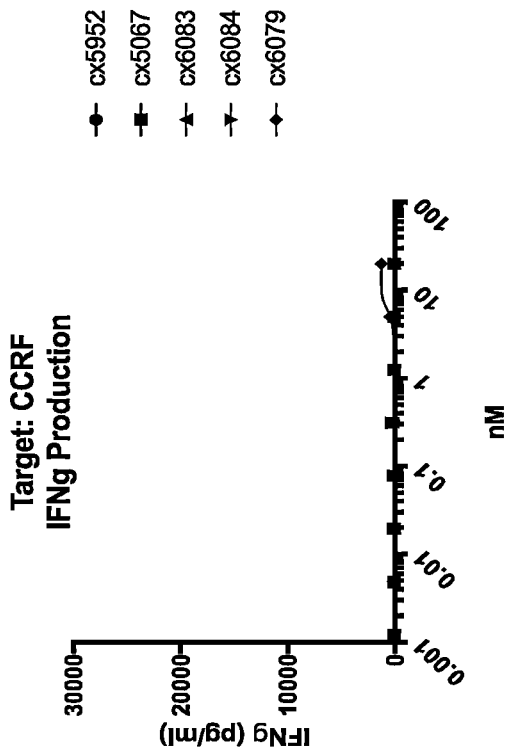
FIG. 16K
FIG. 16L

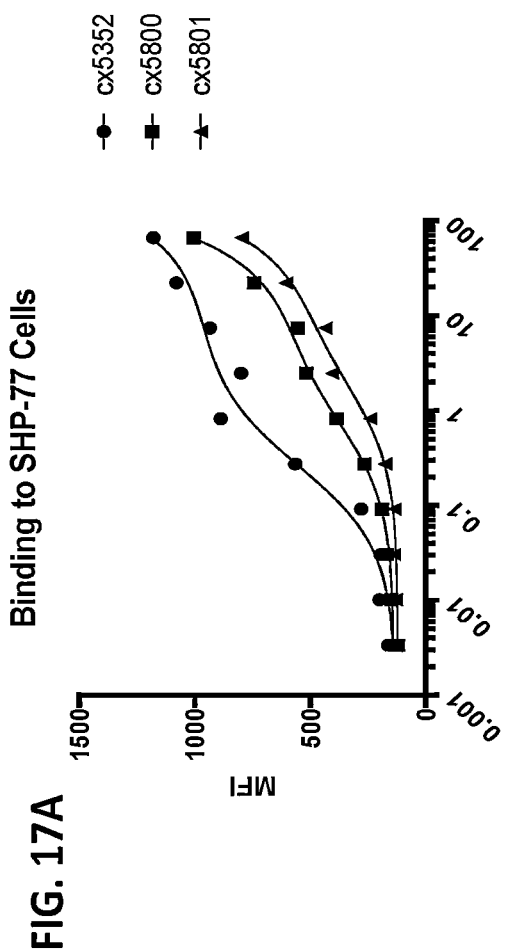
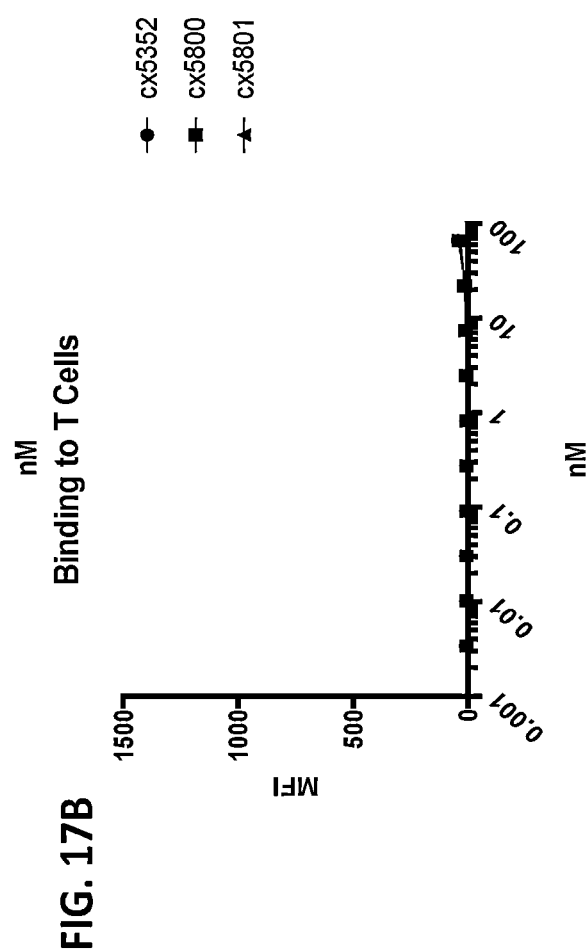
FIG. 17A
FIG. 17B

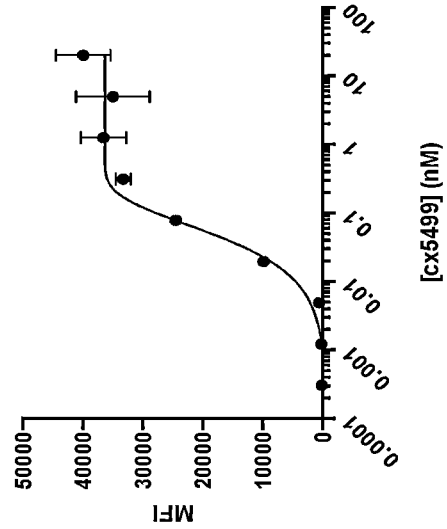
FIG. 18B CD25 Expression on CD4 T-cells
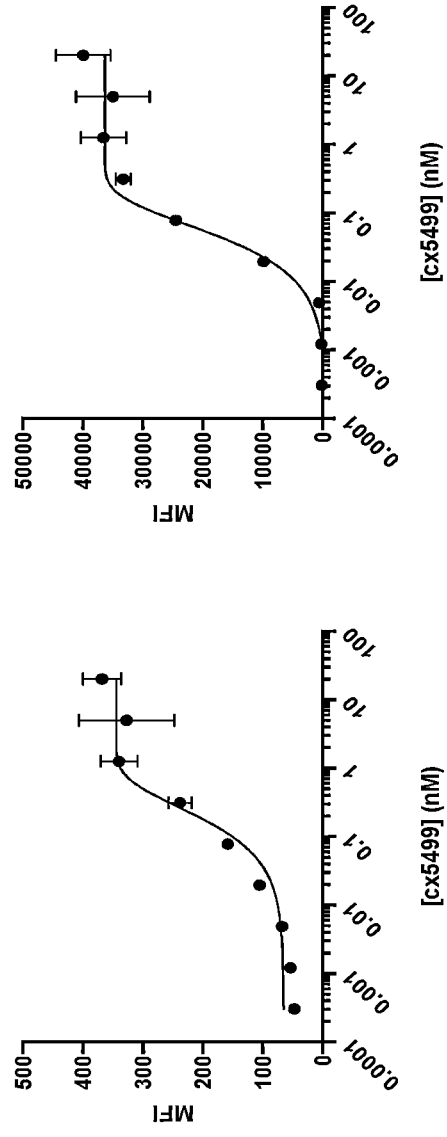
FIG. 18C CD69 Expression on CD4 T-cells
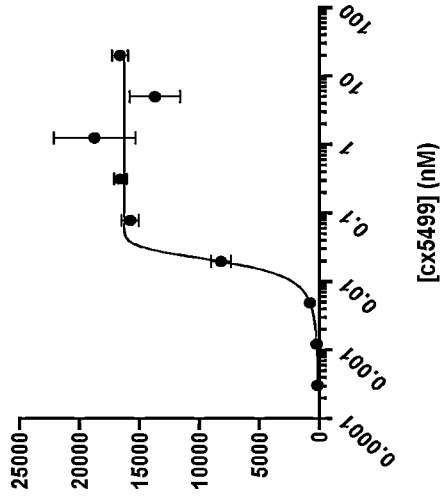
FIG. 18D CD25 Expression on CD8 T-cells
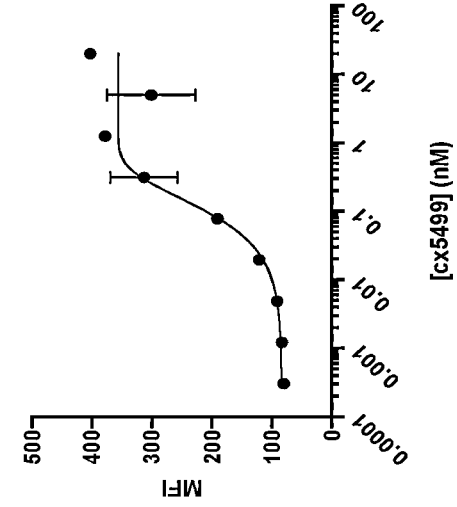
FIG. 18E CD69 Expression on CD8 T-cells

MULTISPECIFIC POLYPEPTIDE CONSTRUCTS HAVING CONSTRAINED CD3 BINDING AND RELATED METHODS AND USES

CROSS-REFERENCE TO RELATED APPLICATIONS

This application is a continuation of U.S. application Ser. No. 16/380,963, filed Apr. 10, 2019, entitled "MULTISPECIFIC POLYPEPTIDE CONSTRUCTS HAVING CONSTRAINED CD3 BINDING AND RELATED METHODS AND USES," which claims priority to U.S. provisional application 62/656,331, filed Apr. 11, 2018, entitled "MULTISPECIFIC POLYPEPTIDE CONSTRUCTS HAVING CONSTRAINED CD3 BINDING AND RELATED METHODS AND USES," the contents of which are incorporated by reference in their entirety for all purposes.

INCORPORATION BY REFERENCE OF SEQUENCE LISTING

The present application is being filed along with a Sequence Listing in electronic format. The content of the electronic Sequence Listing (file name: 7449520002_Seq.xml, date created: Jun. 5, 2023, size: 305,984 bytes) is herein incorporated by reference in its entirety.

FIELD

The invention relates generally to multispecific polypeptides having constrained CD3 binding. In some embodiments, components of the multispecific polypeptides are connected by a non-cleavable linker. Also provided are methods of making and using these multispecific polypeptides in a variety of therapeutic, diagnostic and prophylactic indications.

BACKGROUND

Therapeutic antibodies that cause target cell depletion generally rely on effector functions mediated via interaction with Fc-gamma-receptors (FcγRs) and complement proteins. Effector cells expressing FcγRs are predominately those of the innate immune system. T-cells are not direct effector cells involved in antibody mediated target cell depletion.

CD3 (Cluster of Differentiation 3) T-cell co-receptor is a multimeric protein composed of four distinct polypeptide chains, referred to as the ε, γ, δ, and ζ chains. The CD3 complex serves as the signaling module of the T cell receptor that associates non-covalently with the antigen-binding a/b chains of T cell receptor (TCR).

Because direct engagement of CD3 results in T-cell activation, it is a desirable target for a variety of therapeutic and/or diagnostic indications. Accordingly, there exists a need for antibodies and therapeutics that target the CD3/TCR pathway.

SUMMARY

The present disclosure provides multispecific polypeptide constructs that exhibit constrained CD3 binding. In some embodiments, the multispecific polypeptide construct is composed of a first component comprising an immunoglobulin Fc region and a second component comprising a CD3-binding region, wherein the first and second components are coupled by a linker, such as a non-cleavable linker, wherein the Fc region is positioned N-terminal to the CD3-binding region; and one or both of the first and second components comprises an antigen binding domain that binds a tumor associated antigen (TAA). In some embodiments, the CD3-binding region binds CD3 (CD3ε). In some embodiments, the antigen binding domain is positioned amino-terminally relative to the Fc region and/or carboxy-terminally relative to the CD3 binding region of the multispecific polypeptide construct. In some embodiments, the first component comprises a first antigen binding domain and the second component comprises a second antigen binding domain, wherein each of the antigen binding domains bind a tumor associated antigen (TAA). In some cases, the first antigen binding domain is positioned at the amino terminus of the multispecific construct and the second antigen binding domain is positioned at the carboxy terminus of the multispecific construct. In some embodiments, the first antigen binding domain is positioned amino-terminally relative to the Fc region and/or carboxy-terminally relative to the CD3 binding region of the multispecific polypeptide construct. In particular embodiments of provided multispecific polypeptide constructs, at least one antigen binding domain is positioned carboxy-terminally relative to the CD3 binding region of the multispecific polypeptide construct.

Provided herein is a multispecific polypeptide construct, wherein the multispecific construct comprises in order, from N-terminus to C-terminus: a first antigen binding domain that binds to a tumor-associated antigen (TAA); an immunoglobulin Fc region; a linker, such as a non-cleavable linker, a CD3 binding region that binds CD3 (CD3ε); and a second antigen binding domain that binds a tumor-associated antigen (TAA). Also provided is a multispecific polypeptide construct, wherein the multispecific construct comprises in order, from N-terminus to C-terminus: an immunoglobulin Fc region; a linker, such as a non-cleavable linker; a CD3 binding region that binds CD3 (CD3ε); and an antigen binding domain that binds a tumor-associated antigen (TAA). Provided is a multispecific polypeptide construct, wherein the multispecific construct comprises in order, from N-terminus to C-terminus: an antigen binding domain that binds to a tumor-associated antigen (TAA); an immunoglobulin Fc region; a linker, such as a non-cleavable linker; and a CD3 binding region that binds CD3 (CD3ε).

In some of any of the provided embodiments, the linker is a non-cleavable linker. In some embodiments, the linker is a linker that does not contain a substrate recognition site specific to cleavage by a protease.

In some of any of the provided embodiments, the positioning of the Fc region N-terminal to the CD3 binding region reduces or prevents the ability of the CD3 binding region to bind CD3. In some embodiments, the first component (component #1) and the second component (component #2) of the multispecific polypeptide constructs are linked and binding to CD3 is disallowed, unless the antigen binding domain(s) is bound to its cognate antigen. In some embodiments, component #1 contains at least one antigen binding domain and an Fc region. In some embodiments, component #2 contains at least a CD3 binding region domain and an antigen binding domain, the former of which is capable of binding CD3 (when the multispecific construct is bound to antigen recognized by the antigen binding domain or domains of component #1 or component #2). Thus, linkage of the CD3 binding region to the Fc region as described ensures that the multispecific polypeptide constructs do not bind or otherwise engage CD3 unless the antigen binding domain(s) is bound to its cognate antigen.

This is advantageous as it prevents systemic binding of the CD3 binding region to T-cells and instead focuses the CD3 binding region's ability to bind to site of antigen expression. This is beneficial as it diminishes or eliminates a major binding sink of peripheral T-cells, potentially allowing more favorable distribution and localization at site of antigen expression, e.g., tumor cells or the tumor microenvironment.

When the antigen binding domain(s) is bound to its cognate antigen, the multispecific polypeptide construct, via component #2, is capable of forming an immune synapse between an antigen-expressing cell and a T-cell. This co-engagement mediates antigen dependent T-cell activation, cytotoxicity, cytokine release, degranulation and proliferation. In some embodiments, the multispecific polypeptide constructs are capable of interacting with FcγRs and mediating innate immune effector functions, for example antibody dependent cellular cytotoxicity (ADCC) and antibody dependent cellular phagocytosis (ADCP). In some embodiments, the multispecific polypeptide constructs are capable of interacting with complement proteins, namely C1q, and mediating complement-dependent cytotoxicity.

In some embodiments, the cognate antigen recognized by the antigen binding domain(s) of a provided multispecific polypeptide construct is a tumor associated antigen (TAA).

Thus, among the provided embodiments, the multispecific polypeptide construct is composed of a first component comprising an immunoglobulin Fc region and a second component comprising a CD3-binding region, wherein the first and second components are coupled by a linker, such as a non-cleavable linker, wherein the Fc region is positioned N-terminal to the CD3-binding region; and one or both of the first and second components comprises an antigen binding domain that binds a tumor associated antigen (TAA). In some embodiments, the CD3-binding region binds CD3 (CD3ε). In some embodiments, the antigen binding domain is positioned amino-terminally relative to the Fc region and/or carboxy-terminally relative to the CD3 binding region of the multispecific polypeptide construct. In some embodiments, the first component comprises a first antigen binding domain and the second component comprises a second antigen binding domain, wherein each of the antigen binding domains bind a tumor associated antigen (TAA). In some cases, the first antigen binding domain is positioned at the amino terminus of the multispecific construct and the second antigen binding domain is positioned at the carboxy terminus of the multispecific construct. In some embodiments, the first antigen binding domain is positioned amino-terminally relative to the Fc region and/or carboxy-terminally relative to the CD3 binding region of the multispecific polypeptide construct. In particular embodiments of provided multispecific polypeptide constructs, at least one antigen binding domain is positioned carboxy-terminally relative to the CD3 binding region of the multispecific polypeptide construct.

In some embodiments, the CD3 binding region is an antibody or an antigen binding fragment. In particular embodiments, the antibody or antigen binding fragment is a two chain polypeptide containing a variable heavy (VH) and a variable light (VL) chain. In some embodiments, the antibody or antigen-binding fragment is an Fv. In particular embodiments, the Fv is a disulfide-stabilized Fv (dsFv) containing an interchain disulfide bond between the VH and VL chains.

Provided herein is a multispecific polypeptide construct comprising a first component comprising an immunoglobulin Fc region and a second component comprising a CD3-binding region, wherein the CD3 binding region is an anti-CD3 antibody or antigen binding fragment that is an Fv antibody fragment comprising a variable heavy chain region (VH) and a variable light chain region (VL); the Fc is a heterodimeric Fc comprising a first Fc polypeptide and a second Fc polypeptide and the VH and VL of the anti-CD3 antibody or antigen binding fragment are linked to opposite polypeptides of the heterodimeric Fc; the first and second components are coupled by a non-cleavable linker, wherein the Fc region is positioned N-terminal to the CD3-binding region; and the first component comprises a first antigen binding domain and the second component comprises a second antigen binding domain, wherein each of the antigen binding domains bind a tumor associated antigen (TAA). In some embodiments, the CD3-binding region binds CD3 (CD3ε). In some embodiments, the first antigen binding domain is positioned amino-terminally relative to the Fc region of the multispecific construct and the second antigen binding domain is positioned carboxy-terminally relative to the CD3 binding region of the multispecific construct. In some embodiments, the multispecific construct comprises in order, from N-terminus to C-terminus: the first antigen binding domain that binds to a tumor-associated antigen (TAA); the immunoglobulin Fc region; the non-cleavable linker; the CD3 binding region, wherein the CD3 binding region binds CD3 (CD3ε); and the second antigen binding domain that binds a tumor-associated antigen (TAA).

Provided herein is a multispecific polypeptide construct comprising a first component comprising an immunoglobulin Fc region and a second component comprising a CD3-binding region, wherein: the CD3 binding region is an anti-CD3 antibody or antigen binding fragment that is a disulfide-stabilized Fv antibody fragment (dsFv) comprising a variable heavy chain (VH) and a variable light chain (VL); the Fc is a heterodimeric Fc comprising a first Fc polypeptide and a second Fc polypeptide and the VH and VL of the anti-CD3 antibody or antigen binding fragment are linked to opposite polypeptides of the heterodimeric Fc; the first and second components are coupled by a non-cleavable linker, wherein the Fc region is positioned N-terminal to the CD3-binding region; and one or both of the first and second components comprises an antigen binding domain that binds a tumor associated antigen (TAA). In particular embodiments of provided multispecific polypeptide constructs, at least one antigen binding domain is positioned carboxy-terminally relative to the CD3 binding region of the multispecific polypeptide construct. In some embodiments, the CD3-binding region binds CD3 (CD3ε).

Provided herein is a multispecific polypeptide construct comprising a first component comprising an immunoglobulin Fc region and a second component comprising a CD3-binding region, wherein: the CD3 binding region is an anti-CD3 antibody or antigen binding fragment that is a an Fv antibody fragment comprising a variable heavy chain (VH) and a variable light chain (VL); the Fc is a heterodimeric Fc comprising a first Fc polypeptide and a second Fc polypeptide and the VH and VL of the anti-CD3 antibody or antigen binding fragment are linked to opposite polypeptides of the heterodimeric Fc; the first and second components are coupled by a non-cleavable linker, wherein the Fc region is positioned N-terminal to the CD3-binding region; and one or both of the first and second components comprises an antigen binding domain that binds a tumor associated antigen (TAA), wherein the antigen-binding domain is a single chain antibody fragment, such as an sdAb or an scFv. In particular embodiments of provided multispecific polypeptide constructs, at least one antigen binding domain is positioned carboxy-terminally relative to the CD3 binding region of the multispecific polypeptide construct. In some embodiments, the CD3-binding region binds CD3 (CD3ε).

In embodiments provided herein, the multispecific construct comprises in order, from N-terminus to C-terminus: the first antigen binding domain that binds to a tumor-associated antigen (TAA); the immunoglobulin Fc region; the non-cleavable linker; the CD3 binding region, wherein the CD3 binding region binds CD3 (CD3ε); and the second antigen binding domain that binds a tumor-associated antigen (TAA).

In embodiments provided herein, the multispecific construct comprises in order, from N-terminus to C-terminus: the immunoglobulin Fc region; the non-cleavable linker; the CD3 binding region, wherein the CD3 binding region binds CD3 (CD3ε); and an antigen binding domain that binds a tumor-associated antigen (TAA).

In embodiments provided herein, the multispecific construct comprises in order, from N-terminus to C-terminus: the antigen binding domain that binds to a tumor-associated antigen (TAA); the immunoglobulin Fc region; the non-cleavable linker; and the CD3 binding region, wherein the CD3 binding region binds CD3 (CD3ε).

Provided herein is a multispecific polypeptide construct, wherein the multispecific construct comprises in order, from N-terminus to C-terminus: a first antigen binding domain that binds to a tumor-associated antigen (TAA); an immunoglobulin Fc region; a linker, such as a non-cleavable linker; a CD3 binding region that binds CD3 (CD3ε); and a second antigen binding domain that binds a tumor-associated antigen (TAA). Also provided is a multispecific polypeptide construct, wherein the multispecific construct comprises in order, from N-terminus to C-terminus: an immunoglobulin Fc region; a linker, such as a non-cleavable linker; a CD3 binding region that binds CD3 (CD3ε); and an antigen binding domain that binds a tumor-associated antigen (TAA). Provided is a multispecific polypeptide construct, wherein the multispecific construct comprises in order, from N-terminus to C-terminus: an antigen binding domain that binds to a tumor-associated antigen (TAA); an immunoglobulin Fc region; a linker, such as a non-cleavable linker; and a CD3 binding region that binds CD3 (CD3ε).

In some aspects, the antigen binding domain, or independently each of the antigen binding domains, is selected from an antibody or antigen binding fragment, a natural cognate binding partner, an Anticalin (engineered lipocalin), a Darpin, a Fynomer, a Centyrin (engineered fibroneticin III domain), a cystine-knot domain, an Affilin, an Affibody, or an engineered CH3 domain. In some embodiments, the natural cognate binding partner comprises an extracellular domain or binding fragment thereof of the native cognate binding partner of the TAA, or a variant thereof that exhibits binding activity to the TAA.

In some embodiments, the antigen-binding domain(s) includes one or more copies of an antibody or an antigen-binding fragment thereof. In some embodiments, the antigen-binding domain(s) includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the antigen-binding domain(s) include one or more copies of one or more single domain antibody (sdAb) fragments, for example $V_HH$, $V_{NAR}$, engineered $V_H$ or $V_K$ domains. $V_HHs$ can be generated from camelid heavy chain only antibodies. $V_{NARS}$ can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the one or more antigen binding domains independently bind an antigen that is a tumor associated antigen (TAA). In some examples, the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the Fc region is a homodimeric Fc region. In some embodiments, the immunoglobulin Fc region of the first component is an IgG isotype selected from the group consisting of IgG1 isotype, IgG2 isotype, IgG3 isotype, and IgG4 subclass. In some examples, the Fc region is an Fc region of a human IgG1, a human IgG2, a human IgG3, or a human IgG4, or is an immunologically active fragment thereof. In some embodiments, the Fc region comprises a polypeptide comprises the amino acid sequence set forth in SEQ ID NO: 1 or a sequence of amino acids that has at least 90%, 91%, 92%, 93%, 94%, 95%, 96%, 97%, 98%, 99% sequence identity to SEQ ID NO:1. In some cases, the Fc region comprises a polypeptide comprises the amino acid sequence set forth in SEQ ID NO: 2 or a sequence of amino acids that has at least 90%, 91%, 92%, 93%, 94%, 95%, 96%, 97%, 98%, 99% sequence identity to SEQ ID NO:2. In some of any such embodiments, the Fc region comprises a polypeptide comprises the amino acid sequence set forth in SEQ ID NO: 4 or a sequence of amino acids that has at least 90%, 91%, 92%, 93%, 94%, 95%, 96%, 97%, 98%, 99% sequence identity to SEQ ID NO:4. In some examples, the Fc region comprises a polypeptide comprises the amino acid sequence set forth in SEQ ID NO: 5 or a sequence of amino acids that has at least 90%, 91%, 92%, 93%, 94%, 95%, 96%, 97%, 98%, 99% sequence identity to SEQ ID NO:5. In some examples, the Fc region comprises a polypeptide comprises the amino acid sequence set forth in SEQ ID NO: 6 or a sequence of amino acids that has at least 90%, 91%, 92%, 93%, 94%, 95%, 96%, 97%, 98%, 99% sequence identity to SEQ ID NO:6.

In some embodiments, the immunoglobulin Fc region is a polypeptide comprising an amino acid sequence that is derived from an amino acid sequence selected from the group consisting of SEQ ID NOs: 1-6.

In some embodiments, the immunoglobulin Fc region is a polypeptide comprising an amino acid sequence selected from the group consisting of SEQ ID NOs: 1-6. In some embodiments, the immunoglobulin Fc region is a polypeptide comprising an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NOs: 1-6.

In some embodiments, the Fc region is a heterodimeric Fc region.

In some embodiments, the Fc region is a heterodimer containing a first Fc polypeptide and a second Fc polypeptide wherein one or both of the first and second Fc polypeptides of the heterodimeric Fc region are a variant Fc polypeptide comprising at least one modification to induce heterodimerization compared to an Fc region of human IgG1, human IgG2 or human IgG4. In some embodiments, the at least one modification is in or compared to an Fc region of human IgG1. In some embodiments, the at least one modification is in or compared to the Fc polypeptide set forth in SEQ ID NO:1 or an immunologically active fragment thereof. In some cases, one or both Fc polypeptides of the heterodimeric Fc region comprises at least one modification to induce heterodimerization compared to a polypeptide of a homodimeric Fc region, optionally compared to the Fc polypeptide set forth in SEQ ID NO:1 or an immunologically active fragment thereof. In some embodiments, each of the Fc polypeptides of the heterodimeric Fc independently comprise at least one amino acid modification. In some cases, the at least one modification is selected from a steric modification(s), a knob-into-hole modification(s), a charge mutation(s) to increase electrostatic complementarity of the polypeptides, a modification(s) to alter the isoelectric point (pI variant), or combinations thereof.

In some examples, the amino acid modification is a charge mutation to increase electrostatic complementarity of the polypeptides. In some embodiments, the first and/or second Fc polypeptides comprise a modification in complementary positions, wherein the modification is replacement with an amino acid having an opposite charge to the complementary amino acid of the other polypeptide. In some embodiments, the first or second polypeptide comprise a modification in complementary positions, wherein the modification is replacement with an amino acid having an opposite charge to the complementary amino acid of the other polypeptide. In some embodiments, at least the first or second Fc polypeptides each comprise a modification in complementary positions, wherein the modification is replacement with an amino acid having an opposite charge to the complementary amino acid of the other polypeptide. In some embodiments, the first and second Fc polypeptides each comprise a modification in complementary positions, wherein the modification is replacement with an amino acid having an opposite charge to the complementary amino acid of the other polypeptide.

In some examples, the amino acid modification is a knob-into-hole modification.

In some embodiments, the first Fc polypeptide of the heterodimeric Fc comprises the modification selected from among Thr366Ser, Leu368Ala, Tyr407Val, and combinations thereof and the second Fc polypeptide of the heterodimeric Fc comprises the modification T366W. In some cases, the first and second Fc polypeptides further comprise a modification of a non-cysteine residue to a cysteine residue, wherein the modification of the first polypeptide is at one of a position Ser354 and Y349 and the modification of the second Fc polypeptide is at the other of the position Ser354 and Y349. In some embodiments, the first Fc polypeptide comprises the modifications T366W/S354C and the second Fc polypeptide comprises the modifications T366S/L368A/Y407V/Y349C. In some embodiments, the first Fc polypeptide comprises the modifications L368D/K370S and the second Fc polypeptide comprises the modifications S364K/E357Q.

In some embodiments, the first Fc polypeptide comprises the modifications L368D/K370S and the second Fc polypeptide comprises the modifications S364K/E357Q.

In some embodiments, at least one of the first and second polypeptide comprises the modifications Q295E/N384D/Q418E/N421D.

In some embodiments, one of the first or second Fc polypeptide of the heterodimeric Fc further comprises a modification at residue Ile253. In some instances, the modification is Ile253Arg. In some embodiments, one of the first or second Fc polypeptide of the heterodimeric Fc further comprises a modification at residue His435. In some instances, the modification is His435Arg.

In some embodiments, the Fc region, such as the first and/or second Fc polypeptide comprises a polypeptide that lacks Lys447.

In some of any of the provided embodiments, the first polypeptide of the heterodimeric Fc comprises the sequence of amino acids set forth in any of SEQ ID NOS:82, 86 or 201, and the second polypeptide of the heterodimeric Fc comprises the sequence of amino acids set forth in any of SEQ ID NOS:83, 87, 90, 92, 202 or 205. In some embodiments, the first Fc polypeptide and the second Fc polypeptide comprises sequences selected from the group consisting of SEQ ID NOS: 82 and 83, respectively; SEQ ID NOS: 86 and 87, respectively; SEQ ID NOS: 201 and 202, respectively; SEQ ID NOS: 82 and 90, respectively; SEQ ID NOS: 86 and 92, respectively; and SEQ ID NOS: 201 and 205, respectively.

In some embodiments, the immunoglobulin Fc region is a polypeptide comprising an amino acid sequence that is derived from an amino acid sequence selected from the group consisting of SEQ ID NOs: 1-6 comprising one or modifications. In some embodiments, the immunoglobulin Fc region is a polypeptide comprising an amino acid sequence that is derived from an amino acid sequence selected from the group consisting of SEQ ID NOs: 1-6 comprising one or modifications to prevent glycosylation, to alter Fc receptor interactions, to reduce Fc receptor binding, to enhance the interaction with CD32A, to reduce the complement protein C1q binding, to extend the half-life, to enhance FcRn binding, to alter antibody-dependent cellular cytotoxicity (ADCC) and/or complement-dependent cytotoxicity (CDC), to induce heterodimerization, to prevent dimerization, to stabilize the homodimerization at the CH3:CH3 interface, and combinations thereof.

In some embodiments, modifications within the Fc region reduce binding to Fc-receptor-gamma receptors while having minimal impact on binding to the neonatal Fc receptor (FcRn). In some embodiments, the mutated or modified Fc polypeptide includes the following mutations: Met252Tyr and Met428Leu or Met252Tyr and Met428Val (M252Y, M428L, or M252Y, M428V) using the Kabat numbering system.

In some embodiments, the Fc region comprises a polypeptide comprising at least one modification to enhance FcRn binding. In some examples, the modification is at a position selected from the group consisting of Met252, Ser254, Thr256, Met428, Asn434, and combinations thereof. In some cases, the modification is at a position selected from the group consisting of Met252Y, Ser254T, Thr256E, Met428L, Met428V, Asn434S, and combinations thereof. In some particular embodiments, the modification is at position Met252 and at position Met428. In some cases, the modification is Met252Y and Met428L. In some cases, the modification is Met252Y and Met428V.

In some embodiments, the first polypeptide of the heterodimeric Fc comprises the sequence of amino acids set forth in any of SEQ ID NOS: 94, 96 or 207, and the second polypeptide of the heterodimeric Fc comprises the sequence of amino acids set forth in any of SEQ ID NOS: 98, 100, or 209. In some embodiments, the first Fc polypeptide and the second Fc polypeptide comprises sequences selected from the group consisting of SEQ ID NOS: 94 and 98, respectively; SEQ ID NOS: 96 and 100, respectively; and SEQ ID NOS: 207 and 209, respectively.

In some embodiments, the Fc region comprises a polypeptide comprising at least one modification to enhance FcγR binding. In some cases, the modification is modification at Ser239 or Ile332. In some embodiments, the glycosylation of the Fc region is modified to enhance FcγR binding as compared to an unmodified Fc region. In some examples, the Fc region lacks or has reduced fucose content.

In some embodiments, the Fc region comprises a polypeptide comprising at least one amino acid modification that reduces effector function and/or reduces binding to an effector molecule selected from an Fc gamma receptor or C1q. In some embodiments, the one or more amino acid modification is deletion of one or more of Glu233, Leu234 or Leu235.

In some embodiments, the first polypeptide of the heterodimeric Fc comprises the sequence of amino acids set forth in any of SEQ ID NOS:82, 86, 94 or 96, and the second polypeptide of the heterodimeric Fc comprises the sequence of amino acids set forth in any of SEQ ID NOS:83, 87, 90, 92, 98 or 100. In some embodiments, the Fc region comprises a polypeptide comprising at least one amino acid modification that reduces effector function and/or reduces binding to an effector molecule selected from an Fc gamma receptor or C1q. In some examples, the one or more amino acid modification is deletion of one or more of Glu233, Leu234 or Leu235. In some aspects, the first polypeptide of the heterodimeric Fc comprises the sequence of amino acids set forth in any of SEQ ID NOS: 84, 88, 95 or 97 and the second polypeptide of the heterodimeric Fc comprises the sequence of amino acids set forth in any of SEQ ID NOS: 85, 89, 91, 93, 99 or 101.

In some embodiments, the first polypeptide of the heterodimeric Fc comprises the sequence of amino acids set forth in any of SEQ ID NOS: 84, 88, 95, 97, 203 or 208 and the second polypeptide of the heterodimeric Fc comprises the sequence of amino acids set forth in any of SEQ ID NOS: 85, 89, 91, 93, 99, 101, 204, 206 or 210. In some embodiments, the first Fc polypeptide and the second Fc polypeptide comprises sequences selected from the group consisting of SEQ ID NOS: 84 and 85, respectively; SEQ ID NOS: 88 and 89, respectively; SEQ ID NOS: 203 and 204, respectively; SEQ ID NOS: 95 and 99, respectively; SEQ ID NOS: 97 and 101, respectively; SEQ ID NOS: 208 and 210, respectively; SEQ ID NOS: 84 and 91, respectively; SEQ ID NOS: 88 and 93, respectively; and SEQ ID NOS: 203 and 206, respectively.

In some embodiments, the CD3 binding region is an anti-CD3 antibody or antigen-binding fragment. In some embodiments, the anti-CD3 antibody or antigen binding fragment comprises a variable heavy chain region (VH) and a variable light chain region (VL). In some of any such embodiments, the CD3 binding region is monovalent.

In some embodiments, the anti-CD3 antibody or antigen binding fragment is not a single chain antibody, optionally is not a single chain variable fragment (scFv). In some embodiments, the Fc is a heterodimeric Fc and the VH and VL that comprise the anti-CD3 antibody or antigen binding fragment are linked to opposite polypeptides of the heterodimeric Fc.

In some embodiments, the CD3 binding region is not able to, or is not substantially able to, bind or engage CD3 unless at least one of the antigen binding domains is bound to its TAA. In some aspects, the CD3 binding region is not able to, or is not substantially able, to bind or engage CD3 unless at least two of the antigen binding domains is bound to their TAA(s).

In some embodiments, the multispecific polypeptide construct contains a linker that is a polypeptide linker. In some embodiments, the linker is a polypeptide of up to 25 amino acids in length. In some cases, the linker is a polypeptide of from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is a polypeptide that is 3, 4, 5, 6, 7, 8, 9, 10, 11, 12, 13, 14, 15, 16, 17, 18, 19 or 20 amino acids in length.

In some embodiments, the linker is 3 to 18 amino acids in length. In some embodiments, the linker is 12 to 18 amino acids in length. In some embodiments, the linker is 15 to 18 amino acids in length. In some embodiments, the linker is a polypeptide that is 18 amino acids in length.

In some embodiments, the non-cleavable linker does not contain a substrate recognition site that is specifically recognized for cleavage by a protease. In some embodiments, the protease is produced by an immune effector cell, by a tumor, or by cells present in the tumor microenvironment. In some embodiments, the protease is produced by an immune effector cell and the immune effector cell is an activated T cell, a natural killer (NK) cell, or an NK T cell. In some embodiments, the protease is selected from among matriptase, a matrix metalloprotease (MMP), granzyme B, and combinations thereof. In some embodiments, the protease is granzyme B.

In some embodiments, the linker comprises the amino acid sequence GS, GGS, GGGGS (SEQ ID NO:149), GGGGGS (SEQ ID NO:135) and combinations thereof. In some embodiments, the linker comprises the amino acid sequence (GGS)n, wherein n is 1 to 10. In some embodiments, the linker comprises the amino acid sequence (GGGGS)n (SEQ ID NO: 173), wherein n is 1 to 10. In some embodiments, the linker comprises (GGGGGS)n (SEQ ID NO:172), wherein n is 1 to 4.

In some embodiments, the linker is or comprises GGS. In some embodiments, the linker is or comprises GGGGS (SEQ ID NO: 149). In some embodiments, the linker is or comprises GGGGGS (SEQ ID NO: 135). In some embodiments, the linker is or comprises GGSGGS ("(GGS)$_2$") (SEQ ID NO: 10). In some embodiments, the linker is or comprises GGSGGSGGS ("(GGS)$_3$") (SEQ ID NO: 11). In some embodiments, the linker is or comprises GGSGGSGGSGGS ("(GGS)$_4$") (SEQ ID NO: 12). In some embodiments, the linker is or comprises GGSGGSGGSGGSGGS ("(GGS)$_5$") (SEQ ID NO: 13). In some embodiments, the linker is or comprises GGGGGSGGGGGSGGGGGS (SEQ ID NO: 119). In some embodiments, the linker is or comprises GGSGGGGSGGGGSGGGGS (SEQ ID NO: 147). In some embodiments, the linker is or comprises GGGGSGGGGSGGGGS (SEQ ID NO:170). In some embodiments, the linker is or comprises GGGGG (SEQ ID NO:192).

In some embodiments, the antigen binding domain and the immunoglobulin Fc region of the first component (which in some cases is the first antigen binding domain) are operably linked via one or more further amino acid linkers (referred to herein as an intra-component linker). The intra-component peptide linker of the first component (also called LP1) can be a peptide linker such as any as described in Section 11.3. The intra-component linker present in the first component, i.e. linking the Fc region and an antigen binding domain, can be of various lengths, for example 5, 6, 7, 8, 9, 10, 11, 12, 13, 14, 15, 16, 17, 18, 19, 20 amino acids in length. In some embodiments, these intra-component linkers are composed predominately of the amino acids Glycine and Serine, denoted as GS-linkers herein. In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

In some embodiments, the multispecific polypeptide construct comprises at least (i) a first polypeptide comprising the first Fc polypeptide of the heterodimeric Fc region, the linker and the VH domain of the anti-CD3 antibody or antigen binding fragment thereof; and (ii) a second polypeptide comprising the second Fc polypeptide of the heterodimeric Fc region, the linker and the VL domain of the anti-CD3 antibody or antigen binding fragment thereof, wherein one or both of the first and second polypeptide comprise at least one antigen-binding domain that binds to a tumor associated antigen (TAA). In some embodiments, the VH of the anti-CD3 antibody or antigen-binding fragment is on the same polypeptide as the at least one antigen-binding domain that binds to a tumor associated antigen (TAA). In some embodiments, the polypeptide comprising the VL of the anti-CD3 antibody or antigen-binding fragment does not contain the at least one antigen-binding domain that binds to a tumor associated antigen (TAA). In particular embodiments of provided multispecific polypeptide constructs, at least one antigen binding domain is positioned carboxy-terminally relative to the CD3 binding region of the multispecific polypeptide construct.

In some embodiments, the second component includes one or more copies of the CD3 binding region.

In some embodiments, the CD3 binding region is an anti-CD3 antibody or antigen-binding fragment that includes one or more copies of an antibody or an antigen-binding fragment thereof that is able to bind or engage CD3, such as CD3ε. In some embodiments, the anti-CD3 binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody.

In some embodiments, the anti-CD3 binding domain includes an Fv antibody fragment that binds CD3ε (referred to herein as an anti-CD3ε Fv fragment).

In some embodiments, the anti-CD3ε Fv antibody fragment includes an amino acid sequence selected from the group of SEQ ID NO: 32-81, 191, 196-200, 211, and 212. In some embodiments, the anti-CD3ε Fv antibody fragment includes an amino acid sequence that is at least 90%, 91%, 92%, 93%, 94%, 95%, 96%, 97%, 98%, 99% or more identical to an amino acid sequence selected from the group consisting of SEQ ID NO: 32-81, 191, 196-200, 211, and 212. In some embodiments, the anti-CD3ε Fv antibody fragment includes a combination of an amino acid sequence selected from the group of SEQ ID NO: 32-62, 196-198, and 211 and an amino acid sequence selected from the group consisting of SEQ ID NO: 63-81, 191, 199, 200, and 212. In some embodiments, the anti-CD3ε Fv antibody fragment includes a combination of an amino acid sequence that is at least 90%, 91%, 92%, 93%, 94%, 95%, 96%, 97%, 98%, 99% or more identical to an amino acid sequence selected from the group consisting of SEQ ID NO: 32-62, 196-198, and 211 and an amino acid sequence that is at least 90%, 91%, 92%, 93%, 94%, 95%, 96%, 97%, 98%, 99% or more identical to an amino acid sequence selected from the group consisting of SEQ ID NO: 63-81, 191, 199, 200, and 212.

In some embodiments, the anti-CD3ε Fv antibody fragment is a disulfide stabilized anti-CD3 binding Fv fragment (dsFv).

In some embodiments, the first component includes one or more copies of an antigen-binding domain. In certain embodiments, the first component contains at least two antigen binding domains, such as two antigen binding domains. In some embodiments, the at least two antigen binding domains of the first component bind to the same TAA. In some cases, the at least two antigen binding domains of the first component bind to different epitopes of the same TAA. In some instances, the at least two antigen binding domains of the first component bind to the same epitope of the same TAA. In some embodiments, the at least two antigen binding domain of the first component bind to different TAAs.

In some embodiments, the second component includes one or more copies of an antigen-binding domain. In certain embodiments, the second component contains at least two antigen binding domains, such as two antigen binding domains. In some embodiments, the at least two antigen binding domains of the second component bind to the same TAA. In some cases, the at least two antigen binding domains of the second component bind to different epitopes of the same TAA. In some instances, the at least two antigen binding domains of the second component binds to a same epitope of the same TAA. In some embodiments, the at least two antigen binding domains of the second component bind to different TAAs.

In some embodiments, the first component contains a first antigen binding domain and the antigen binding domain of the second component is a second antigen binding domain. In some embodiments, the multispecific antigen binding domain comprises at least a first antigen binding domain and a second antigen binding domain, wherein the first antigen binding domain and second antigen binding domain bind to the same TAA. In some cases, the first antigen binding domain and the second antigen binding domain bind different epitopes of the same TAA. In some instances, the first antigen binding domain and the second antigen binding domain bind the same epitope of the same TAA. In some embodiments, the multispecific antigen binding domain comprises at least a first antigen binding domain and a second antigen binding domain wherein the first antigen binding domain and the second antigen binding domain bind different TAAs.

In some embodiments, the antigen binding domain of the second component (which in some cases is the second antigen binding domain) and the CD3 binding region are operably linked via one or more further amino acid linkers (referred to herein as an intra-component linker). The intra-component peptide linker of the second component (also called LP2) can be a peptide linker such as any as described in Section 11.3. The intra-component linker of present in the second component, i.e. linking the CD3 binding region and an antigen binding domain, can be of various lengths, for example 5, 6, 7, 8, 9, 10, 11, 12, 13, 14, 15, 16, 17, 18, 19, 20 amino acids in length. In some embodiments, the intra-component linker of the second component is composed predominately of the amino acids Glycine and Serine, denoted as GS-linkers herein. In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

Provided herein is a multispecific polypeptide construct, the multispecific polypeptide construct comprising a first component comprising a heterodimeric Fc region and a second component comprising an anti-CD3 antibody or antigen-binding fragment comprising a variable heavy chain region (VH) and a variable light chain region (VL), wherein: the VH and VL that comprise the anti-CD3 antibody or antigen binding fragment are linked to opposite polypeptides of the heterodimeric Fc; the first and second components are coupled by a linker, wherein the heterodimeric Fc region is positioned N-terminal to the anti-CD3 antibody or antigen-binding fragment; and one or both of the first and second components comprises an antigen binding domain that binds a tumor associated antigen (TAA).

In some embodiments, the linker is a polypeptide of up to 50 amino acids in length. In some embodiments, the linker is a polypeptide of up to 25 amino acids in length. In some embodiments, the linker is a polypeptide of up to 15 amino acids in length.

In any of the provide embodiments, the one or more antigen binding domain that binds TAA results in monovalent, bivalent, trivalent, or tetravalent binding to the TAA. In some embodiments, the one or more antigen binding domains that bind TAA independently are selected from an sdAb, an scFv or a Fab. In some embodiments, the one or more antigen binding domains that binds a TAA is a single chain molecule, such as a single chain antibody fragment containing a VH and a VL, for example an sdAb or an scFv. In some embodiments the one or more antigen binding domains that binds a TAA is a sdAb, such as a V$_H$H or a VH$_{NAR}$. In some embodiments, at least one of the antigen binding domains is a Fab containing a first chain comprising a VH-CH1 (Fd) and a second chain comprising a VL-CL.

In some embodiments, the antigen binding domain that binds the TAA is attached to the VH of the anti-CD3 binding domain. In some embodiments, the antigen binding domain that binds the TAA is attached to the same side (e.g., knob or hole) of the heterodimeric Fc to which the VH of the anti-CD3 binding domain is attached. In some embodiments, the antigen binding domain that binds the TAA is a sdAb attached to the VH of the anti-CD3 binding domain. In some embodiments, the antigen binding domain that binds the TAA is a sdAb attached to same side (e.g., knob or hole) of the heterodimeric Fc domain to which the VH of the anti-CD3 binding domain is attached. In some embodiments, the antigen binding domain that binds the TAA is a V$_H$H or a VH$_{NAR}$ that is attached to the VH of the anti-CD3 binding domain. In some embodiments, the antigen binding domain that binds the TAA is a V$_H$H or a VH$_{NAR}$ that is attached to the same side (e.g., knob or hole) of the heterodimeric Fc domain to which the VH of the anti-CD3 binding domain is attached. In some embodiments, the antigen binding domain that binds the TAA is a V$_H$H attached to the VH of the anti-CD3 binding domain. In some embodiments, the antigen binding domain that binds the TAA is a V$_H$H attached to the same side (e.g., knob or hole) of the heterodimeric Fc domain to which the VH of the anti-CD3 binding domain is attached. In some embodiments, the antigen binding domain that binds the TAA is a VH$_{NAR}$ attached to the VH of the anti-CD3 binding domain. In some embodiments, the antigen binding domain that binds the TAA is a VH$_{NAR}$ attached to the same side (e.g., knob or hole) or the Fc domain to which the VH of the anti-CD3 binding domain is attached.

In some embodiments, the multispecific polypeptide construct comprises at least (i) a first polypeptide comprising the first Fc polypeptide of the heterodimeric Fc region, the linker and the VH domain of the anti-CD3 antibody or antigen binding fragment; and (ii) a second polypeptide comprising the second Fc polypeptide of the heterodimeric Fc region, the linker and the VL domain of the anti-CD3 antibody or antigen binding fragment, wherein one or both of the first and second polypeptide comprise at least one antigen-binding domain that binds to a tumor associated antigen (TAA). In some instances, only one of the first or second polypeptide comprises the at least one antigen-binding domain that binds a TAA.

In some embodiments, the at least one of the antigen binding domain(s) is a Fab. In some embodiments, the multispecific polypeptide construct comprises: (i) a first polypeptide comprising the first Fc polypeptide of the heterodimeric Fc region, the linker and the VH domain of the anti-CD3 antibody or antigen binding fragment; (ii) a second polypeptide comprising the second Fc polypeptide of the heterodimeric Fc region, the linker and the VL domain of the anti-CD3 antibody or antigen binding fragment, and (iii) a third polypeptide comprising a VH-CH1 (Fd) or VL-CL of a Fab antibody fragment that binds to a tumor-associated antigen, wherein the first and/or second polypeptide further comprises the other of the VH-CH1 (Fd) or VL-CL of the Fab antibody fragment. In some cases, only one of the first or second polypeptide comprises the other of the VH-CH1 (Fd) or VL-CL of the Fab antibody fragment. In some embodiments, both the first or second polypeptide comprises the other of the VH-CH1 (Fd) or VL-CL of the Fab antibody fragment. In some cases, the other of the VH-CH1 (Fd) or VL-CL of the Fab antibody fragment is positioned amino-terminally relative to the Fc region and/or carboxy-terminally relative to the CD3 binding region of one of the first or second polypeptide of the multispecific polypeptide construct. In some embodiments, the other of the VH-CH1 (Fd) or VL-CL of the Fab antibody fragment is positioned amino-terminally relative to the Fc region of the first polypeptide or second polypeptide and carboxy-terminally relative to the CD3 binding region of the other of the first or second polypeptide.

In some embodiments, the at least one antigen binding domain is positioned amino-terminally relative to the Fc region and/or is positioned carboxy-terminally relative to the CD3 binding region of one of the first or second polypeptide of the multispecific polypeptide construct. In some cases, the at least one antigen binding domain is positioned amino-terminally relative to the Fc region of the multispecific construct and the second antigen binding domain is positioned carboxy-terminally relative to the CD3 binding region of the multispecific construct. In particular embodiments of provided multispecific polypeptide constructs, at least one antigen binding domain is positioned carboxy-terminally relative to the CD3 binding region of the multispecific polypeptide construct. In some embodiments, the at least one antigen binding domain is a sdAb. In some embodiments the at least one antigen binding domain that is a sdAb is positioned carboxy-terminally to the CD3 binding region of the multispecific construct. In some embodiments the at least one antigen binding domain that is a sdAb is positioned amino-terminally to the Fc region of the multispecific construct. In some embodiments the at least one antigen binding domain is a $V_HH$. In some embodiments, the at least one antigen binding domain that is a $V_HH$ is positioned carboxy-terminally to the CD3 binding region of the multispecific construct. In some embodiments the at least one antigen binding domain that is a $V_HH$ is positioned amino-terminally to the Fc region of the multispecific construct.

In some embodiments, the multispecific polypeptide construct comprises a first linking peptide (LP1) between the first antigen binding domain and the immunoglobulin Fc polypeptide region (Fc region). In some embodiments, the multispecific polypeptide construct comprises a second linking peptide (LP2) between the anti-CD3 binding domain (CD3 binding region) and the second antigen binding domain. In some embodiments, the multispecific polypeptide construct comprises a first linking peptide (LP1) between the first antigen binding domain and the immunoglobulin Fc polypeptide region (Fc region) and a second linking peptide (LP2) between the anti-CD3 binding domain (CD3 binding region) and the second antigen binding domain.

In some embodiments, the multispecific polypeptide construct has the structural arrangement from N-terminus to C-terminus as follows: first antigen binding domain-LP1-immunoglobulin Fc polypeptide linker region (Fc region)-linker-anti-CD3 binding domain-LP2-second antigen binding domain. In some embodiments, the multispecific polypeptide construct has the structural arrangement from N-terminus to C-terminus as follows: second antigen binding domain-LP2-immunoglobulin Fc polypeptide linker region (Fc region)-linker-anti-CD3 binding domain (CD3 binding region)-LP1-first antigen binding domain.

In some embodiments, the two linking peptides LP1 and LP2 are not identical to each other. In some cases, LP1 or LP2 is independently a peptide of about 1 to 20 amino acids in length. In some examples, LP1 or LP2 independently comprise a peptide that is or comprises any Gly-Ser linker as set forth in SEQ ID NOs: 10-13, 119, 135, 147, 149.

In some embodiments, the multispecific construct is a construct having any of the structural arrangement shown in FIG. 1. In some embodiments, the construct is a bispecific construct that has a structural arrangement from N-terminus to C-terminus as follows. The N-terminal end of the bispecific construct includes a first antigen binding domain that binds a tumor associated antigen (TAA). The first binding domain binds a first epitope on the TAA target. Coupled to the first antigen binding domain is a central immunoglobulin Fc polypeptide region that regulates FcγR interactions and/or FcRn interaction. In some embodiments, the central immunoglobulin Fc polypeptide region is heterodimeric. The immunoglobulin Fc polypeptide region is coupled to a linker located at a position C-terminal to the end of the immunoglobulin Fc polypeptide region. The linker is attached to an anti-CD3 binding sequence located C-terminal to the Fc region, which, in some cases, is at the distal end of the second component. The C-terminus of the bispecific construct includes a second antigen binding domain that binds a TAA. In some embodiments, the second antigen binding domain binds the same TAA as the first antigen binding domain located within the first component. In some embodiments, the second antigen binding domain binds a second epitope on the TAA, wherein the second epitope is non-competitive with the first epitope on the TAA. In some embodiments, the second antigen binding domain binds a distinct TAA from that of the first antigen binding domain.

In some of any of the provided embodiments, the anti-CD3 antibody or antigen binding fragment is an Fv antibody fragment. In some embodiments, the Fv antibody fragment comprises a disulfide stabilized anti-CD3 binding Fv fragment (dsFv). In some embodiments, the anti-CD3 binding sequence is an Fv antibody fragment that is engineered to include a disulfide linkage between the variable heavy chain (VH) and variable light chain (VL) regions, thereby producing a disulfide stabilized anti-CD3 binding Fv fragment (dsFv). In some embodiments, the VH and VL domains that comprise the anti-CD3 Fv are operably linked to opposite members of a heterodimeric Fc region. In these embodiments, the anti-CD3 Fv binds CD3 in a monovalent fashion. In aspects as provided, the anti-CD3 dsFv does not engage CD3 unless the multispecific polypeptide construct is bound to a cognate antigen.

In some embodiments, each of the first antigen binding domain and the second antigen binding domain of the bispecific construct includes one or more copies of an antibody or an antigen-binding fragment thereof. In some embodiments, each of the first antigen binding domain and the second antigen binding domain of the bispecific construct includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the antigen binding domain, or independently each of the antigen binding domains, is an antibody or antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the each of the first antigen binding domain and the second antigen binding domain of the bispecific construct includes one or more copies of one or more single domain antibody (sdAb) fragments, for example $V_HH$, $V_{NAR}$, engineered $V_H$ or $V_K$ domains. $V_HH$s can be generated from natural camelid heavy chain only antibodies, genetically modified rodents that produce heavy chain only antibodies, or naïve/synthetic camelid or humanized camelid single domain antibody libraries. $V_{NARS}$ can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the antibody or antigen-binding fragment is an sdAb. In some cases, the sdAb is a human or humanized sdAb. In some aspects, the sdAb is $V_HH$, $V_{NAR}$, an engineered VH domain or an engineered VK domain. In some examples, the antibody or antigen-binding fragment thereof is an scFv. In some cases, the antibody or antigen-binding fragment thereof is a Fab.

In some of any of the provided embodiments, the anti-CD3 antibody or antigen-binding fragment comprises a VH CDR1 comprising the amino acid sequence TYAMN (SEQ ID NO: 16); a VH CD2 comprising the amino acid sequence RIRSKYNNYATYYADSVKD (SEQ ID NO: 17); a VH CDR3 comprising the amino acid sequence HGNFGN-SYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21).

In some of any of the provided embodiments, the anti-CD3 antibody or antigen-binding fragment comprises a VH CDR1 comprising the amino acid sequence GFTFN-TYAMN (SEQ ID NO: 211); a VH CDR2 comprising the amino acid sequence RIRSKYNNYATY (SEQ ID NO:212); a VH CDR3 comprising the amino acid sequence HGNFGNSYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21).

In some of any of the provided embodiments, the anti-CD3 antibody or antigen-binding fragment comprises a VH CDR1 sequence that includes at least the amino acid sequence GFTFNTYAMN (SEQ ID NO: 211); a VH CDR2 sequence that includes at least the amino acid sequence RIRSKYNNYATY (SEQ ID NO: 212); a VH CDR3 sequence that includes at least the amino acid sequence HGNFGNSYVSWFAY (SEQ ID NO: 18), a VL CDR1 sequence that includes at least the amino acid sequence GSSTGAVTTSNYAN (SEQ ID NO: 229); a VL CDR2 sequence that includes at least the amino acid sequence GTNKRAP RAP (SEQ ID NO: 230); and a VL CDR3 sequence that includes at least the amino acid sequence ALWYSNHWV (SEQ ID NO: 225).

In some of any of the provided embodiments, the anti-CD3 antibody or antigen-binding fragment comprises: a VH having the amino acid sequence of any of SEQ ID NOS: 14, 32-62, 196-198, and 211 or a sequence that exhibits at least 90%, 91%, 92%, 93%, 94%, 95%, 96%, 97%, 98% or 99% sequence identity to any of SEQ ID NOS: 14, 32-62, 196-198, and 211; and a VL having the amino acid sequence of any of SEQ ID NOS: 15, 63-81, 191, 199, 200, and 212 or a sequence that exhibits at least 90%, 91%, 92%, 93%, 94%, 95%, 96%, 97%, 98% or 99% sequence identity to any of SEQ ID NOS: 15, 63-81, 191, 199, 200, and 212.

In some embodiments, the anti-CD3 antibody or antigen-binding fragment is an Fv. In some embodiments, the anti-CD3 Fv comprises: a VH having the amino acid sequence of any of SEQ ID NOS: 14, 32-43, 45-47, 48, 196 and 211 or a sequence that exhibits at least 90%, 91%, 92%, 93%, 94%, 95%, 96%, 97%, 98% or 99% sequence identity to any of SEQ ID NOS: 14, 32-43, 45-47, 48, 196 and 211; and a VL having the amino acid sequence of any of SEQ ID NOS: 15, 63, 65-71, 73, 75, 77, and 199 or a sequence that exhibits at least 90%, 91%, 92%, 93%, 94%, 95%, 96%, 97%, 98% or 99% sequence identity to any of SEQ ID NOS: 15, 63, 65-71, 73, 75, 77, and 199. In some cases, the anti-CD3 dsFv comprises the amino acid sequence of SEQ ID NO: 14 and the amino acid sequence of SEQ ID NO: 15. In other cases, the anti-CD3 Fv comprises the amino acid sequence of SEQ ID NO: 196 and the amino acid sequence of SEQ ID NO:199.

In some embodiments, the VH and VL chain regions of the CD3 binding domain each independently comprise at least one amino acid modification. In some embodiments, the at least one amino acid modification of the VH and VL chain regions of the CD3 binding domain increase the stability of the CD3 binding domain. In some embodiments, the at least one amino acid modification of the VH and VL chain regions of the CD3 binding domain increase the ability of the CD3 binding domain to bind CD3. In some embodiments, the at least one amino acid modification of the VH and VL chain regions of the CD3 binding domain increase the stability of the CD3 binding domain by creating a disulfide linkage between the VH and VL chain regions.

In some embodiments, the CD3 binding region has a disulfide stabilized linkage between the VH and VL regions. In some embodiments, the anti-CD3 antibody or antigen-binding fragment is disulfide stabilized Fv (dsFv). In some embodiments, the disulfide stabilized anti-CD3 Fv comprises an anti-CD3 VH with the mutation 44 to Cys and an anti-CD3 VL with the mutation 100 to Cys by Kabat numbering. In some embodiments, the disulfide stabilized anti-CD3 Fv comprises an anti-CD3 VH with the mutation G44C and an anti-CD3 VL with the mutation G100C by Kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, the anti-CD3 dsFv comprises: a VH having the amino acid sequence of any of SEQ ID NOS: 44, 49-62, 197 and 198 or a sequence that exhibits at least 90%, 91%, 92%, 93%, 94%, 95%, 96%, 97%, 98% or 99% sequence identity to any of SEQ ID NOS: 44, 49-62, 197 and 198; and a VL having the amino acid sequence of any of SEQ ID NOS: 64, 72, 74, 76, 78-81, 191, 200 and 212 or a sequence that exhibits at least 90%, 91%, 92%, 93%, 94%, 95%, 96%, 97%, 98% or 99% sequence identity to any of SEQ ID NOS: 64, 72, 74, 76, 78-81, 191, 200 and 212. In some cases, the anti-CD3 dsFv comprises the amino acid sequence of SEQ ID NO: 44 and the amino acid sequence of SEQ ID NO: 72. In some embodiments, the anti-CD3 dsFv comprises the amino acid sequence of SEQ ID NO: 198 and the amino acid sequence of SEQ ID NO: 200. In some embodiments, the anti-CD3 dsFv comprises the amino acid sequence of SEQ ID NO: 197 and the amino acid sequence of SEQ ID NO: 200.

In some embodiments, the multispecific construct also includes an agent conjugated to the multispecific construct.

In some embodiments, the agent is a therapeutic agent. In some embodiments, the agent is a detectable moiety. In some embodiments, the detectable moiety is a diagnostic agent. In some embodiments, the agent is conjugated to the multispecific construct via a linker. In some embodiments, the linker is a non-cleavable linker.

In some embodiments, the multispecific construct described herein is used in conjunction with one or more additional agents or a combination of additional agents. Suitable additional agents include current pharmaceutical and/or surgical therapies for an intended application, such as, for example, cancer. For example, the multispecific construct can be used in conjunction with an additional chemotherapeutic or anti-neoplastic agent.

In some embodiments, the multispecific construct and additional agent are formulated into a single therapeutic composition, and the multispecific construct and additional agent are administered simultaneously. In some embodiments, the multispecific construct and additional agent are separate from each other, e.g., each is formulated into a separate therapeutic composition, and the multispecific construct and the additional agent are administered simultaneously, or the multispecific construct and the additional agent are administered at different times during a treatment regimen. For example, the multispecific construct is administered prior to the administration of the additional agent, the multispecific construct is administered subsequent to the administration of the additional agent, or the multispecific construct and the additional agent are administered in an alternating fashion. As described herein, the multispecific construct and additional agent are administered in single doses or in multiple doses.

In some embodiments, the multispecific construct naturally contains one or more disulfide bonds. In some embodiments, the multispecific construct can be engineered to include one or more disulfide bonds.

The disclosure also provides an isolated nucleic acid molecule or polynucleotide encoding at least a portion of a multispecific construct described herein and/or one or more nucleic acid molecules encoding a multispecific construct described herein, such as for example, at least a first nucleic acid encoding at least a portion of the first component of the multispecific construct and a second nucleic acid encoding at least a portion of the second component of the multispecific construct, as well as vectors that include these isolated nucleic acid sequences.

Among the provided embodiments is a polynucleotide(s) encoding any of the provided multispecific polypeptide constructs. Also provided is a polynucleotide encoding a polypeptide chain of any of the provided multispecific polypeptide constructs. Further provided is a polynucleotide, comprising a first nucleic acid sequence encoding a first polypeptide of any of the provided multispecific constructs and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping. In some cases, the first nucleic acid sequence and second nucleic acid sequence are operably linked to the same promoter. In some embodiments, the multispecific polypeptide construct comprises a third polypeptide chain, and the polynucleotide further comprises a third nucleic acid encoding the third polypeptide of the multispecific construct. In some embodiments, the third nucleic acid is separated from the first and/or second polypeptide by an internal ribosome entry site (IRES), or a nucleic acid encoding a self-cleaving peptide or a peptide that causes ribosome skipping and/or the third nucleic acid sequence is operably linked to the same promoter as the first and/or second nucleic acid sequence. In some examples, the nucleic acid encoding a self-cleaving peptide or a peptide that causes ribosome skipping is selected from a T2A, a P2A, a E2A or a F2A (SEQ ID NOS: 159-164, or encoded by the sequence set forth in SEQ ID NO: 165)

Provided herein is a vector comprising any of the provided polynucleotides. In some embodiments, the vector is an expression vector. In some examples, the vector is a viral vector or a eukaryotic vector, optionally wherein the eukaryotic vector is a mammalian vector.

Provided is a cell, comprising any of the provided polynucleotides or vectors. In some cases, the cell is recombinant or isolated. In some examples, the cell is a mammalian cell. In some examples, the cell is a HEK293 or CHO cell.

The disclosure provides methods of producing a multispecific construct by culturing a cell under conditions that lead to expression of the multispecific construct, wherein the cell comprises such a nucleic acid molecule(s). In some embodiments, the cell comprises such a vector.

Provided herein is a method of producing a multispecific polypeptide construct, the method comprising introducing into a cell any of the provided polynucleotides or vectors and culturing the cell under conditions to that lead to expression of the multispecific construct to produce the multispecific polypeptide construct. Also provided is a method of producing a multispecific polypeptide construct, the method comprising culturing any of the provided cells under conditions in which the multispecific polypeptide is expressed or produced by the cell. In some cases, the cell is a mammalian cell. In some examples, the cell is a HEK293 or CHO cell. In some embodiments, the method further includes isolating or purifying the multispecific polypeptide construct from the cell. In some cases, the multispecific polypeptide construct is a heterodimer.

Provided herein is a multispecific polypeptide construct produced by any of the provided methods.

Provided herein is a method of stimulating or inducing an immune response, the method comprising contacting a target cell and a T cell with the any of the provided multispecific polypeptide constructs or pharmaceutical compositions, said target cell expressing a tumor associated antigen recognized by the multispecific polypeptide construct. In some embodiments, the target cell is a tumor cell expressing the tumor associated antigen (TAA).

In some embodiments, the contacting is carried out ex vivo or in vitro. In some embodiments, the contacting is carried out in vivo in a subject.

Provided is a method of stimulating or inducing an immune response in a subject, the method comprising administering, to a subject in need thereof, a therapeutically effective amount of any of the provided multispecific conjugates or pharmaceutical compositions. In some cases, the method increases cell-mediated immunity. In some embodiments, the method increases T-cell activity. In some embodiments, the method increases cytolytic T-cell (CTL) activity. In some examples, the immune response is increased against a tumor or cancer. In some embodiments, the method treats a disease or condition in the subject.

The present disclosure also provides methods of treating, preventing, delaying the progression of or otherwise ameliorating a symptom of one or more pathologies or alleviating a symptom associated with such pathologies, by administering a multispecific polypeptide construct of the disclosure to a subject in which such treatment or prevention is desired. Provided herein is a method of treating a disease or condition in a subject, the method comprising administering, to a subject in need thereof, a therapeutically effective amount of any of the provided multispecific conjugates or pharmaceutical compositions. In some embodiments, the disease or condition is a tumor or a cancer.

In some embodiments of any of the provided method, the subject, such as the subject to be treated is, e.g., human or other mammal. In some embodiments of any of the provided method, the subject is a human. In some embodiments, the subject is a non-human mammal, such as a non-human primate, companion animal (e.g., cat, dog, horse), farm animal, work animal, or zoo animal. In some embodiments, the subject is a rodent.

A multispecific polypeptide construct of the disclosure used in any of the embodiments of these methods and uses can be administered at any stage of the disease. For example, such a multispecific polypeptide construct can be administered to a patient suffering cancer of any stage, from early to metastatic. The terms subject and patient are used interchangeably herein.

A multispecific polypeptide construct of the disclosure used in any of the embodiments of these methods and uses can be used in a treatment regimen comprising neoadjuvant therapy.

A multispecific polypeptide construct of the disclosure used in any of the embodiments of these methods and uses can be administered either alone or in combination with one or more additional agents, including small molecule inhibitors, other antibody-based therapies, polypeptide or peptide-based therapies, nucleic acid-based therapies and/or other biologics. In some embodiments, a multispecific polypeptide construct is administered in combination with one or more additional agents such as, by way of non-limiting example, a chemotherapeutic agent, such as an alkylating agent, an anti-metabolite, an anti-microtubule agent, a topoisomerase inhibitor, a cytotoxic antibiotic, and any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteasome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art. In some embodiments, the multispecific polypeptide construct and the additional agent(s) are formulated in a single composition. In some embodiments, the multispecific polypeptide construct and the additional agent(s) are administered as two or more separate compositions. In some embodiments, the multispecific polypeptide construct and the additional agent(s) are administered simultaneously. In some embodiments, the multispecific polypeptide construct and the additional agent(s) are administered sequentially.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent(s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC).

In some embodiments, the checkpoint inhibitor is an inhibitor of a target selected from the group consisting of CTLA-4, LAG-3, PD-1, PDL1, TIGIT, TIM-3, B7H3, B7H4, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSF1R inhibitor, an α-CCR4 inhibitor, a TGF-beta, a myeloid-derived suppressor cell, or a T-regulatory cell. In some embodiments, the agonist is selected from the group consisting of OX40, GITR, CD137, CD28, ICOS, CD27, and HVEM. In some embodiments, the checkpoint inhibitor is an antibody that binds a target selected from CTLA-4, PD-1, and/or PD-L1. In some embodiments, the checkpoint inhibitor is an anti-CTLA4 antibody, an anti-PD-1 antibody, and an anti-PD-L1 antibody, and/or combinations thereof. In some embodiments, the checkpoint inhibitor is an anti-CTLA4 antibody such as, e.g., Yervoy™. In some embodiments, the checkpoint inhibitor is an anti-PD-1 antibody such as, e.g., Opdivo™ and/or Keytruda™.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a PDL1 inhibitor. In some embodiments, the inhibitor is a TIGIT inhibitor. In some embodiments, the inhibitor is a TIM-3 inhibitor. In some embodiments, the inhibitor is a B7H3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSF1R inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is OX40. In some embodiments, the agonist is GITR. In some embodiments, the agonist is CD137. In some embodiments, the agonist is CD28. In some embodiments, the agonist is ICOS. In some embodiments, the agonist is CD27. In some embodiments, the agonist is HVEM.

In some embodiments, the multispecific polypeptide construct is administered during and/or after treatment in combination with one or more additional agents such as, for example, a chemotherapeutic agent, an anti-inflammatory agent, and/or a an immunosuppressive agent. In some embodiments, the multispecific polypeptide construct and the additional agent are formulated into a single therapeutic composition, and the multispecific polypeptide construct and additional agent are administered simultaneously. Alternatively, the multispecific polypeptide construct and additional agent are separate from each other, e.g., each is formulated into a separate therapeutic composition, and the multispecific polypeptide construct and the additional agent are administered simultaneously, or the multispecific polypeptide construct and the additional agent are administered at different times during a treatment regimen. For example, the multispecific polypeptide construct is administered prior to the administration of the additional agent, the multispecific polypeptide construct is administered subsequent to the administration of the additional agent, or the multispecific polypeptide construct and the additional agent are administered in an alternating fashion. As described herein, the multispecific polypeptide construct and additional agent are administered in single doses or in multiple doses.

In some embodiments, the multispecific polypeptide construct and the additional agent(s) are administered simultaneously. For example, the multispecific polypeptide construct and the additional agent(s) can be formulated in a single composition or administered as two or more separate compositions. In some embodiments, the multispecific polypeptide construct and the additional agent(s) are administered sequentially, or the multispecific polypeptide construct and the additional agent are administered at different times during a treatment regimen.

In addition to the elements described above, the multispecific polypeptide construct can contain additional elements such as, for example, amino acid sequence N- or C-terminal of the multispecific polypeptide construct. For example, a multispecific polypeptide construct can include a targeting moiety to facilitate delivery to a cell or tissue of interest. Multispecific polypeptide construct can be conjugated to an agent, such as a therapeutic agent, a detectable moiety or a diagnostic agent. Examples of agents are disclosed herein.

The multispecific polypeptide construct can also include any of the conjugated agents, linkers and other components described herein in conjunction with a multispecific polypeptide construct of the disclosure.

The disclosure also pertains to immunoconjugates comprising a multispecific polypeptide construct conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents for use in targeting diseased T cells such as in a T cell-derived lymphoma include, for example, dolastatins and derivatives thereof (e.g. auristatin E, AFP, MMAD, MMAF, MMAE). In some embodiments, the agent is a dolastatin. In some embodiments, the agent is an auristatin or derivative thereof. In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the linker between the multispecific polypeptide construct and the cytotoxic agent is cleavable. In some embodiments, the linker is non-cleavable. In some embodiments, two or more linkers are present. The two or more linkers are all the same, e.g., cleavable or non-cleavable, or the two or more linkers are different, e.g., at least one cleavable and at least one non-cleavable.

The multispecific polypeptide constructs and conjugates thereof are useful in methods for treating a variety of disorders and/or diseases. Non-limiting examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

Also provided is a pharmaceutical composition comprising any of the multispecific polypeptide constructs provided herein and a pharmaceutically acceptable carrier. In some cases, the pharmaceutical composition is sterile. Pharmaceutical compositions according to the disclosure can include a multispecific polypeptide construct of the disclosure and a carrier. These pharmaceutical compositions can be included in kits, such as, for example, diagnostic kits.

One skilled in the art will appreciate that the antibodies of the disclosure have a variety of uses. For example, the proteins of the disclosure are used as therapeutic agents for a variety of disorders. The antibodies of the disclosure are also used as reagents in diagnostic kits or as diagnostic tools, or these antibodies can be used in competition assays to generate therapeutic reagents.

BRIEF DESCRIPTION OF DRAWINGS

FIGS. 2A and B is a schematic of various FRα-targeting constrained CD3 constructs composed of two polypeptides, Chain 1 and Chain 2. As shown in FIG. 2A, Chain 1 contains a FRα sdAb (antigen binding domain), linked to a heterodimeric Fc "hole," linked via a non-cleavable linker (ranging from 3 amino acids in cx1356 to 18 amino acids in cx681) to anti-CD3 VL domain, linked to a second FRα sdAb; and Chain 2 contains a FRα sdAb, linked to a complementary heterodimeric Fc "knob", linked via the same non-cleavable linker as above to anti-CD3 VH domain, linked to second FRα sdAb. When co-expressed the CD3 binding domain is properly assembled via the association of the VL:VH on the hole and knob, respectively (FIG. 2B). An exemplary anti-CD3 is a disulfide-stabilized Fv (dsFv) containing a variable light (VL) chain with the mutation G100C and a variable heavy (VH) chain with a mutation G44C.

FIG. 5A and FIG. 5C show binding to Ovcar5 cells (a FRα positive ovarian cancer cell line). FIG. 5B and FIG. 5D depict the lack of binding to T-cells. FIG. 5A and FIG. 5B display histograms of the normalized cell counts vs fluorescence at 100 nM of each construct. The secondary anti-human APC antibody only control is shown in the filled black trace, while the positive control anti-CD3 binding is shown in the open trace, and cx1356 and cx681 are shown in the gray shaded traces in FIG. 5A and FIG. 5B. The full titration of each construct on the various cell types are shown in FIG. 5C and FIG. 5D.

FIGS. 6A, C, and E show binding to A375 cells (a B7H3 positive human melanoma cell line). FIGS. 6B, D, and F show the lack of binding to isolated T cells.

FIG. 7A-B show the kinetics of CD3 signaling by 2 nM of various constructs on antigen positive and negative cells, respectively. FIG. 7C-D show the magnitude of CD3 agonizing capacity by 2 nM of various constructs on antigen positive and negative cells, respectively. FIG. 7E-F show the potency of CD3 agonizing capacity of various constructs with differing linker lengths on antigen positive and negative cells, respectively. A Jurkat CD3 NFAT-GFP reporter cell line was used to assess CD3 signaling. Constrained CD3 binding proteins only effectively engage and cluster CD3 on T cells when bound to a second antigen on target cells.

FIG. 8A and FIG. 8C depict the capacity to mediate CD3 signaling in the presence of B7H3 positive A375 cells, while FIG. 8B and FIG. 8D show the inability to mediate CD3 signaling in the presence of B7H3 negative CCRF-CEM cells. A Jurkat CD3 NFAT-GFP reporter cell line was used to assess CD3 agonism.

FIGS. 10A and 10B depict the ability of representative B7H3-targeting constrained CD3 engaging constructs to induce T-cell mediated cytotoxicity in a target dependent manner. FIG. 10A depicts the capacity of these constructs to induce T-cell mediated cytotoxicity in the presence of B7H3 positive A375 cells, while FIG. 10B depicts the capacity of these constructs to induce T-cell mediated cytotoxicity in the presence of B7H3 negative CCRF-CEM cells. Cytotoxicity was assessed by determining the overlap area of red target cells and green dying cells.

FIGS. 10C and 10D depict the ability of representative B7H3-targeting constrained CD3 engaging constructs to induce T-cell mediated cytotoxicity in a target dependent manner. FIG. 10C depicts the capacity of these constructs to induce T-cell mediated cytotoxicity in the presence of B7H3 positive A375 cells, while FIG. 10C depicts the capacity of these constructs to induce T-cell mediated cytotoxicity in the presence of B7H3 negative CCRF-CEM cells. Cytotoxicity was assessed by determining the overlap area of red target cells and green dying cells.

FIGS. 11D-11K depict the ability of representative B7H3-targeting constrained CD3 engaging constructs to induce T-cell activation in a target dependent manner. B7H3-target-dependent CD4+ T-cell activation is shown by expression of the T cell activation markers CD25 (FIG. 11D) and CD71 (FIG. 11F). B7H3-target-dependent CD8+ T-cell activation is shown by expression of the T cell activation markers CD25 (FIG. 11H) and CD71 (FIG. 11J). T-cell activation was not observed in the absence of B7H3 positive cells, based on T cell activation marker CD25 as shown in CD4+ T cells (FIG. 11E) or CD8+ T cells (FIG. 11I) or based on T cell activation marker CD71 as shown in CD4+ T cells (FIG. 11G) or CD8+ T cells (FIG. 11K)

FIG. 12A shows the production of IFNγ from T-cells cultured with B7H3 positive A375 cells and in the presence of B7H3 negative CCRF-CEM cells in the presence of the representative B7H3-targeting CD3 engaging constructs.

FIG. 12B shows the production of IFNγ from T-cells cultured with B7H3 positive A375 cells and in the presence of B7H3 negative CCRF-CEM cells in the presence of the representative B7H3-targeting CD3 engaging constructs.

FIG. 13A shows binding to B7H3 positive A375 cells. FIG. 13B shows the lack of binding to B7H3 negative CCRF-CEM cells and isolated T-cells.

FIG. 13C shows that engaging B7H3 positive A375 cells with a construct hat is bivalent and bi-epitopic to B7H3 (cx5187) induced more potent CD3 signaling than constructs that are monovalent to B7H3 (cx5873 and cx5965). FIG. 13D shows the lack of activation of T-cells in the presence of B7H3 negative CCRF-CEM cells. A Jurkat CD3 NFAT-GFP reporter cell line was used to assess CD3 agonism.

FIG. 14A and FIG. 14B depict the ability of representative B7H3-targeting constrained CD3 engaging constructs to induce T-cell mediated cytotoxicity in a target dependent manner. FIG. 14A shows that targeting B7H3 positive A375 cells with a construct that is bivalent and bi-epitopic to B7H3 (cx5187) induced more potent T-cell mediated cytotoxicity than constructs that are monovalent to B7H3 (cx5873 and cx5965). FIG. 14B depicts the lack of T-cell mediated cytotoxicity against B7H3 negative CCRF-CEM cells.

FIG. 15A-D depict the ability of representative B7H3-targeting constrained CD3 engaging molecules to activate T-cells in the presence of B7H3 positive A375 cells, but not in the presence of B7H3 negative CCRF-CEM cells. FIGS. 15A and 15B show that targeting B7H3 positive A375 cells with a construct that is bivalent and bi-epitopic to B7H3 (cx5187), induced more potent CD25 expression on CD4+ and CD8+ T-cells than constructs that are monovalent to B7H3 (cx5873 and cx5965). FIGS. 15C and 15D show the lack of CD25 expression on CD4+ and CD8+ T-cells in the presence of B7H3 negative CCRF-CEM cells.

FIGS. 16C-16J demonstrate the ability of representative B7H3-targeting constrained CD3 engaging constructs to elicit T cell activation in the presence of B7H3-positive A375 cells but not in the presence of CCRF-CEM B7H3-negative cells, as assessed by: expression of CD25 on CD4+ T cells (FIGS. 16C and 16D, respectively), CD25 expression on CD8+ T cells (FIGS. 16E and 16F, respectively), CD71 expression on CD4+ T cells (FIGS. 16G and 16H, respectively), CD71 expression on CD8+ T cells (FIGS. 16I and 16J, respectively).

FIGS. 16K and 16L demonstrate the ability of representative B7H3-targeting constrained CD3 engaging constructs to elicit T cell cytokine production in the presence of B7H3-positive A375 cells (FIG. 16K) but not in the presence of CCRF-CEM B7H3-negative cells (FIG. 16L).

FIGS. 17A and 17B demonstrate that representative monovalent (cx5800 and cx5801) and bivalent (cx5352) DLL3-targeting constrained CD3 engaging constructs bound to a DLL3 expressing cell line, SHP-77 (FIG. 17A), but not to isolated T-cells (FIG. 17B). Binding was assessed by flow cytometry.

FIG. 18A-18E demonstrate the ability of a representative DLL3-targeting constrained CD3 engaging construct, cx5499 to elicit T-cell mediated cytotoxicity and T-cell activation in the presence of DLL3-positive SHP-77 cells. FIG. 18A demonstrates the ability of the representative DLL3-targeting constrained CD3 engaging constructs to elicit T-cell mediated cytotoxicity in the presence of DLL3-positive SHP-77 cells. FIGS. 18C-18D demonstrate the ability of representative DLL3-targeting constrained CD3 engaging constructs to elicit T cell activation in the presence of DLL3-positive SHP-77 cells, as assessed by: expression of CD25 on CD4+ T cells (FIG. 18B), CD69 expression on CD4+ T cells (FIG. 18C), CD25 expression on CD8+ T cells (FIG. 18D) and CD69 expression on CD8+ T cells (FIG. 18E).

DETAILED DESCRIPTION

The present disclosure provides constrained T-cell engaging fusion proteins in the form of multispecific polypeptide constructs that bind at least CD3 and a second antigen. The multispecific polypeptide constructs provided herein include at least a first component that includes one or more copies of an antigen-binding domain that binds an antigen operably linked to an immunoglobulin Fc region, a second component that includes one or more copies of at least a binding domain that binds CD3 (referred to herein as an anti-CD3 binding domain or a CD3 binding region, which are terms that are used interchangeably herein), and a linker, such as a polypeptide linker, that joins the first component and the second component. In some embodiments, the antigen is a tumor associated antigen (TAA). In some embodiments, the linker is a non-cleavable linker. In some embodiments, the linker does not contain a substrate recognition site that is specifically recognized by a protease, such as a protease that is granzyme B, an MMP or matriptase.

Figure 1:
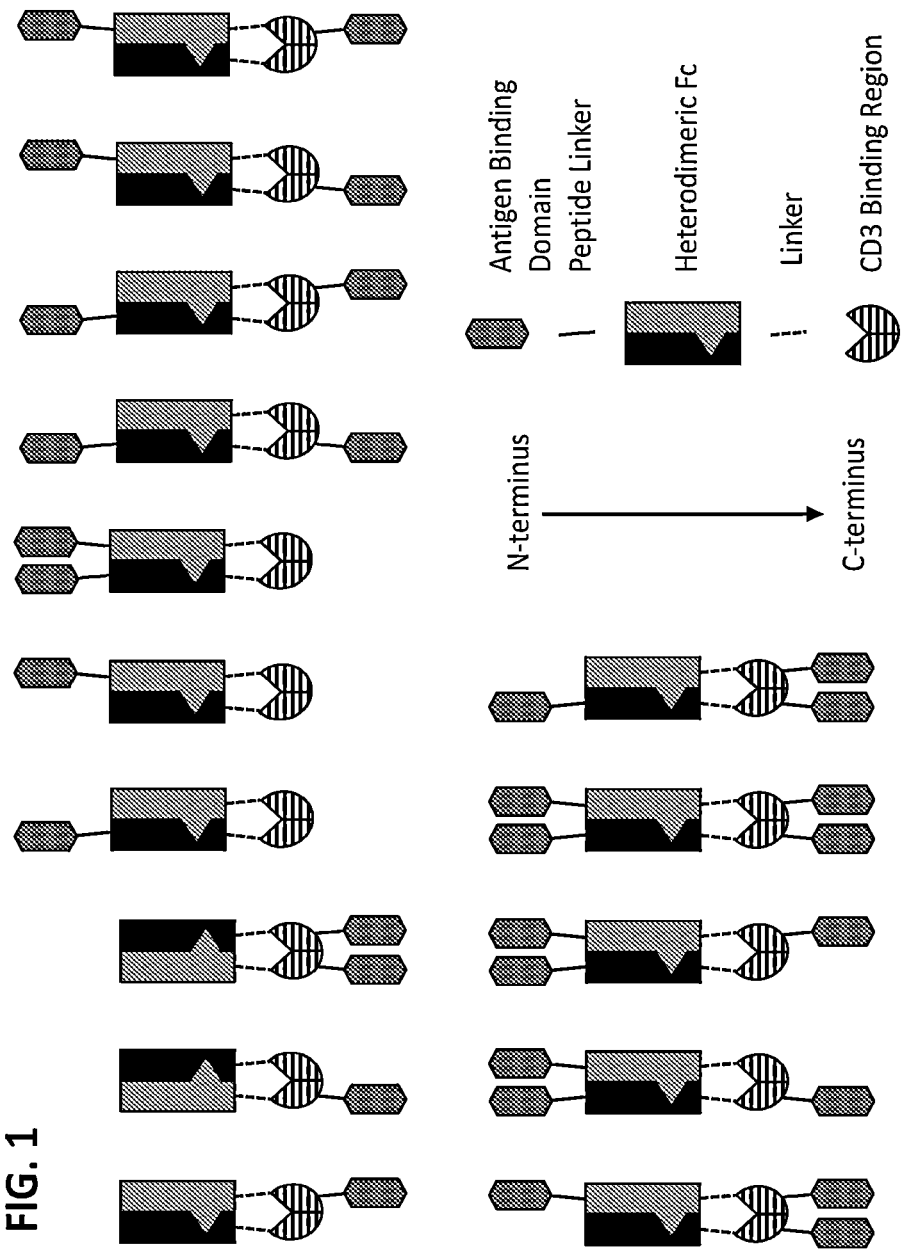
FIG. 1 is a schematic of the basic components of the multispecific polypeptide constructs of the present disclosure having constrained CD3 binding. The antigen binding domain(s) are positioned at the amino and/or carboxy termini. The Fc region, such as a heterodimeric Fc region, is positioned N-terminal to the CD3 binding region. This positioning of the Fc in close proximity to the CD3 binding region obstructs CD3 binding. The linker can be a non-cleavable linker as provided herein.

The provided multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments the antigen binding domain(s) is positioned on the amino-terminal (N-term) region of the multispecific polypeptide construct. In some embodiments, the antigen binding domain(s) is positioned on the carboxy-terminal (C-term) region of the multispecific polypeptide construct. In some embodiments, the antigen binding domain(s) is positioned on both the N- and C-terminal regions of the multispecific polypeptide construct. Various configurations of a multispecific polypeptide construct as provided herein are shown in FIG. 1.

The provided multispecific polypeptide constructs exhibit constrained T-cell engaging activity because such constructs only substantially bind to CD3 once an antigen is bound via the antigen-binding domain. This is exemplified in the Examples and Figures provided herein, which demonstrate the ability of constrained CD3-engaging proteins to efficiently bind TAA positive cells, while having little to no binding of T cells. This unique property allows constrained CD3-engaging proteins to distribute to sites where TAA is present without binding to peripheral T cells. This format is distinct from other CD3 engaging multispecific constructs, in that constitutive CD3 binding is disallowed or eliminated, providing a significant benefit by avoiding peripheral T-cell binding and permitting superior distribution to the site(s) where antigen is present as recognized by the antigen binding domain. Furthermore, other CD3 engaging constructs mediate antigen-dependent T-cell activation. However, the multispecific polypeptide constructs provided herein mediate both antigen dependent T-cell binding and activation.

The constrained T-cell engaging activity of the provided multispecific polypeptide constructs is due, in some aspects, to the positioning of the Fc region N-terminal to the CD3-binding region. In some embodiments, such positioning reduces, attenuates, dampens and/or prevents CD3 binding by the CD3 binding region. In the absence of antigen binding by the antigen binding domain, the multispecific polypeptide constructs provided herein demonstrate reduced or eliminated CD3 binding and T-cell activating capacity. In some embodiments, in the presence of an antigen binding event mediated by the antigen binding domain(s) of the multispecific polypeptide constructs, the capacity to bind CD3 by the CD3 binding region is greatly enhanced. In some embodiments, in the presence of an antigen binding event mediated by the antigen binding domains(s) of the multispecific polypeptide constructs, the capacity to activate T-cells is greatly enhanced. Engagement of its cognate antigen by the antigen binding domain(s) within the multispecific polypeptide construct leads to subsequent T-cell engagement and mediates antigen-dependent T-cell activation, such as cytotoxicity, cytokine release, degranulation and proliferation. In some embodiments, the provided multispecific polypeptide constructs can be used to increase an immune response, such as to enhance T-cell activity, including cytolytic (or cytotoxic) T-cell activity. The modulation of the immune response can, in some aspects, treat a disease or condition in a subject.

In some embodiments, the one or more antigen binding domains bind an antigen on a tumor cell or a cell of the tumor microenvironment. In some aspects, the provided multispecific polypeptide constructs can be used to increase immune responses, such as T-cell activity, e.g. cytotoxicity activity, against a tumor or cancer. In some embodiments, the provided multispecific polypeptide constructs can be used to treat a tumor or cancer in the subject.

In some embodiments, the multispecific polypeptide constructs of the disclosure ensure that there will be no binding of T-cells via CD3 in peripheral blood, as the CD3 binding region of these constructs is constrained or otherwise blocked and/or inhibited by the presence of the Fc region. Thus, the multispecific polypeptide constructs of the disclosure provide a number of advantages. In some aspects, these constructs limit the sink effect caused by binding all T-cells. In some aspects, these constructs reduce systemic toxicity.

In some embodiments, the provided multispecific polypeptide constructs of the disclosure allow for controlled biodistribution to a desired site in a subject, such as, for example, a site of tumor-associated antigen (TAA) expression. Sites of TAA expression include, for example, tumor and the surrounding tumor microenvironment.

In some embodiments, the multispecific polypeptide constructs of the disclosure exhibit specificity for CD3 and one or more other antigen. In some embodiments, the multispecific polypeptide constructs can contain more than one antigen binding domain able to bind one or more TAA, such as 2, 3 or 4 antigen binding domains, see e.g. FIG. 1. In some embodiments, the one or more antigen binding domains bind the same antigen. In some embodiments, the multispecific polypeptide constructs include more than one antigen binding domains that bind distinct epitopes on the same antigen. In some embodiments, the multispecific polypeptide constructs include more than one antigen binding domains that bind one or more distinct antigens. In some embodiments, the multispecific polypeptide constructs include more than one antigen binding domains that bind distinct epitopes on the same antigens as well as include additional antigen binding domains that bind to one or more distinct antigens. In some aspects, the provided multispecific polypeptide constructs are bispecific polypeptide constructs, such that they are able to bind to CD3 and to another antigen, such as a TAA, via binding of the antigen-binding domain of the multispecific polypeptide construct. In some examples, the provided multispecific polypeptide constructs are bispecific polypeptide constructs that provide multivalent engagement of one or more TAA through the use of a first antigen-binding domain and a second antigen-binding domain. For example, in some embodiments, the bispecific polypeptide constructions include a first antigen-binding single domain antibody (sdAb) and a second antigen-binding sdAb.

In some embodiments, the multispecific polypeptide constructs provided herein exist in two states in terms of capacity to bind CD3 and subsequently activate T-cells: (1) the "inactive" state occurs when there is no binding of any or all of the antigen binding domain(s), such that the CD3 binding is constrained and T-cell interaction is obviated, and (2) the "active" state occurs upon antigen binding by any or all of the antigen binding domain(s), such that the CD3 binding region is able to bind CD3 and the T-cell interaction is allowed.

In some embodiments, the Fc region is linked to the CD3 binding domain via a linker or linkers. In some embodiments, the Fc region is linked to the CD3 binding region via a non-cleavable linker or linkers, such as any as described.

In some embodiments, the Fc region is a homodimeric Fc region. In some embodiments, the Fc region is a heterodimeric Fc region. In some embodiments, the Fc region is a monomeric Fc region. In some embodiments, the Fc region of the multispecific polypeptide constructs are capable of interacting with FcγRs and mediating innate immune effector functions, for example, antibody dependent cellular toxicity (ADCC) and antibody dependent cellular phagocytosis (ADCP). In some embodiments, the Fc region of the multispecific polypeptide constructs are capable of interacting with complement proteins, namely C1q, and mediating complement dependent cytotoxicity. Thus, in some aspects, the multispecific polypeptide constructs of the disclosure allow for multiple immune effector mechanisms, including innate immune effectors and T-cells.

In some embodiments, the multispecific polypeptide constructs of the disclosure allow for T-cell and NK cell mediated cytotoxicity to occur simultaneously. In some cases, such activity can occur in a multispecific polypeptide construct in which is contained a first antigen binding domain, e.g., a first anti-TAA antigen binding domain, and a second antigen binding domain, e.g., a second anti-TAA antigen binding domain, that can target distinct and/or non-competing epitopes on a given TAA.

It is contemplated that the constrained CD3 engaging constructs are amenable for use with any TAA-binding domain, allowing better therapeutic exposure within the tumor or tumor-microenvironment by avoiding interactions with peripheral T-cells and mediating potent TAA-dependent T-cell cytotoxicity. In some embodiments, the second portion or component contains a CD3 binding region that is monovalent to CD3, such that there will be no activation of T-cell unless there is TAA present.

In some aspects, the multispecific polypeptide constructs of the disclosure provide a number of advantages over current bispecific therapeutics. The multispecific polypeptide constructs of the disclosure are smaller than a conventional therapeutic antibody, e.g., 150 kDa vs. 125 kDa, which will allow for better target, e.g. tumor, penetration. In some aspects, the size of the entire multispecific polypeptide construct provides long half-life for the construct. In some aspects, the multispecific polypeptide constructs of the disclosure exhibit reduced systemic toxicity or toxicity of any area outside the tumor and/or tumor microenvironment, since CD3 binding by the CD3 binding region depends on TAA engagement before CD3 engagement will occur.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

I. Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and antigen-binding portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, fully human, domain antibody, single chain, Fab, and F(ab')$_2$ fragments, Fvs, scFvs, and a Fab expression library. Typically, an "antigen-binding fragment" contains at least one CDR of an immunoglobulin heavy and/or light chain that binds to at least one epitope of the antigen of interest. In this regard, an antigen-binding fragment may comprise 1, 2, 3, 4, 5, or all 6 CDRs of a variable heavy chain (VH) and variable light chain (VL) sequence from antibodies that bind the antigen, such as generally six CDRs for an antibody containing a VH and a VL ("CDR1," "CDR2" and "CDR3" for each of a heavy and light chain), or three CDRs for an antibody containing a single variable domain. Antigen binding fragments include single domain antibodies, such as those only containing a VH or only containing a VL, including, for example, $V_HH$, $V_{NAR}$, engineered $V_H$ or $V_K$ domains.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, IgG$_3$, IgG$_4$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any specific portion of an antigen targeted by an antibody, antibody fragment or other binding domain. The term "epitope" includes any protein region to which specific binding is directed. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal, central, or C-terminal peptides of a polypeptide. In addition, antibodies may be raised against linear or discontinuous epitopes of a polypeptide. An antibody is said to specifically bind an antigen when the dissociation constant is ≤1 µM; for example, in some embodiments ≤100 nM and in some embodiments, ≤10 nM and does not display binding to other proteins either closely related or distinct.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity and is equal to the dissociation constant $K_d$. (See, generally, Davies et al. (1990) Annual Rev Biochem 59:439-473). An antibody of the present disclosure is said to specifically bind to EGFR, when the binding constant ($K_d$) is ≤1 µM, for example, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length, for example, in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, for example, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, for example, in some embodiments, at least 80%, 90%, 95%, and in some embodiments 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. In some embodiments, amino- and carboxy-termini of fragments or analogs occur near boundaries of functional domains. Structural and functional domains can be identified by comparison of the nucleotide and/or amino acid sequence data to public or proprietary sequence databases. Computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

In some embodiments, amino acid substitutions are those that: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, for example, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to EGFR, under suitable binding conditions. Typically, polypeptide analogs comprise a conservative amino acid substitution (or addition or deletion) with respect to the naturally-occurring sequence. Analogs typically are at least 20 amino acids long, for example, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., a fluorophore, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, a composition refers to any mixture of two or more products, substances, or compounds, including cells. It may be a solution, a suspension, liquid, powder, a paste, aqueous, non-aqueous or any combination thereof.

The term "pharmaceutical composition" refers to a composition suitable for pharmaceutical use in a mammalian subject, often a human. A pharmaceutical composition typically comprises an effective amount of an active agent (e.g., multispecific polypeptide construct) and a carrier, excipient, or diluent. The carrier, excipient, or diluent is typically a pharmaceutically acceptable carrier, excipient or diluent, respectively.

The terms "treating," "treatment," or "therapy" of a disease or disorder as used herein mean slowing, stopping or reversing the disease or disorders progression, as evidenced by decreasing, cessation or elimination of either clinical or diagnostic symptoms, by administration of a pharmaceutical composition of the disclosure either alone or in combination with another compound as described herein. "Treating," "treatment," or "therapy" also means a decrease in the severity of symptoms in an acute or chronic disease or disorder or a decrease in the relapse rate. As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS). "Preventing," "prophylaxis," or "prevention" of a disease or disorder refers to administration of a pharmaceutical composition, either alone or in combination with another compound, to prevent the occurrence or onset of a disease or disorder or some or all of the symptoms of a disease or disorder or to lessen the likelihood of the onset of a disease or disorder.

The terms "effective amount" or "therapeutically effective amount" refer to a quantity and/or concentration of a composition that when administered into a patient either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present.

Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Other chemistry terms herein are used according to conventional usage in the art, as exemplified by The McGraw-Hill Dictionary of Chemical Terms (Parker, S., Ed., McGraw-Hill, San Francisco (1985)).

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

II. Multispecific Polypeptide Constructs

Provided herein is a multispecific polypeptide construct containing a first component containing an immunoglobulin Fc region and a second component comprising a CD3-binding region, wherein the first and second components are coupled by a linker, wherein the Fc region is positioned N-terminal to the CD3-binding region; and one or both of the first and second components comprises an antigen binding domain that binds a tumor associated antigen (TAA). In some embodiments, the linker is a non-cleavable linker. In some embodiments, the linker does not contain a substrate recognition that is specifically recognized for cleavage by a protease.

In some embodiments, the multispecific polypeptide construct contains in order, from N-terminus to C-terminus: an immunoglobulin Fc region; a linker; a CD3 binding region that binds CD3 (CD3ε); and an antigen binding domain that binds a tumor-associated antigen (TAA). In some embodiments, the multispecific polypeptide construct contains in order, from N-terminus to C-terminus: an antigen binding domain that binds to a tumor-associated antigen (TAA); an immunoglobulin Fc region; a linker; and a CD3 binding region that binds CD3 (CD3ε). In some embodiments, the multispecific polypeptide construct contains at least a first antigen binding domain that binds a TAA and a second antigen binding domain that binds a TAA. In some embodiments, the multispecific polypeptide construct contains, in order, from N-terminus to C-terminus: a first antigen binding domain that binds to a tumor-associated antigen (TAA); an immunoglobulin Fc region; a linker; a CD3 binding region that binds CD3 (CD3ε); and a second antigen binding domain that binds a tumor-associated antigen (TAA).

Each of the components of the multispecific polypeptide constructs of the disclosure is described in more detail below.

1. Anti-CD3 Binding Domains:

The multispecific polypeptide constructs of the disclosure include one or more copies of an anti-CD3 binding domain. The anti-CD3 binding domains of the disclosure activate T cells via engagement of CD3ε on the T cells. The anti-CD3 binding domains of the disclosure agonize, stimulate, activate, and/or otherwise augment CD3-mediated T cell activation. Biological activities of CD3 include, for example, T cell activation and other signaling through interaction between CD3 and the antigen-binding subunits of the T-Cell Receptor (TCR). For example, the anti-CD3 binding domains of the disclosure completely or partially activate T cells via engagement of CD3ε on T cells by partially or completely modulating, e.g., agonizing, stimulating, activating or otherwise augmenting CD3-mediated T cell activation.

In preferred embodiments, the anti-CD3 binding domains of the disclosure specifically bind the epsilon chain of CD3, also known as CD3ε. The anti-CD3ε binding domains of the disclosure activate T cells via engagement of CD3ε on the T cells. The anti-CD3ε binding domains of the disclosure include monoclonal antibodies, such as, for example, mammalian monoclonal antibodies, primate monoclonal antibodies, fully human monoclonal antibodies, as well as humanized monoclonal antibodies and chimeric antibodies, as well as antigen-binding fragments thereof. In some embodiments, the anti-CD3ε binding domain includes one or more copies of an antibody or an antigen-binding fragment thereof.

In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence TYAMN (SEQ ID NO: 16); a VH CD2 sequence that includes at least the amino acid sequence RIRSKYNNYATYYADSVKD (SEQ ID NO: 17); and a VH CDR3 sequence that includes at least the amino acid sequence HGNFGNSYVSWFAY (SEQ ID NO: 18). In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence GFTFNTYAMN (SEQ ID NO: 211); a VH CDR2 sequence that includes at least the amino acid sequence RIRSKYNNYATY (SEQ ID NO: 212); and a VH CDR3 sequence that includes at least the amino acid sequence HGNFGNSYVSWFAY (SEQ ID NO: 18).

In some embodiments, the anti-CD3ε binding domain includes a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a VH CDR1 sequence that includes at least the amino acid sequence TYAMN (SEQ ID NO: 16); a VH CDR2 sequence that includes at least the amino acid sequence RIRSKYNNYATYYADSVKD (SEQ ID NO: 17); a VH CDR3 sequence that includes at least the amino acid sequence HGNFGNSYVSWFAY (SEQ ID NO: 18), a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a VH CDR1 sequence that includes at least the amino acid sequence GFTFNTYAMN (SEQ ID NO: 211); a VH CDR2 sequence that includes at least the amino acid sequence RIRSKYNNYATY (SEQ ID NO: 212); a VH CDR3 sequence that includes at least the amino acid sequence HGNFGNSYVSWFAY (SEQ ID NO: 18), a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a VH CDR1 sequence that includes at least the amino acid sequence GFTFNTYAMN (SEQ ID NO: 211); a VH CDR2 sequence that includes at least the amino acid sequence RIRSKYNNYATY (SEQ ID NO: 212); a VH CDR3 sequence that includes at least the amino acid sequence HGNFGNSYVSWFAY (SEQ ID NO: 18), a VL CDR1 sequence that includes at least the amino acid sequence GSSTGAVTTSNYAN AN (SEQ ID NO: 229); a VL CDR2 sequence that includes at least the amino acid sequence GTNKRAP (SEQ ID NO: 230); and a VL CDR3 sequence that includes at least the amino acid sequence ALWYSNHWV (SEQ ID NO: 225).

In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence TYAMN (SEQ ID NO: 16); a VH CDR2 sequence that includes a sequence that is at least 90%, 91%, 92%, 93%, 94%, 95%, 96%, 97%, 98%, 99% or more identical to the amino acid sequence RIRSKYNNYATYYADSVKD (SEQ ID NO: 17); and a VH CDR3 sequence that includes a sequence that is at least 90%, 91%, 92%, 93%, 94%, 95%, 96%, 97%, 98%, 99% or more identical to the amino acid sequence HGNFGNSYVSWFAY (SEQ ID NO: 18).

In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence GFTFNTYAMN (SEQ ID NO: 211); a VH CDR2 sequence that includes a sequence that is at least 90%, 91%, 92%, 93%, 94%, 95%, 96%, 97%, 98%, 99% or more identical to the amino acid sequence RIRSKYNNYATY (SEQ ID NO: 212); and a VH CDR3 sequence that includes a sequence that is at least 90%, 91%, 92%, 93%, 94%, 95%, 96%, 97%, 98%, 99% or more identical to the amino acid sequence HGNFGNSYVSWFAY (SEQ ID NO: 18).

In some embodiments, the anti-CD3ε binding domain includes a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RSSTGAVTTSNYAN (SEQ ID NO: 19); a VL CDR2 sequence that includes a sequence that is at least 90%, 91%, 92%, 93%, 94%, 95%, 96%, 97%, 98%, 99% or more identical to the amino acid sequence GTNKRAP (SEQ ID NO: 20); and a VL CDR3 sequence that includes a sequence that is at least 90%, 91%, 92%, 93%, 94%, 95%, 96%, 97%, 98%, 99% or more identical to the amino acid sequence ALWYSNLWV (SEQ ID NO: 21).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence TYAMN (SEQ ID NO: 16); a VH CD2 sequence that is at least 90%, 91%, 92%, 93%, 94%, 95%, 96%, 97%, 98%, 99% or more identical to the amino acid sequence RIRSKYNNYATYYADSVKD (SEQ ID NO: 17); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 18), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 19); a VL CDR2 sequence that is at least 90%, 91%, 92%, 93%, 94%, 95%, 96%, 97%, 98%, 99% or more identical to the amino acid sequence GTNKRAP (SEQ ID NO: 20); and a VL CDR3 sequence that is at least 90%, 91%, 92%, 93%, 94%, 95%, 96%, 97%, 98%, 99% or more identical to the amino acid sequence ALWYSNLWV (SEQ ID NO: 21).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 211); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 212); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 18), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 19); a VL CDR2 sequence that is at least 90%, 91%, 92%, 93%, 94%, 95%, 96%, 97%, 98%, 99% or more identical to the amino acid sequence GTNKRAP (SEQ ID NO: 20); and a VL CDR3 sequence that is at least 90%, 91%, 92%, 93%, 94%, 95%, 96%, 97%, 98%, 99% or more identical to the amino acid sequence ALWYSNLWV (SEQ ID NO: 21).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 211); a VH CDR2 sequence that is at least 90%, 91%, 92%, 93%, 94%, 95%, 96%, 97%, 98%, 99% or more identical to amino acid sequence RIRSKYNNYATY (SEQ ID NO: 212); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 18), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 229); a VL CDR2 sequence that is at least 90%, 91%, 92%, 93%, 94%, 95%, 96%, 97%, 98%, 99% or more identical to the amino acid sequence GTNKRAP (SEQ ID NO: 230); and a VL CDR3 sequence that is at least 90%, 91%, 92%, 93%, 94%, 95%, 96%, 97%, 98%, 99% or more identical to the amino acid sequence ALWYSNHWV (SEQ ID NO: 225).

In some embodiments, the anti-CD3ε binding domain includes a VH CDR1 sequence that includes at least the amino acid sequence GFTFSTYAMN (SEQ ID NO: 227); a VH CDR2 sequence that includes at least the amino acid sequence RIRSKYNNYATY (SEQ ID NO: 228); a VH CDR3 sequence that includes at least the amino acid sequence HGNFGDSYVSKWFAY (SEQ ID NO: 224), a VL CDR1 sequence that includes at least the amino acid sequence GSSTGAVTTSNYAN (SEQ ID NO: 229); a VL CDR2 sequence that includes at least the amino acid sequence GTNKRAP (SEQ ID NO: 230); and a VL CDR3 sequence that includes at least the amino acid sequence ALWYSNHWV (SEQ ID NO: 225).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFSTYAMN (SEQ ID NO: 227); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 228); a VH CDR3 sequence that is at least 90%, 91%, 92%, 93%, 94%, 95%, 96%, 97%, 98%, 99% or more identical to the amino acid sequence HFNFGDSYVSWFAY (SEQ ID NO: 224), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 229); a VL CDR2 sequence that is at least 90%, 91%, 92%, 93%, 94%, 95%, 96%, 97%, 98%, 99% or more identical to the amino acid sequence GTNKRAP (SEQ ID NO: 230); and a VL CDR3 sequence that is at least 90%, 91%, 92%, 93%, 94%, 95%, 96%, 97%, 98%, 99% or more identical to the amino acid sequence ALWYSNHWV (SEQ ID NO: 225).

In some embodiments, the anti-CD3ε binding domain includes a CDR3 that includes at least amino acids VLWYSNRWV (SEQ ID NO:226). In some embodiments, the anti-CD3ε binding domain includes a CDR3 that is at least 90%, 91%, 92%, 93%, 94%, 95%, 96%, 97%, 98%, 99% or more identical to the amino acids VLWYSNRWV (SEQ ID NO:226).

In some embodiments, the anti-CD3ε binding domain includes one or more copies of an antibody or an antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some embodiments, the anti-CD3 binding domain includes an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is not a single chain antibody. For example, in some aspects, the CD3 binding region is not a single chain variable fragment (scFv).

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described in Section 11.2. In such embodiments, the variable heavy chain (VH) and variable light chain (VL) of the CD3 binding region are linked on opposite chains of the heterodimeric Fc.

In some embodiments, the anti-CD3ε Fv antibody fragment includes an amino acid sequence selected from the group of SEQ ID NO: 32-81. In some embodiments, the anti-CD3ε Fv antibody fragment includes an amino acid sequence that is at least 90%, 91%, 92%, 93%, 94%, 95%, 96%, 97%, 98%, 99% or more identical to an amino acid sequence selected from the group consisting of SEQ ID NO: 32-81. In some embodiments, the anti-CD3ε Fv antibody fragment includes a combination of an amino acid sequence selected from the group of SEQ ID NO: 32-62 and an amino acid sequence selected from the group consisting of SEQ ID NO: 63-81. In some embodiments, the anti-CD3ε Fv antibody fragment includes a combination of an amino acid sequence that is at least 90%, 91%, 92%, 93%, 94%, 95%, 96%, 97%, 98%, 99% or more identical to an amino acid sequence selected from the group consisting of SEQ ID NO: 32-62 and an amino acid sequence that is at least 90%, 91%, 92%, 93%, 94%, 95%, 96%, 97%, 98%, 99% or more identical to an amino acid sequence selected from the group consisting of SEQ ID NO: 63-81 an amino acid sequence.

In some embodiments, the anti-CD3ε binding domain thereof includes a combination of a heavy chain variable region amino acid sequence and a light chain variable region amino acid sequence comprising an amino acid sequence selected from the group of SEQ ID NO: 32-81. In some embodiments, the anti-CD3ε binding domain thereof includes a combination of a heavy chain variable region amino acid sequence selected from the group of SEQ ID NO: 32-62 and a light chain variable region amino acid sequence comprising an amino acid sequence selected from the group of SEQ ID NO: 63-81.

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 14, 15, 32-81, 191, 196-200, 211, and 212. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 14, 15, 32-81, 191, 196-200, 211, and 212. In some embodiments, the anti-CD3ε binding domain thereof is an Fv fragment that includes a combination of heavy chain variable amino acid sequence selected from the group of SEQ ID NO: 14, 32-62, 196-198, and 211 and light chain variable amino acid sequence selected from the group consisting of SEQ ID NO: 15, 63-81, 191, 199, 200, and 212. In some embodiments, the anti-CD3ε binding domain thereof is an Fv fragment that includes a combination of heavy chain variable amino acid sequence that is at least 90%, 91%, 92%, 93%, 94%, 95%, 96%, 97%, 98%, 99% or more identical to an amino acid sequence selected from the group consisting of SEQ ID NO: 14, 32-62, 196-198, and 211 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 15, 63-81, 191, 199, 200, and 212.

In some embodiments, the anti-CD3ε binding domain thereof includes a combination of a heavy chain variable region amino acid sequence and a light chain variable region amino acid sequence comprising an amino acid sequence selected from the group of SEQ ID NO: 32-81, 191, 196-200, 211, and 212. In some embodiments, the anti-CD3ε binding domain thereof includes a combination of a heavy chain variable region amino acid sequence selected from the group of SEQ ID NO: 32-62, 196-198, and 211 and a light chain variable region amino acid sequence comprising an amino acid sequence selected from the group of SEQ ID NO: 63-81, 191, 199, 200, and 212.

In some embodiments, the anti-CD3ε Fv antibody fragment includes a combination of an amino acid sequence that is at least 90%, 91%, 92%, 93%, 94%, 95%, 96%, 97%, 98%, 99% or more identical to an amino acid sequence selected from the group consisting of SEQ ID NO: 14, 32-43, 45-47, 48, 196 and 211 and an amino acid sequence that is at least 90%, 91%, 92%, 93%, 94%, 95%, 96%, 97%, 98%, 99% or more identical to an amino acid sequence selected from the group consisting of SEQ ID NO: 15, 63, 65-71, 73, 75, 77, and 199. In some embodiments, the anti-CD3ε Fv antibody fragment includes a combination of an amino acid sequence selected from the group of SEQ ID NO: 14, 32-43, 45-47, 48, 196 and 211 and an amino acid sequence selected from the group consisting of SEQ ID NO: 15, 63, 65-71, 73, 75, 77, and 199.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 14. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 15. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 14 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 15. In some embodiments, the anti-CD3ε binding domain thereof includes a variable heavy chain (VH) comprising the amino acid sequence of SEQ ID NO: 14. In some embodiments, the anti-CD3ε binding domain includes a variable light chain (VL) comprising the amino acid sequence of SEQ ID NO: 15. In some embodiments, the anti-CD3ε binding domain thereof includes a variable heavy chain (VH) comprising the amino acid sequence of SEQ ID NO: 14 and a variable light chain (VL) comprising the amino acid sequence of SEQ ID NO: 15.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 196. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 199. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 196 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 199. In some embodiments, the anti-CD3ε binding domain thereof includes a variable heavy chain (VH) comprising the amino acid sequence of SEQ ID NO: 196. In some embodiments, the anti-CD3ε binding domain includes a variable light chain (VL) comprising the amino acid sequence of SEQ ID NO: 199. In some embodiments, the anti-CD3ε binding domain thereof includes a variable heavy chain (VH) comprising the amino acid sequence of SEQ ID NO: 196 and a variable light chain (VL) comprising the amino acid sequence of SEQ ID NO: 199.

In particular embodiments, the Fv is a disulfide stabilized Fv fragment (dsFv) in which the the $V_H$-$V_L$ heterodimer is stabilized by an interchain disulfide bond. In some embodiments, the interchain disulfide bond is engineered by mutation of position in framework positions of the VH and/or VL chain. In some embodiments, the disulfide stabilized anti-CD3 Fv comprises an anti-CD3 VH with the mutation 44 to Cys and an anti-CD3 VL with the mutation 100 to Cys by Kabat numbering. For example, in some embodiments, the VH chain contains the mutation G44C and the VL chain contains the mutation G100C, each by kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, the anti-CD3ε Fv antibody fragment includes a combination of an amino acid sequence that is at least 90%, 91%, 92%, 93%, 94%, 95%, 96%, 97%, 98%, 99% or more identical to an amino acid sequence selected from the group consisting of SEQ ID NO: 44, 49-62, 197 and 198 and an amino acid sequence that is at least 90%, 91%, 92%, 93%, 94%, 95%, 96%, 97%, 98%, 99% or more identical to an amino acid sequence selected from the group consisting of SEQ ID NO: 64, 72, 74, 76, 78-81, 191, 200 and 212. In some of any such embodiments, the anti-CD3 Fv is a dsFv that has a VH chain containing the mutation G44C and a VL chain containing the mutation G100C, each by kabat numbering. In some embodiments, the anti-CD3ε Fv antibody fragment includes a combination of an amino acid sequence selected from the group of SEQ ID NO: 44, 49-62, 197 and 198 and an amino acid sequence selected from the group consisting of SEQ ID NO: 64, 72, 74, 76, 78-81, 191, 200 and 212.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 44. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 72. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 44 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 72. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 44. In some embodiments, the anti-CD3ε binding domain includes a variable light chain (VL) comprising the amino acid sequence of SEQ ID NO: 72. In some embodiments, the anti-CD3ε binding domain thereof includes a variable heavy chain (VH) comprising the amino acid sequence of SEQ ID NO: 44 and a variable light chain (VL) comprising the amino acid sequence of SEQ ID NO: 72.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 198. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 200. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 198 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 200. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 198. In some embodiments, the anti-CD3ε binding domain includes a variable light chain (VL) comprising the amino acid sequence of SEQ ID NO: 200. In some embodiments, the anti-CD3ε binding domain thereof includes a variable heavy chain (VH) comprising the amino acid sequence of SEQ ID NO: 198 and a variable light chain (VL) comprising the amino acid sequence of SEQ ID NO: 200.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 197. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 200. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 197 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 200. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 197. In some embodiments, the anti-CD3ε binding domain includes a variable light chain (VL) comprising the amino acid sequence of SEQ ID NO: 200. In some embodiments, the anti-CD3ε binding domain thereof includes a variable heavy chain (VH) comprising the amino acid sequence of SEQ ID NO: 197 and a variable light chain (VL) comprising the amino acid sequence of SEQ ID NO: 200.

2. Immunoglobulin Fc polypeptides:

The first component of the multispecific polypeptide constructs of the disclosure includes an immunoglobulin Fc region. In some embodiments, the immunoglobulin Fc region is an IgG isotype selected from the group consisting of IgG1 isotype, IgG2 isotype, IgG3 isotype, and IgG4 subclass. In some embodiments, the Fc region is a human Fc. In some embodiments, the immunoglobulin Fc region is a polypeptide comprising an amino acid sequence selected from the group consisting of SEQ ID NOs: 1-6. In some embodiments, the immunoglobulin Fc region contains an Fc chain that is an immunologically active fragment of any of SEQ ID Nos: 1-6. In some embodiments, the immunoglobulin Fc region contains an Fc polypeptide chain that is at least 50%, 60%, 65%, 70%, 75%, 80%, 85%, 90%, 91%, 92%, 93%, 94%, 95%, 96%, 97%, 98%, or 99% identical to the amino acid sequence of any of SEQ ID NOs: 1-6 or an immunologically active fragment thereof.

In some embodiments, the multispecific polypeptide construct is a dimer formed by polypeptides, each containing an Fc. In some specific embodiments, identical or substantially identical polypeptides will be dimerized to create a homodimer. In some embodiments, the dimer is a homodimer in which the two polypeptides of the multispecific polypeptide construct are the same. In other cases, the Fc region is formed by Fc domains that are mutated or modified to promote heterodimerization in which different polypeptides can be dimerized to yield a heterodimer. Thus, in some embodiments, the dimer is a heterodimer in which two polypeptide chains of the multispecific polypeptide construct are different. Exemplary modifications to promote heterodimerization are known, including any as described below.

In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments, such functions can be altered, such as reduced or enhanced, in an Fc for use with the provided multispecific polypeptide constructs.

In some embodiments, the Fc region of the provided multispecific polypeptide constructs exhibit one or more effector functions. In some cases, the Fc region is capable of providing Fc-mediated effector functions, such as for example, ADCC (e.g., release of granzyme B by NK cells), ADCP, and/or CDC. Thus, in some embodiments in which the multispecific polypeptide constructs contain a cleavable linker, cleavage of the linker can produce two components that each have biological activity: the CD3-binding region that is able to bind and engage CD3 on a T cell and the Fc region linked to the TAA-antigen binding domain that can exhibit target-specific effector function. In particular embodiments provided herein, the multispecific polypeptide constructs contain a non-cleavable linker and may, in some aspects, not exhibit an independent Fc-mediated effector function.

In some embodiments, the Fc region includes an Fc polypeptide that is mutated or modified to alter one or more effector functions. Various examples of mutations to Fc polypeptides to alter, such as reduce, effector function are known, including any as described below. In some embodiments, reference to amino acid substitutions in an Fc region is by EU numbering by Kabat (also called Kabat numbering) unless described with reference to a specific SEQ ID NO. EU numbering is known and is according to the most recently updated IMGT Scientific Chart (IMGT®, the international ImMunoGeneTics information System®, imgt.org/IMGTScientificChart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

In some embodiments, provided multispecific polypeptide constructs that contain an Fc region that exhibits reduced effector functions, may be a desirable candidate for applications in which constrained CD3 binding is desired yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multispecific polypeptide constructs and/or cleaved components thereof lack FcγR binding (hence likely lacking ADCC activity), but retains FcRn binding ability. The primary cells for mediating ADCC, NK cells, express FcγRIII only, whereas monocytes express FcγRT, FcγRII and FcγRIII. Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the multispecific polypeptide construct or cleaved components thereof is unable to bind C1q and hence lacks CDC activity. See, e.g., C1q and C3ε binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., Blood 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Intl. Immunol.* 18(12):1759-1769 (2006)).

In some embodiments, the immunoglobulin Fc region or immunologically active fragment thereof is an IgG isotype. For example, the immunoglobulin Fc region of the fusion protein is of human IgG1 isotype, having an amino acid sequence:

```
                                                           (SEQ ID NO: 1)
PAPE LLGGPS VFLFPPKPKD TLMISRTPEV TCVVVDVSHE DPEVKFNWYV

DGVEVHNAKT KPREEQYNST YRVVSVLTVL HQDWLNGKEY KCKVSNKALP

APIEKTISKA KGQPREPQVY TLPPSRDELT KNQVSLTCLV KGFYPSDIAV

EWESNGQPEN NYKTTPPVLD SDGSFFLYSK LTVDKSRWQQ GNVFSCSVMH

EALHNHYTQK SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, an IgG1 Fc polypeptide or a variant thereof such as any described below can be made in a G1 m1 or G1 m3 allotype. In some embodiments, the Fc region can contain amino acids of the human G1 m1 allotype, such as residues containing Asp (D) and Leu (L) at positions 356 and 358, e.g. as set forth in SEQ ID NO:1. In some cases, an Fc polypeptide can contain amino acid substitutions E356D and M358L to reconstitute residues of allotype G1 m1. In other embodiments, the Fc region can contain amino acids of the human G1 m3 allotype, such as residues Glu (E) and Met (M) at positions 356 and 358 by EU numbering, e.g. as set forth in SEQ ID NOS: 194 and 195. In some cases, an Fc polypeptide can contain amino acid substitutions D356E and L358M to reconstitute residues of allotype G1 m3. In some embodiments, the human IgG1 Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11, the contents of each of which are hereby incorporated by reference in their entireties.

In some embodiments, the Fc region, such as the human IgG1 Fc region is modified to enhance ADCC activity or CDC activity. Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the human IgG1 Fc region fusion proteins of the present disclosure lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line. In some embodiments, the human IgG1 Fc region is modified at amino acid Asn297 (Boxed, Kabat Numbering) to prevent glycosylation of the fusion protein, e.g., Asn297Ala (N297A) or Asn297Asp (N297D).

In some embodiments, the Fc region is altered to provide reduced Fc-mediated effector functions, such as via reduced Fc receptor binding, e.g. binding to FcγR binding but generally not FcRn binding. In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In some embodiments, the Fc region of the fusion protein is modified at amino acid Leu235 (Boxed in SEQ ID NO:1 above, Kabat Numbering) to alter Fc receptor interactions, e.g., Leu235Glu (L235E) or Leu235Ala (L235A). In some embodiments, the Fc region of the fusion protein is modified at amino acid Leu234 (Boxed in SEQ ID NO:1 above, Kabat Numbering) to alter Fc receptor interactions, e.g., Leu234Ala (L234A). In some embodiments, the Fc region of the fusion protein is altered at both amino acid 234 and 235, e.g., Leu234Ala and Leu235Ala (L234A/L235A) or Leu234Val and Leu235Ala (L234V/L235A). In preferred embodiments, modifications within the Fc region reduce binding to Fc-receptor-gamma receptors while have minimal impact on binding to the neonatal Fc receptor (FcRn).

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, *J. Biol Chem* Vol. 281(33) 23514-23524), Met428Leu and Asn434Ser (M428L, N434S) (Zalevsky et al 2010 *Nature Biotech, Vol.* 28(2) 157-159) (EU index of Kabat et al 1991 *Sequences of Proteins of Immunological Interest*). In some embodiments, the mutated or modified Fc polypeptide includes the following mutations: Met252Tyr and Met428Leu or Met252Tyr and Met428Val (M252Y, M428L, or M252Y, M428V) using the Kabat numbering system.

In some embodiments, the Fc region of the fusion protein is lacking an amino acid at one or more of the following positions to reduce Fc receptor binding: Glu233 (E233), Leu234 (L234), or Leu235 (L235). In these embodiments, Fc deletion of these three amino acids reduces the complement protein C1q binding.

```
                                                           (SEQ ID NO: 2)
PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK
```

```
TTPPVLDSDG SFFLYSKLTV DKSRWQQGNV FSCSVMHEAL

HNHYTQKSLS LSPGK
```

In some embodiments, the Fc region is mutated in one or more of the following positions to reduce Fc receptor binding: Glu233 (E233), Leu234 (L234), or Leu235 (L235). The one or more mutations can include E233P, L234V and/or L235A.

In some embodiments, the Fc region of the fusion protein is altered at Gly236 (boxed in SEQ ID NO:1 above) to reduce Fc receptor binding. For example, wherein Gly236 is deleted from the fusion protein. In some embodiments, the human IgG1 Fc region is modified at amino acid Gly236 to enhance the interaction with CD32A, e.g., Gly236Ala (G236A).

In particular embodiments, the mutations of the Fc region to reduce Fc effector function, e.g. via reducing Fc receptor binding to FcγR, include mutations from among any of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G or E233P/L234V/L235A/G236del.

In some embodiments, the human IgG1 Fc region lacks Lys447 (EU index of Kabat et al 1991 Sequences of Proteins of Immunological Interest).

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the immunoglobulin Fc region or immunologically active fragment of the fusion protein is of human IgG2 isotype, having an amino acid sequence:

```
                                                    (SEQ ID NO: 3)
PAPPVAGPSV FLFPPKPKDT LMISRTPEVT CVVVDVSHED PEVQFNWYVD

GVEVHNAKTK PREEQFNSTF RVVSVLTVVH QDWLNGKEYK CKVSNKGLPA

PIEKTISKTK GQPREPQVYT LPPSREEMTK NQVSLTCLVK GFYPSDISVE

WESNGQPENN YKTTPPMLDS DGSFFLYSKL TVDKSRWQQG NVFSCSVMHE

ALHNHYTQKS LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG2 Fc region is modified at amino acid Asn297 (Boxed, to prevent to glycosylation of the antibody, e.g., Asn297Ala (N297A) or Asn297Asp (N297D). In some embodiments, the human IgG2 Fc region lacks Lys447 (EU index of Kabat et al 1991 *Sequences of Proteins of Immunological Interest*).

In some embodiments, the immunoglobulin Fc region or immunologically active fragment of the fusion protein is of human IgG3 isotype, having an amino acid sequence:

```
                                                    (SEQ ID NO: 4)
PAPELLGGPS VFLFPPKPKD TLMISRTPEV TCVVVDVSHE DPEVQFKWYV

DGVEVHNAKT KPREEQYNST FRVVSVLTVL HQDWLNGKEY KCKVSNKALP

APIEKTISKT KGQPREPQVY TLPPSREEMT KNQVSLTCLV KGFYPSDIAV

EWESSGQPEN NYNTTPPMLD SDGSFFLYSK LTVDKSRWQQ GNIFSCSVMH

EALHNRFTQK SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In some embodiments, the human IgG3 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region lacks Lys447 (EU index of Kabat et al 1991 Sequences of Proteins of Immunological Interest).

In some embodiments, the immunoglobulin Fc region or immunologically active fragment of the fusion protein is of human IgG4 isotype, having an amino acid sequence:

```
                                                  (SEQ ID NO: 5)
PAPEFLGGPS VFLFPPKPKD TLMISRTPEV TCVVVDVSHE DPEVKFNWYV

DGVEVHNAKT KPREEQFNST YRVVSVLTVL HQDWLNGKEY KCKVSNKGLP

SSIEKTISKA KGQPREPQVY TLPPSQEEMT KNQVSLTCLV KGFYPSDIAV

EWESNGQPEN NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 5.

In some embodiments, the immunoglobulin Fc region or immunologically active fragment of the fusion protein is of human IgG4 isotype, having an amino acid sequence:

```
                                                  (SEQ ID NO: 6)
PAPELLGGPS VFLFPPKPKD TLMISRTPEV TCVVVDVSQE DPEVQFNWYV

DGVEVHNAKT KPREEQYNST YRVVSVLTVL HQDWLNGKEY KCKVSNKGLP

SSIEKTISKA KGQPREPQVY TLPPSQEEMT KNQVSLTCLV KGFYPSDIAV

EWESNGQPEN NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 6.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG4 Fc region lacks Lys447 (EU index of Kabat et al 1991 *Sequences of Proteins of Immunological Interest*).

In some embodiments, the human IgG Fc region is modified to stabilize the homodimerization at the CH3:CH3 interface by introducing two disulfide bonds by changing Ser354 to Cys (S354C) and Tyr349 to Cys (Y349C) (S354C/Y349C).

In particular embodiments of multispecific polypeptide constructs provided herein, the human IgG Fc region is modified to induce heterodimerization. Various methods are known for promoting heterodimerization of complementary Fc polypeptides, see e.g. Ridgway et al, Protein Eng. 9:617-621 (1996); Merchant et al, Nat. Biotechnol. 16(7): 677-81 (1998); Moore et al. (2011) MAbs, 3:546-57; Von Kreudenstein et al. MAbs, (2013) 5:646-54; Gunasekaran et al. (2010) J. Biol. Chem., 285:19637-46; Leaver-Fay et al. (2016) Structure, 24:641-51; Ha et al. (2016) Frontiers in Immunology, 7:1; Davis et al. (2010) Protein Eng Des Sel, 23:195-202; published international PCT Appl. No. WO 1998/050431, WO 2009/089004, WO2011143545 WO 2014/067011, WO 2012/058768, WO2018027025; published U.S. patent Appl. No. US20140363426, US20150307628, US20180016354, US20150239991; and U.S. patent Nos. U.S. Pat. Nos. 5,731,168, 7,183,076, 9,701,759, 9,605,084, and 9,650,446. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. For example, in some embodiments, the Fc polypeptides of a heterodimer includes a mutation to alter charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (Guneskaran et al. (2010) JBC, 285: 19637-19646). When co-expressed in a cell, association between the chains is possible but the chains do not substantially self-associate due to charge repulsion. Other strategies for generating a heterodimeric Fc include mixing human IgG and IgA CH3 domain segments to create a complementary CH3 heterodimer, which is referred to as a SEED Fc.

Methods and variants for heterodimerization also include those described in published international PCT App.

WO2014/145806, including "knobs and holes" mutations (also called "skew" variants), mutations that relate to "electrostatic steering" or "charge pairs," and pI variants. Heterodimeric variants also include any as described in U.S. published Appl. No. US2012/0149876 or US2018/011883.

In some embodiments, to promote heterodimerization both polypeptides of the Fc heterodimer contain paired or complementary amino acid modifications. Exemplary paired amino acid modification of polypeptides of an Fc fusion are set forth in Table 1.

TABLE 1

Paired amino acids of Heterodimeric Fc

| First Fc polypeptide | Second Fc Polypeptide |
|---|---|
| T366W | T366S/L368W/Y407V |
| T366W/S354C | T366S/L368A/Y407V/Y349C |
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q347R/D399V/F405T |
| L360E/K409W/Y349C | Q347R/399V/F405T/S354C |
| K370E/K409W | E357N/D399V/F405T |

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first Fc polypeptide that is modified to contain protuberance (hole) amino acids include replacement of a native or original amino acid with an amino acid that has at least one side chain which projects from the interface of the first Fc polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second Fc polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 A2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731,168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

For example, in some embodiments the heterodimeric Fc includes a polypeptide having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (Reviewed in Carter, 2001 Journal of Immunological Methods, 248: 7-15).

In particular embodiments, a multispecific polypeptide construct contains a first and second Fc able to mediate Fc heterodimerization contains a first Fc polypeptide containing mutations T366W and S354C and a second Fc polypeptide containing mutations T366S, L368A, Y407V and Y349C. In some embodiments, the first Fc polypeptide is selected from an Fc polypeptide comprising the sequence set forth in SEQ ID NO: 201 or 207 and the second Fc polypeptide is selected from an Fc polypeptide comprising the sequence set forth in SEQ ID NO: 202, 205 or 209. In some embodiments, the first Fc polypeptide is or comprises the sequence of amino acids set forth in any of SEQ ID NOS: 82, 86, 94 or 96 and the second Fc polypeptide is or comprises the sequence of amino acids set forth in any of SEQ ID NOS: 83, 87, 90, 92, 98 or 100.

In some embodiments, the Fc polypeptide exhibits features providing Fc-mediated effector functions. In particular examples, the first Fc polypeptide is or comprises the sequence set forth in SEQ ID NOs:201 and a second Fc polypeptide that is or comprises SEQ ID NO: 202 or 205. In some embodiments, the first Fc polypeptide is or comprises the sequence set forth in SEQ ID NO: 82 and the second Fc polypeptide is or comprises the sequence set forth in SEQ ID NO: 83 or 90. In some embodiments, the first Fc polypeptide is or comprises the sequence set forth in SEQ ID NO: 86 and the second Fc polypeptide is or comprises the sequence set forth in SEQ ID NO: 87 or 92. The first and second Fc polypeptide can be formatted on either polypeptide chain of the construct.

In some embodiments, one or both of the first and second Fc polypeptides can further include one or more amino acid mutations to further reduce one or more Fc effector functions, such as reduced Fc receptor binding. Exemplary mutations to reduce Fc effector functions include any as described. In some embodiments, the modification can be a deletion of one or more positions Glu233 (E233), Leu234 (L234), or Leu235 (L235), such as a deletion of amino acids Glu233 (E233), Leu234 (L234), and Leu235 (L235). In some embodiments, the first Fc polypeptide is selected from an Fc polypeptide comprising the sequence set forth in SEQ ID NO: 203 or 208 and the second Fc polypeptide is selected from an Fc polypeptide comprising the sequence set forth in SEQ ID NO: 204, 206 or 210. In some embodiments, the first Fc polypeptide is or comprises the sequence of amino acids set forth in any of SEQ ID NOS: 84, 88, 95 or 97 and the second Fc polypeptide is or comprises the sequence of amino acids set forth in any of SEQ ID NOS: 85, 89, 91, 93, 99 or 101.

In particular examples, the first Fc polypeptide is or comprises the sequence set forth in SEQ ID NOs:203 and a second Fc polypeptide that is or comprises SEQ ID NO: 204 or 206. In some embodiments, the first Fc polypeptide is or comprises the sequence set forth in SEQ ID NO: 84 and the second Fc polypeptide is or comprises the sequence set forth in SEQ ID NO: 85 or 91. In some embodiments, the first Fc polypeptide is or comprises the sequence set forth in SEQ ID NO: 88 and the second Fc polypeptide is or comprises the sequence set forth in SEQ ID NO: 89 or 93. The first and second Fc polypeptide can be formatted on either polypeptide chain of the construct.

In some embodiments, the first Fc polypeptide or second Fc polypeptide further includes mutations M252Y and/or M428V. In particular examples, the first Fc polypeptide is or comprises the sequence set forth in SEQ ID NO:207 and the second Fc polypeptide is or comprises the sequence set forth in SEQ ID NO:209. In some embodiments, the first Fc polypeptide is or comprises the sequence set forth in SEQ ID NO:94 and the second Fc polypeptide is or comprises the sequence set forth in SEQ ID NO: 98. In some embodiments, the first Fc polypeptide is or comprises the sequence set forth in SEQ ID NO:96 and the second Fc polypeptide is or comprises the sequence set forth in SEQ ID NO: 100. In other examples, the first Fc polypeptide is or comprises the sequence set forth in SEQ ID NO:208 and the second Fc polypeptide is or comprises the sequence set forth in SEQ ID NO:210. In some embodiments, the first Fc polypeptide is or comprises the sequence set forth in SEQ ID NO:95 and the second Fc polypeptide is or comprises the sequence set forth in SEQ ID NO: 99. In some embodiments, the first Fc polypeptide is or comprises the sequence set forth in SEQ ID NO:97 and the second Fc polypeptide is or comprises the sequence set forth in SEQ ID NO: 101. The first and second Fc polypeptide can be formatted on either polypeptide chain of the construct.

Additional examples of variants that can facilitate the promotion of heterodimers are any combination or pair of steric variants (e.g. skew variants) of a first Fc polypeptide and a second Fc polypeptide from among: S364K/E357Q and L368D/K370S; L368D/K370S and S364K; L368E/K370S and S364K; T411T/E360E/Q362E and D401K; L368D/K370S and S364K/E357L, K370S and S364K/E357Q and T366S/L368A/Y407V and T366W or 366S/L368A/Y407V/Y349C and T366W/S354C), where each pair represents mutations in the first Fc polypeptide and second Fc polypeptide. In particular embodiments, a provided construct contains a first and second Fc polypeptide containing the pair of mutations L368D/K370S and S364K and E357Q.

An additional mechanism that can be used in the generation of heterodimers is sometimes referred to as "electrostatic steering" as described in Gunasekaran et al., J. Biol. Chem. 285(25):19637 (2010). This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". In one embodiments, a first Fc polypeptide can contain mutations D221E/P228E/L368E and a second Fc polypeptide can contain mutations D221R/P228R/K409R. In another embodiments, a first Fc polypeptide can contain mutations C220E/P228E/368E and a second Fc polypeptide can contain mutations C220R/E224R/P228R/K409R.

In some embodiments, heterodimerization can be facilitated by pI variants. In some aspects, a pI variant can include those that increase the pI of the protein (basic changes). In other aspects, the pI variant can include those that decrease the pI of the protein (acidic changes). In some cases, all combinations of these variants can be done, including combinations in which one Fc polypeptide may be wild type, or a variant that does not display a significantly different pI from wild-type, and the other Fc polypeptide can be either more basic or more acidic. Alternatively, each Fc polypeptide can be changed, one to more basic and one to more acidic. In some embodiments, at least one Fc polypeptide is a negative pI variant Fc containing mutations Q295E/N384D/Q418E/N421D.

In some embodiments, a combination of steric heterodimerization variants (e.g. knob and hole) and pI or charge pair variants can be used.

In particular embodiments, the provided constructs contains (a) a first Fc polypeptide comprising the skew variants S364K/E357Q; and b) a second Fc polypeptide containing skew variants L368D/K370S and the pI variants N208D/Q295E/N384D/Q418E/N421D. In some embodiments, one or both of the first and second polypeptide can contain further mutations to reduce Fc effector activity, such as the exemplary mutations E233P/L234V/L235A/G236del/S267K. An example of such a first Fc polypeptide and a second Fc polypeptide able to mediate Fc heterodimeriztion comprise the sequences set forth in SEQ ID NOs:194 and 195. The first and second Fc polypeptide can be formatted on either polypeptide chain of the construct.

The resulting multispecific polypeptide constructs can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

Techniques for recovery of heterodimers from homodimers based on a differential affinity of the heterodimers for an affinity reagent are known. In some aspects, such techniques include designing a heterodimer so that one of the Fc polypeptide chains does not bind to the affinity reagent protein A. In some cases, one of the polypeptide chain can contain one or more amino acid substitution to abrogate or reduce affinity for the protein A reagent in one of the polypeptides of the Fc heterodimer, see e.g. WO2017134440, WO2010151792, Jendeberg et al. (Jendeberg et al., (1997) J. Immunol. Methods, 201(1): 25-34. In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, for example Ile253Arg (I253R). In some embodiments, the modification may be H435R or H435R/Y436F. In some embodiments, an Fc polypeptide of an Fc heterodimer can contain a modification so that it is capable of binding protein A but not protein G (pA+/pG−). Exemplary pA+/pG− amino acid modifications include an Fc containing serine at position 428, serine at position 434 and optionally histidine at position 436, with reference to human IgG1 or comprising these residues at the corresponding positions in human IgG 2, 3, or 4. In some aspects, such amino acid modifications in one IgG Fc polypeptide at positions 428, 434 and optionally 436 reduces or prevents the binding of protein G, enhancing the purification of the protein.

In some embodiments, any of such modifications to confer differential affinity to an affinity reagent can be combined with any one or more other amino acid modifications described above. For example, the I253R modification maybe combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed. Similar modifications can be employed by combining T366S/L368A/Y407V and H453R.

In some embodiments, the Fc regions of the heterodimeric molecule additionally can contain one or more other Fc mutation, such as any described above. In some embodiments, the heterodimer molecule contains an Fc region with a mutation that reduces effector function.

In some embodiments, one Fc polypeptide of a heterodimeric Fc comprises the sequence of amino acids set forth in any of SEQ ID NOS:201 (e.g. SEQ ID NO:82), 86, 207 (e.g. SEQ ID NO:94), or 96, and the other Fc polypeptide of the heterodimeric Fc contains the sequence of amino acids set forth in any of SEQ ID NOS:201 (e.g. SEQ ID NO:83), 87, 205 (e.g. SEQ ID NO:90), 92, 209 (e.g. SEQ ID NO:98), or 100. In some embodiments, one Fc polypeptide of a heterodimeric Fc comprises the sequence of amino acids set forth in any of SEQ ID NOS: 203 (e.g. SEQ ID NO:84), 88, 208 (e.g. SEQ ID NO:95), or 97 and the other Fc polypeptide of the heterodimeric Fc comprises the sequence of amino acids set forth in any of SEQ ID NOS: 204 (e.g. SEQ ID NO:85), 89, 206 (e.g. SEQ ID NO:91), 93, 210 (e.g. SEQ ID NO:99), or 101.

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTH-TCPPC (SEQ ID NO: 7), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 8).

In some embodiments, the fusion protein has a modified hinge from IgG4, which is modified to prevent or reduce strand exchange, e.g., Ser228Pro (S228P), having the sequence ESKYGPPCPPC (SEQ ID NO: 9). In some embodiments, the fusion protein contains linker polypeptides. In other embodiments, the fusion protein contains linker and hinge polypeptides.

3. Linkers

The provided multispecific polypeptide constructs contain a linker that joins or couples the first component containing the immunoglobulin Fc region and the second component containing the CD3 binding region. In some embodiments, the linker is a non-cleavable linker. In some embodiments, the linker does not contain a substrate recognition site that is specifically recognized for cleavage by the protease. Thus, linkers in the provided multispecific polypeptide constructs do not include an amino acid sequence that can serve as a substrate for a protease, such as an extracellular protease. For example, the non-cleavable linker does not include a cleavage sequence containing at least one peptide bond which lies within a cleavable peptide sequence of a protease.

In some embodiments, the linker is positioned at the end of the C-terminal region of the Fc region, such that the Fc region is N-terminal to the CD3 binding region. Because the provided multispecific polypeptide constructs are multimers, such as dimers, the provided constructs include a linker joining the first Fc polypeptide and a first domain (e.g. VH) of the CD3 binding region of the first polypeptide and the second Fc polypeptide and second domain (e.g. VL) of the CD3 binding region of the second polypeptide. Typically, the linkers present in the first and second polypeptides of the multispecific polypeptide construct are the same. Thus, in some embodiments, each domain of the CD3 binding domain is linked via a linker, such as the same linker, to opposite polypeptides of the Fc, such as heterodimeric Fc.

Various polypeptide linkers for use in fusion proteins are known (see e.g. Chen et al. (2013) Adv. Drug. Deliv. 65:1357-1369; and International PCT publication No. WO 2014/099997, WO2000/24884; U.S. Pat. Nos. 5,258,498; 5,525,491; 5,525,491; 6,132,992).

In some embodiments, the linker is chosen so that, when the CD3 binding region is joined to the Fc region of the multispecific polypeptide conjugate, the CD3 binding region is constrained and not able to, or not substantially able to, bind or engage CD3 on the surface of a cell, e.g. T cell, upon contact of the multispecific polypeptide construct with the cell. Various assays can be employed to assess binding or engagement of CD3 by the multispecific polypeptide construct, including assays to assess T cell binding, NFAT activation using a reporter system, cytolytic T cell activity, cytokine production and/or expression of T cell activation markers. Exemplary assays are shown in the provided Examples. Typically, the linker also is one that ensures correct folding of the polypeptide construct, does not exhibit a charge that would be inconsistent with the activity or function of the linked polypeptides or form bonds or other interactions with amino acid residues in one or more of the domains that would impede or alter activity of the linked polypeptides. In some embodiment, the linker is a polypeptide linker. The polypeptide linker can be a flexible linker or a rigid linker or a combination of both.

In some aspects, the linker is a short, medium or long linker. In some embodiments, the linker is up to 40 amino acids in length. In some embodiments, the linker is up to 25 amino acids in length. In some embodiments, the linker is at least or is at least about 2 amino acids in length. In some aspects, a suitable length is, e.g., a length of at least one and typically fewer than about 40 amino acid residues, such as 2-25 amino acid residues, 5-20 amino acid residues, 5-15 amino acid residues, 8-12 amino acid. In some embodiments, the linker is from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is 2, 3, 4, 5, 6, 7, 8, 9, 10, 11, 12, 13, 14, 15, 16, 17, 18, 19 or 20 amino acids in length.

In certain aspects, the longer the linker length, the greater the CD3 binding when the multispecific polypeptide conjugate is bounds to its antigen, e.g. TAA. Thus, in some aspects, the linker is greater than 12 amino acids in length, such as greater than 13, 14, 15, 16, 17 or 18 amino acids in length. In some embodiments, the linker is 12 to 40 amino acids in length, 12 to 30 amino acids, 12 to 24 amino acids, 12 to 18 acids, 12 to 15 amino acids, 15 to 40 amino acids, 15 to 30 amino acids, 15 to 24 amino acids, 15 to 18 amino acids, 18 to 40 amino acids, 18 to 30 amino acids, 18 to 24 amino acids, 24 to 40 amino acids, 24 to 30 amino acids or 30 to 40 amino acids.

The linkers can be naturally-occurring, synthetic or a combination of both. Particularly suitable linker polypeptides predominantly include amino acid residues selected from Glycine (Gly), Serine (Ser), Alanine (Ala), and Threonine (Thr). For example, the linker may contain at least 75% (calculated on the basis of the total number of residues present in the peptide linker), such as at least 80%, at least 85%, or at least 90% of amino acid residues selected from Gly, Ser, Ala, and Thr. The linker may also consist of Gly, Ser, Ala and/or Thr residues only. In some embodiments, the linker contains 1-25 glycine residues, 5-20 glycine residues, 5-15 glycine residues, or 8-12 glycine residues. In some aspects, suitable peptide linkers typically contain at least 50% glycine residues, such as at least 75% glycine residues. In some embodiments, a peptide linker comprises glycine residues only. In some embodiments, a peptide linker comprises glycine and serine residues only.

In some embodiments, these linkers are composed predominately of the amino acids Glycine and Serine, denoted as GS-linkers herein. In some embodiments, the linker contains (GGS)n, wherein n is 1 to 10, such as 1 to 5, for example 1 to 3, such as GGS(GGS)n (SEQ ID NO:171), wherein n is 0 to 10. In particular embodiments, the linker contains the sequence (GGGGS)n (SEQ ID NO: 173), wherein n is 1 to 10 or n is 1 to 5, such as 1 to 3. In further embodiments, the linker contains (GGGGGS)n (SEQ ID NO:172), wherein n is 1 to 4, such as 1 to 3. The linker can include combinations of any of the above, such as repeats of 2, 3, 4, or 5 GS, GGS, GGGGS, and/or GGGGGS linkers may be combined. In some embodiments, such a linker is 2, 3, 4, 5, 6, 7, 8, 9, 10, 11, 12, 13, 14, 15, 16, 17, 18 or 19 amino acids in length.

In some embodiments, the linker is (in one-letter amino acid code): GGS, GGGGS (SEQ ID NO: 149), or GGGGGS (SEQ ID NO: 135). In some embodiments, the GS-linker comprises an amino acid sequence of GGSGGS, i.e., $(GGS)_2$ (SEQ ID NO: 10); GGSGGSGGS, i.e., $(GGS)_3$ (SEQ ID NO: 11); GGSGGSGGSGGS, i.e., $(GGS)_4$ (SEQ ID NO: 12); GGSGGSGGSGGSGGS, i.e., $(GGS)_5$ (SEQ ID NO: 13); GGGGGSGGGGGSGGGGGS, i.e., $(G5S)_3$ (SEQ ID NO: 119), GGSGGGGSGGGGSGGGGS (SEQ ID NO: 147) and GGGGSGGGGSGGGGS (SEQ ID NO:170). In some embodiments, the linker is GGGG (SEQ ID NO:103). In some embodiments, the linker is GGGGG (SEQ ID NO:192). In some of any of the above examples, serine can be replaced with alanine (e.g., (Gly4Ala) or (Gly3Ala)).

In some embodiments, the linker includes a peptide linker having the amino acid sequence $Gly_x$-Xaa-$Gly_y$-Xaa-$Gly_z$ (SEQ ID NO:174), wherein each Xaa is independently selected from Alanine (Ala), Valine (Val), Leucine (Leu), Isoleucine (Ile), Methionine (Met), Phenylalanine (Phe), Tryptophan (Trp), Proline (Pro), Glycine (Gly), Serine (Ser), Threonine (Thr), Cysteine (Cys), Tyrosine (Tyr), Asparagine (Asn), Glutamine (Gln), Lysine (Lys), Arginine (Arg), Histidine (His), Aspartate (Asp), and Glutamate (Glu), and wherein x, y, and z are each integers in the range from 1-5. In some embodiments, each Xaa is independently selected from the group consisting of Ser, Ala, and Thr. In a specific variation, each of x, y, and z is equal to 3 (thereby yielding a peptide linker having the amino acid sequence Gly-Gly-Gly-Xaa-Gly-Gly-Gly-Xaa-Gly-Gly-Gly (SEQ ID NO:175), wherein each Xaa is selected as above.

In some embodiments, the linker is serine-rich linkers based on the repetition of a (SSSSG)n (SEQ ID NO:185) motif where n is at least 1, though n can be 2, 3, 4, 5, 6, 7, 8 and 9.

In some cases, it may be desirable to provide some rigidity into the peptide linker. This may be accomplished by including proline residues in the amino acid sequence of the peptide linker. Thus, in some embodiments, a linker comprises at least one proline residue in the amino acid sequence of the peptide linker. For example, a peptide linker can have an amino acid sequence wherein at least 25% (e.g., at least 50% or at least 75%) of the amino acid residues are proline residues. In one particular embodiment, the peptide linker comprises proline residues only.

In some aspects, a peptide linker comprises at least one cysteine residue, such as one cysteine residue. For example, in some embodiments, a linker comprises at least one cysteine residue and amino acid residues selected from the group consisting of Gly, Ser, Ala, and Thr. In some such embodiments, a linker comprises glycine residues and cysteine residues, such as glycine residues and cysteine residues only. Typically, only one cysteine residue will be included per peptide linker. One example of a specific linker comprising a cysteine residue includes a peptide linker having the amino acid sequence $Gly_m$-Cys-$Gly_n$, wherein n and m are each integers from 1-12, e.g., from 3-9, from 4-8, or from 4-7. In a specific variation, such a peptide linker has the amino acid sequence GGGGG-C-GGGGG (SEQ ID NO:177).

In some embodiments, the linker of the fusion protein is a structured or constrained linker. In particular embodiments, the structured linker contains the sequence (AP)n or (EAAAK)n (SEQ ID NO:178), wherein n is 2 to 20, preferably 4 to 10, including but not limited to, AS-(AP)n-GT (SEQ ID NO:179) or AS-(EAAAK)n-GT (SEQ ID NO:180), wherein n is 2 to 20, such as 2, 3, 4, 5, 6, 7, 8, 9, 10, 11, 12, 13, 14 or 15. In other embodiments, the linker comprises the sequences (GGGGA)n (SEQ ID NO:181), (PGGGS)n (SEQ ID NO:182), (AGGGS)n (SEQ ID NO:183) or GGS-(EGKSSGSGSESKST)n-GGS (SEQ ID NO:184, wherein n is 2 to 20. In some embodiments, the linker is SSSASASSA (SEQ ID NO:186), GSPGSPG (SEQ ID NO:187), or ATTTGSSPGPT (SEQ ID NO:176). In some embodiments, such linkers, by virtue of their structure, may be more resistant to proteolytic degradation, thereby offering an advantage when injected in vivo.

In some embodiments, the linker is not a cleavable linker (used interchangeably with non-cleavable linker). In some embodiments, the linker is not cleavable by a protease. In some embodiments, a linker that is not a cleavable linker or that is not cleavable by a protease is one that is generally stable for in vivo delivery or recombinant production. In some aspects, a linker that is not cleavable by a protease includes those that do not contain at least one peptide bond which preferably lies within a cleavable peptide sequence or recognition site of a protease. In particular embodiments, a non-cleavable linker is not a target substrate for a protease, such that it is not preferentially or specifically cleaved by a protease compared to a linker that contains a substrate recognition site for the same protease.

In some embodiments, the linker does not contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the linker does not include a P1-P1' scissile bond sequence that is recognized by a protease.

In some aspects, a non-cleavable linker or a linker that does not contain a substrate recognition site that is specifically recognized for cleavage by a protease is one whose cleavage by a protease is substantially less than cleavage of a target substrate of the protease. Typically, a protease exhibits specificity or preference for cleavage of a particular target substrate compared to another non-target substrate. Such a degree of specificity can be determined based on the rate constant of cleavage of a sequence, e.g. linker sequence, which is a measure of preference of a protease for its substrate and the efficiency of the enzyme. Any method to determine the rate of increase of cleavage over time in the presence of various concentrations of substrate can be used to calculate the specificity constant. For example, a substrate is linked to a fluorogenic moiety, which is released upon cleavage by a protease. By determining the rate of cleavage at different protease concentrations the specificity constant for cleavage ($k_{cat}/K_m$) can be determined for a particular protease towards a particular linker. In some embodiments, a non-cleavable linker, or a linker that does not contain a substrate recognition site that is specifically recognized for cleavage by a protease, is a linker that, if cleaved at all, is cleaved by a protease at a rate of less than $1\times10^4$ $M^{-1}S^{-1}$, or less than $5\times10^3$ $M^{-1}S$, less than $1\times10^3$ $M^{-1}S$, or less than $1\times10^2$ $M^{-1}S$ or less.

In some embodiments, the linkers in the multispecific constructs provided herein do not contain a substrate recognition site for a protease that include, for example, matrix metalloproteases (MMP), cysteine proteases, serine proteases and plasmin activators. In particular embodiments, the linker does not contain a substrate recognition site for a protease that is a protease that is produced by a tumor, an activated immune effector cell (e.g. a T cell or a NK cell), or a cell in a tumor microenvironment.

In some embodiments, the linker does not contain a substrate recognition site that is specifically recognized by one or more of the following enzymes or proteases: ADAMS, ADAMTS, e.g. ADAMS; ADAMS; ADAM10; ADAM12; ADAM15; ADAM17/TACE; ADAMDEC1; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; Cysteine proteinases, e.g., Cruzipain; Legumain; Otubain-2; KLKs, e.g., KLK4, KLK5, KLK6, KLK7, KLK8, KLK10, KLK11, KLK13, or KLK14; Metallo proteinases, e.g., Meprin; Neprilysin; PSMA; BMP-1; MMPs, e.g., MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, Granzyme B, Guanidinobenzoatase, HtrA1, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof. In some embodiments, the linker does not contain a substrate recognition site that is specifically recognized by granzyme B, a matriptase or an MMP, such as MMP-2.

In some embodiments, the linker does not comprise an amino acid that is a substrate for Granzyme B. In some embodiments, the linker does not contain an amino acid sequence having the general formula P4 P3 P2 P1 ↓P1' (SEQ ID NO: 150), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, the linker does not contain an amino acid sequence having the general formula P4 P3 P2 P1 ↓P1' (SEQ ID NO: 151), wherein P4 is amino acid I or L; P3 is amino acid E; P2 is amino acid P or A; P1 is amino acid D; and P1' is amino acid I, V, T, S, or G.

In some embodiments, the linker does not contain the amino acid sequence LEAD (SEQ ID NO: 22), LEPD (SEQ ID NO: 142), or LEAE (SEQ ID NO:143). In some embodiments, the linker does not contain the amino acid sequence IEPDI (SEQ ID NO:136), LEADT (SEQ ID NO:137), IEPDG (SEQ ID NO:138), IEPDV (SEQ ID NO:139), IEPDS (SEQ ID NO:140), IEPDT (SEQ ID NO:141), IEPDP (SEQ ID NO:144), LEPDG (SEQ ID NO:152) or LEADG (SEQ ID NO:153).

In some embodiments, the linker does not comprise an amino acid that is a substrate for matriptase. In some embodiments, the linker does not comprises the sequence P1QAR↓(A/V) (SEQ ID NO: 154), wherein P1 is any amino acid. In some embodiments, the linker does not comprises the sequence RQAR(A/V) (SEQ ID NO: 155). In some embodiments, the linker does not comprise the amino acid sequence RQAR (SEQ ID NO: 23). In some embodiments, the linker does not comprise the amino acid sequence RQARV (SEQ ID NO: 156)

In some embodiments, the linker does not comprise an amino acid that is a substrate for one or more matrix metalloproteases (MMPs). In some embodiments, the MMP is MMP-2. In some embodiments, the linker does not contain a sequence having the general formula P3 P2 P1 ↓P1' (SEQ ID NO: 157), wherein P3 is P, V or A; P2 is Q or D; P1 is A or N; and P1' is L, I or M. In some embodiments, the linker does not contain the general formula P3 P2 P1 ↓P1' (SEQ ID NO: 158), wherein P3 is P; P2 is Q or D; P1 is A or N; and P1' is L or I. In some embodiments, the linker does not comprise the amino acid sequence PAGL (SEQ ID NO: 24).

In some embodiments, the linker is not a linker comprising the amino acid sequence set forth as TGLEADGSPAGL-GRQARVG (SEQ ID NO: 25); TGLEAD-GSRQARVGPAGLG (SEQ ID NO: 26); TGSPAGLEADGSRQARVGS (SEQ ID NO: 27); TGPAGLGLEADGSRQARVG (SEQ ID NO: 28); TGRQARVGLEADGSPAGLG (SEQ ID NO: 29); TGSRQARVGPAGLEADGS (SEQ ID NO: 30); and TGPAGLGSRQARVGLEADGS (SEQ ID NO: 31); GPAGLGLEPDGSRQARVG (SEQ ID NO: 104); GGSGGGGIEPDIGGSGGS (SEQ ID NO: 105); GGSGGGGLEADTGGSGGS (SEQ ID NO: 106); GSIEP-DIGS (SEQ ID NO: 107); GSLEADTGS (SEQ ID NO: 108); GGSGGGGIEPDGGGSGGS (SEQ ID NO: 109); GGSGGGGIEPDVGGSGGS (SEQ ID NO: 110); GGSGGGGIEPDSGGSGGS (SEQ ID NO: 111); GGSGGGGIEPDTGGSGGS (SEQ ID NO: 112); GGGSLEPDGSGS (SEQ ID NO: 113); and GPAGLG-LEADGSRQARVG (SEQ ID NO: 114), GGEGGGGSGGSGGGS (SEQ ID NO: 115); GSSAGSEA-GGSGQAGVGS (SEQ ID NO: 116); GGSGGGGLEAE-GSGGGGS (SEQ ID NO: 117); GGSGGG-GIEPDPGGSGGS(SEQ ID NO: 118); TGGSGGGGIEPDIGGSGGS (SEQ ID NO: 148).

4. Antigen Binding Domains:

The multispecific polypeptide constructs of the present disclosure include at least one antigen binding domain, such as at least a first antigen binding domain and a second antigen binding domain. In some aspects, the antigen binding domain, or independently each of the antigen binding domains, is selected from an antibody or antigen binding fragment, a natural cognate binding partner, an Anticalin (engineered lipocalin), a Darpin, a Fynomer, a Centyrin (engineered fibroneticin III domain), a cystine-knot domain, an Affilin, an Affibody, or an engineered CH3 domain. In some embodiments, the natural cognate binding partner comprises an extracellular domain or binding fragment thereof of the native cognate binding partner of the TAA, or a variant thereof that exhibits binding activity to the TAA.

In some embodiments, a TAA is a counter-structure that is present primarily on tumor cells of a mammalian subject but generally not found on normal cells of the mammalian subject. A tumor specific antigen need not be exclusive to tumor cells but the percentage of cells of a particular mammal that have the tumor associated antigen is sufficiently high or the levels of the tumor associated antigen on the surface of the tumor are sufficiently high such that it can be targeted by anti-tumor therapeutics, such as multispecific polypeptide constructs as provided, and provide prevention or treatment of the mammal from the effects of the tumor. In some embodiments, in a random statistical sample of cells from a mammal with a tumor, at least 50% of the cells displaying a TAA are cancerous. In other embodiments, at least 60%, 70%, 80%, 85%, 90%, 95%, or 99% of the cells displaying a TAA are cancerous.

In some embodiments, the antigen binding domain, or independently each of the antigen binding domains, such as the first antigen-binding domain and the second antigen binding domains, includes one or more copies of an antibody or an antigen-binding fragment thereof. In some embodiments, the antigen binding domain, or independently each of the antigen binding domains, includes one or more copies of an antibody or an antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some embodiments, the antigen binding domain, or independently each of the antigen binding domains, such as the first antigen-binding domain and the second antigen binding domains, is a single chain antibody. In some examples, the single chain is an scFv, a scAb, a single domain heavy chain antibody, or a single domain light chain antibody. In some embodiments, each of the first antigen-binding domain and the second antigen binding domains includes one or more single domain antibody (sdAb) fragments, for example $V_H H$, $V_{NAR}$, engineered $V_H$ or $V_K$ domains. $V_H Hs$ can be generated from natural camelid heavy chain only antibodies, genetically modified rodents that produce heavy chain only antibodies, or naïve/synthetic camelid or humanized camelid single domain antibody libraries. $V_{NARS}$ can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the antigen binding domain or independently each of the antigen binding domains, such as the first antigen-binding domain and/or the second antigen binding domains, of the multispecific polypeptide constructs contains at least one sdAb or an scFv that binds a TAA. In some embodiments, the at least one scFv or sdAb that binds a TAA is positioned amino-terminally relative to the Fc region and/or carboxy-terminally relative to the CD3 binding region of the multispecific polypeptide construct. In some embodiments, the multispecific polypeptide construct contains only one scFv or sdAb that binds to a TAA, which can be positioned either amino-terminally relative to the Fc region and/or carboxy-terminally relative to the CD3 binding region. In some embodiments, the multispecific polypeptide construct contains two scFvs or sdAbs that bind to a TAA, positioned amino-terminally relative to the Fc region and/or carboxy-terminally relative to the CD3 binding region. In some embodiments, the multispecific polypeptide construct contains three scFv or sdAb, in which two are positioned amino-terminally relative to the Fc region or carboxy-terminally relative to the CD3 binding region, and the third is positioned at the other end of the multispecific polypeptide construct.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to a tumor-associated antigen; and a second polypeptide comprising a second Fc polypeptide of the heterodimeric Fc region, the linker, a VL domain of the anti-CD3 antibody or antigen binding fragment (e.g. Fv) and, optionally, the same or different scFv or sdAb that binds to a tumor-associated antigen. The scFv or sdAb that binds to a TAA can be positioned amino terminally relative to an Fc polypeptide of the heterodimeric Fc and/or carboxy-terminally relative to a VH or VL chain of the CD3 binding region. In some embodiments, the antigen binding domain, or independently each of the antigen binding domains, of the multispecific polypeptide constructs contains VH and VL sequences assembled as FABs or scFvs. In some embodiments, the antigen binding domain, or independently each of the antigen binding domains, of the multispecific polypeptide constructs contains binding domains as single domain antibodies (sdAbs).

In some embodiments, the antigen binding domain or independently each of the antigen binding domains, such as the first antigen-binding domain and the second antigen binding domains, contains more than one chain. In some embodiments, the antigen binding domain or independently each of the antigen binding domains, such as the first antigen-binding domain and/or the second antigen binding domains, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds a TAA. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) and VL-CL, that binds to a TAA, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to a TAA, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to a tumor-associated antigen; a second polypeptide comprising a second Fc polypeptide of the heterodimeric Fc region, the linker and, optionally, the same VH-CH1 (Fd) or VL-CL of the Fab antibody fragment that binds to a tumor-associated antigen, and a third polypeptide comprising the other of the VH-CH1 (Fd) or VL-CL of the Fab antibody fragment that binds to the TAA.

In some embodiments, the antigen binding domain, or independently each of the antigen binding domains, is or includes an extracellular domain or binding fragment thereof of the native cognate binding partner of the TAA, or a variant thereof that exhibits binding activity to the TAA.

In some embodiments, each of the antigen binding domains, such as each of the first antigen-binding domain and the second antigen binding domains, bind the same antigen. In some embodiments, each of the first antigen-binding domain and the second antigen binding domains bind a different antigen. In some embodiments, each of the antigen binding domains, such as each of the first antigen-binding domain and the second antigen binding domains, bind the same tumor associated antigen (TAA). In some embodiments, each of the antigen binding domains, such as each of the first antigen-binding domain and the second antigen binding domains, bind a different TAA. In some embodiments, each of the antigen binding domains, such as each of the first antigen-binding domain and the second antigen binding domains, bind a different epitope on the same TAA. In some embodiments, each of the antigen binding domains, such as each of the first antigen-binding domain and the second antigen binding domains, bind the same epitope on the same TAA.

In some embodiments, the antigen binding domains results in monovalent, bivalent, trivalent, or tetravalent binding to the TAA. In some embodiments, bivalent binding to the TAA comprises two antigen binding domains that bind the same epitope of the same antigen (e.g. mono-epitopic). In some embodiments, bivalent binding to the TAA comprises two antigen binding domains that bind different epitopes of the same antigen (e.g. bi-epitopic). In some embodiments, monovalent binding to the TAA comprises one antigen binding domain that binds one epitope of the antigen (e.g. mono-epitopic).

In some embodiments, the TAA is selected from the group consisting of 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, at least one antigen binding domain, or independently each antigen binding domain, binds the tumor associated antigen (TAA) folate receptor alpha (FRα). For example, the antigen binding domain contains the binding domain as an sdAb that binds FRα. Exemplary FRα-binding sdAbs are set forth in SEQ ID NOS: 120, 121, and 122.

In some embodiments, at least one antigen binding domain, or independently each antigen binding domain, binds the tumor associated antigen (TAA) cMET. For example, the antigen binding domain contains the binding domain as a sdAb that binds cMET. An exemplary cMET-binding sdAb is set forth in SEQ ID NO: 123 (U.S. Pat. No. 9,346,884).

In some embodiments, at least one antigen binding domain, or independently each antigen binding domain, binds the tumor associated antigen (TAA) B7H3. For example, the antigen binding domain contains the binding domain as an scFv that binds B7H3. An exemplary B7H3-binding scFv is set forth in SEQ ID NO: 124. In some embodiments, the antigen binding domain is a sdAb, such as a VHH. Exemplary B7H3-binding sdAbs are set forth in any of SEQ ID NOS: 214-218. In some embodiments, the antigen binding domain is or contains a Fab antibody fragment comprising a VH-CH1 (Fd) and LC. An exemplary B7H3 Fd is set forth in SEQ ID NO: 127 and an exemplary B7H3 LC is set forth in SEQ ID NO: 128 (PCT Publication No, WO2017/030926).

In some embodiments, at least one antigen binding domain, or independently each antigen binding domain, binds the tumor associated antigen (TAA) CD20. In some embodiments, such an antigen-binding domain contains a VH set forth in SEQ ID NO: 189 and a VL set forth in SEQ ID NO: 190 or a sequence that exhibits at least at or about 85%, 90%, 95%, 96%, 97%, 98%, 98%, or 99% sequence identity to SEQ ID NO: 189 or SEQ ID NO:190. For example, the antigen binding domain contains the binding domain as an scFv that binds CD20. Exemplary CD20-binding scFvs are set forth in SEQ ID NO: 125 and 213 (U.S. Pub. No. US 2005/0123546).

In some embodiments, at least one antigen binding domain, or independently each antigen binding domain, binds the tumor associated antigen (TAA) DLL3. For example, the antigen binding domain contains the binding domain as an scFv that binds DLL3. Exemplary DLL3-binding scFv is set forth in SEQ ID NO: 126 and 188 (U.S. Pub. No. US 2017/0037130). In some embodiments, the antigen binding domain is a sdAb, such as a VHH. Exemplary DLL3-binding sdAbs are set forth in any of SEQ ID NO: 219 or SEQ ID NO:220. In some embodiments, the antigen binding domain is or contains a Fab antibody fragment comprising a Fd and LC that binds DLL3. An exemplary DLL3 Fd is set forth in SEQ ID NO: 133 and an exemplary DLL3 LC is set forth in SEQ ID NO: 134 (U.S. Pat. No. 8,044,178).

In some embodiments, at least one antigen binding domain, or independently each antigen binding domain, binds the tumor associated antigen (TAA) 5T4. An exemplary 5T4 Fd is set forth in SEQ ID NO: 129 and an exemplary 5T4 LC is set forth in SEQ ID NO: 130. In some embodiments, the antibody binding domain comprises a VH-CH1 (Fd) or VL-CL as set forth in SEQ ID NOS: 167 and 168 (U.S. Pat. No. 8,044,178).

In some embodiments, at least one antigen binding domain, or independently each antigen binding domain, binds the tumor associated antigen (TAA) gpNMB. In some embodiments, the antigen binding domain is or contains a Fab fragment comprising a Fd and LC chain. An exemplary gpNMB Fd is set forth in SEQ ID NO: 131 and an exemplary gpNMB LC is set forth in SEQ ID NO: 132.

In some embodiments, the antigen binding domain is linked, directly or indirectly via a linker, to the Fc region and/or to the CD3 binding region. In some embodiments, linkage is via a linker. In some embodiments, the linker is a linking peptide (LP), which can include any flexible or rigid linker as described in Section 11.3, although generally peptides linking the antigen binding domain or domains is not a cleavable liker.

In some embodiments, the multispecific polypeptide construct comprises a first linking peptide (LP1) between the first antigen binding domain and the Fc region. In some embodiments, the multispecific polypeptide construct comprises a second linking peptide (LP2) between the CD3 binding region and the second antigen binding domain. In some embodiments, the multispecific polypeptide construct comprises a first linking peptide (LP1) between the first antigen binding domain and the Fc region and a second linking peptide (LP2) between the CD3 binding region and the second antigen binding domain. In some aspects, the multispecific polypeptide construct has the structural arrangement from N-terminus to C-terminus as follows: first antigen binding domain-LP1-Fc region-linker-CD3 binding region-LP2-second antigen binding domain. In some embodiments, the two linking peptides are not identical to each other.

In some embodiments, the LP1 or LP2 is independently a peptide of about 1 to 20 amino acids in length. In some embodiments, the LP1 or LP2 is independently a peptide that is or comprises any Gly-Ser linker as set forth in SEQ ID NOs: 10-13, 119, 135, 147, 149 or GGS.

III. Pharmaceutical Composition

Provided herein are compositions of any of the provided multispecific polypeptide constructs. It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed., Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol.

32(2):210-8 (2000), Wang W. "Lyophilization and development of solid protein pharmaceuticals." Int. J. Pharm. 203 (1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In some embodiments, the multispecific polypeptide constructs, conjugated multispecific polypeptide constructs, and compositions thereof—referred to collectively herein as the Therapeutic(s) and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the multispecific polypeptide construct or a conjugated thereof and a pharmaceutically acceptable carrier. Where a multispecific polypeptide construct includes a fragment of an antibody, the smallest fragment of the antibody that specifically binds to the target protein can be used. For example, based upon the variable-region sequences of an antibody, peptide molecules can be designed that retain the ability of the antibody to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL' (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, or intraspinally.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the multispecific polypeptide construct are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the Therapeutics are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the Therapeutics can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

In some embodiments, the pharmaceutical composition comprises a pharmaceutically-acceptable excipient, for example a filler, binder, coating, preservative, lubricant, flavoring agent, sweetening agent, coloring agent, a solvent, a buffering agent, a chelating agent, or stabilizer. Examples of pharmaceutically-acceptable fillers include cellulose, dibasic calcium phosphate, calcium carbonate, microcrystalline cellulose, sucrose, lactose, glucose, mannitol, sorbitol, maltol, pregelatinized starch, corn starch, or potato starch. Examples of pharmaceutically-acceptable binders include polyvinylpyrrolidone, starch, lactose, xylitol, sorbitol, maltitol, gelatin, sucrose, polyethylene glycol, methyl cellulose, or cellulose. Examples of pharmaceutically-acceptable coatings include hydroxypropyl methylcellulose (HPMC), shellac, corn protein zein, or gelatin. Examples of pharmaceutically-acceptable disintegrants include polyvinylpyrrolidone, carboxymethyl cellulose, or sodium starch glycolate. Examples of pharmaceutically-acceptable lubricants include polyethylene glycol, magnesium stearate, or stearic acid. Examples of pharmaceutically-acceptable preservatives include methyl parabens, ethyl parabens, propyl paraben, benzoic acid, or sorbic acid. Examples of pharmaceutically-acceptable sweetening agents include sucrose, saccharine, aspartame, or sorbitol. Examples of pharmaceutically-acceptable buffering agents include carbonates, citrates, gluconates, acetates, phosphates, or tartrates.

Sustained-release preparations can be prepared. Suitable examples of sustained-release preparations include semipermeable matrices of solid hydrophobic polymers containing the antibody, which matrices are in the form of shaped articles, e.g., films, or microcapsules. In some embodiments, the pharmaceutical composition further comprises an agent for the controlled or sustained release of the product, such as injectable microspheres, bio-erodible particles, polymeric compounds (polylactic acid, polyglycolic acid), beads, or liposomes. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Further provided are kits comprising the pharmaceutical compositions (or articles of manufacture) described herein. The pharmaceutical compositions can be included in a container, pack, or dispenser together with instructions for administration. The kits described herein may also include other materials desirable from a commercial and user standpoint, including other buffers, diluents, filters, needles, syringes, and package inserts with instructions for performing any methods described herein.

The formulation can also contain more than one multispecific polypeptide construct as necessary for the particular indication being treated, for example, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2 or more, about 3 or more, about 4 or more, about 5 or more, about 6 or more, or about 7 or more) doses are given in a week. In some embodiments, multiple doses are given over the course of days, weeks, months, or years. In some embodiments, a course of treatment is about 1 or more doses (such as about 2 or more does, about 3 or more doses, about 4 or more doses, about 5 or more doses, about 7 or more doses, about 10 or more doses, about 15 or more doses, about 25 or more doses, about 40 or more doses, about 50 or more doses, or about 100 or more doses).

In some embodiments, the pharmaceutical composition is administered to a subject. Generally, dosages and routes of administration of the pharmaceutical composition are determined according to the size and condition of the subject, according to standard pharmaceutical practice. For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. The optimal dosage and treatment regime for a particular patient can readily be determined by one skilled in the art of medicine by monitoring the patient for signs of disease and adjusting the treatment accordingly.

IV. Methods of Use and Therapeutic Administration

Also provided are methods for using and uses of the multispecific polypeptide constructs. Such methods and uses include therapeutic methods and uses, for example, involving administration of the molecules or compositions containing the same, to a subject having a disease, condition, or disorder, such as a tumor or cancer. In some embodiments, the molecule and/or composition is administered in an effective amount to effect treatment of the disease or disorder. Uses include uses of the multispecific polypeptide constructs in such methods and treatments, and in the preparation of a medicament in order to carry out such therapeutic methods. In some embodiments, the methods are carried out by administering the multispecific polypeptide constructs, or compositions comprising the same, to the subject having or suspected of having the disease or condition. In some embodiments, the methods thereby treat the disease or condition or disorder in the subject.

In one embodiment, a multispecific polypeptide construct of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. A multispecific polypeptide construct is administered to the subject. A multispecific polypeptide construct is administered to the subject and will generally have an effect due to its binding with the target(s).

In some embodiments, provided herein is a method of modulating an immune response in a subject by administering a therapeutically effective amount of any of the provided multispecific conjugates or pharmaceutical compositions. In some embodiments, the method of modulating an immune response increases or enhances an immune response in a subject. For example, the increase or enhanced response may be an increase in cell-mediated immunity. In some examples, the method increases T-cell activity, such as cytolytic T-cell (CTL) activity. In some embodiments, the modulated (e.g., increased) immune response is against a tumor or cancer.

Administration of the multispecific polypeptide construct may activate innate immune cells via engagement of FcγRs through the Fc-region of the multispecific polypeptide construct. Administration of the multispecific polypeptide construct may agonize, stimulate, activate, and/or augment innate immune cell effector functions, including ADCC, cytokine release, degranulation and/or ADCP. In examples where a multispecific polypeptide construct contains a cleavable linker, administration of the multispecific polypeptide construct may activate T-cell once the linker(s) joining the first and second component is cleaved by a protease thereby allowing the anti-CD3 binding portion to bind CD3ε on the T cells. Administration of the multispecific polypeptide construct may agonize, stimulate, activate, and/or augment CD3-mediated T cell activation, cytotoxicity, cytokine release and/or proliferation.

In some embodiments, the provided methods are for treating a disease or condition in a subject by administering a therapeutically effective amount of any of the provided multispecific conjugates or pharmaceutical compositions. In some embodiments, the disease or condition is a tumor or a cancer. Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

In some embodiments, the pharmaceutical composition can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

A therapeutically effective amount of a multispecific polypeptide construct of the disclosure relates generally to the amount needed to achieve a therapeutic objective. As noted above, this may be a binding interaction between the multispecific polypeptide construct and its target antigen(s) that, in certain cases, agonize, stimulate, activate, and/or augment FcγR-mediated innate immune cell activation or CD3-mediated T cell activation. The amount required to be administered will furthermore depend on the binding affinity of the multispecific polypeptide construct for its specific antigen(s), and will also depend on the rate at which an administered multispecific polypeptide construct is depleted from the free volume other subject to which it is administered. Common ranges for therapeutically effective dosing of a multispecific polypeptide construct may be, by way of nonlimiting example, from about 0.01 µg/kg body weight to about 10 mg/kg body weight. In some embodiments, the therapeutically effective dosing of a multispecific polypeptide construct of the disclosure may be, by way of nonlimiting example, from about 0.01 mg/kg body weight to about 5-10 mg/kg body weight. Common dosing frequencies may range, for example, from twice daily to once a week.

Efficaciousness of treatment is determined in association with any known method for diagnosing or treating the particular disorder. Methods for the screening of multispecific polypeptide construct that possess the desired specificity include, but are not limited to, enzyme linked immunosorbent assay (ELISA) and other immunologically mediated techniques known within the art. A variety of means are known for determining if administration of the provided multispecific polypeptide constructs sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity.

The multispecific polypeptide construct are also useful in a variety of diagnostic and prophylactic formulations. In one embodiment, a multispecific polypeptide construct is administered to patients that are at risk of developing one or more of the aforementioned disorders. A patient's or organ's predisposition to one or more of the disorders can be determined using genotypic, serological or biochemical markers.

In another embodiment of the disclosure, a multispecific polypeptide construct is administered to human individuals diagnosed with a clinical indication associated with one or more of the aforementioned disorders. Upon diagnosis, a multispecific polypeptide construct is administered to mitigate or reverse the effects of the clinical indication.

Combination Therapies

In some embodiments, the multispecific polypeptide constructs, conjugated multispecific polypeptide constructs, and compositions thereof—referred to collectively herein as the Therapeutic(s)—are administered in conjunction with one or more additional agents, or a combination of additional agents. Suitable additional agents include current pharmaceutical and/or surgical therapies for an intended application. For example, the Therapeutic(s) can be used in conjunction with an additional chemotherapeutic or antineoplastic agent. For example, the Therapeutic(s) and additional agent are formulated into a single therapeutic composition, and the Therapeutic(s) and additional agent are administered simultaneously. In some embodiments, the Therapeutic(s) and additional agent are separate from each other, e.g., each is formulated into a separate therapeutic composition, and the Therapeutic(s) and the additional agent are administered simultaneously, or the Therapeutic(s) and the additional agent are administered at different times during a treatment regimen. For example, the Therapeutic(s) is administered prior to the administration of the additional agent, the Therapeutic(s) is administered subsequent to the administration of the additional agent, or the Therapeutic(s) and the additional agent are administered in an alternating fashion. As described herein, the Therapeutic(s) and additional agent are administered in single doses or in multiple doses. In some embodiments, the additional agent is coupled or otherwise attached to the Therapeutic(s). Suitable additional agents are selected according to the purpose of the intended application (i.e., killing, prevention of cell proliferation, hormone therapy or gene therapy). Such agents may include but is not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radiopaque dyes, radioactive isotopes, fluorogenic compounds, magnetic labels, nanoparticles, marker compounds, lectins, compounds that alter cell membrane permeability, photochemical compounds, small molecules, liposomes, micelles, gene therapy vectors, viral vectors, and the like. Finally, combinations of agents or combinations of different classes of agents may be used.

In one embodiment, the multispecific polypeptide constructs are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is still detectable at effective concentrations at the site of treatment.

For example, the combination therapy can include one or more multispecific polypeptide constructs of the disclosure co-formulated with, and/or co-administered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more multispecific polypeptide constructs described herein may be used in combination with two or more of the therapeutic agents described herein. Such combination therapies may advantageously utilize lower dosages of the administered therapeutic agents, thus avoiding possible toxicities or complications associated with the various monotherapies.

In other embodiments, one or more multispecific polypeptide constructs of the disclosure can be co-formulated with, and/or co-administered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl) methyl] methylamino] benzoyl]-L-glutamic acid); and inhibitors of pyrimidine biosynthesis, e.g., dihydroorotate dehydrogenase (DHODH) inhibitors. Suitable therapeutic agents for use in combination with the antibodies of the disclosure include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppressants, e.g., cyclosporin, tacrolimus (FK-506); and mTOR inhibitors, e.g., sirolimus (rapamycin—RAPAMUNE™ or rapamycin derivatives, e.g., soluble rapamycin derivatives (e.g., ester rapamycin derivatives, e.g., CCI-779); agents that interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Suitable therapeutic agents for use in combination with the antibodies of the disclosure are immunosuppressants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs. Additional examples of therapeutic agents that can be combined with a multispecific polypeptide construct include one or more of: 6-mercaptopurines (6-MP); azathioprine sulphasalazine; mesalazine; olsalazine; chloroquine/hydroxychloroquine (PLAQUENIL); pencillamine; aurothiornalate (intramuscular and oral); azathioprine; coichicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

V. Exemplary Embodiments

Among the provided embodiments are:
1. A multispecific polypeptide construct, the multispecific polypeptide construct comprising a first component comprising an immunoglobulin Fc region and a second component comprising a CD3-binding region, wherein:
the first and second components are coupled by a non-cleavable linker, wherein the Fc region is positioned N-terminal to the CD3-binding region; and one or both of the first and second components comprises an antigen binding domain that binds a tumor associated antigen (TAA).
2. The multispecific polypeptide construct of embodiment 1, wherein the CD3-binding region binds CD3 (CD3ε).
3. The multispecific construct of embodiment 1 or embodiment 2, wherein the antigen binding domain is positioned amino-terminally relative to the Fc region and/or carboxy-terminally relative to the CD3 binding region of the multispecific polypeptide construct.
4. The multispecific polypeptide construct of any of embodiments 1-3, wherein the first component comprises a first antigen binding domain and the second component comprises a second antigen binding domain, wherein each of the antigen binding domains bind a tumor associated antigen (TAA).
5. The multispecific polypeptide construct of embodiment 4, wherein the first antigen binding domain is positioned amino-terminally relative to the Fc region of the multispecific construct and the second antigen binding domain is positioned carboxy-terminally relative to the CD3 binding region of the multispecific construct.
6. A multispecific polypeptide construct, wherein the multispecific construct comprises in order, from N-terminus to C-terminus:
a first antigen binding domain that binds to a tumor-associated antigen (TAA);
an immunoglobulin Fc region;
a non-cleavable linker;
a CD3 binding region that binds CD3 (CD3ε); and
a second antigen binding domain that binds a tumor-associated antigen (TAA).
7. A multispecific polypeptide construct, wherein the multispecific construct comprises in order, from N-terminus to C-terminus:
an immunoglobulin Fc region;
a non-cleavable linker;
a CD3 binding region that binds CD3 (CD3ε); and
an antigen binding domain that binds a tumor-associated antigen (TAA).
8. A multispecific polypeptide construct, wherein the multispecific construct comprises in order, from N-terminus to C-terminus:
an antigen binding domain that binds to a tumor-associated antigen (TAA);
an immunoglobulin Fc region;
a non-cleavable linker; and
a CD3 binding region that binds CD3 (CD3ε).
9. The multispecific polypeptide construct of any of embodiments 1-8, wherein the Fc region is a homodimeric Fc region.
10. The multispecific polypeptide construct of any of embodiments 1-9, wherein the Fc region is an Fc region of a human IgG1, a human IgG2, a human IgG3, or a human IgG4, or is an immunologically active fragment thereof.
11. The multispecific polypeptide construct of any of embodiments 1-10, wherein the Fc region comprises a polypeptide comprises the amino acid sequence set forth in SEQ ID NO: 1 or a sequence of amino acids that has at least 90%, 91%, 92%, 93%, 94%, 95%, 96%, 97%, 98%, 99% sequence identity to SEQ ID NO:1.
12. The multispecific polypeptide construct of any of embodiments 1-10, wherein the Fc region comprises a polypeptide comprises the amino acid sequence set forth in SEQ ID NO: 2 or a sequence of amino acids that has at least 90%, 91%, 92%, 93%, 94%, 95%, 96%, 97%, 98%, 99% sequence identity to SEQ ID NO:2;
the Fc region comprises a polypeptide comprises the amino acid sequence set forth in SEQ ID NO: 4 or a sequence of amino acids that has at least 90%, 91%, 92%, 93%, 94%, 95%, 96%, 97%, 98%, 99% sequence identity to SEQ ID NO:4; or
the Fc region comprises a polypeptide comprises the amino acid sequence set forth in SEQ ID NO: 5 or a sequence of amino acids that has at least 90%, 91%, 92%, 93%, 94%, 95%, 96%, 97%, 98%, 99% sequence identity to SEQ ID NO:5.
13. The multispecific polypeptide construct of any of embodiments 1-6, 9 and 12, wherein the Fc region is a heterodimeric Fc region.
14. The multispecific polypeptide construct of embodiment 13, wherein one or both Fc polypeptides of the heterodimeric Fc region comprises at least one modification to induce heterodimerization compared to a polypeptide of a homodimeric Fc region, optionally compared to the Fc polypeptide set forth in SEQ ID NO:1 or an immunologically active fragment thereof.
15. The multispecific polypeptide construct of embodiment 14, wherein each of the Fc polypeptides of the heterodimeric Fc independently comprise at least one amino acid modification.
16. The multispecific polypeptide construct of embodiment 15, wherein each of the Fc polypeptides of the heterodimeric Fc comprise a knob-into-hole modification or comprise a charge mutation to increase electrostatic complementarity of the polypeptides.
17. The multispecific polypeptide construct of embodiment 16, wherein the amino acid modification is a knob-into-hole modification.
18. The multispecific polypeptide construct of any of embodiments 13-17, wherein the first Fc polypeptide of the heterodimeric Fc comprises the modification selected from among Thr366Ser, Leu368Ala, Tyr407Val, and combinations thereof and the second Fc polypeptide of the heterodimeric Fc comprises the modification T366W.
19. The multispecific polypeptide construct of embodiment 18, wherein the first and second Fc polypeptides further comprises a modification of a non-cysteine residue to a cysteine residue, wherein the modification of the first polypeptide is at one of the position Ser354 and Y349 and the modification of the second Fc polypeptide is at the other of the position Ser354 and Y349.
20. The multispecific polypeptide construct of embodiment 16, wherein the amino acid modification is a charge mutation to increase electrostatic complementarity of the polypeptides.
21. The multispecific polypeptide construct of any of embodiments 13-16 and 20, wherein the first and/or second Fc polypeptides or each of the first and second Fc polypeptide comprise a modification in complementary positions, wherein the modification is replacement with an amino acid having an opposite charge to the complementary amino acid of the other polypeptide.
22. The multispecific polypeptide construct of any of embodiments 14-21, wherein one of the first or second Fc polypeptide of the heterodimeric Fc further comprises a modification at residue Ile253.
23. The multispecific polypeptide construct of embodiment 22, wherein the modification is Ile253Arg.
24. The multispecific polypeptide construct of any of embodiments 14-23, wherein one of the first or second Fc polypeptide of the heterodimeric Fc further comprises a modification at residue His435.

25. The multispecific polypeptide construct of embodiment 24, wherein the modification is His435Arg.
26. The multispecific polypeptide construct of any of embodiments 1-25, wherein the Fc region comprises a polypeptide that lacks Lys447.
27. The multispecific polypeptide construct of any of embodiments 1-26, wherein the Fc region comprises a polypeptide comprising at least one modification to enhance FcRn binding.
28. The multispecific polypeptide construct of embodiment 27, wherein the modification is at a position selected from the group consisting of Met252, Ser254, Thr256, Met428, Asn434, and combinations thereof
29. The multispecific polypeptide construct of embodiment 28, wherein the modification is at a position selected from the group consisting of Met252Y, Ser254T, Thr256E, Met428L, Met428V, Asn434S, and combinations thereof
30. The multispecific polypeptide construct of embodiment 28, wherein the modification is at position Met252 and at position Met428.
31. The multispecific polypeptide construct of embodiment 30, wherein the modification is Met252Y and Met428L.
32. The multispecific polypeptide construct of embodiment 30, wherein the modification is Met252Y and Met428V.
33. The multispecific polypeptide construct of any of embodiments 13-32, wherein the first polypeptide of the heterodimeric Fc comprises the sequence of amino acids set forth in any of SEQ ID NOS:82, 86, 94 or 96, and the second polypeptide of the heterodimeric Fc comprises the sequence of amino acids set forth in any of SEQ ID NOS:83, 87, 90, 92, 98 or 100.
34. The multispecific polypeptide construct of any of embodiments 1-33, wherein the Fc region comprises a polypeptide comprising at least one amino acid modification that reduces effector function and/or reduces binding to an effector molecule selected from an Fc gamma receptor or C1q.
35. The multispecific polypeptide construct of embodiment 34, wherein the one or more amino acid modification is deletion of one or more of Glu233, Leu234 or Leu235.
36. The multispecific polypeptide construct of any of embodiments 13-32, 34 and 35, wherein the first polypeptide of the heterodimeric Fc comprises the sequence of amino acids set forth in any of SEQ ID NOS: 84, 88, 95 or 97 and the second polypeptide of the heterodimeric Fc comprises the sequence of amino acids set forth in any of SEQ ID NOS: 85, 89, 91, 93, 99 or 101.
37. The multispecific polypeptide construct of any of embodiments 1-32, wherein the Fc region comprises a polypeptide comprising at least one modification to enhance FcγR binding.
38. The multispecific polypeptide construct of embodiment 37, wherein the modification is modification at Ser239 or Ile332.
39. The multispecific polypeptide construct of any of embodiments 1-32 and 37, wherein the glycosylation of the Fc region is modified to enhance Fc☐R binding as compared to an unmodified Fc region.
40. The multispecific polypeptide construct of embodiment 39, wherein the Fc region lacks or has reduced fucose content.
41. The multispecific polypeptide construct of any of embodiments 1-40, wherein the CD3 binding region is an anti-CD3 antibody or antigen-binding fragment.
42. The multispecific polypeptide construct of embodiment 41, wherein the anti-CD3 antibody or antigen binding fragment comprises a variable heavy chain region (VH) and a variable light chain region (VL).
43. The multispecific polypeptide construct of any of embodiments 1-42, wherein the CD3 binding region is monovalent.
44. The multispecific polypeptide construct of any of embodiments 41-43, wherein the anti-CD3 antibody or antigen binding fragment is not a single chain antibody, optionally is not a single chain variable fragment (scFv).
45. The multispecific polypeptide construct of embodiment 42 or embodiment 44, wherein the Fc is a heterodimeric Fc and the VH and VL that comprise the anti-CD3 antibody or antigen binding fragment are linked to opposite polypeptides of the heterodimeric Fc.
46. The multispecific polypeptide construct of any of embodiments 1-45, wherein the CD3 binding region is not able to, or is not substantially able to, bind or engage CD3 unless at least one of the antigen binding domain is bound to its TAA.
47. The multispecific polypeptide construct of any of embodiments 1-46, wherein the CD3 binding region is not able to, or is not substantially able, to bind or engage CD3 unless at least two of the antigen binding domain is bound to its TAA.
48. The multispecific polypeptide construct of any of embodiments 1-47, wherein the linker is a polypeptide linker.
49. The multispecific polypeptide construct of embodiment 48, wherein the linker is a polypeptide of up to 25 amino acids in length.
50. The multispecific polypeptide construct of embodiment 48 or embodiment 49, wherein the linker is a polypeptide of from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids.
51. The multispecific polypeptide construct of any of embodiments 48-50, wherein the linker is a polypeptide that is 3, 4, 5, 6, 7, 8, 9, 10, 11, 12, 13, 14, 15, 16, 17, 18, 19 or 20 amino acids in length.
52. The multispecific polypeptide construct of any of embodiments 48-51, wherein the linker is a polypeptide that is 3 to 18 amino acids in length.
53. The multispecific polypeptide construct of any of embodiments 48-51, wherein the linker is a polypeptide that is 12 to 18 amino acids in length.
54. The multispecific polypeptide construction of any of embodiments 48-51, wherein the linker is a polypeptide that is 15 to 18 amino acids in length.

55. A multispecific polypeptide construct, the multispecific polypeptide construct comprising a first component comprising a heterodimeric Fc region and a second component comprising an anti-CD3 antibody or antigen-binding fragment comprising a variable heavy chain region (VH) and a variable light chain region (VL), wherein:
the VH and VL that comprise the anti-CD3 antibody or antigen binding fragment are linked to opposite polypeptides of the heterodimeric Fc;
the first and second components are coupled by a non-cleavable linker, wherein the heterodimeric Fc region is positioned N-terminal to the anti-CD3 antibody; and
one or both of the first and second components comprises an antigen binding domain that binds a tumor associated antigen (TAA).

56. The multispecific polypeptide construct of any of embodiments 52-55, wherein the non-cleavable linker does not contain a substrate recognition site that is specifically recognized for cleavage by a protease.

57. The multispecific polypeptide construct of embodiment 56, wherein the protease is produced by an immune effector cell, by a tumor, or by cells present in the tumor microenvironment.

58. The multispecific polypeptide construct of embodiment 57, wherein the protease is produced by an immune effector cell and the immune effector cell is an activated T cell, a natural killer (NK) cell, or an NK T cell.

59. The multispecific polypeptide construct of any of embodiments 56-58, wherein the protease is selected from among matriptase, a matrix metalloprotease (MMP), Granzyme B, and combinations thereof 60. The multispecific polypeptide construct of embodiment 59, wherein the protease is granzyme B.

61. The multispecific polypeptide construct of any of embodiments 1-60, wherein the non-cleavable linker comprises GS, GGS, GGGGS (SEQ ID NO:149), GGGGGS (SEQ ID NO:135) and combinations thereof 62. The multispecific polypeptide construct of any of embodiments 1-61, wherein the non-cleavable linker comprises (GGS)n, wherein n is 1 to 10.

63. The multispecific polypeptide construct of any of embodiments 1-62, wherein the non-cleavable linker comprises (GGGGS)n (SEQ ID NO: 173), wherein n is 1 to 10.

64. The multispecific polypeptide construct of any of embodiments 1-62, wherein the non-cleavable linker comprises (GGGGGS)n (SEQ ID NO:172), wherein n is 1 to 4.

65. The multispecific polypeptide construct of any of embodiments 1-64, wherein the non-cleavable linker comprises GGS.

66. The multispecific polypeptide construct of any of embodiments 1-64, wherein the non-cleavable linker comprises GGGGS (SEQ ID NO: 149).

67. The multispecific polypeptide construct of any of embodiments 1-64, wherein the non-cleavable linker comprises GGGGGS (SEQ ID NO: 135).

68. The multispecific polypeptide construct of any of embodiments 1-64, wherein the non-cleavable linker comprises (GGS)2 (SEQ ID NO: 10).

69. The multispecific polypeptide construct of any of embodiments 1-64, wherein the non-cleavable linker comprises GGSGGSGGS (SEQ ID NO: 11).

70. The multispecific polypeptide construct of any of embodiments 1-64, wherein the non-cleavable linker comprises GGSGGSGGSGGS (SEQ ID NO: 12).

71. The multispecific polypeptide construct of any of embodiments 1-64, wherein the non-cleavable linker comprises GGSGGSGGSGGSGGS (SEQ ID NO: 13).

72. The multispecific polypeptide construct of any of embodiments 1-64, wherein the non-cleavable linker comprises GGGGGSGGGGGSGGGGGS (SEQ ID NO: 119).

73. The multispecific polypeptide construct of any of embodiments 1-64, wherein the non-cleavable linker comprises GGSGGGGSGGGGSGGGGS (SEQ ID NO: 147)

74. The multispecific polypeptide construct of any of embodiments 1-64, wherein the non-cleavable linker comprises and GGGGSGGGGSGGGGS (SEQ ID NO:170).

75. The multispecific polypeptide construct of any of embodiments 45-74, wherein the multispecific polypeptide construct comprises at least (i) a first polypeptide comprising the first Fc polypeptide of the heterodimeric Fc region, the linker and the VH domain of the anti-CD3 antibody or antigen binding fragment; and (ii) a second polypeptide comprising the second Fc polypeptide of the heterodimeric Fc region, the linker and the VL domain of the anti-CD3 antibody or antigen binding fragment, wherein one or both of the first and second polypeptide comprise at least one antigen-binding domain that binds to a tumor associated antigen (TAA).

76. The multispecific polypeptide construct of any of embodiments 1-75, wherein one or more antigen binding domain that binds TAA results in monovalent, bivalent, trivalent, or tetravalent binding to the TAA.

77. The multispecific polypeptide construct of embodiment 75, wherein only one of the first or second polypeptide comprises the at least one antigen-binding domain that binds a TAA.

78. The multispecific polypeptide construct of embodiment 75 or embodiment 77, wherein the at least one antigen binding domain is positioned amino-terminally relative to the Fc region and/or is positioned carboxy-terminally relative to the CD3 binding region of one of the first or second polypeptide of the multispecific polypeptide construct.

79. The multispecific polypeptide construct of embodiment 75 or embodiment 77, wherein the at least one antigen binding domain is positioned amino-terminally relative to the Fc region of the multispecific construct and the second antigen binding domain is positioned carboxy-terminally relative to the CD3 binding region of the multispecific construct.

80. The multispecific polypeptide construct of any of embodiments 1-79, wherein the antigen binding domain, or independently each of the antigen binding domains, comprises an extracellular domain or binding fragment thereof of the native cognate binding partner of the TAA, or a variant thereof that exhibits binding activity to the TAA.

81. The multispecific polypeptide construct of any of embodiments 1-79, wherein the antigen binding domain, or independently each of the antigen binding domains, is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

82. The multispecific polypeptide construct of embodiment 81, wherein the antibody or antigen-binding fragment thereof is a Fv, a scFv, a Fab, a single domain antibody (sdAb), a VNAR, or a VHH.

83. The multispecific polypeptide construct of embodiment 81 or embodiment 82, wherein the antibody or antigen-binding fragment is an sdAb.

84. The multispecific polypeptide construct of embodiment 83, wherein the sdAb is a human or humanized sdAb.

85. The multispecific polypeptide construct of embodiment 83 or embodiment 84, wherein the sdAb is VHH, VNAR, an engineered VH domain or an engineered VK domain.

86. The multispecific polypeptide construct of embodiment 81 or embodiment 82, wherein the antibody or antigen-binding fragment thereof is an scFv.

87. The multispecific polypeptide construct of embodiment 81 or embodiment 82, wherein the antibody or antigen-binding fragment thereof is a Fab.

88. The multispecific polypeptide construct of embodiment 87, wherein the multispecific polypeptide construct comprises:
(i) a first polypeptide comprising the first Fc polypeptide of the heterodimeric Fc region, the linker and the VH domain of the anti-CD3 antibody or antigen binding fragment;
(ii) a second polypeptide comprising the second Fc polypeptide of the heterodimeric Fc region, the linker and the VL domain of the anti-CD3 antibody or antigen binding fragment, and
(iii) a third polypeptide comprising a VH-CH1 (Fd) or VL-CL of a Fab antibody fragment that binds to a tumor-associated antigen, wherein the first and/or second polypeptide further comprises the other of the VH-CH1 (Fd) or VL-CL of the Fab antibody fragment.

89. The multispecific polypeptide construct of embodiment 88, wherein only one of the first or second polypeptide comprises the other of the VH-CH1 (Fd) or VL-CL of the Fab antibody fragment.

90. The multispecific polypeptide construct of embodiment 89, wherein both the first or second polypeptide comprises the other of the VH-CH1 (Fd) or VL-CL of the Fab antibody fragment.

91. The multispecific polypeptide construct of embodiment 89 or embodiment 90, wherein the other of the VH-CH1 (Fd) or VL-CL of the Fab antibody fragment is positioned amino-terminally relative to the Fc region and/or at the carboxy-terminally relative to the CD3 binding region of one of the first or second polypeptide of the multispecific polypeptide construct.

92. The multispecific polypeptide construct of any of embodiments 89-91, wherein the other of the VH-CH1 (Fd) or VL-CL of the Fab antibody fragment is positioned amino-terminally relative to the Fc region of the first polypeptide or second polypeptide and at the carboxy-terminally relative to the CD3 binding region of the other of the first or second polypeptide.

93. The multispecific polypeptide construct of any of embodiments 1-92, wherein the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

94. The multispecific polypeptide construct of any of embodiments 1-93, wherein multispecific antigen binding domain comprises at least a first antigen binding domain and a second antigen binding domain, wherein the first antigen binding domain and second antigen binding domain bind to the same TAA.

95. The multispecific polypeptide construct of embodiment 94, wherein the first antigen binding domain and the second antigen binding domain binds a different epitope of the same TAA.

96. The multispecific polypeptide construct of embodiment 94, wherein the first antigen binding domain and the second antigen binding domain binds the same epitope of the same TAA.

97. The multispecific polypeptide construct of any of embodiments 1-96, wherein multispecific antigen binding domain comprises at least a first antigen binding domain and a second antigen binding domain wherein the first antigen binding domain and the second antigen binding domain bind a different TAA.

98. The multispecific polypeptide construct of any of embodiments 5-97, wherein the multispecific polypeptide construct comprises a first linking peptide (LP1) between the first antigen binding domain and the Fc region.

99. The multispecific polypeptide construct of any of embodiments 5-98, wherein the multispecific polypeptide construct comprises a second linking peptide (LP2) between the CD3 binding region and the second antigen binding domain.

100. The multispecific polypeptide construct of any of embodiments 5-99, wherein the multispecific polypeptide construct comprises a first linking peptide (LP1) between the first antigen binding domain and the Fc region and a second linking peptide (LP2) between the CD3 binding region and the second antigen binding domain, and wherein the multispecific polypeptide construct has the structural arrangement from N-terminus to C-terminus as follows: first antigen binding domain-LP1-Fc region-non-cleavable linker-CD3 binding region-LP2-second antigen binding domain.

101. The multispecific polypeptide construct of embodiment 100, wherein the two linking peptides are identical to each other.

102. The multispecific polypeptide construct of embodiment 100, wherein the two linking peptides are not identical to each other.

103. The multispecific polypeptide construct of any of embodiments 98-102, wherein LP1 or LP2 is independently a peptide of about 1 to 20 amino acids in length.

104. The multispecific polypeptide of embodiment 103, wherein LP1 or LP2 independently comprise a peptide that is or comprises any Gly-Ser linker as set forth in SEQ ID NOs: 10-13, 119, 135, 147, 149 or GGS.

105. The multispecific polypeptide construct of any of embodiments 41-104, wherein the anti-CD3 antibody or antigen binding fragment is an Fv antibody fragment.

106. The multispecific polypeptide construct of embodiment 105, wherein the Fv antibody fragment comprises a disulfide stabilized anti-CD3 binding Fv fragment (dsFv).

107. The multispecific polypeptide construct of any of embodiments 41-106, wherein:
the anti-CD3 antibody or antigen-binding fragment comprises a VH CDR1 comprising the amino acid sequence TYAMN (SEQ ID NO: 16) or SEQ ID NO:211; a VH CD2 comprising the amino acid sequence RIRSKYN-NYATYYADSVKD (SEQ ID NO: 17) or SEQ ID NO:212; a VH CDR3 comprising the amino acid sequence HGNFGNSYVSWFAY (SEQ ID NO: 18), a VL CDR1 comprising the amino acid sequence RSST-GAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21): or
the anti-CD3 antibody or antigen-binding fragment comprises a VH CDR1 sequence that includes at least the amino acid sequence GFTFNTYAMN (SEQ ID NO: 211); a VH CDR2 sequence that includes at least the amino acid sequence RIRSKYNNYATY (SEQ ID NO: 212); a VH CDR3 sequence that includes at least the amino acid sequence HGNFGNSYVSWFAY (SEQ ID NO: 18), a VL CDR1 sequence that includes at least the amino acid sequence GSSTGAVTTSNYAN (SEQ ID NO: 229); a VL CDR2 sequence that includes at least the amino acid sequence GTNKRAP RAP (SEQ ID NO: 230); and a VL CDR3 sequence that includes at least the amino acid sequence ALWYSNHWV (SEQ ID NO: 225).

108. The multispecific polypeptide construct of embodiment 106 or embodiment 107, wherein the anti-CD3 dsFv comprises:
a VH having the amino acid sequence of any of SEQ ID NOS: 14 and 32-62 or a sequence that exhibits at least 90%, 91%, 92%, 93%, 94%, 95%, 96%, 97%, 98% or 99% sequence identity to any of SEQ ID NOS: 14 and 32-62; and
a VL having the amino acid sequence of any of SEQ ID NOS: 15 and 63-81 or a sequence that exhibits at least 90%, 91%, 92%, 93%, 94%, 95%, 96%, 97%, 98% or 99% sequence identity to any of SEQ ID NOS: 14 and 32-62.

109. The multispecific polypeptide construct of any of embodiments 106-108, wherein the anti-CD3 dsFv comprises the amino acid sequence of SEQ ID NO: 14 and the amino acid sequence of SEQ ID NO: 15.

110. The multispecific polypeptide construct of any of embodiments 102-104, wherein the anti-CD3 dsFv comprises the amino acid sequence of SEQ ID NO: 44 and the amino acid sequence of SEQ ID NO: 72.

111. The multispecific polypeptide construct of any of embodiments 1-109, wherein the multispecific polypeptide construct is conjugated to an agent.

112. The multispecific polypeptide construct of embodiment 111, wherein the agent is a therapeutic agent, an antineoplastic agent, a toxin or fragment thereof, a detectable moiety or a diagnostic agent.

113. The multispecific polypeptide construct of embodiment 112, wherein the agent is conjugated to the multispecific polypeptide construct via a linker.

114. A polynucleotide(s) encoding the multispecific polypeptide constructs of any of embodiments 1-113.

115. A polynucleotide encoding a polypeptide chain of any of the multispecific polypeptide constructs of any of embodiments 1-113.

116. A polynucleotide, comprising a first nucleic acid sequence encoding a first polypeptide of a multispecific construct of any of embodiments 1-115 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

117. The polynucleotide of embodiment 116, wherein the first nucleic acid sequence and second nucleic acid sequence are operably linked to the same promoter.

118. The polynucleotide of embodiment 116 or embodiment 117, wherein the multispecific polypeptide construct comprises a third polypeptide chain, and the polynucleotide further comprises a third nucleic acid encoding the third polypeptide of the multispecific construct.

119. The polynucleotide of embodiment 118, wherein the third nucleic acid is separated from the first and/or second polypeptide by an internal ribosome entry site (IRES), or a nucleic acid encoding a self-cleaving peptide or a peptide that causes ribosome skipping and/or the third nucleic acid sequence is operably linked to the same promoter as the first and/or second nucleic acid sequence.

120. The polynucleotide of any of embodiments 116-119, wherein the nucleic acid encoding a self-cleaving peptide or a peptide that causes ribosome skipping is selected from a T2A, a P2A, a E2A or a F2A.
121. A vector, comprising the polynucleotide of any of embodiments 114-120.
122. The vector of embodiment 121 that is an expression vector.
123. The vector of embodiment 121 or 122 that is a viral vector or a eukaryotic vector, optionally wherein the eukaryotic vector is a mammalian vector.
124. A cell, comprising polynucleotide or polynucleotides of any of embodiments 114-120, or a vector or vectors of any of embodiments 121-123.
125. The cell of embodiment 124, wherein the cell is recombinant or isolated.
126. The cell of embodiment 125, wherein the cell is a mammalian cell.
127. The cell of embodiment 126, wherein the cell is a HEK293 or CHO cell.
128. A method of producing a multispecific polypeptide construct, the method comprising introducing into a cell a polynucleotide or polynucleotides of any of embodiments 114-120 or a vector or vectors of any of embodiments 121-123 and culturing the cell under conditions to produce the multispecific polypeptide construct.
129. A method of producing a multispecific polypeptide construct, the method comprising culturing the cell of any of embodiments 124-127 under conditions in which the multispecific polypeptide is produced by the cell.
130. The cell of embodiment 128 or 129, wherein the cell is a mammalian cell.
131. The cell of embodiment 130, wherein the cell is a HEK293 or CHO cell.
132. The method of embodiment 128 or embodiment 129, further comprising isolating or purifying the multispecific polypeptide construct from the cell.
133. The method of any of embodiments 128-132, wherein the multispecific polypeptide construct is a heterodimer.
134. A multispecific polypeptide construct produced by the method of any of embodiments 128-133.
135. A pharmaceutical composition comprising the multispecific polypeptide construct of any of embodiments 1-113 or embodiment 134 and a pharmaceutically acceptable carrier.
136. The pharmaceutical composition of embodiment 135 that is sterile.
137. A method of stimulating or inducing an immune response, the method comprising contacting a target cell and a T cell with the multispecific polypeptide construct of any of embodiments 1-113 or embodiment 134 or the pharmaceutical composition of embodiments 109 or embodiment 110, said target cell expressing a tumor associated antigen recognized by the multispecific polypeptide construct.
138. The method of embodiment 137, wherein the target cell is a tumor cell expressing the tumor associated antigen (TAA).
139. The method of embodiment 137 or embodiment 138, wherein the contacting is carried out ex vivo or in vitro.
140. The method of any of embodiments 137-149, wherein the contacting is carried out in vivo in a subject.
141. A method of stimulating or inducing an immune response in a subject, the method comprising administering, to a subject in need thereof, a therapeutically effective amount of the multispecific conjugate of any of embodiments 1-113 or embodiment 134 or the pharmaceutical composition of embodiments 109 or embodiment 110.
142. The method of any of embodiments 137-141, which increases cell-mediated immunity.
143. The method of any of embodiments 137-142, which increases T-cell activity.
144. The method of any of embodiments 137-143, which increases cytolytic T-cell (CTL) activity.
145. The method of any of embodiments 137-144, wherein the immune response is increased against a tumor or cancer.
146. The method of any of embodiments 137-145, wherein the method treats a disease or condition in the subject.
147. A method of treating a disease or condition in a subject, the method comprising administering, to a subject in need thereof, a therapeutically effective amount of the multispecific conjugate of any of embodiments 1-113 or the pharmaceutical composition of embodiments 135 or embodiment 136.
148. The method of embodiment 146 or embodiment 147, wherein the disease or condition is a tumor or a cancer.
149. The method of any of embodiments 140-148, wherein said subject is a human.

VI. EXAMPLES

The following examples are included for illustrative purposes only and are not intended to limit the scope of the invention.

Example 1: Method of Producing Multispecific Constructs with Constrained CD3 Binding Example 1 describes the generation and expression of multispecific polypeptide constructs containing a CD3 binding region that exhibits constrained CD3 binding. The multispecific constructs were generated in various configurations, as shown in FIG. 1, FIGS. 2A-2B, FIGS. 3A-3C and FIGS. 4A-4B, to contain a heterodimeric Fc region of an immunoglobulin coupled by a linker (e.g. a non-cleavable linker) to the CD3 binding region, and one or more antigen binding domains that binds a tumor associated antigen (TAA) positioned amino-terminally relative to the Fc region and/or carboxy-terminally relative to the CD3 binding region of the multispecific polypeptide construct.

A. Design and Generation of Constructs

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; and a variable light (VL) domain of an anti-CD3 antibody. The second polypeptide chain generally included in order, from the N-terminus to C-terminus, a second Fc polypeptide (e.g. an Fc knob polypeptide); the same non-cleavable linker as the first polypeptide chain; and a variable heavy (VH) domain of an anti-CD3 antibody. The anti-CD3 antibody included either a disulfide-stabilized (dsFv) antibody (anti-CD3 VH with the mutation G44C and VL with the mutation G100C) or contained a non-disulfide stabilized Fv antibody, as set forth in Tables E1.1 and E1.2. Various exemplary Fc polypeptide pairs to facilitate heterodimerization of the polypeptide chains were used as set forth in Tables E1.1 and Table E1.2. One or both of the polypeptide chains additionally encoded one or more TAA antigen binding domain amino-terminal to the Fc domain and/or carboxy-terminal to the CD3 binding region, in various configurations. Similar constructs can be generated using other heterodimeric Fc configurations, including other knob-into-hole configurations, such as any as described; other CD3-binding regions, including other anti-CD3 antibodies, including dsFv or other monovalent fragments; or other TAA antigen-binding fragments, such as scFv, sdAb or Fab formats can also be used.

Among generated constructs, the non-cleavable linker included linkers ranging from 3-18 amino acids in size. Examples of non-cleavable linkers used in exemplary generated molecules were GGS (e.g. contained in exemplary construct cx1356), GGSGGS (SEQ ID NO:10, contained in exemplary construct cx1357), GGSGGSGGS (SEQ ID NO:11, contained in exemplary construct cx1358), GGSGGSGGSGGS (SEQ ID NO:12, contained in exemplary construct cx1359), GGSGGSGGSGGSGGS (SEQ ID NO:13, contained in exemplary construct cx1360), and GGGGGSGGGGGSGGGGGS (SEQ ID NO:119, contained in exemplary construct cx5823 and cx5952) or GGSGGGGSGGGGSGGGGS (SEQ ID NO: 147, contained in exemplary construct cx681).

Any antigen binding domain that binds to a TAA can be employed in the provided multispecific polypeptide constructs. Exemplary generated proteins contained an antigen binding domain that binds Folate Receptor Alpha (FRα), B7H3 (CD276), or Delta-like 3 (DLL3). The antigen-binding domain can include single chain fragments (e.g. sdAb or scFv) or two chain antigen-binding fragments (Fabs). When the TAA was provided as a single chain fragment, e.g. sdAb or scFv, the TAA antigen binding domain was linked at the N-terminus to one or both polypeptide chains of the Fc heterodimer (e.g. hole and/or knob) by a peptide linker, e.g. PGGGG (SEQ ID NO:102) and/or was linked at the C-terminus to one or both domains (e.g. VH and/or VL) of the CD3 binding region by a peptide linker, e.g. GGGG (SEQ ID NO:103). Other similar peptide linkers can be employed.

When the TAA was provided as a Fab antigen-binding fragment the construct was composed of a VH and CH1 linked directly to one or both Fc polypeptides without a linker, as well as a light chain composed of a VL and CL. These TAA binding Fabs can be located on the amino- or carboxy-terminus of the heterodimeric Fc.

Multispecific polypeptide constructs were generated containing 1, 2, 3 or 4 TAA antigen binding domain, such as to provide for monovalent, bivalent, trivalent, or tetravalent binding, respectively. In some cases, the TAA antigen binding domains were the same (mono-epitopic). In some cases, the TAA antigen binding domains were different, such that the generated multispecific polypeptide constructs exhibited specificity for at least two different TAAs, to different epitopes of the same TAA (bi-epitopic) or the same epitopes of the same TAA (mono-epitopic).

Figure 3A:
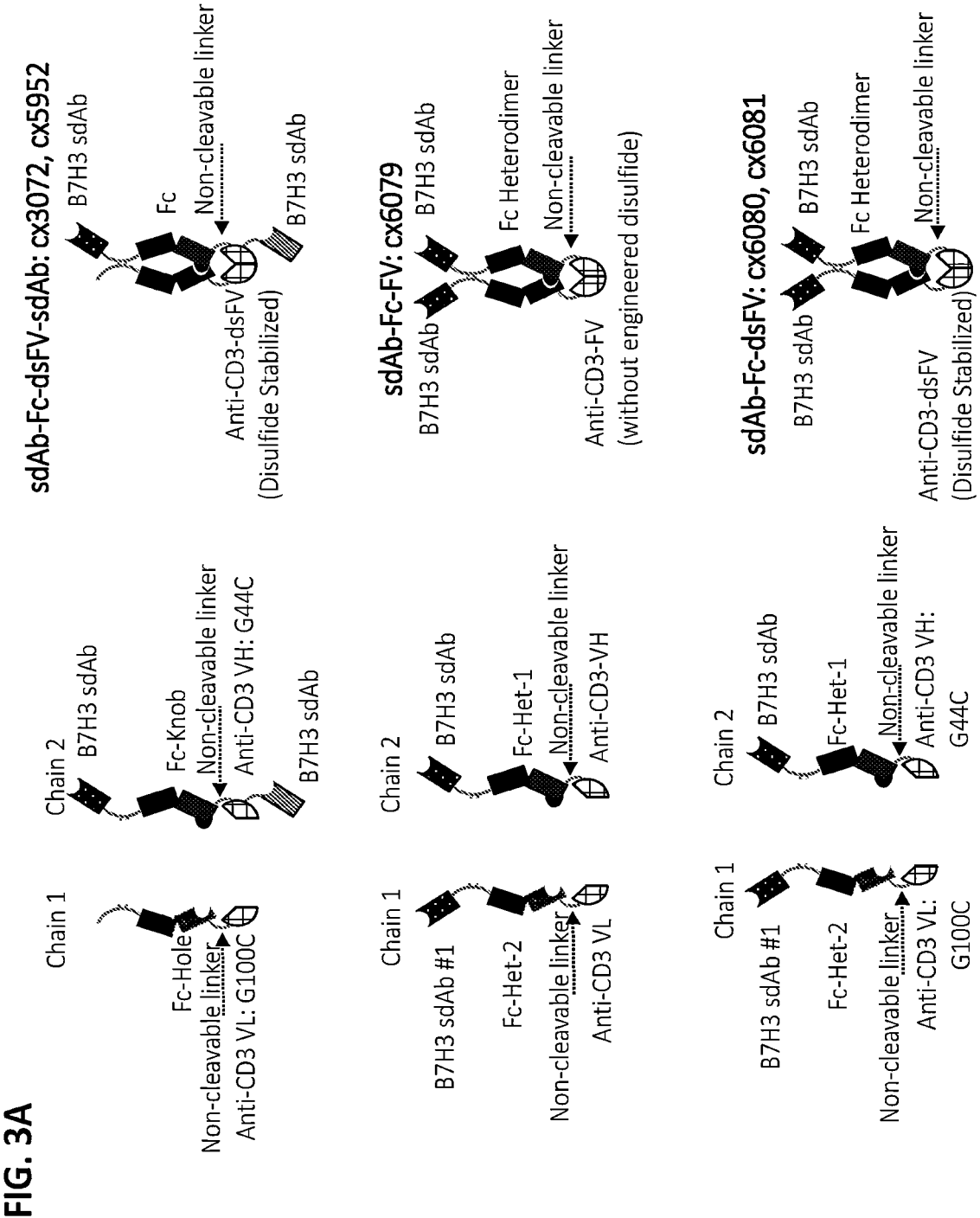
FIG. 3A is a schematic of various B7H3-targeting constrained CD3 constructs composed of two polypeptides, Chain 1 and Chain 2. Chain 1 contains either a heterodimeric Fc "hole," linked via a non-cleavable linker to an anti-CD3 VL domain modified at G100C (top); a B7H3-targeting sdAb linked to a heterodimeric Fc "hole," linked via a non-cleavable linker to an anti-CD3 VL domain (middle); or an B7H3-targeting sdAb linked to a heterodimeric Fc "hole," linked via a non-cleavable linker to an anti-CD3 VL domain modified at G100C (bottom). Chain 2 contains either a B7H3-targeted sdAb, linked to a complementary heterodimeric Fc "knob," linked via the linker as above to an anti-CD3 VH domain modified at G44C linked to second B7H3 sdAb (top); a B7H3-targeted sdAb, linked to a complementary heterodimeric Fc "knob," linked via the linker as above to an anti-CD3 VH domain (middle); or a B7H3-targeted sdAb, linked to a complementary heterodimeric Fc "knob," linked via the linker as above to an anti-CD3 VH domain modified by G44C (bottom). When co-expressed the CD3 binding domain is properly assembled via the association of the VL:VH on the hole and knob, respectively. Where denoted the VH:VL interaction is stabilized by an engineered disulfide bond between the modified residues G44C in the VH domain and G100C in the VL domain.
Figure 3B:
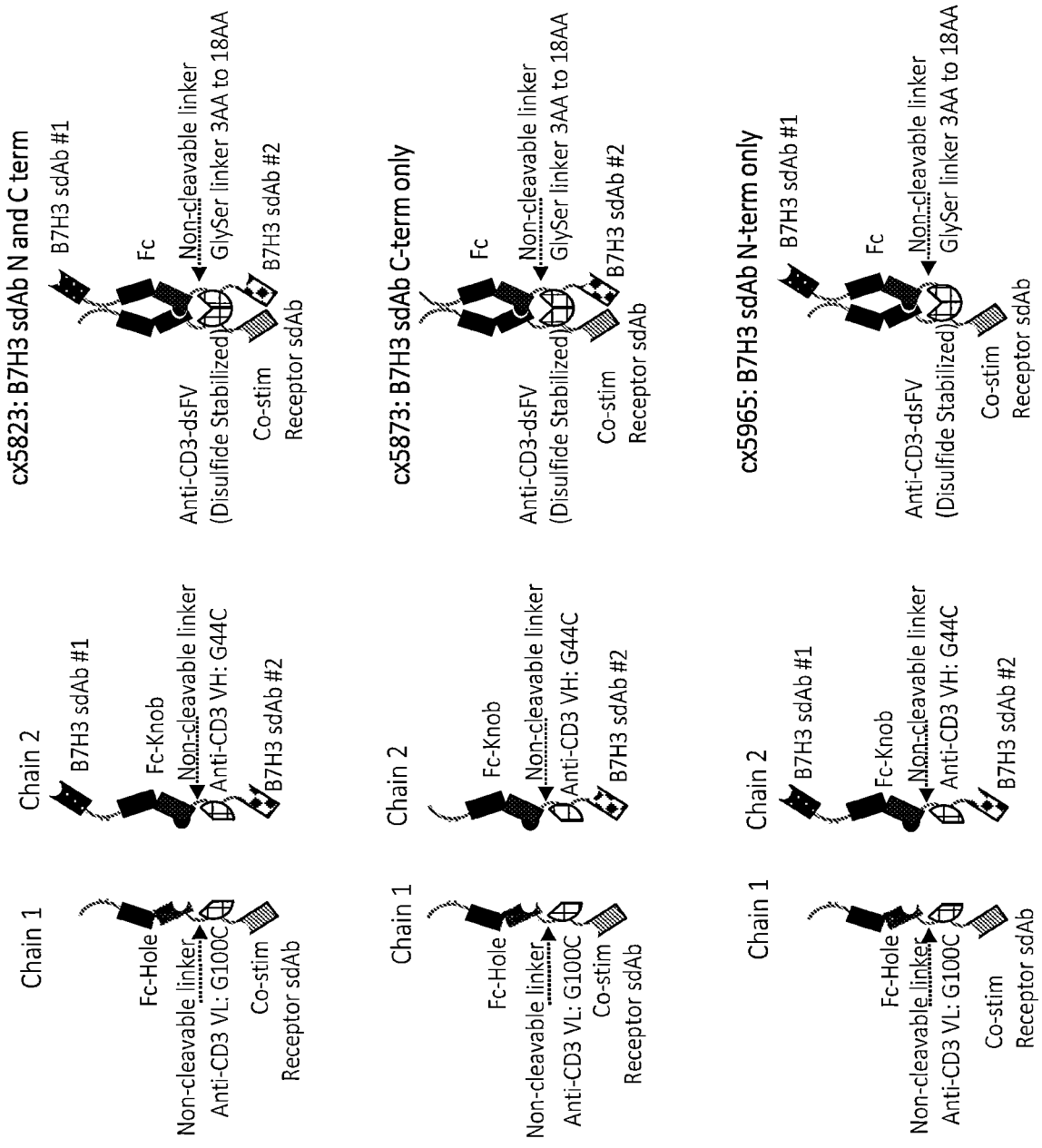
FIG. 3B is a schematic of various B7H3-targeting constrained CD3 constructs composed of two polypeptides, Chain 1 and Chain 2. Chain 1 contains a heterodimeric Fc "hole," linked via a non-cleavable linker to an anti-CD3 VL domain modified at G100C linked to a co-stimulatory receptor targeting sdAb. Chain 2 contains either a B7H3-targeted sdAb, linked to a complementary heterodimeric Fc "knob," linked via the linker as above to an anti-CD3 VH domain modified at G44C linked to second B7H3-targeted sdAb (top); a heterodimeric Fc "knob," linked via the linker as above to an anti-CD3 VH domain modified at G44C linked to a B7H3-targeted sdAb (middle); or a B7H3-targeted sdAb, linked to a complementary heterodimeric Fc "knob," linked via the linker as above to an anti-CD3 VH domain modified by G44C (bottom). When co-expressed the CD3 binding domain is properly assembled via the association of the VL:VH on the hole and knob, respectively. VH:VL interaction is stabilized by an engineered disulfide bond between the modified residues G44C in the VH domain and G100C in the VL domain. The resulting constructs are engage B7H3 either in bivalent (top) or monovalent (middle and bottom) manner. All the constructs herein express contain a co-stimulatory receptor targeting sdAb.
Figure 4A:
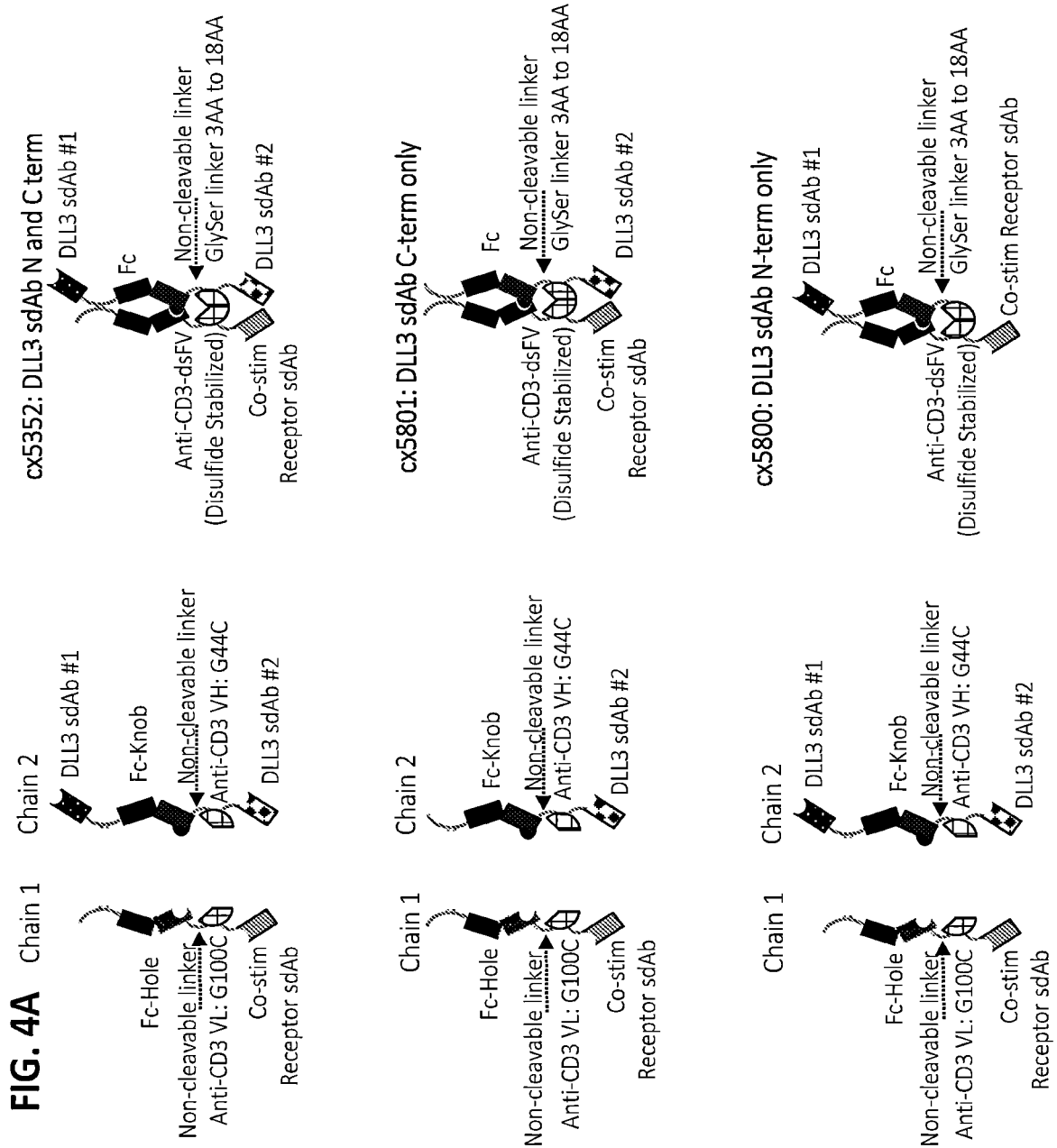
FIG. 4A is a schematic of various DLL3-targeting constrained CD3 constructs composed of two polypeptides, Chain 1 and Chain 2. Chain 1 contains a heterodimeric Fc "hole", linked via a non-cleavable linker to an anti-CD3 VL domain modified at G100C linked to a co-stimulatory receptor targeting sdAb. Chain 2 contains either a DLL3-targeted sdAb, linked to a complementary heterodimeric Fc "knob", linked via the linker as above to an anti-CD3 VH domain modified at G44C linked to second DLL3-targeted sdAb (top); a heterodimeric Fc "knob", linked via the linker as above to an anti-CD3 VH domain modified at G44C linked to a DLL3-targeted sdAb (middle); or a DLL3-targeted sdAb, linked to a complementary heterodimeric Fc "knob", linked via the linker as above to an anti-CD3 VH domain modified by G44C (bottom). When co-expressed the CD3 binding domain is properly assembled via the association of the VL:VH on the hole and knob, respectively. VH:VL interaction is stabilized by an engineered disulfide bond between the modified residues G44C in the VH domain and G100C in the VL domain. The resulting constructs are engage DLL3 either in bivalent (top) or monovalent (middle and bottom) manner. All the constructs herein express contain a co-stimulatory receptor targeting sdAb.
Figure 4B:
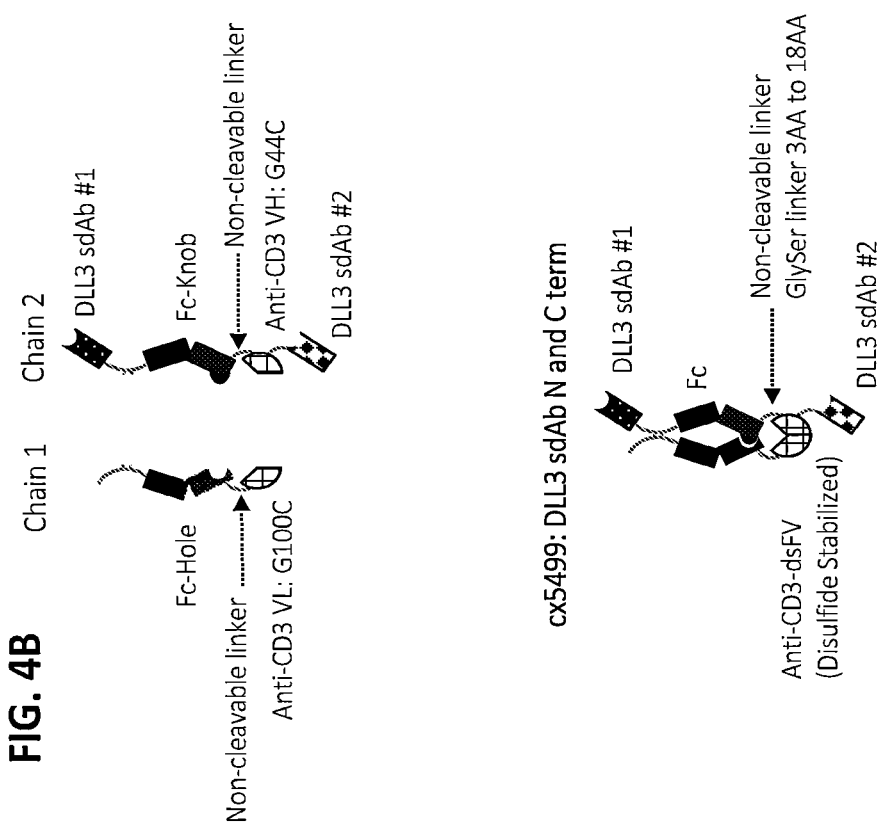
FIG. 4B is a schematic of a DLL3-targeting constrained CD3 construct, cx5499 composed of two polypeptides, Chain 1 and Chain 2. cx5499 is identical to cx5352 shown in FIG. 4A (top), but lacking co-stimulatory receptor targeting sdAb on the C-terminus of Chain 1. When co-expressed the CD3 binding domain is properly assembled via the association of the VL:VH on the hole and knob, respectively. VH:VL interaction is stabilized by an engineered disulfide bond between the modified residues G44C in the VH domain and G100C in the VL domain. The resulting constructs are engage DLL3 either in bivalent (top) or monovalent (middle and bottom) manner.

Among the generated proteins were constructs in which the TAA antigen binding domains were composed as single domain antibodies (sdAbs). Polynucleotides were generated to encode polypeptide chains of exemplary multispecific polypeptide constructs containing non-cleavable linkers. These included constructs designated cx1356, cx1357, cx1358, cx1359, cx1360, and cx681, targeting FRα as depicted in FIG. 2B; cx3072, cx5952, cx6079, cx6080, cx6081, cx5823, cx5873, and cx5965, targeting B7H3 as depicted in FIGS. 3A and 3B; and cx5352, cx5499, cx5800, and cx5801 targeting DLL3 as depicted in FIGS. 4A and 4B. Notably, some constructs were generated wherein the VH domain of the dsFv anti-CD3 antibody and the sdAb were both linked to the same side (e.g. hole or knob side) of the Fc heterodimer (e.g. cx3072 and cx5952, shown in FIG. 3A). Constructs were engineered without a disulfide stabilized Fv or were engineered with a disulfide linkage stabilizing the VH and VL domains of the anti-CD3 antibody. Some of the exemplary constructs generated additionally contained a sdAb (containing a CDR1, a CDR2 and a CDR3 set forth in SEQ ID Nos: 221, 222 and 223, respectively) targeting 4-1BB co-stimulatory receptor (e.g. cx5823, cx5873, cx5965, cx5352, cx5801, cx5800). A list of exemplary constrained CD3 binding constructs having sdAb TAA domains is given below in Table E1.1.

TABLE E1.1

Exemplary Constrained CD3 engaging constructs

| Construct ID | Chain | N-term sdAb (Target) | Fc | Linker | CD3 Binding Domain | C-term sdAb (Target) | Disulfide Stabilized |
|---|---|---|---|---|---|---|---|
| cx681 | 1 | FRα sdAb1 (SEQ ID NO: 120) | IgG1-Knob (SEQ ID NO: 82, 86 or 201) | GGSGGGGSGGGGS GGGGS (SEQ ID NO: 147) | VH34 (SEQ ID NO: 198) | FRα sdAb2 (SEQ ID NO: 121) | yes |
|  | 2 | FRα sdAb1 (SEQ ID NO: 120) | IgG1-Hole (SEQ ID NO: 83, 87 or 202) | GGSGGGGSGGGGS GGGGS (SEQ ID NO: 147) | VL21 (SEQ ID NO: 200) | FRα sdAb2 (SEQ ID NO: 121) |  |
| cx1356 | 1 | FRα sdAb1 (SEQ ID NO: 120) | IgG1-Knob (SEQ ID NO: 82, 86 or 201) | GGS | VH34 (SEQ ID NO: 198) | FRα sdAb2 (SEQ ID NO: 121) | yes |
|  | 2 | FRα sdAb1 (SEQ ID NO: 120) | IgG1-Hole (SEQ ID NO: 83, 87 or 202) | GGS | VL21 (SEQ ID NO: 200) | FRα sdAb2 (SEQ ID NO: 121) |  |
| cx1357 | 1 | FRα sdAb1 (SEQ ID NO: 120) | IgG1-Knob (SEQ ID NO: 82, 86 or 201) | GGSGGS (SEQ ID NO: 10) | VH34 (SEQ ID NO: 198) | FRα sdAb2 (SEQ ID NO: 121) | yes |

TABLE E1.1-continued

Exemplary Constrained CD3 engaging constructs

| Construct ID | Chain | N-term sdAb (Target) | Fc | Linker | CD3 Binding Domain | C-term sdAb (Target) | Disulfide Stabilized |
|---|---|---|---|---|---|---|---|
| | 2 | FRα sdAb1 (SEQ ID NO: 120) | IgG1-Hole (SEQ ID NO: 83, 87 or 202) | GGSGGS (SEQ ID NO: 10) | VL21 (SEQ ID NO: 200) | FRα sdAb2 (SEQ ID NO: 121) | |
| cx1358 | 1 | FRα sdAb1 (SEQ ID NO: 120) | IgG1-Knob (SEQ ID NO: 82, 86 or 201) | GGSGGSGGS (SEQ ID NO: 11) | VH34 (SEQ ID NO: 198) | FRα sdAb2 (SEQ ID NO: 121) | yes |
| | 2 | FRα sdAb1 (SEQ ID NO: 120) | IgG1-Hole (SEQ ID NO: 83, 87 or 202) | GGSGGSGGS (SEQ ID NO: 11) | VL21 (SEQ ID NO: 200) | FRα sdAb2 (SEQ ID NO: 121) | |
| cx1359 | 1 | FRα sdAb1 (SEQ ID NO: 120) | IgG1-Knob (SEQ ID NO: 82, 86 or 201) | GGSGGSGGSGGS (SEQ ID NO: 12) | VH34 (SEQ ID NO: 198) | FRα sdAb2 (SEQ ID NO: 121) | yes |
| | 2 | FRα sdAb1 (SEQ ID NO: 120) | IgG1-Hole (SEQ ID NO: 83, 87 or 202) | GGSGGSGGSGGS (SEQ ID NO: 12) | VL21 (SEQ ID NO: 200) | FRα sdAb2 (SEQ ID NO: 121) | |
| cx1360 | 1 | FRα sdAb1 (SEQ ID NO: 120) | IgG1-Knob (SEQ ID NO: 82, 86 or 201) | GGSGGSGGSGGSGGSGS (SEQ ID NO: 13) | VH34 (SEQ ID NO: 198) | FRα sdAb2 (SEQ ID NO: 121) | yes |
| | 2 | FRα sdAb1 (SEQ ID NO: 120) | IgG1-Hole (SEQ ID NO: 83, 87 or 202) | GGSGGSGGSGGSGGSGS (SEQ ID NO: 13) | VL21 (SEQ ID NO: 200) | FRα sdAb2 (SEQ ID NO: 121) | |
| cx5823 | 1 | B7H3 sdAb4 (SEQ ID NO: 214) | xELL-Knob (SEQ ID NO: 88) | GGGGSGGGGSGGGGGS (SEQ ID NO: 119) | VH13 (SEQ ID NO: 44) | B7H3 sdAb5 (SEQ ID NO: 216) | yes |
| | 2 | None | xELL-Hole (SEQ ID NO: 93) | GGGGSGGGGSGGGGGS (SEQ ID NO: 119) | VL10 (SEQ ID NO: 72) | Co-stim Receptor sdAb | |
| cx5952 | 1 | B7H3 sdAb4 (SEQ ID NO: 214) | xELL-Knob (SEQ ID NO: 88) | GGGGSGGGGSGGGGGS (SEQ ID NO: 119) | VH13 (SEQ ID NO: 44) | B7H3 sdAb5 (SEQ ID NO: 216) | yes |
| | 2 | None | xELL-Hole (SEQ ID NO: 93) | GGGGSGGGGSGGGGGS (SEQ ID NO: 119) | VL10 (SEQ ID NO: 72) | None | |
| cx6079 | 1 | B7H3 sdAb4 (SEQ ID NO: 214) | Fc-Het-1 (SEQ ID NO: 194) | GGGGSGGGGSGGGGS (SEQ ID NO: 170) | VH32 (SEQ ID NO: 196) | None | no |
| | 2 | B7H3 sdAb4 (SEQ ID NO: 214) | Fc-Het-2 (SEQ ID NO: 195) | GGGGSGGGGSGGGGS (SEQ ID NO: 170) | VL20 (SEQ ID NO: 199) | None | |
| cx6080 | 1 | B7H3 sdAb4 (SEQ ID NO: 214) | Fc-Het-1 (SEQ ID NO: 194) | GGGGSGGGGSGGGGS (SEQ ID NO: 170) | VH33 (SEQ ID NO: 197) | None | yes |
| | 2 | B7H3 sdAb4 (SEQ ID NO: 214) | Fc-Het-2 (SEQ ID NO: 195) | GGGGSGGGGSGGGGS (SEQ ID NO: 170) | VL21 (SEQ ID NO: 200) | None | |
| cx6081 | 1 | B7H3 sdAb4 (SEQ ID NO: 214) | Fc-Het-1 (SEQ ID NO: 194) | GGGGSGGGGSGGGGS (SEQ ID NO: 170) | VH13 (SEQ ID NO: 44) | None | yes |
| | 2 | B7H3 sdAb4 (SEQ ID NO: 214) | Fc-Het-2 (SEQ ID NO: 195) | GGGGSGGGGSGGGGS (SEQ ID NO: 170) | VL10 (SEQ ID NO: 72) | None | |

TABLE E1.1-continued

Exemplary Constrained CD3 engaging constructs

| Construct ID | Chain | N-term sdAb (Target) | Fc | Linker | CD3 Binding Domain | C-term sdAb (Target) | Disulfide Stabilized |
|---|---|---|---|---|---|---|---|
| cx5841 | 1 | B7H3 sdAb4 (SEQ ID NO: 214) | xELL-Knob (SEQ ID NO: 84, 88 or 203) | GGGGSGGGGSG GGGS (SEQ ID NO: 119) | VH13 (SEQ ID NO: 44) | B7H3 sdAb3 (SEQ ID NO: 217) | yes |
|  | 2 | None | xELL-Hole (SEQ ID NO: 91, 93 or 206) | GGGGSGGGGSG GGGS (SEQ ID NO: 119) | VL10 (SEQ ID NO: 72) | Co-stim Receptor sdAb |  |
| cx5187 | 1 | B7H3 sdAb4 (SEQ ID NO: 214) | xELL-Knob (SEQ ID NO: 84, 88 or 203) | GGGGSGGGGSG GGGS (SEQ ID NO: 119) | VH13 (SEQ ID NO: 44) | B7H3 sdAb3 (SEQ ID NO: 217) | yes |
|  | 2 | None | xELL-Hole (SEQ ID NO: 91, 93 or 206) | GGGGSGGGGSG GGGS (SEQ ID NO: 119) | VL10 (SEQ ID NO: 72) | Co-stim Receptor sdAb |  |
| cx5499 | 1 | DLL3 sdAb1 (SEQ ID NO: 219) | xELL-Knob (SEQ ID NO: 84, 88 or 203) | GGGGSGGGGSG GGGS (SEQ ID NO: 119) | VH13 (SEQ ID NO: 44) | DLL3 sdAb2 (SEQ ID NO: 220) | yes |
|  | 2 | None | xELL-Hole (SEQ ID NO: 91, 93 or 206) | GGGGSGGGGSG GGGS (SEQ ID NO: 119) | VL10 (SEQ ID NO: 72) | None |  |
| cx3072 | 1 | B7H3 sdAb2 (SEQ ID NO: 215) | IgG1-Knob (SEQ ID NO: 82, 86 or 201) | GGGGSGGGGSG GGGS (SEQ ID NO: 119) | VH13 (SEQ ID NO: 44) | B7H3 sdAb1 (SEQ ID NO: 218) | yes |
|  | 2 | None | IgG1-Knob (SEQ ID NO: 83, 87 or 202) | GGGGSGGGGSG GGGS (SEQ ID NO: 119) | VL10 (SEQ ID NO: 72) | None |  |
| cx5873 | 1 | None | xELL-Knob (SEQ ID NO: 84, 88 or 203) | GGGGSGGGGSG GGGS (SEQ ID NO: 119) | VH13 (SEQ ID NO: 44) | B7H3 sdAb3 (SEQ ID NO: 217) | yes |
|  | 2 | None | xELL-Hole (SEQ ID NO: 91, 93 or 206) | GGGGSGGGGSG GGGS (SEQ ID NO: 119) | VL10 (SEQ ID NO: 72) | Co-stim Receptor sdAb |  |
| cx5965 | 1 | B7H3 sdAb4 (SEQ ID NO: 214) | xELL-Knob (SEQ ID NO: 84, 88 or 203) | GGGGSGGGGSG GGGS (SEQ ID NO: 119) | VH13 (SEQ ID NO: 44) | none | yes |
|  | 2 | None | xELL-Hole (SEQ ID NO: 91, 93 or 206) | GGGGSGGGGSG GGGS (SEQ ID NO: 119) | VL10 (SEQ ID NO: 72) | Co-stim Receptor sdAb |  |
| cx5352 | 1 | DLL3 sdAb1 (SEQ ID NO: 219) | xELL-Knob (SEQ ID NO: 84, 88 or 203) | GGGGSGGGGSG GGGS (SEQ ID NO: 119) | VH13 (SEQ ID NO: 44) | DLL3 sdAb2 (SEQ ID NO: 220) | yes |
|  | 2 | None | xELL-Hole (SEQ ID NO: 91, 93 or 206) | GGGGSGGGGSG GGGS (SEQ ID NO: 119) | VL10 (SEQ ID NO: 72) | Co-stim Receptor sdAb |  |

TABLE E1.1-continued

Exemplary Constrained CD3 engaging constructs

| Construct ID | Chain | N-term sdAb (Target) | Fc | Linker | CD3 Binding Domain | C-term sdAb (Target) | Disulfide Stabilized |
|---|---|---|---|---|---|---|---|
| cx5800 | 1 | DLL3 sdAb1 (SEQ ID NO: 219) | xELL-Knob (SEQ ID NO: 84, 88 or 203) | GGGGSGGGGGSG GGGGS (SEQ ID NO: 119) | VH13 (SEQ ID NO: 44) | None | yes |
|  | 2 | None | xELL-Hole (SEQ ID NO: 91, 93 or 206) | GGGGSGGGGGSG GGGGS (SEQ ID NO: 119) | VL10 (SEQ ID NO: 72) | Co-stim Receptor sdAb |  |
| cx5801 | 1 | None | xELL-Knob (SEQ ID NO: 84, 88 or 203) | GGGGSGGGGGSG GGGGS (SEQ ID NO: 119) | VH13 (SEQ ID NO: 44) | DLL3 sdAb2 (SEQ ID NO: 220) | yes |
|  | 2 | None | xELL-Hole (SEQ ID NO: 91, 93 or 206) | GGGGSGGGGGSG GGGGS (SEQ ID NO: 119) | VL10 (SEQ ID NO: 72) | Co-stint Receptor sdAb |  |

Figure 3C:
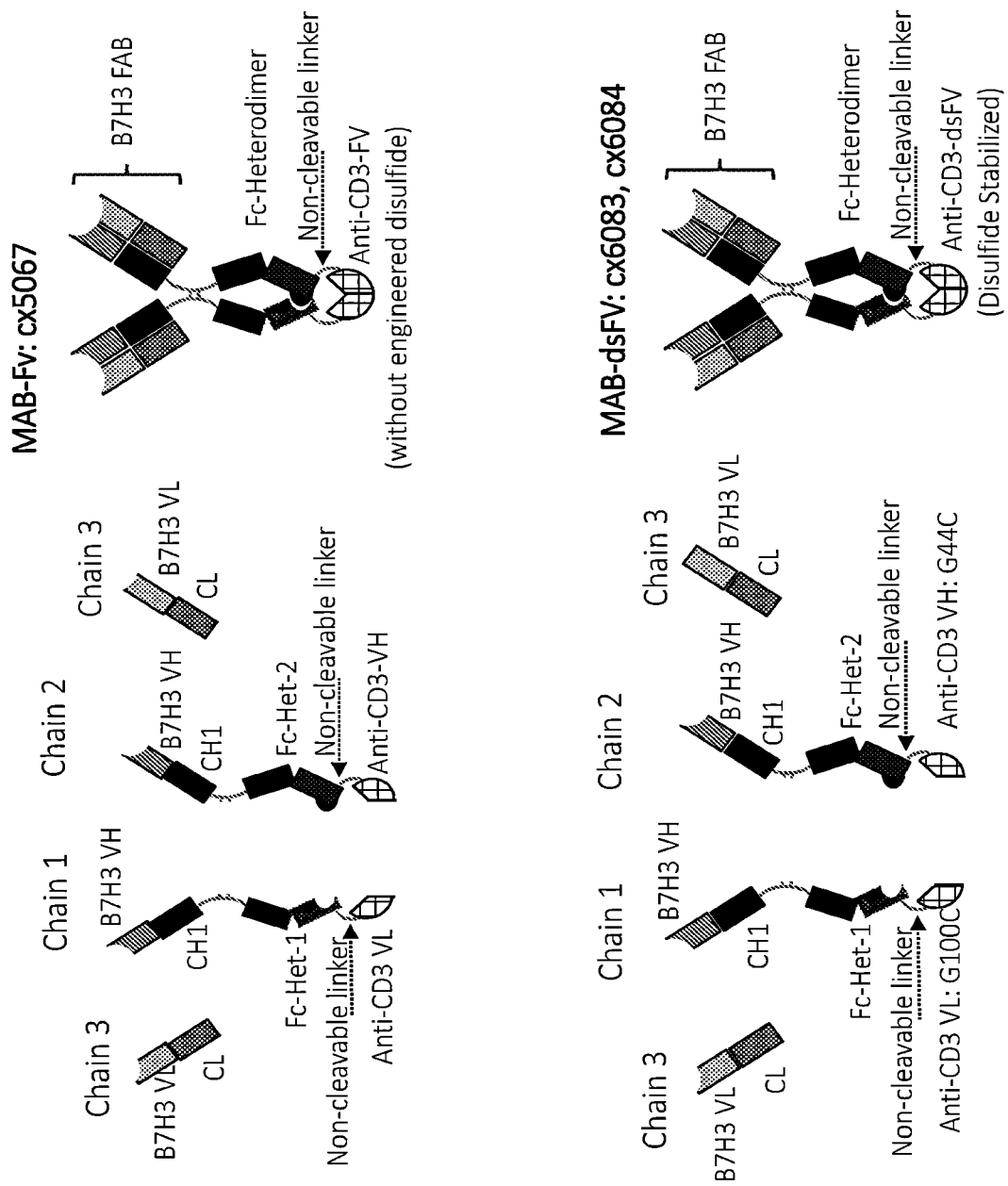
FIG. 3C is a schematic of various B7H3-targeting constrained CD3 constructs composed of three polypeptides, Chain 1, Chain 2 and Chain 3, wherein the B7H3 targeting domain is a FAB. Chain 1 contains a BH73-targeting VH, an IgG Constant Heavy 1 (CH1) linked via a hinge to a first member of a heterodimeric Fc (Fc-Het-1), linked via the linker as above to an anti-CD3 VL domain that either lacks (top) or contains the modification of G100C (bottom). Chain 2 contains a BH73-targeting VH, an IgG Constant Heavy 1 (CH1) linked via a hinge to a second member of a heterodimeric Fc (Fc-Het-2), linked via the linker as above to an anti-CD3 VH domain that either lacks (top) or contains the modification of G44C (bottom). Chain 3 contains a complementary B7H3-targeting VL domain linked to human Ig Constant Light (CL) region. When co-expressed the CD3 binding domain is properly assembled via the association of the VL:VH on the complimentary heterodimeric Fc regions. Where denoted the VH:VL interaction is stabilized by an engineered disulfide bond between the modified residues G44C in the VH domain and G100C in the VL domain.

Exemplary generated constructs also included constructs in which the TAA antigen binding domains were composed as a Fab (designated MAB formats). In this example, an anti-B7H3 Fab was used composed of a heavy chain Fd set forth in SEQ ID NO:127 and a light chain set forth in SEQ ID NO:128. Polynucleotides were generated to encode polypeptide chains of exemplary multispecific polypeptide constructs containing non-cleavable linkers. These included cx5067, cx6083, and cx6084, as depicted in FIG. 3C. Constructs were engineered without a disulfide stabilized anti-CD3 antibody Fv or were engineered with a disulfide linkage stabilizing the VH and VL domains of the anti-CD3 antibody (anti-CD3 VH with the mutation G44C and VL with the mutation G100C). A list of exemplary Fab constructs is provided below in Table E1.2.

B. Expression and Purification of Generated Constructs

Separate plasmids encoding each chain of the heterodimeric constrained CD3 binding protein were transiently transfected at an equimolar ratio into mammalian cells (either HEK293 or CHO) using polyethylenimine. Recombinant protein secreted into the supernatant was collected after 3-14 days, and purified by protein A chromatography, followed by either preparative size exclusion chromatography (SEC) or flow-through hydrophobic interaction chromatography (HIC). In some cases, heterodimeric protein was enriched for during purification due to a mutation designed into one chain of the heterodimeric Fc at position I253R or H435R (e.g. in the hole-Fc) such that it did not bind protein A, and thus homodimers of I253R or H435R were not purified. The second chromatography step by SEC

TABLE E1.2

Exemplary B7H3-targeted constrained CD3 engaging constructs

| Construct ID | Chain | N-term Domain | Fc | Linker | CD3 Binding Domain | C-term sdAb (Target) | Disulfide Stabilized |
|---|---|---|---|---|---|---|---|
| cx5067 | 1 | B7H3-Fab (SEQ ID NOs: 127, 128) | Fc-Het-1 (SEQ ID NO: 194) | GGGGSGGGSGGGG S (SEQ ID NO: 170) | VH32 (SEQ ID NO: 196) | None | no |
|  | 2 | B7H3-Fab (SEQ ID NOs: 127, 128) | Fc-Het-2 (SEQ ID NO: 195) | GGGGSGGGSGGGG S (SEQ ID NO: 170) | VL20 (SEQ ID NO: 199) | None |  |
| cx6083 | 1 | B7H3-Fab (SEQ ID NOs: 127, 128) | Fc-Het-1 (SEQ ID NO: 194) | GGGGSGGGSGGGG S (SEQ ID NO: 170) | VH33 (SEQ ID NO: 197) | None | yes |
|  | 2 | B7H3-Fab (SEQ ID NOs: 127, 128) | Fc-Het-2 (SEQ ID NO: 195) | GGGGSGGGSGGGG S (SEQ ID NO: 170) | VL21 (SEQ ID NO: 200) | None |  |
| cx6084 | 1 | B7H3-Fab (SEQ ID NOs: 127, 128) | Fc-Het-1 (SEQ ID NO: 194) | GGGGSGGGSGGGG S (SEQ ID NO: 170) | VH13 (SEQ ID NO: 44) | None | yes |
|  | 2 | B7H3-Fab (SEQ ID NOs: 127, 128) | Fc-Het-2 (SEQ ID NO: 195) | GGGGSGGGSGGGG S (SEQ ID NO: 170) | VL10 (SEQ ID NO: 72) | None |  |

(AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multi-specific polypeptide constructs, containing properly paired species of heterodimeric Fc and the anti-CD3 Fv (e.g. disulfide stabilized anti-CD3 Fv). Purified heterodimeric constrained CD3 binding protein was stable and did not accumulate cross-paired species upon prolonged incubation at 4° C. or increased protein concentration.

Example 2: Assessment of Binding of Constrained CD3 Binding Constructs to Cancer Cells and Primary T Cells by Flow Cytometry This Example describes studies assessing binding of exemplary constructs to T cells or to cancer cells. These studies were carried out in single cultures containing either only the T cells or only the cancer cells in isolation from each other.

A. FR-Alpha Binding

Binding of exemplary multispecific polypeptide constructs of the disclosure containing an antigen-binding domain directed against Folate Receptor Alpha (FRα) to CD3 on the surface of primary T cells and to FRα expressing cells (Ovcar-5) was assessed by flow cytometry. The tumor antigen binding domains of the tested constructs bind the Folate Receptor Alpha (FRα), which is not expressed on the primary T cells. The tested constructs included cx1356 and cx681, containing a non-cleavable linker of 3 amino acids in cx1356 or a non-cleavable linker of 18 amino acids in cx681 (see FIG. 2B and Table E1.1).

Figure 5A:
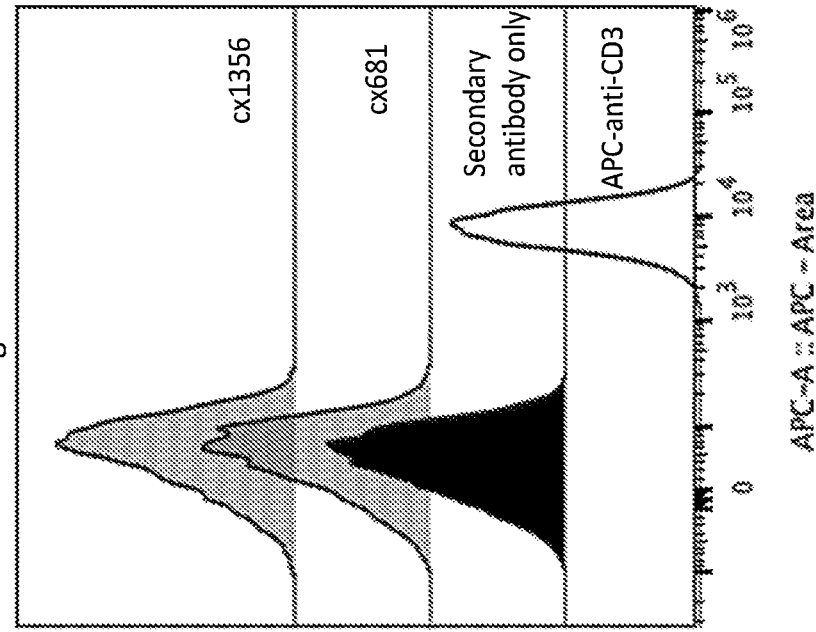
FIG. 5A-D depict cellular binding by representative FRα-targeting constrained CD3 engaging constructs, cx1356 and cx681.
Figure 5B:
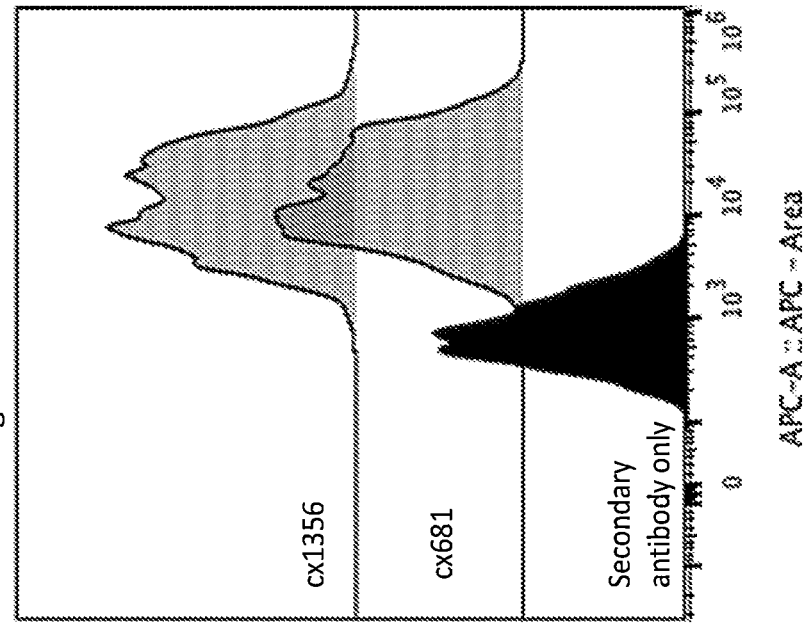
Figure 5C:
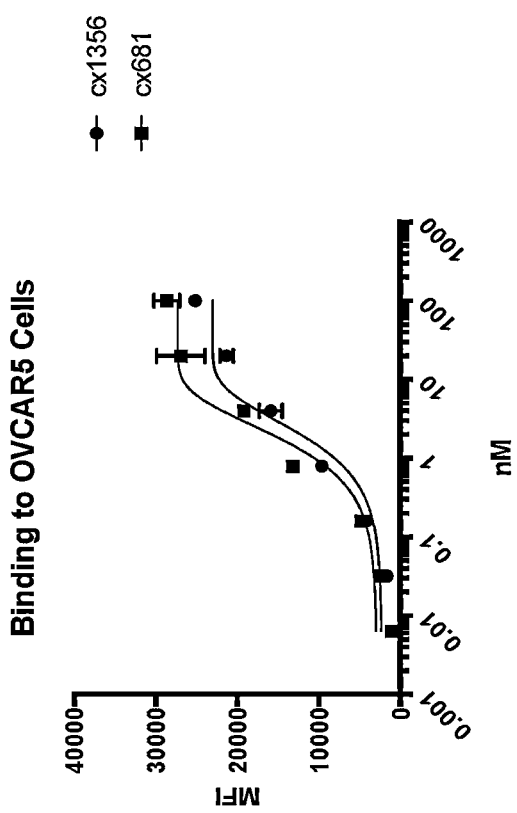
Figure 5D:
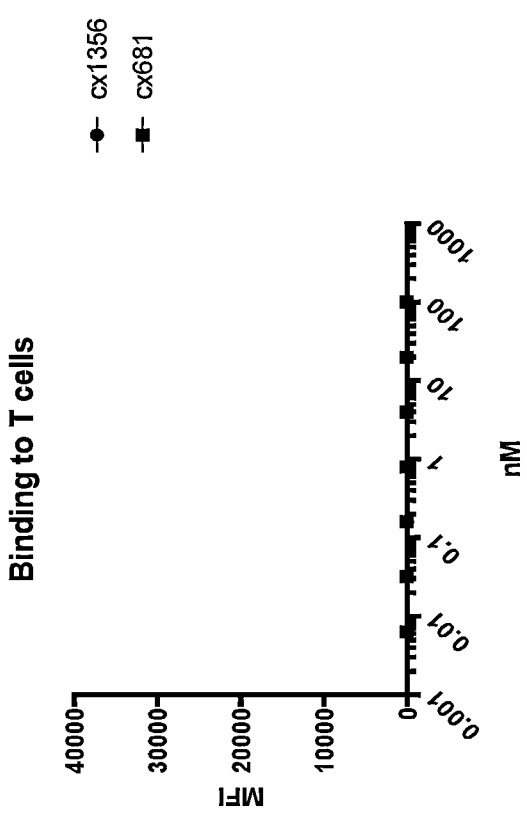

For the studies described in FIGS. 5A and 5B, 100 nM of each construct, cx1356 or cx681 was used and assessed for binding to either the Ovcar-5 cells or primary T-cells. An anti-CD3 antibody was included as a control. A titration of the constrained CD3 engaging constructs on either FRα expressing cells (Ovcar-5; FIG. 5C) or isolated primary T-cells (FRα negative; FIG. 5D), was conducted to assess binding. Bound constructs were detected using fluorophore-conjugated anti-human IgG Fc secondary antibody.

The tested FRα-targeting constructs with various linkers between the Fc and the component of the CD3 binding domains were found to bind FRα expressing cells (Ovcar-5) (FIGS. 5A and 5C), but lacked the capacity to bind T-cells (FIGS. 5B and 5D). These results are consistent with a finding that binding to CD3 on T cells in isolation is constrained in the provided formats.

B. B7H3 Binding

Binding of exemplary multispecific constructs containing an antigen-binding domain directed against B7H3 were assessed for binding to B7H3 positive A375 tumor cells or primary T-cells. The constructs were generated containing antigen-binding domain(s) that were either sdAbs or a FABs, and that were positioned either only N-terminal to the Fc or both N-terminal to the Fc and C-terminal to the anti-CD3 binding domain (see FIGS. 3A and 3C and Table E1.1). Among the various formats of constructs tested included: sdAb-Fc-dsFV-sdAb (cx3072, cx5952) sdAb-Fc-FV (cx6079), sdAb-Fc-dsFV (cs6080, cx6081), MAB-FV (cx5067) and MAB-dsFV (cx6083, cx6084), where the FV represents the anti-CD3 binding domain composed of VH and VL domain pairs and "ds" notes disulfide stabilized via an engineered interdomain disulfide bond.

Figure 6A:
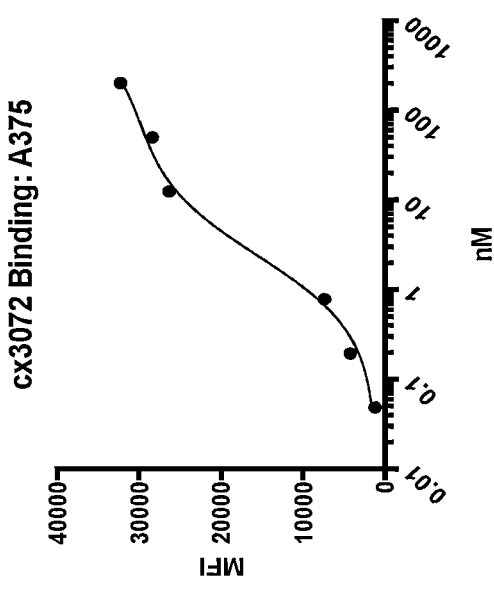
FIG. 6A-F depict cellular binding by representative B7H3-targeting constrained CD3 engaging constructs.
Figure 6B:
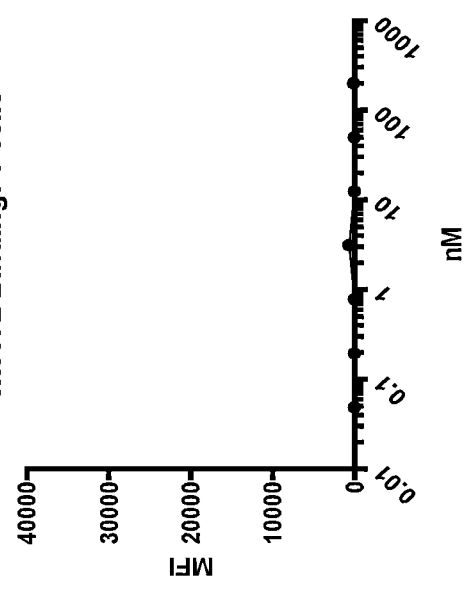
Figure 6C:
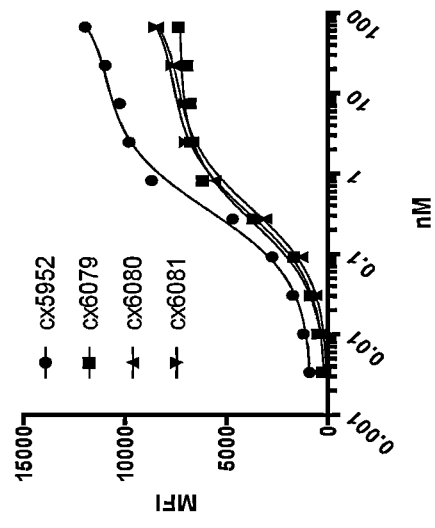
Figure 6D:
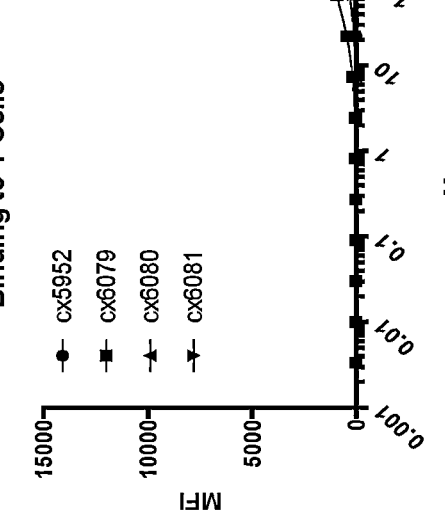
Figure 6E:
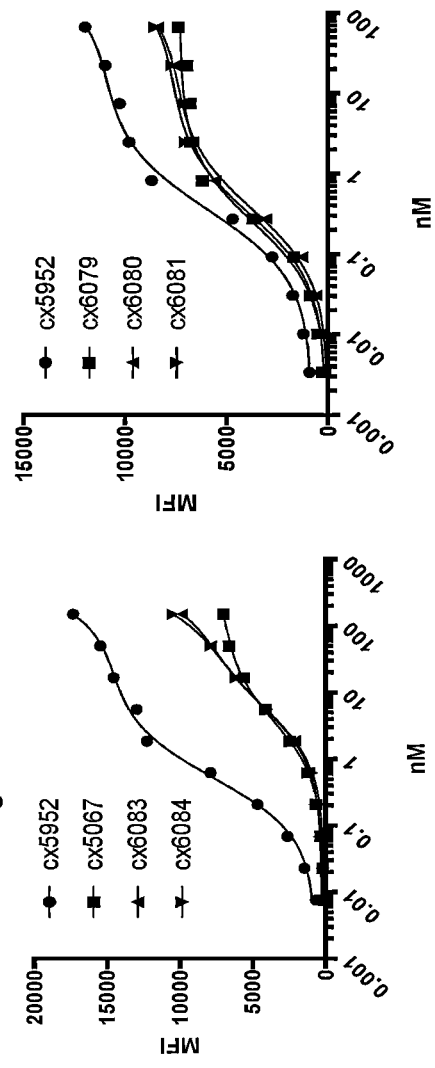
Figure 6F:
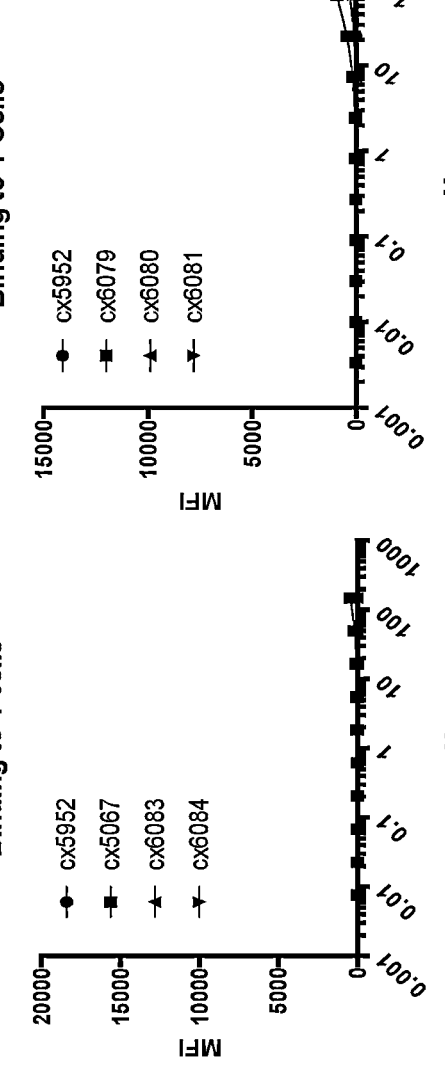

FIGS. 6A-F demonstrate that these constructs are capable of binding to B7H3 but not T-cells in isolation. Binding was assessed as described above via flow cytometry using a fluorophore-conjugated anti-human Fc secondary antibody. cx3072 bound to A375 cells with high affinity (FIG. 6A) but not to isolated T-cells (FIG. 6B). The tested sdAb-Fc-dsFV-sdAb (cx5952) displayed higher binding affinity compared to a FAB containing MAB-FV (cx5067) and MAB-dsFV constructs (cx6083, cx6084) (FIG. 6C). The B7H3-targeting sdAb containing constructs (cx5952, cx6079, cx6080, and cx6081) bound to B7H3 positive cells with similar affinities (depicted in FIG. 6E), with cx5952 displaying higher maximal binding. cx6079, cx6080 and cx6081 contain two identical B7H3-targeting sdAbs, whereas cx5952, and cx3072 contain two distinct B7H3-targeting sdAb that bind different epitopes. The MAB-FV, cx5067, contains two identical B7H3-targeting FAB domains. Notably none of the exemplary B7H3-targeted constrained CD3 engaging constructs bound isolated primary human T-cells, as depicted in FIGS. 6B, 6D, and 6F. These results further support that binding to CD3 on T cells in isolation is constrained in the provided formats.

Example 3: Assessment of CD3 Signaling Activity in Co-Cultures with Antigen-Expressing Target Cells and Impact of Linker Length on Activity The effect of various length linkers between the Fc and the component domains (VH and VL) that comprise the CD3 binding region on T-cell activating capacity was tested using a Jurkat reporter assay. The CD3 reporter cells were developed from Jurkat cells that naturally express CD3 and were engineered to express NFAT-driven green fluorescence protein (GFP). Agonism of CD3 results in NFAT signaling and production of green fluorescence.

Antigen targeting constrained CD3 engaging constructs were titrated onto co-cultures of target cells and Jurkat CD3 reporter cells. In this assay, target cells included either IGROV1 (FRα positive) or NCI-460 (FRα negative). For reporter assays utilizing adherent antigen expressing target cells, target cells were seeded, allowed to settle at room temperature for uniform distribution, and incubated for several hours at 37° C. to permit adherence prior to addition of reporter cells and antigen targeting constrained CD3 engaging constructs. Assay plates were serially imaged using an IncuCyte ZOOM system and CD3 reporter cell activation was determined by measuring GFP expression as the total integrated green object in the well.

FRα-targeting constrained CD3 engaging constructs, generated as described in Example 1 containing GlySer-based linkers of varying lengths as listed in Table E3 were used in these assays.

TABLE E3

Tested Linker Lengths

| SEQ ID NO | Linker |
|---|---|
| — | gs3: GGS |
| 10 | gs6: GGSGGS |
| 11 | gs9: GGSGGSGGS |
| 12 | gs12: GGSGGSGGSGGS |
| 13 | gs15: GGSGGSGGSGGSGGS |

TABLE E3-continued

Tested Linker Lengths

| SEQ ID NO | Linker |
|---|---|
| 119 | gs18: GGGGGSGGGGGSGGGGGS |
| 147 | gs18: GGSGGGGSGGGGSGGGGS |

Figure 7A:
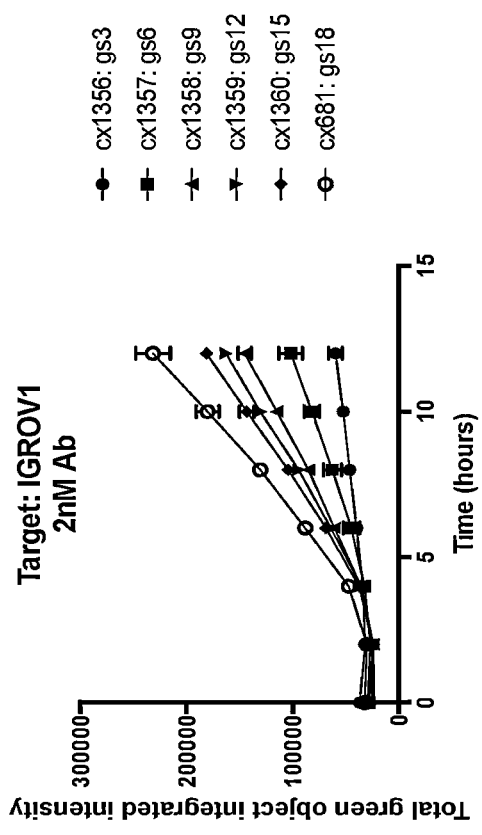
FIG. 7A-F depict the impact of linker length on the capacity to agonize CD3 in the presence of FRα positive IGROV1 cells (FIG. 7A, 7C, 7E), or FRα negative NCI-H460 cells (FIG. 7B, 7D, 7F).
Figure 7B:
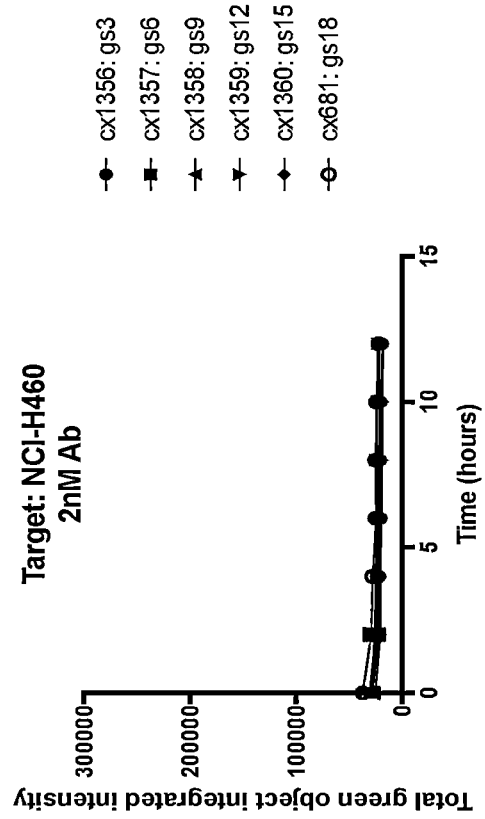
Figures 7C, 7D:
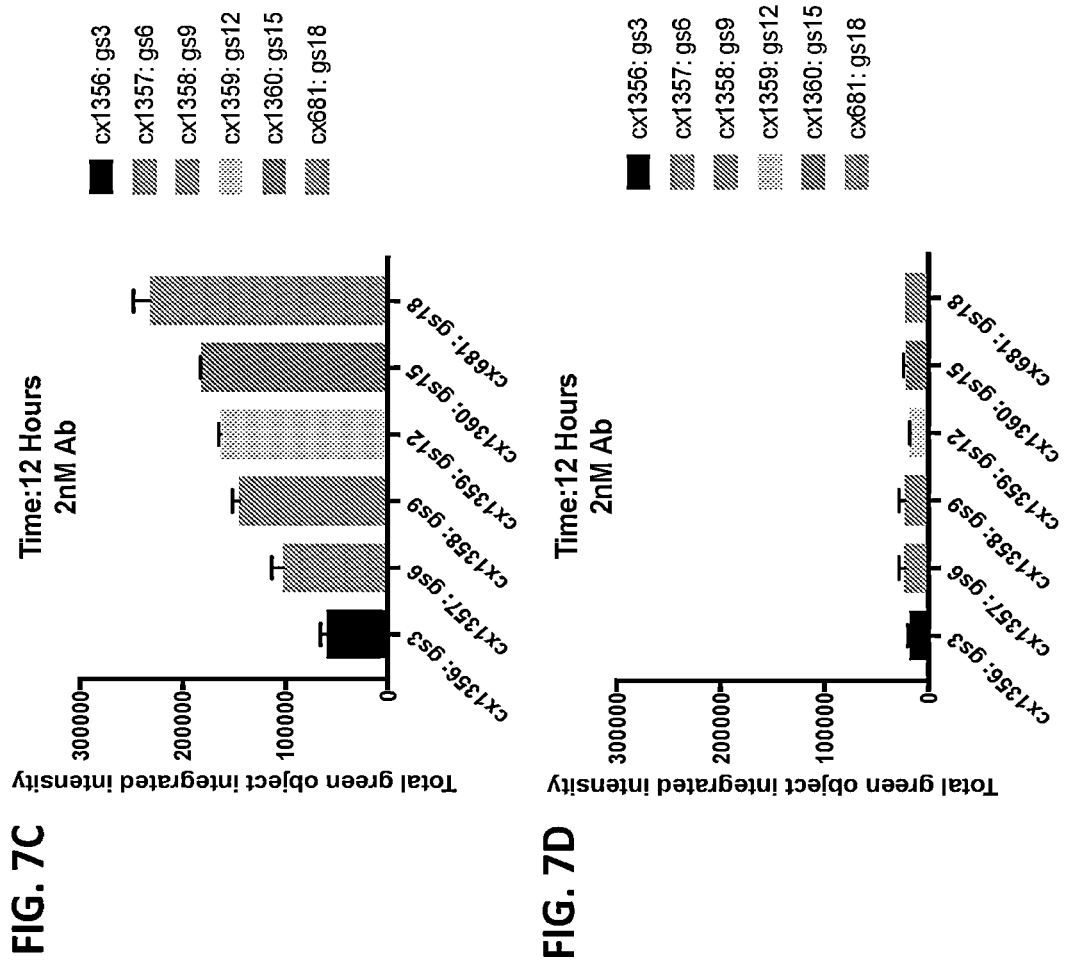
Figure 7E:
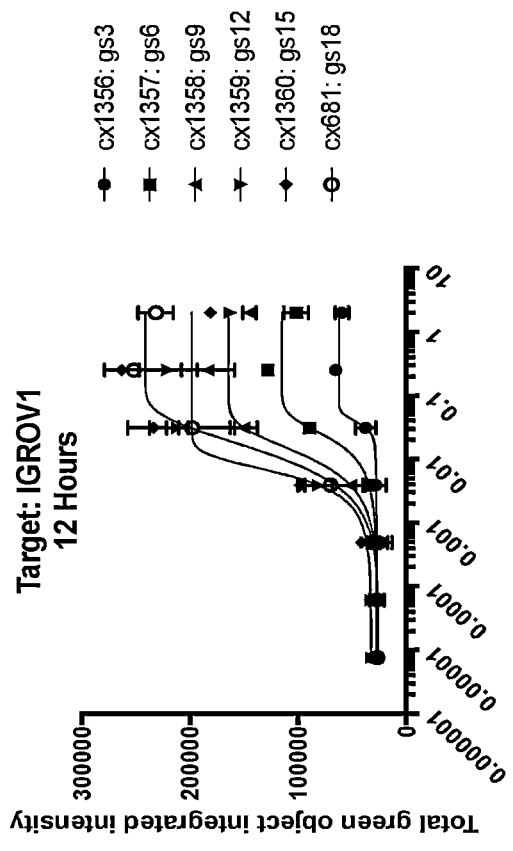
Figure 7F:
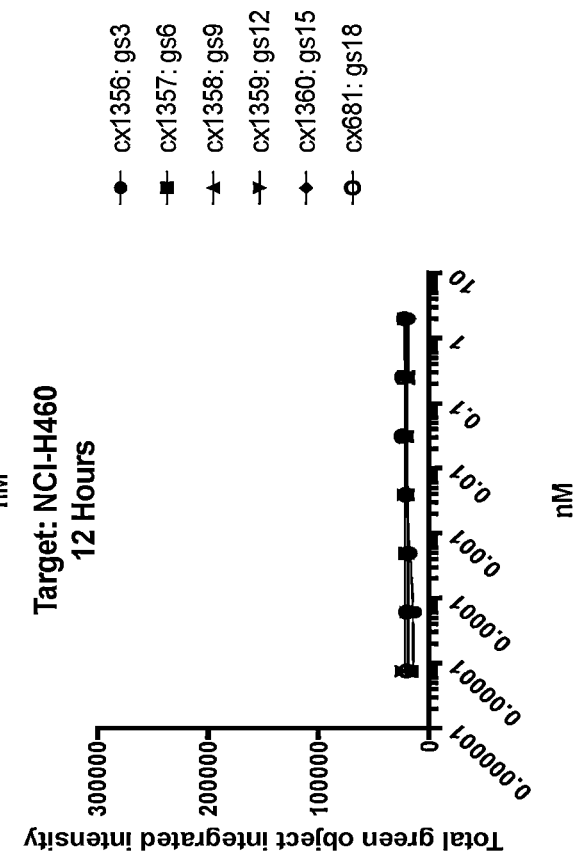

As shown in FIGS. 7A-7F, the T-cell activating activity as determined by fluorescent intensity was dependent on co-culture with FRα-antigen expressing target cells. The length of the linker and T-cell activating capacity were positively correlated. T-cell activating capacity was shown to directly relate to linker length, indicating shorter linkers restrict CD3 binding to a greater extent (see FIGS. 7A, 7C and 7E). Importantly, T-cell engagement of the constructs is dependent on TAA-binding, as these constructs did not demonstrate a T-cell binding capacity in isolation (e.g. solution form when unbound to target TAA) as shown above in Example 2. Further, no observable fluorescence was measured in co-cultures with FRα negative cells (FIGS. 7B, 7D and 7E). Together, these constructs displayed restricted or substantially reduced binding to CD3, yet were capable of activating T-cells in a target dependent manner.

Example 4: Assessment of T Cell Activating Activity of B7H3-Targeted Constrained CD3 Binding Constructs Constructs containing either a B7H3-targeted sdAb or a Fab as the tumor-associated antigen-binding domain were assessed for T-cell activating activity in a T cell reporter assay and in a T cell cytotoxicity assay. Activity of B7H3-targeted constrained CD3 engaging constructs that were formatted with an anti-B7H3 sdAb (e.g. cx5823, cx6079, cx6080, cs6081, cx3072 and cx5952) or anti-B7H3 MAB constructs formatted with a Fab (e.g. cx5067, cx6083 or cx6084) as the antigen-binding domain(s) were assessed (see FIGS. 3A-3C and Table E1.1). All tested constructs, except cx5067 and cx6079, contained a disulfide-stabilized anti-CD3 Fv (dsFv) containing an interchain disulfide bond created by the modification of anti-CD3 VH G44C paired with VL G100C. The anti-CD3 Fv of cx5067, designated MAB-Fv, was not disulfide-stabilized.

A. T Cell Reporter Activity

Figure 8A:
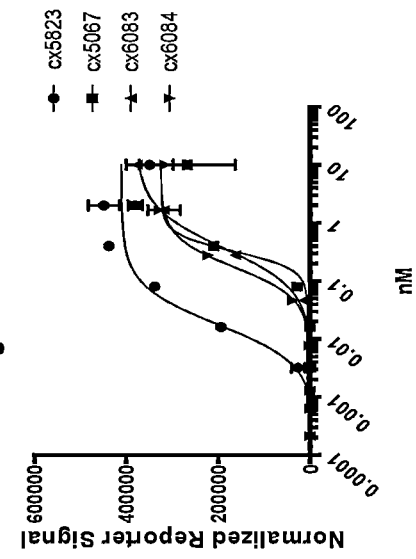
FIG. 8A-D depict the ability of representative B7H3-targeting constrained CD3 engaging constructs to agonize CD3 in a target dependent manner.
Figure 8C:
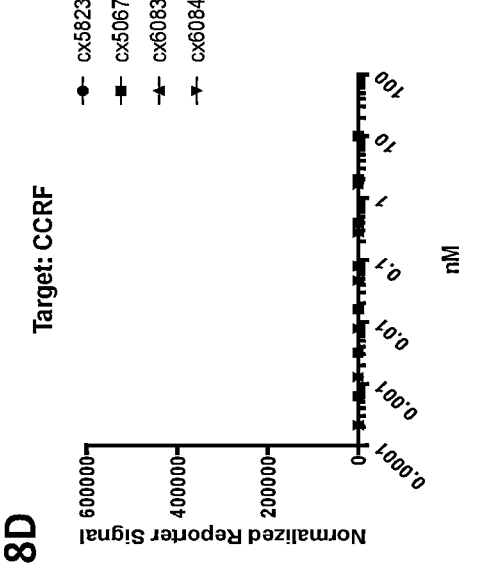
Figure 8B:
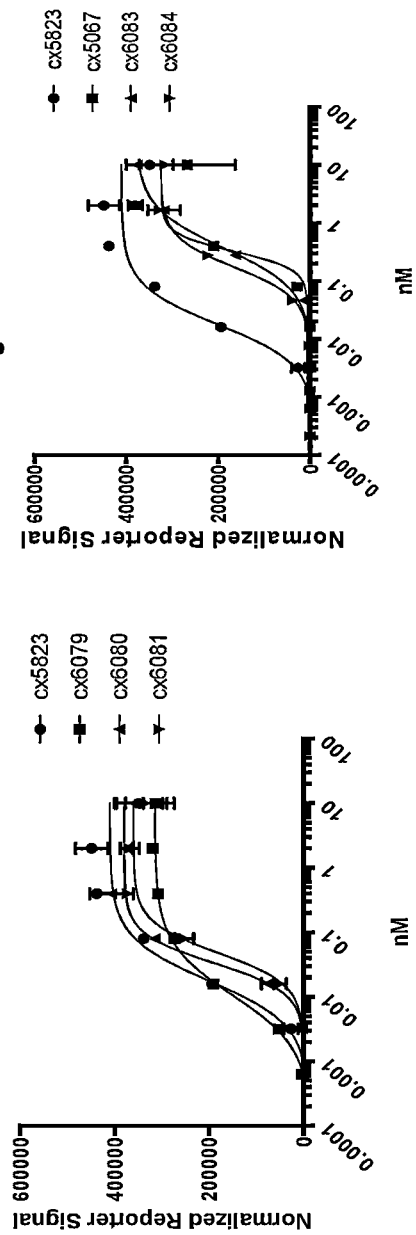
Figure 8D:
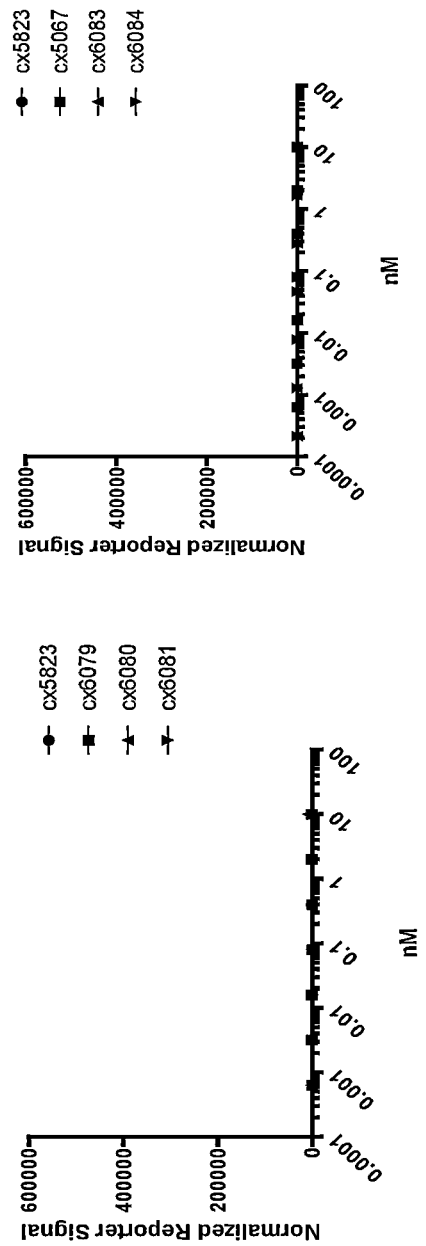

The NFAT-GFP CD3 Jurkat reporter described in Example 3 was used to compare the CD3 agonistic properties of B7H3-targeted constrained CD3 engaging constructs when co-cultured in the presence of B7H3-positive cells (A375) or non-target CCRF-CEM cells that naturally lack B7H3 expression. In this assay, anti-B7H3 sdAb constructs, cx5823, cx6079, cx6080 and cx6081, or anti-B7H3 Fabs constructs, cx5067, cx6083 and cx6084, were used as the B7H3-targeting domains. As shown in FIG. 8A, the constructs containing B7H3-targeted sdAb displayed similar potencies of antigen-dependent CD3 activation. As shown in FIG. 8C the exemplary cx5823 construct containing B7H3-targeted sdAbs was found to be superior at mediating antigen-dependent CD3 activation compared to the constructs containing B7H3-targeted Fabs. Although cx5823 is formatted with a binding domain for a costimulatory receptor, it is unlikely that this component contributed to the difference in results, since Jurkat T cells do not express the costimulatory receptor. None of the constructs demonstrated activity against the B7H3-negative CCRF-CEM cells (FIGS. 8B and 8D).

B. Cytotoxicity

To further assess activity of the molecules, exemplary B7H3-targeted constructs cx3072 and cx5952 (each formatted as sdAb-dsFv), cx6083 and cx6084 (MAB-dsFv), cx5067 (MAB-Fv), cx6079 (sdAb-Fv), and cx6080 and cx 6081 (sdAb-dsFv) were tested in a T-cell-mediated cytotoxicity assay. Target cells included the B7H3 positive cell line, A375, and either modified A375 cells, wherein B7H3 gene was disrupted by CRISPR (A375:B7H3 KD), or CCRF-CEM cells that naturally lacked B7H3 expression. Target cells were seeded at $1.0 \times 10^4$ cells per well, allowed to settle at room temperature for uniform distribution, and incubated for several hours at 37° C. Primary T cells were negatively enriched from PBMCs isolated from healthy human donor leukopaks and added at a 10:1 T cell-to-target cell ratio. Green caspase-3/7 reagent was added, which fluorescently labels nuclear DNA of cells undergoing apoptosis was added. Multispecific constructs with constrained CD3 engaging activity were titrated onto the co-culture and assay plates were serially imaged using an IncuCyte ZOOM system. Target cell death was determined by measuring total red/green overlap object area.

Figure 9A:
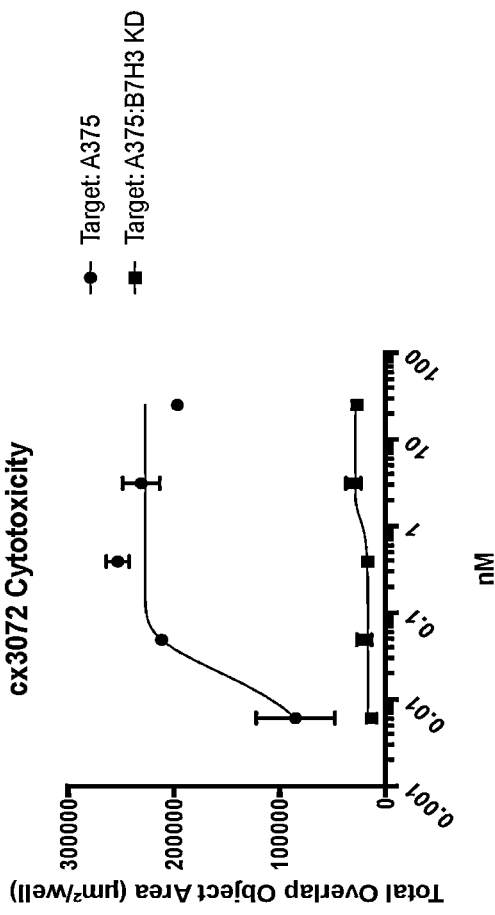
FIG. 9A depicts the ability of a representative B7H3-targeting constrained CD3 engaging construct (cx3072) to induce T-cell mediated cytotoxicity in a target dependent manner. Target cells were labeled with cytoID red label and dying cells were visualized by addition of Caspase 3/7 green reagent. Cytotoxicity was assessed by determining the overlap area of red target cells and green dying cells. A B7H3 negative A375 cell line, generated by CRISPR technology was used to test antigen specific T-cell mediated cytotoxicity. cx3072 was unable to elicit T-cell mediated cytotoxicity of these B7H3 deficient cells.
Figure 9B:
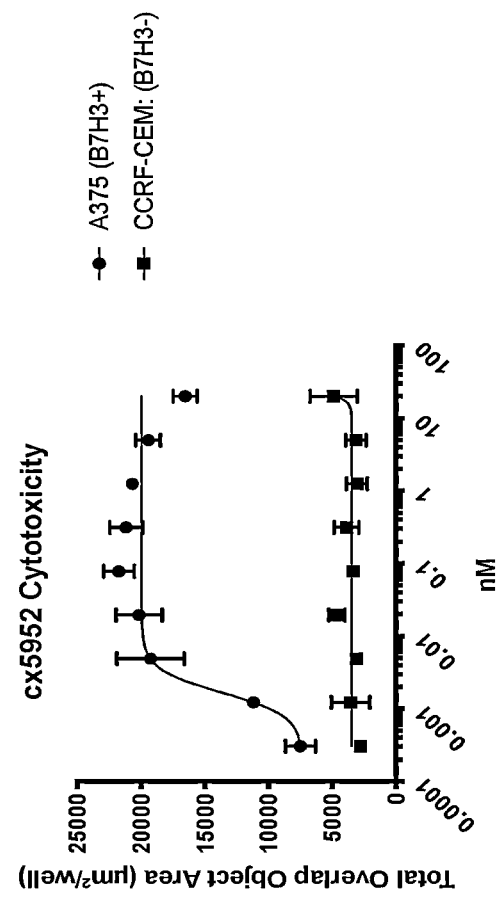
FIG. 9B shows the ability of cx5952 to induce T-cell mediated cytotoxicity in the presence of B7H3 positive A375 cells, but not in the presence of B7H3 negative CCRF-CEM cells.

As shown in FIGS. 9A and 9B, exemplary constructs cx3072 and cx5952 containing sdAb B7H3-targeted antigen-binding domains induced potent T-cell-mediated cytotoxicity of B7H3 positive (A375) but not B7H3 negative cell lines.

When compared to exemplary B7H3-targeting constrained CD3 engagers with Fab B7H3-targeting domains (cx5067, cx6083 and cx6084), the exemplary cx5952 sdAb B7H3-targeting constrained CD3 engager mediated enhanced target-dependent T-cell cytotoxicity (FIG. 10A). No measurable T cell cytotoxicity was observed against the B7H3 negative cell line CCRF-CEM for any of the tested constructs, consistent with the capacity to potently induce antigen-dependent T-cell activation (FIG. 10B). Of the constructs tested, representative MAB-dsFV constructs cx6084 and cx6083 contained the engineered disulfide, whereas the representative MAB-FV construct cx5067 lacked this stabilizing modification. Notably cx6083 and cx5067 are identical with the exception of the presence (cx6083) or absence (cx5067) of the engineered disulfide within the anti-CD3 FV domain (depicted in FIG. 3C). The engineered disulfide was created by the modification of G44C within VH and G100C within VL. As shown in FIG. 10A, cx6083 displayed superior potency in mediating target-dependent T-cell cytotoxicity compared to cx5067, suggesting that the incorporation of the inter-domain disulfide is beneficial in T-cell mediated cytotoxicity, likely by enhancing proper association of the VH and VL domains that comprise the anti-CD3 FV.

When compared to other exemplary B7H3-targeting constrained CD3 engagers with sdAb B7H3-targeting domains (cx6079, cx6080 and cx6081), the exemplary cx5952 sdAb B7H3-targeting constrained CD3 engager mediated enhanced target-dependent T-cell cytotoxicity (FIG. 10C). No measurable T cell cytotoxicity was observed against the B7H3 negative cell line CCRF-CEM for any of the tested constructs, consistent with the capacity to potently induce antigen-dependent T-cell activation (FIG. 10D). Of the constructs tested, sdAb-dsFV constructs cx5952, cx6080 and cx6081 contained the engineered disulfide linkage, whereas the sdAb-FV construct cx6079 lacked this stabilizing modification. The engineered disulfide was created by the modification of G44C within VH and G100C within VL. Notably, cx5952 was engineered to have two distinct B7H3 targeting domains, one located at the amino terminal and one located at the carboxy terminal. cx6079, cx6080, and cx6081 were engineered to have two identical B7H3 targeting domains, both located at the amino terminal (see FIG. 3A).

C. T Cell Modulation

To further assess T cell modulation, exemplary multispecific CD3 constrained binding constructs was assessed by monitoring the ability of the constructs to modulate T cell activation markers. To assess T cell activation, suspension cells from T cell cytotoxicity assays above, involving culture of T cells with B7H3 positive (A375) or B7H3 negative cell lines (CCRF-CEM) in the presence of an exemplary B7H3-targeted constrained CD3 engaging construct, cx5952, were collected. Cells were stained with a live/dead stain and fluorophore-conjugated anti-CD4, anti-CD8, anti-CD25, anti-CD69, and/or anti-CD71 antibodies. Cells were analyzed using a SONY SA3800 spectral analyzer and CD4+ or CD8+ T cell activation was determined by measuring expression levels of CD25, CD69 or CD71 or percent CD25-, CD69- or CD71-positive.

Figure 11A:
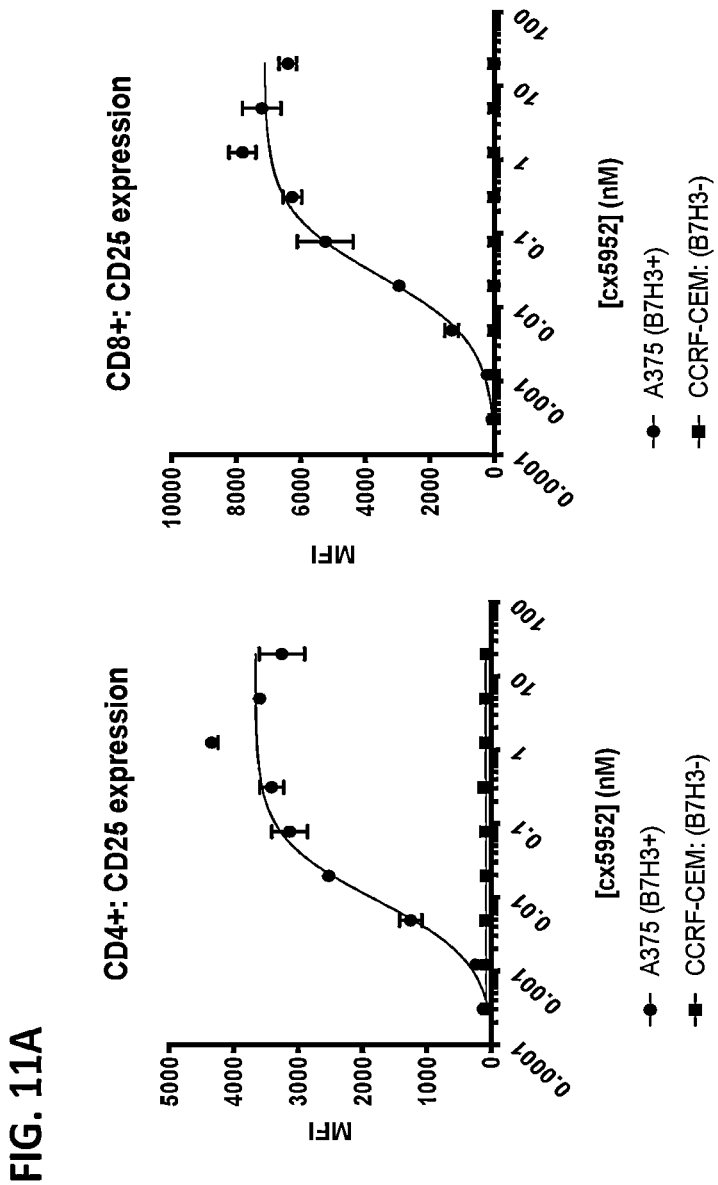
FIGS. 11A-C depict the ability of a representative B7H3-targeting constrained CD3 engaging construct (cx5952) to induce T-cell mediated T-cell activation in a target dependent manner. T-cell activation of CD4+ or CD8+ T cells was assessed by expression of the T cell activation markers CD25 (FIG. 11A), CD69 (FIG. 11B), and CD71 (FIG. 11C).
Figure 11B:
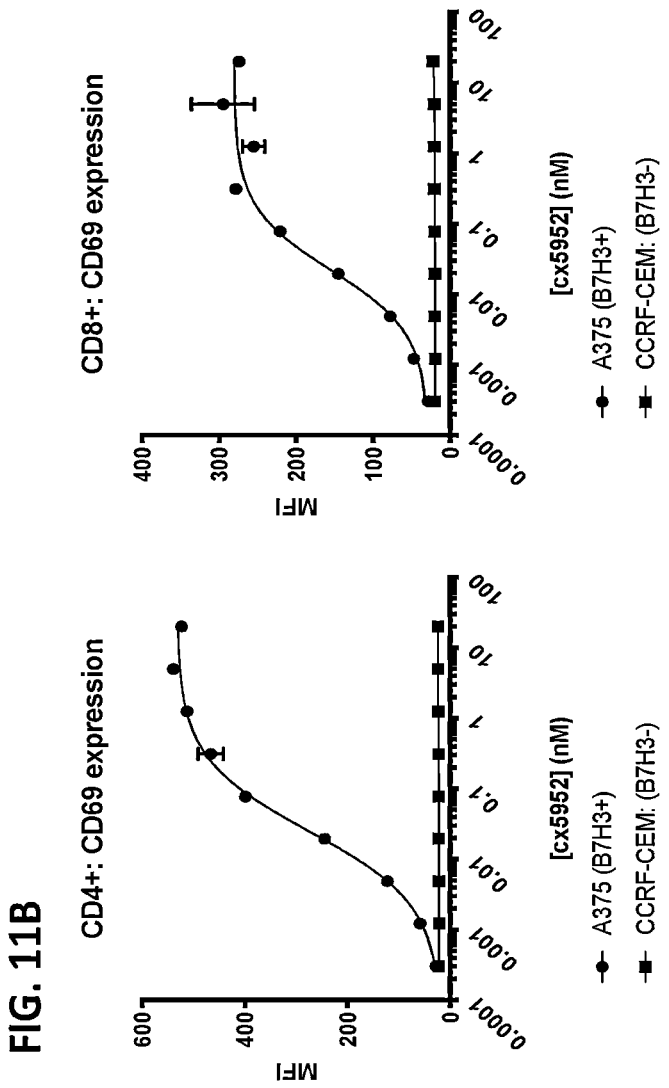
Figure 11C:
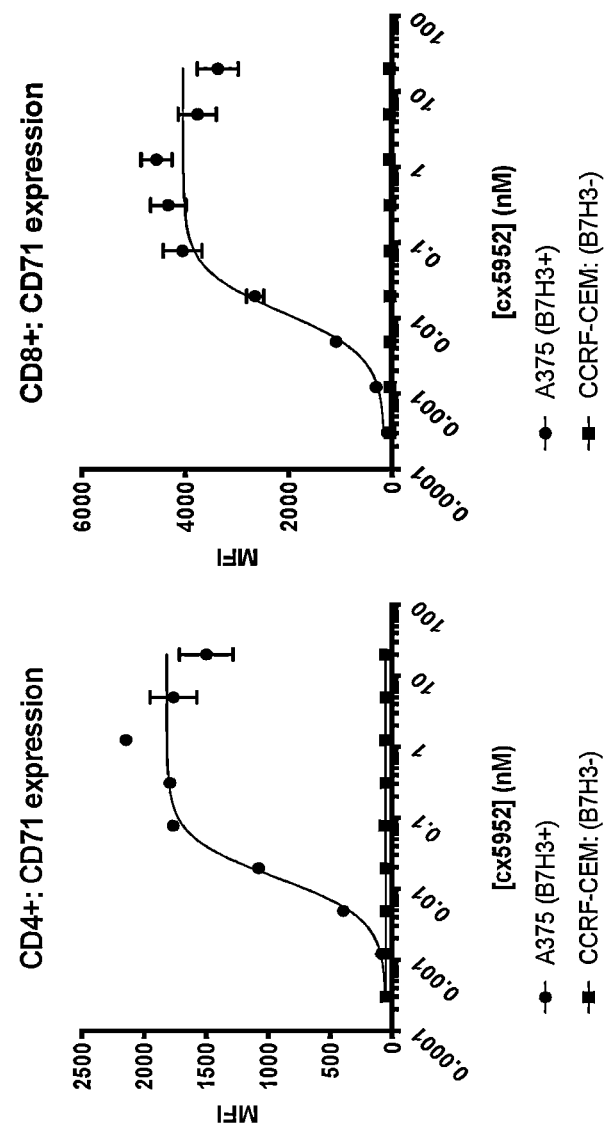

Results are shown for CD25 expression (FIG. 11A), CD69 expression (FIG. 11B) and CD71 expression (FIG. 11C) on CD4+ and CD8+ T cells following the co-culture with B7H3 positive (A375) or B7H3 negative cell lines (CCRF-CEM) in the presence of cx5952. The results showed that cx5952 mediated a dose-dependent B7H3-dependent T-cell activation via CD3 binding, as evidenced by increased expression of CD25, CD69 and CD71 in CD4+ and CD8+ T cells.

Figure 11D:
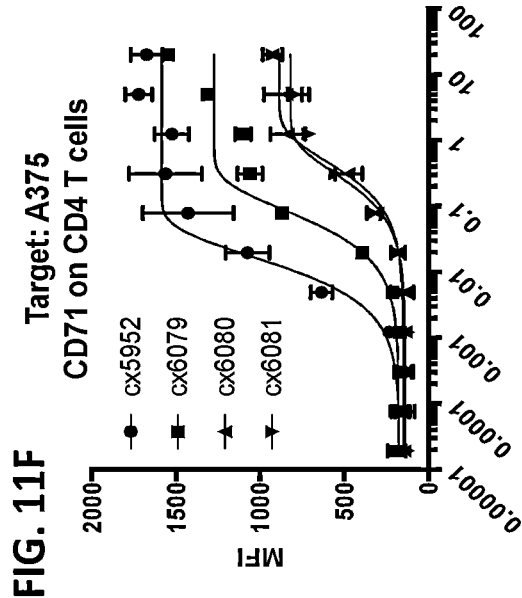
Figure 11F:
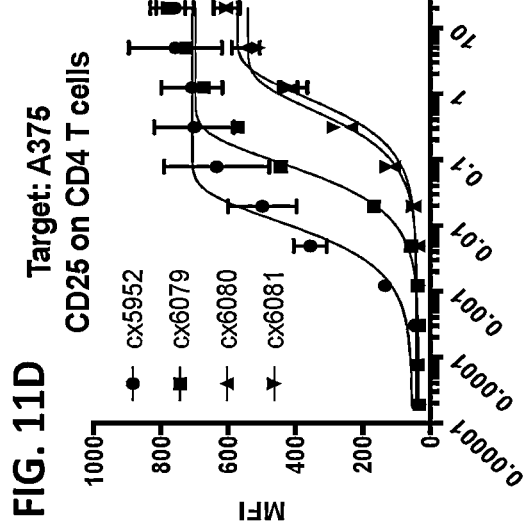
Figure 11E:
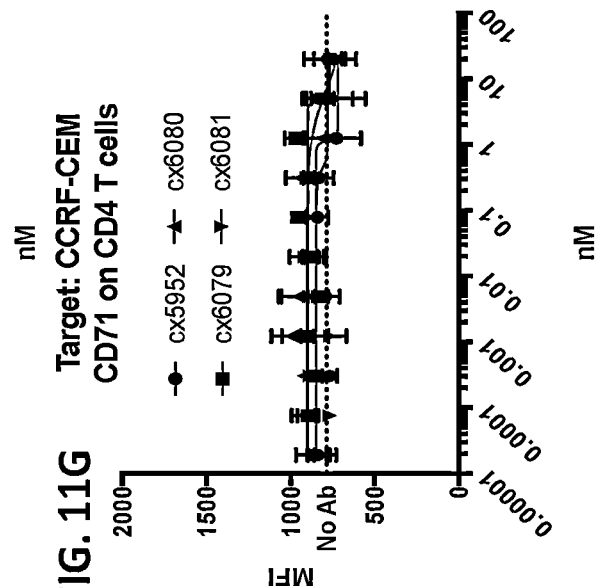
Figure 11G:
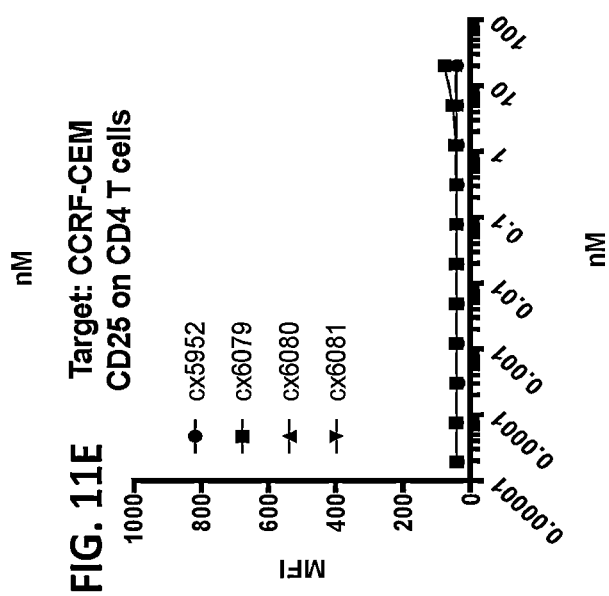

When compared to the other exemplary B7H3-targeting constrained CD3 engagers with sdAb B7H3-targeting domains (cx6079, cx6080 and cx6081), the exemplary cx5952 sdAb B7H3-targeting constrained CD3 engager mediated increased T cell activation as evidenced by increased expression of CD25 in CD4+ T cells (FIG. 11D) and in CD8+ T cells (FIG. 11H) and increased expression of CD71 in CD4+ T cells (FIG. 11F) and in CD8+ T cells (FIG. 11J). Increased expression of the surface markers on T cells was not observed in the presence of the B7H3-targeting constrained CD3 engager constructs in cultures with B7H3 negative cell lines (FIGS. 11E and 11G for CD4+ T cells and FIGS. 11I and 11K for CD8+ T cells).

D. T Cell Cytokine Production

Figure 12A:
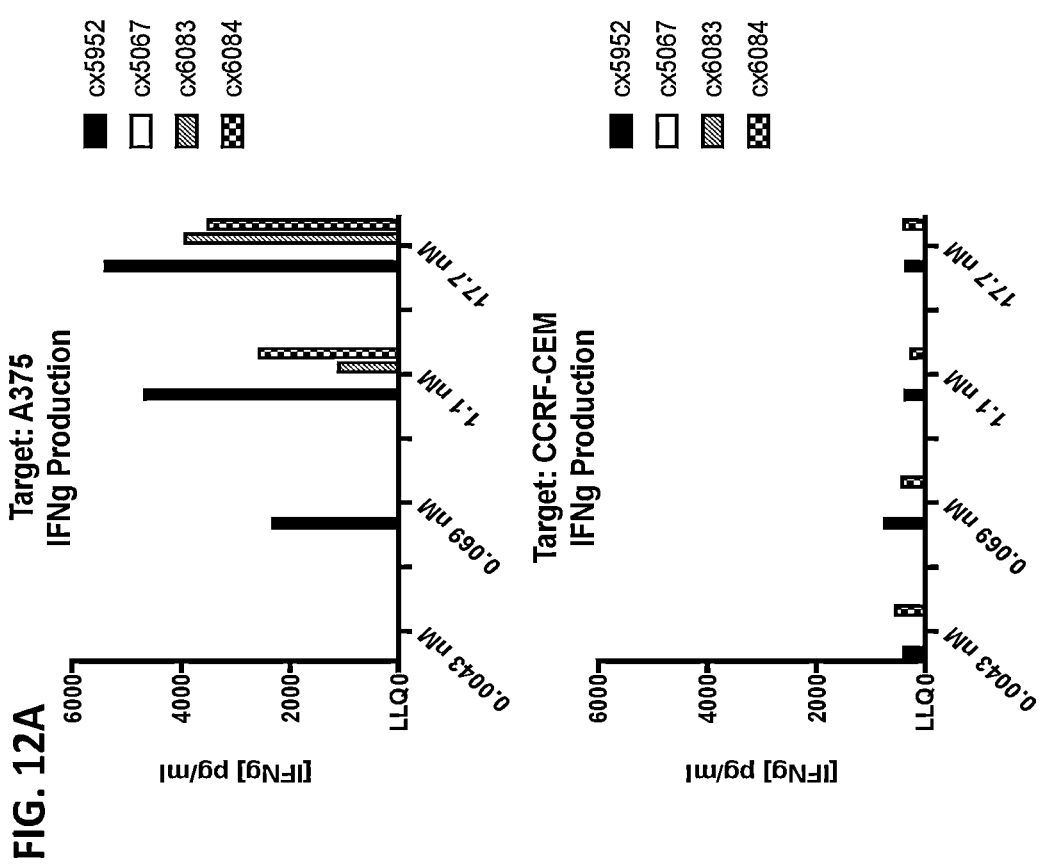
FIG. 12A depicts the ability of representative B7H3-targeting constrained CD3 engaging constructs to induce IFNγ production in a target dependent manner.

Supernatants from T cell cytotoxicity tumor cell co-culture assays, involving co-culture of T cells with B7H3 positive, A375 or negative, CCRF-CEM cells in the presence of cx5952, cx6083, cx6084 or cx5067, were analyzed for IFNγ content by sandwich ELISA. A standard curve was generated from which cytokine concentration values of supernatant samples were interpolated. Samples that had absorbance values below the lower limit of detection were assigned a cytokine concentration equal to half that of the lowest standard concentration. As shown in FIG. 12A, the representative sdAb-Fc-dsFV-sdAb construct, cx5952, was superior to the tested B7H3-targeted FAB containing constructs, cx6083, cx6084 and cx5067 at eliciting target-dependent cytokine release from activated T-cells. Importantly, the MAB-dsFV constructs, cx6083 and cx6084 were superior to the MAB-FV construct, cx5067, demonstrating the importance of interdomain disulfide stabilizing modification for enhancing T-cell function.

Figure 12B:
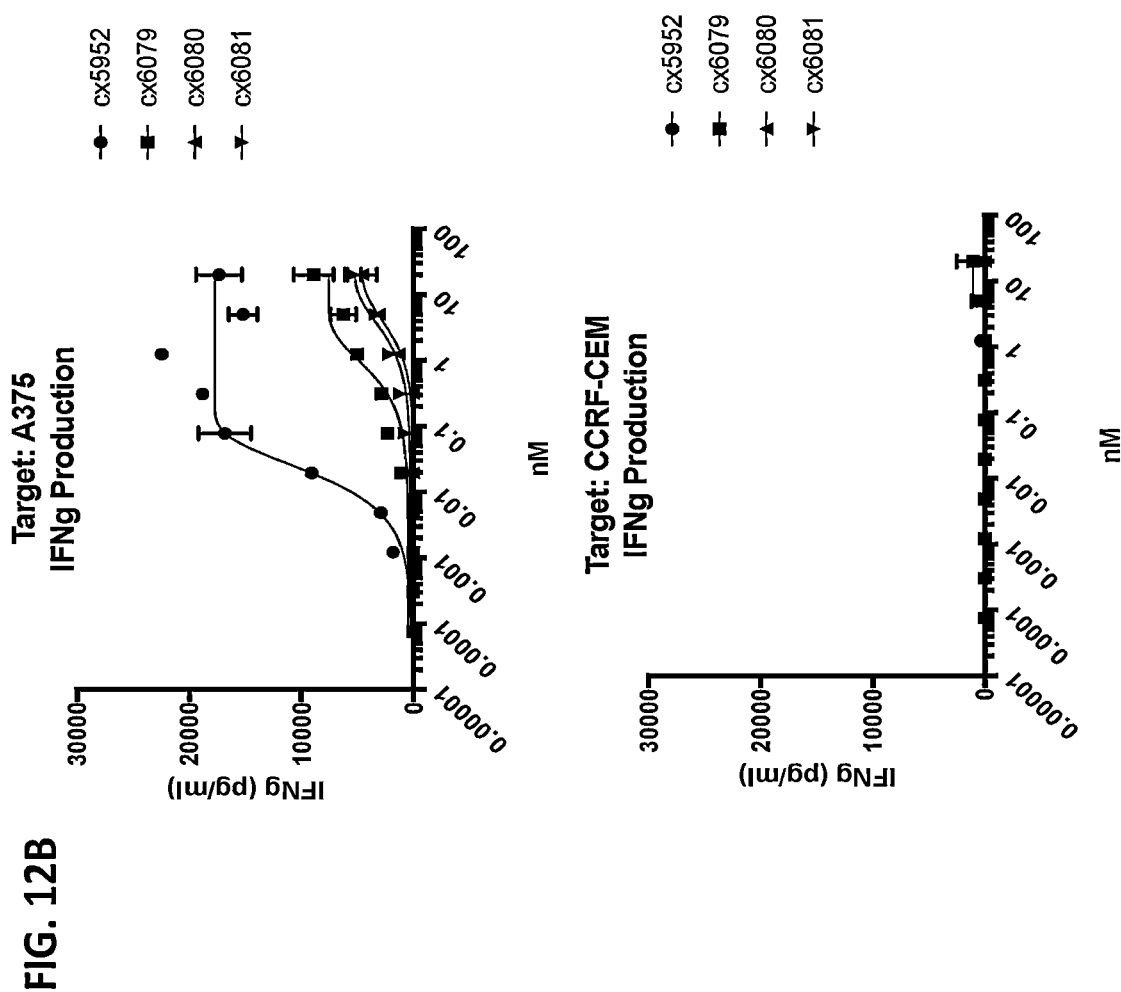
FIG. 12B depicts the ability of representative B7H3-targeting constrained CD3 engaging constructs to induce IFNγ production in a target dependent manner.

When compared to the other exemplary B7H3-targeting constrained CD3 engagers with sdAb B7H3-targeting domains (cx6079, cx6080 and cx6081), the exemplary cx5952 sdAb B7H3-targeting constrained CD3 engager mediated substantially increased production of IFNγ in the presence of B7H3-target cells T cells but not in cultures with B7H3 negative cell lines (FIG. 12B)

E. Summary

These observations further support that the antigen-targeted constrained CD3 format provided herein lack or exhibit reduced T-cell binding in isolation while maintaining potent B7H3-dependent T-cell cytotoxicity inducing capacities. Without wishing to be bound by theory, together these results show that utilization of antigen targeted sdAbs instead of a Fabs may reduce the immune synapse distance between the TAA expressing tumor cell and the CD3 expressing T-cells and enhance T cell activity and cytotoxicity. Notably, it was found that the inclusion of an interchain disulfide bond created by the modification of anti-CD3 VH G44C paired with VL G100C greatly enhanced the activity of constrained CD3 engaging constructs. Further, the more potent B7H3-dependent T cell activity by cx5952 compared to other sdAb B7H3-targeting domain constructs suggests that the positioning of the B7H3-targeting sdAb C-terminal to the anti-CD3 binding domain or the fact that cx5952 binds two distinct epitopes on B7H3 whereas the other constructs tested bind to a single epitope in a bivalent manner, contributed to this enhanced activity.

Example 5: Assessment of CD3-Constrained Multispecific Constructs Containing Single or Multiple B7H3-Binding Targeting Domains Activity of constructs containing a monovalent sdAb antigen-binding domain (positioned at either the N or C-terminus) was compared to activity of dual binding (bivalent) constructs that contained antigen-targeting sdAbs positioned at both the N and C-termini. Binding was assessed substantially as described in Example 2 and T cell activity was assessed in the Jurkat reporter assay and T cell cytotoxicity assays substantially as described in Examples 3 and 4.

A. Binding

Figure 13A:
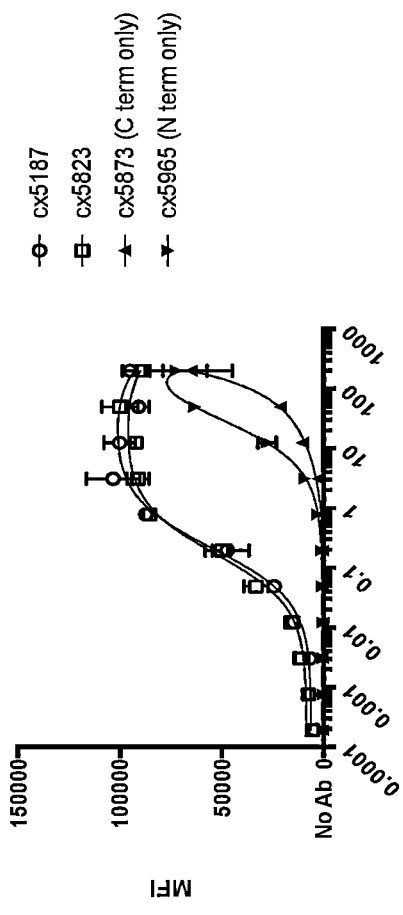
FIGS. 13A and 13B depict cellular binding of representative B7H3-targeting constrained CD3 engaging constructs. cx5187 and cx5823 each contain two B7H3 binding domains while complex cx5873 and cx5965 each contain one B7H3 binding domain.
Figure 13B:
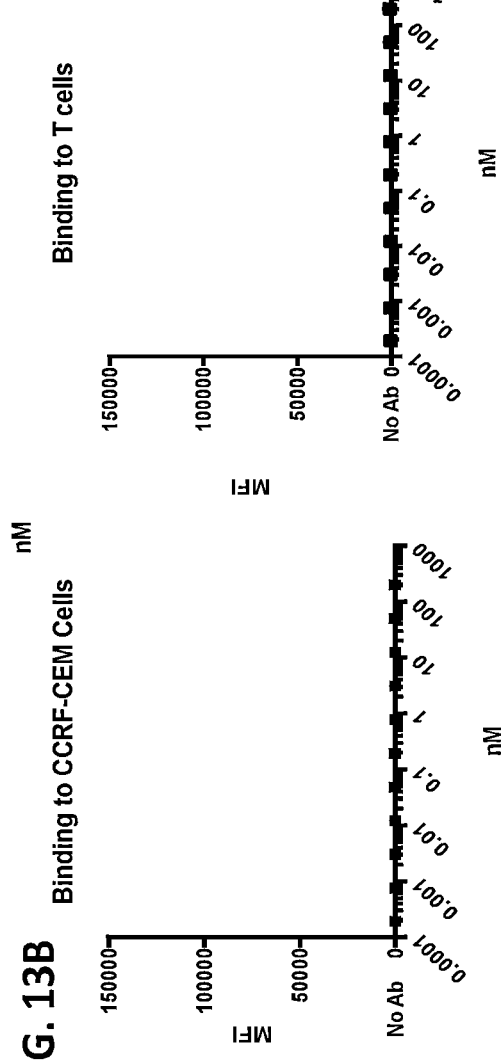

As shown in FIG. 13A the bivalent B7H3-targeting constrained CD3 engaging constructs, cx5187 and cx5823, displayed higher affinity binding to B7H3 positive A375 cells, compared to the monovalent versions, cx5873 and cx5965. None of these constructs displayed any detectable binding to B7H3 negative CCRF-CEM cells or isolated T-cells (FIG. 13B).

B. T Cell Reporter Activity

Figure 13C:
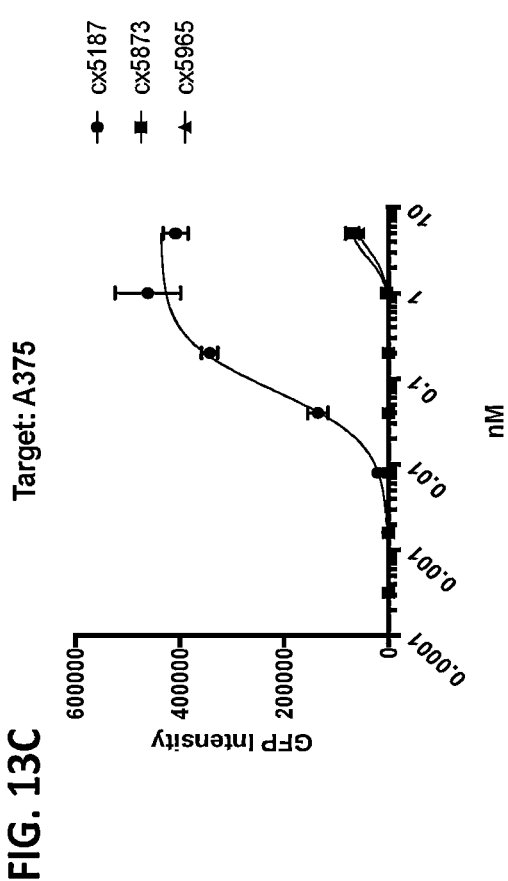
FIG. 13C and FIG. 13D depict the ability of representative B7H3-targeting constrained CD3 engaging constructs to agonize CD3 in a target dependent manner.
Figure 13D:
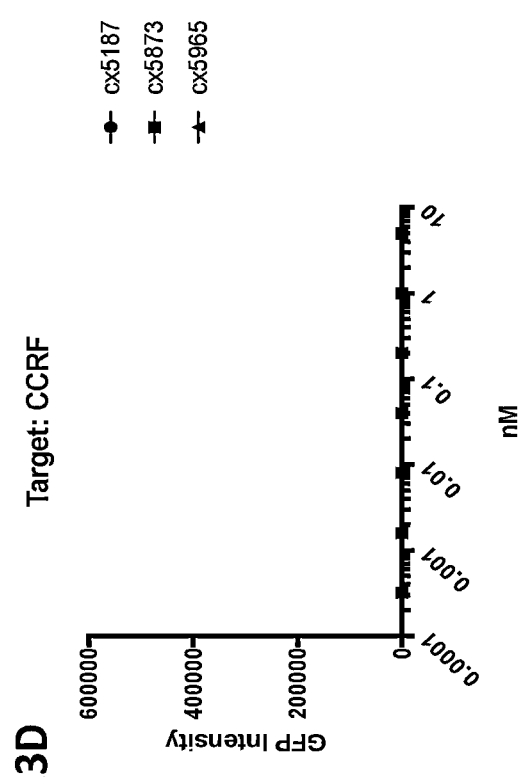

B7H3 Antigen-dependent CD3 agonistic capacities of antigen-targeted constrained CD3 engaging constructs that engage the antigen in a monovalent or bivalent manner were assessed using CD3-NFAT Jurkat reporter cells, in an assay substantially as described above. As shown in FIG. 13C, substantially increased fluorescence reporter activity was observed in the presence of the exemplary bivalent B7H3-targeted construct cx5187 compared to reporter activity for the exemplary monovalent constructs cs5873 and cx5965. No reporter activity was observed when constructs were incubated with Jurkat reporter cells co-cultured with B7H3-negative CCRF target cells (FIG. 13D).

C. Cytotoxic Activity

Cytotoxicity of B7H3-targeted CD3 constrained binding constructs was assessed against a melanoma cell line, A375, and a T-cell acute lymphoblastic leukemia cell line, CCRF-CEM, which were used as B7H3 positive and negative cell lines, respectively. Cytotoxicity was assessed substantially as described in Example 4. As shown in FIG. 14A an exemplary bivalent B7H3-targeted constrained CD3 engaging construct, cx5187, displayed enhanced target-dependent T-cell mediated cytotoxicity compared to the monovalent versions of the constructs, cx5873 and cx5965. In these assays, no cytotoxicity was observed in the absence of B7H3 expression of the target cells, as shown in FIG. 14B wherein the CCRF-CEM cells were used as target cells.

D. T Cell Modulation

T cell modulation was assessed by monitoring expression of CD25, substantially as described in Example 4, in suspension cells from T cell cytotoxicity assays above, involving culture of T cells with B7H3 positive (A375) or B7H3 negative cell lines (CCRF-CEM) in the presence of cx5187, cx5873 or cx5965. As shown in FIGS. 15A and 15B, an exemplary bivalent B7H3-targeted constrained CD3 engaging construct, cx5187, displayed enhanced target-dependent T-cell mediated activation compared to the monovalent versions of the constructs, cx5873 and cx5965, as evidenced by enhanced potency of CD25 upregulation on CD4 and CD8 T-cells. In these assays, no T-cell activation was observed in the absence of B7H3 expression of the target cells, as shown in FIGS. 15C and 15D, wherein the CCRF-CEM cells were used as target cells. These results demonstrated that the B7H3-targeting constrained CD3 engaging constructs induced potent antigen-dependent activation of both CD4 and CD8 T-cells.

D. Summary

Together, these results demonstrate that bivalent antigen-targeted constrained CD3 engaging constructs displayed superior antigen-dependent CD3 binding and activity than the monovalent antigen-targeted constrained CD3 engaging constructs. These results are consistent with a finding that constructs containing dual antigen-binding domains positioned at both the N and C-termini have superior binding and T cell activity than monovalent constructs containing only a single monovalent antigen-binding domain. Furthermore, without wishing to be bound by theory, positioning one of the sdAbs C-terminal to the CD3 binding domain may form a more optimal immune synapse compared to constructs wherein the sdAbs are only positioned N-terminal to the Fc as the latter may increase the immune synapse distance.

Example 6: Assessment of a CD3-Constrained Multispecific Constructs Containing B7113-Targeting sdAb and Fab Domains Constructs containing either B7H3-targeted sdAb(s) or a Fab as the tumor-associated antigen-binding domain were assessed for T-cell activating activity. Activity of B7H3-targeted constrained CD3 engaging constructs that were formatted with anti-B7H3 sdAbs (e.g. cx5952 and cx6079) or anti-B7H3 MAB constructs formatted with a Fab (e.g. cx5067, cx6083 or cx6084) as the antigen-binding domain (s) were assessed (see FIGS. 3A and 3C and Table E1.1 and E1.2). All tested constructs, except cx6079 and cx5067, contained a disulfide-stabilized anti-CD3 Fv (dsFv) containing an interchain disulfide bond created by the modification of anti-CD3 VH G44C paired with VL G100C. The anti-CD3 Fv of cx5067, designated MAB-Fv, and the anti-CD3 Fv of cx6079, designated sdAb-Fc-Fv, were not disulfide-stabilized. Additionally, cx5952 was engineered to contain two distinct B7H3-targeting sdAb domains, with one located N-terminal to the Fc domain and one located C-terminal to the CD3-binding domain. By contrast, cx6079 was engineered to contain two identical B7H3-targeting sdAb domains, both located N-terminal to the Fc domain. The Fvs of all three Fab constructs were engineered to be N-terminal to the Fc domain.

A. Cytotoxicity

Figure 16A:
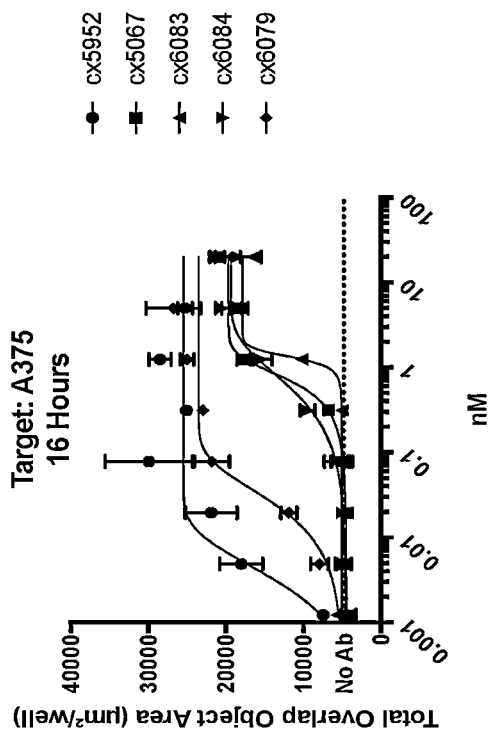
FIGS. 16A and 16B demonstrate the ability of representative B7H3-targeting constrained CD3 engaging constructs to elicit T-cell mediated cytotoxicity in the presence of B7H3-positive A375 cells (FIG. 16A) but not in the presence of CCRF-CEM B7H3-negative cells (FIG. 16B).
Figure 16B:
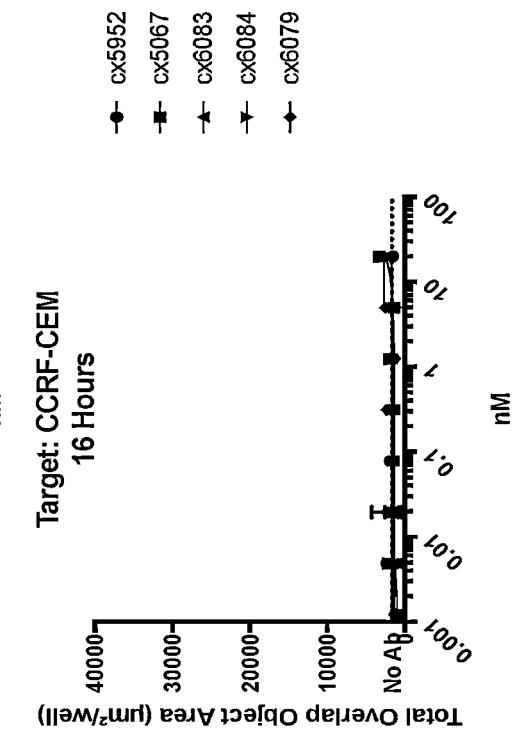
Figure 16G:
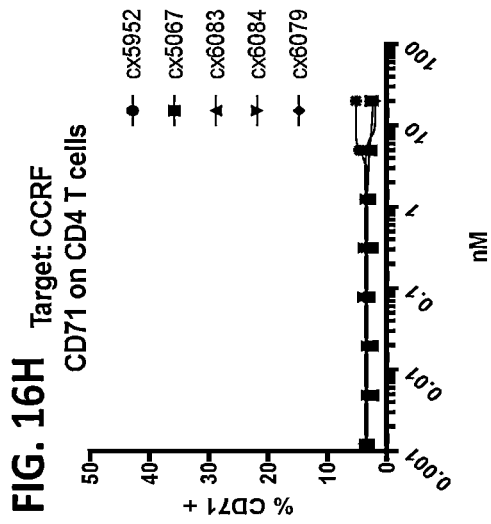
Figure 16I:
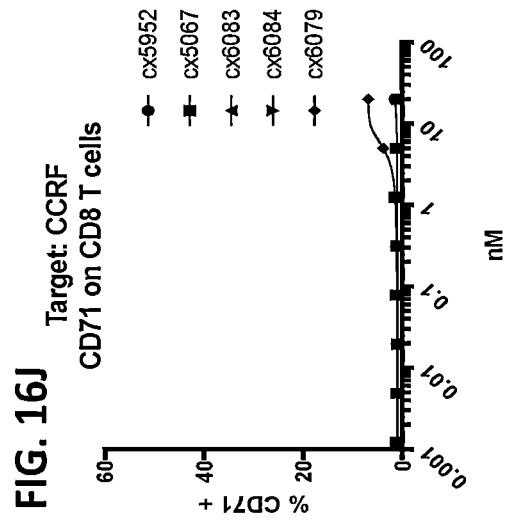
Figure 16H:
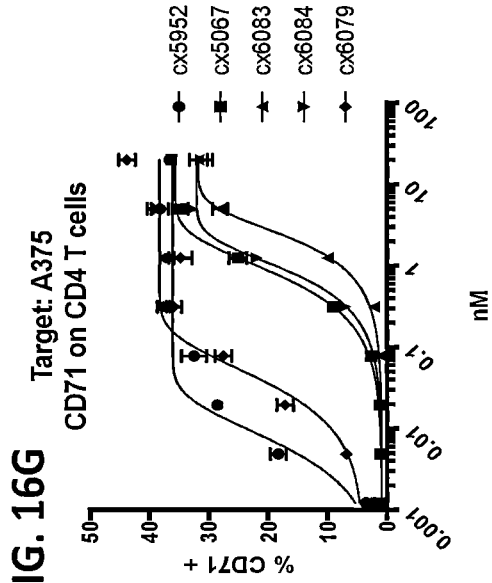
Figure 16J:
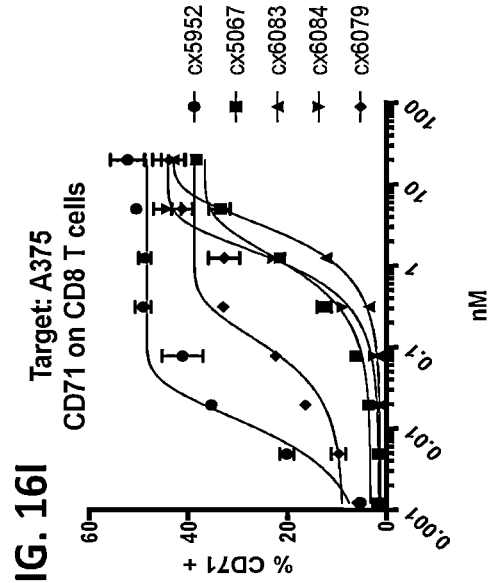

Cytotoxicity of B7H3-targeted CD3 constrained binding constructs was assessed substantially as described in Example 4. Cytotoxicity was assessed against a melanoma cell line, A375, and a T-cell acute lymphoblastic leukemia cell line, CCRF-CEM, which were used as B7H3 positive and negative cell lines, respectively. As shown in FIG. 16A the exemplary constrained CD3 engaging constructs formatted with B7H3-targeting sdAbs, cx5952 and cx6079, were superior at eliciting antigen-dependent T-cell cytotoxicity compared to to the anti-B7H3 MAB constructs formatted with a Fab, cx5067, cx6083, and cx6084. Notably, cx5952 was more potent than cx6079, suggesting the positioning of the B7H3-targeting sdAb C-terminal to the anti-CD3 binding domain and/or the stabilization of the anti-CD3 FV via engineered disulfide contributed to this enhanced activity. In these assays, no cytotoxicity was observed in the presence of B7H3-negative CRF-CEM cells target cells, as shown in FIG. 16B.

B. T Cell Modulation

To further assess T cell modulation, exemplary multispecific CD3 constrained binding constructs were assessed by monitoring the ability of the constructs to modulate T cell activation markers, substantially as described in Example 4. To assess T cell activation, suspension cells from T cell cytotoxicity assays above, involving culture of T cells with B7H3 positive (A375) or B7H3 negative cell lines (CCRF-CEM) in the presence of an exemplary B7H3-targeted constrained CD3 engaging constructs, were collected. Tested constructs included anti-B7H3 constructs formatted with sdAbs (e.g. cx5952 and cx6079) and anti-B7H3 constructs formatted with a Fab (e.g. cx5067, cx6083 and cx6084)

Cells were stained with a live/dead stain and fluorophore-conjugated anti-CD4, anti-CD8, anti-CD25 and/or anti-CD71 antibodies. Cells were analyzed using a SONY SA3800 spectral analyzer and CD4+ or CD8+ T cell activation was determined by measuring expression levels of CD25 or CD71 or percent CD25- or CD71-positive.

Results are shown for CD25 expression (FIG. 16C-F) and CD71 expression (FIG. 16G-J) on CD4+ and CD8+ T cells following the co-culture with B7H3 positive (A375) or B7H3 negative cell lines (CCRF-CEM) in the presence of the described constructs. The results showed that cx5952 mediated a dose-dependent B7H3-dependent T-cell activation via CD3 binding, as evidenced by increased expression of CD25 and CD71 in CD4+ and CD8+ T cells. cx5952 was the most potent over other B7H3-targeted constrained CD3 engaging constructs and inducing T-dependent T-cell activation.

C. T Cell Cytokine Production

Supernatants from T cell cytotoxicity tumor cell co-culture assays, involving co-culture of T cells with B7H3 positive, A375 or negative, CCRF-CEM cells in the presence of cx5952, cx6079, cx6083, cx6084 or cx5067, were analyzed for IFNγ content by sandwich ELISA. A standard curve was generated from which cytokine concentration values of supernatant samples were interpolated. Samples that had absorbance values below the lower limit of detection were assigned a cytokine concentration equal to half that of the lowest standard concentration. As shown in FIG. 16K, the representative sdAb-Fc-dsFV-sdAb construct, cx5952, was superior to the tested B7H3-targeted FAB containing constructs, cx6083, cx6084 and cx5067 at eliciting target-dependent cytokine release from activated T-cells. This is consistent with the finding from the antigen dependent cytotoxicity and activation assays. Importantly, the MAB-dsFV constructs, cx6083 and cx6084 were superior to the MAB-FV construct, cx5067, demonstrating the importance of interdomain disulfide stabilizing modification for enhancing T-cell function.

D. Summary

Together, these results demonstrate that constrained anti-CD3 constructs formatted with anti-B7H3 sdAb binding domains were superior at eliciting antigen-dependent T-cell cytotoxicity compared to the anti-B7H3 MAB constructs formatted with a Fab B7H3 binding domain. Further, that cx5952 was more potent than cx6079 suggested that the positioning of the B7H3-targeting sdAb C-terminal to the CD3 binding domain, the stabilization of the anti-CD3 FV via engineered disulfide, or both, contribute to enhanced activity. Without wishing to be bound by theory, positioning one of the sdAbs C-terminal to the CD3 binding domain may form a more optimal immune synapse compared to constructs wherein the sdAbs are only positioned N-terminal to the Fc as the latter may increase the immune synapse distance.

Example 7: Assessment of CD3-Constrained Multispecific Constructs Containing Single or Multiple Antigen-Binding DLL3-Targeting Domains This example describes the assessment and characterization of exemplary generated DLL3-targeted constrained CD3 engaging constructs in human primary T cell in vitro assays.

Binding and activity of DLL3-targeted constrained CD3 engaging constructs that were formatted with an anti-DLL3 sdAb (e.g. cx5352, cx5800, cx5801, and cx5499) as the antigen-binding domain(s) were assessed (see FIGS. 4A-4B and Table E1.1). All tested constructs contained a disulfide-stabilized anti-CD3 Fv (dsFv) containing an interchain disulfide bond created by the modification of anti-CD3 VH G44C paired with VL G100C. Further, the DLL-3-targeted constructs were engineered to contain a co-stimulatory receptor sdAb C-terminal to the CD3 dsFv, except for cx5499, which did not contain this co-stimulatory receptor sdAb domain.

A. Binding

Binding was assessed substantially as described in Example 2. As shown in FIG. 17A the bivalent DLL3-targeting constrained CD3 engaging constructs, cx5352 displayed higher affinity binding to DLL3 positive, SHP-77 cells compared to the monovalent versions, cx5800 and cx5801. None of the constructs tested displayed binding to DLL3-negative primary T cells, as depicted in FIG. 17B. These binding assays were conducted by flow cytometry, wherein bound constructs were detected using a fluorophore-conjugated anti-human IgG Fc secondary antibody.

A. T Cell Reporter Activity

Figure 17C:
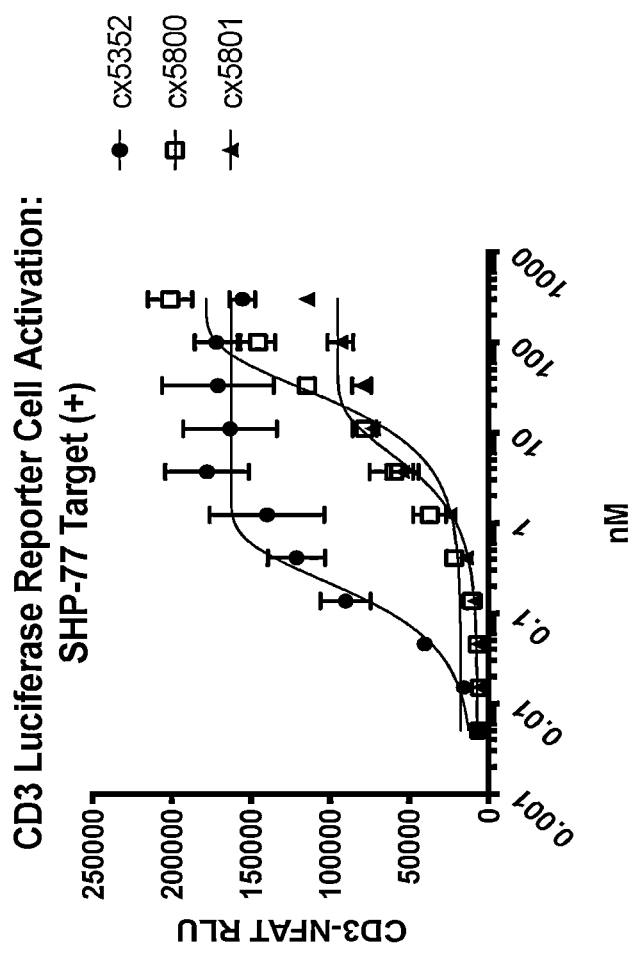
FIG. 17C depicts the ability of representative DLL3-targeting constrained CD3 engaging constructs to agonize CD3 signaling in the presence of DLL3 positive SHP-77 cells. Engaging DLL3 positive cells with a construct that is bivalent and bi-epitopic to DLL3 (cx5352) induced more potent T-cell activation than constructs that are monovalent to DLL3 (cx5800 and cx5801). A Jurkat CD3 NFAT-Luciferase reporter cell line was used to assess CD3 signaling.

T cell activity was assessed in a reporter assay substantially as described in Example 2, except that Jurkat cells expressing NFAT-driven Luciferase were used and luciferase activity was monitored. NFAT-driven Luciferase CD3 Jurkat reporter cells were co-cultured with SHP-77 (DLL3-positive) target cells in the presence of monovalent and bivalent constructs containing antigen-binding domains against the DLL3 antigen (see FIG. 4A). Specifically, as shown in FIG. 17C, the exemplary bivalent construct cx5352 induced substantially greater luciferase activity in this assay compared to the exemplary monovalent constructs cx5800 and cx5801. These results are consistent with results observed with B7H3-targeted constructs, thereby indicating that the activity of the constructs is not specific to a particular target antigen.

C. Cytotoxicity

Figure 18A:
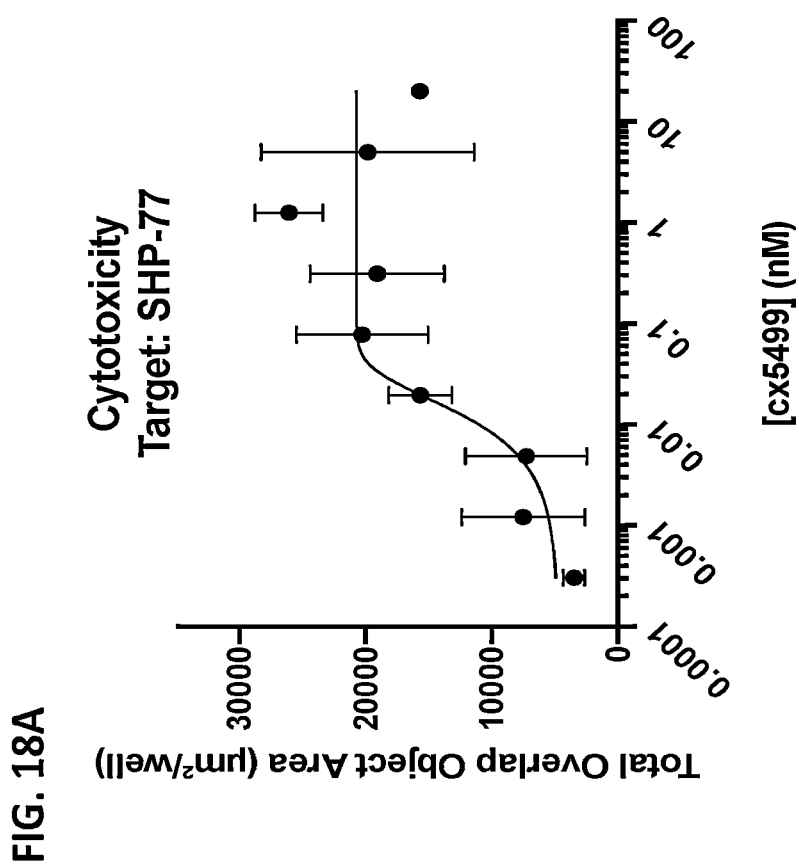

Cytotoxicity of cx5499, a DLL3-targeted CD3 constrained binding construct formatted with two distinct sdAb binding domains located at its amino and carboxy termini, was assessed against a DLL3 expressing cell line, SHP-77, using an assay substantially as described in Example 4. As shown in FIG. 18A, cx5499 induced potent T-cell mediated cytotoxicity directed toward the SHP-77 cell line.

D. T Cell Modulation

To further assess T cell modulation, exemplary multispecific CD3 constrained binding constructs were assessed by monitoring the ability of the constructs to modulate T cell activation markers. To assess T cell activation, suspension cells from T cell cytotoxicity assays above, involving culture of T cells with DLL3 positive SHP-77 cells in the presence of cx5499, in the presence of an exemplary DLL3-targeted constrained CD3 engaging constructs, were collected. Cells were stained with a live/dead stain and fluorophore-conjugated anti-CD4, anti-CD8, anti-CD25 and/or anti-CD69 antibodies. Cells were analyzed using a SONY SA3800 spectral analyzer and CD4+ or CD8+ T cell activation was determined by measuring expression levels of CD25 or CD69 or percent CD25- or CD69-positive.

FIG. 18B and FIG. 18D depict results for CD25 expression on CD4 T cells or CD8 T cells, respectively, upon culture of T cells with DLL3 positive, SHP-77 cells, in the presence of an exemplary DLL3-targeted constrained CD3 engaging construct, cx5499. FIG. 18C and FIG. 18E depict results for CD69 expression on CD4 cells or CD8 T cells, respectively, upon culture of T cells with DLL3 positive, SHP-77 cells, in the presence of an exemplary DLL3-targeted constrained CD3 engaging construct, cx5499. The results showed that cx5499 mediated a dose-dependent DLL3-dependent T-cell activation via CD3 binding, as evidenced by increased expression of CD25 and CD69 on CD4+ and CD8+ T cells.

E. Summary

Together, these results demonstrate that constrained anti-CD3 constructs formatted with anti-DLL3 sdAb binding domains are capable of binding to a DLL3-expressing cell line, SHP-77, and eliciting antigen-dependent T-cell cytotoxicity and activation. This result is consistent with a finding that the constrained CD3 engaging constructs of the disclosure have broad applicability to specifically target numerous tumor antigens and elicit T-cell cytotoxicity and activation against target-expressing cells.

While the invention has been described in conjunction with the detailed description thereof, the foregoing description is intended to illustrate and not limit the scope of the disclosure, which is defined by the scope of the appended claims. Other aspects, advantages, and modifications are within the scope of the following claims.

SEQUENCE TABLE

| SEQ ID NO | SEQUENCE | DESCRIPTION |
|---|---|---|
| 1 | PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK | IgG1 Fc |

SEQUENCE TABLE

| SEQ ID NO | SEQUENCE | DESCRIPTION |
|---|---|---|
| 2 | PAPGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK | xELL Fc |
| 3 | PAPPVAGPSV FLFPPKPKDT LMISRTPEVT CVVVDVSHED PEVQFNWYVD GVEVHNAKTK PREEQFNSTF RVVSVLTVVH QDWLNGKEYK CKVSNKGLPA PIEKTISKTK GQPREPQVYT LPPSREEMTK NQVSLTCLVK GFYPSDISVE WESNGQPENN YKTTPPMLDS DGSFFLYSKL TVDKSRWQQG NVFSCSVMHE ALHNHYTQKS LSLSPGK | IgG2 Fc |
| 4 | PAPELLGGPS VFLFPPKPKD TLMISRTPEV TCVVVDVSHE DPEVQFKWYV DGVEVHNAKT KPREEQYNST FRVVSVLTVL HQDWLNGKEY KCKVSNKALP APIEKTISKT KGQPREPQVY TLPPSREEMT KNQVSLTCLV KGFYPSDIAV EWESSGQPEN NYNTTPPMLD SDGSFFLYSK LTVDKSRWQQ GNIFSCSVMH EALHNRFTQK SLSLSPGK | IgG3 Fc |
| 5 | PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | IgG4 Fc |
| 6 | PAPELLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | IgG4 Fc |
| 7 | EPKSSDKTHTCPPC | Hinge |
| 8 | DKTHTCPPC | Hinge |
| 9 | ESKYGPPCPPC | Hinge |
| 10 | GGSGGS | (GGS)$_2$ |
| 11 | GGSGGSGGS | (GGS)$_3$ |
| 12 | GGSGGSGGSGGS | (GGS)$_4$ |
| 13 | GGSGGSGGSGGSGGS | (GGS)$_5$ |
| 14 | EVQLVESGGGLVQPKGSLKLSCAASGFTFNTYAMNWVRQAPGKGLEWVA RIRSKYNNYATYYADSVKDRFTISRDDSQSILYLQMNNLKTEDTAMYYCVR HGNFGNSYVSWFAYWGQGTLVTVSA | anti-CD3 VH |
| 15 | QAVVTQESALTTSPGETVTLTCRSSTGAVTTSNYANWVQEKPDHLFTGLIG GTNKRAPGVPARFSGSLIGDKAALTITGAQIEDEAIYFCALWYSNLWVFGG GTKLTVL | anti-CD3 VL |
| 16 | TYAMN | anti-CD3 VH CDR1 |
| 17 | RIRSKYNNYATYYADSVKD | anti-CD3 VH CDR2 |
| 18 | HGNFGNSYVSWFAY | anti-CD3 VH CDR3 |
| 19 | RSSTGAVTTSNYAN | anti-CD3 VL CDR1 |
| 20 | GTNKRAP | anti-CD3 VL CDR2 |
| 21 | ALWYSNLWV | anti-CD3 VL CDR3 |
| 22 | LEAD | Granzyme B substrate |

-continued

| SEQ ID NO | SEQUENCE | DESCRIPTION |
|---|---|---|
| 23 | RQAR | Granzyme B substrate |
| 24 | PAGL | MMP substrate |
| 25 | TGLEADGSPAGLGRQARVG | Linker |
| 26 | TGLEADGSRQARVGPAGLG | Linker |
| 27 | TGSPAGLEADGSRQARVGS | Linker |
| 28 | TGPAGLGLEADGSRQARVG | Linker |
| 29 | TGRQARVGLEADGSPAGLG | Linker |
| 30 | TGSRQARVGPAGLEADGS | Linker |
| 31 | TGPAGLGSRQARVGLEADGS | Linker |
| 32 | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCVRHGNFGNSYVSWFAYWGQGTLVTVSS | anti-CD3 VH1 |
| 33 | EVKLVESGGGLVQPGGSLRLSCAASGFTFNTYAMNWVRQAPGKGLEWVARIRSKYNNYATYYADSVKDRFTISRDDSKSSLYLQMNNLKTEDTAMYYCVRHGNFGNSYVSWFAYWGQGTLVTVSS | anti-CD3 VH2 |
| 34 | EVKLVESGGGLVKPGRSLRLSCAASGFTFNTYAMNWVRQAPGKGLEWVARIRSKYNNYATYYADSVKDRFTISRDDSKSILYLQMNNLKIEDTAMYYCVRHGNFGNSYVSWFAYWGQGTLVTVSS | anti-CD3 VH3 |
| 35 | EVKLVESGGGLVKPGRSLRLSCAASGFTFNTYAMNWVRQAPGKGLEWVARIRSKYNNYATYYADSVKDRFTISRDDSKSILYLQMNSLKIEDTAMYYCVRHGNFGNSYVSWFAYWGQGTLVTVSS | anti-CD3 VH4 |
| 36 | EVKLVESGGGLVKPGRSLRLSCAASGFTFNTYAMNWVRQAPGKGLEWVARIRSKYNNYATYYADSVKDRFTISRDDSKSILYLQMNSLKIEDTAMYYCVRHGNFGNSYVSWFAYWGQGTLVTVSS | anti-CD3 VH5 |
| 37 | EVQLLESGGGLVQPGGSLRLSCAASGFTFSTYAMNWVRQAPGKGLEWVSRIRSKYNNYATYYADSVKGRFTISRDDSKNTLYLQMNSLRAEDTAVYYCVRHGNFGNSYVSWFAYWGQGTLVTVSS | anti-CD3 VH6 |
| 38 | EVQLVESGGGLVQPGGSLRLSCAASGFTFSTYAMSWVRQAPGKGLEWVGRIRSKYNNYATYYADSVKGRFTISRDDSKNTLYLQMNSLRAEDTAVYYCVRHGNFGDSYVSWFAYWGQGTLVTVSS | anti-CD3 VH7 |
| 39 | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVS | anti-CD3 VH8 |
| 40 | EVQLVESGGGLVQPGGSLRLSCAASGFTFNTYAMNWVRQAPGKGLEWVARIRSKYNNYATYYADSVKGRFTISRDDSKNTLYLQMNSLRAEDTAVYYCVRHGNFGNSYVSWFAYWGQGTTVTVSS | anti-CD3 VH9 |
| 41 | EVQLVESGGGLVQPGGSLRLSCAASGFTFNTYAMNWVRQAPGKGLEWVARIRSKYNNYATYYADSVKGRFTISRDDSKNTLYLQMNSLRAEDTAVYYCVRHGNFGNSYVSYFAYWGQGTTVTVSS | anti-CD3 VH10 |
| 42 | EVQLVESGGGLVQPKGSLKLSCAASGFTFNTYAMNWVRQAPGKGLEWVARIRSKYNNYATYYADSVKDRFTISRDDSQSILYLQMNNLKTEDTAMYYCVRHGNFGNSYVSWFAYWGQGTLVTVSS | anti-CD3 VH11 |
| 43 | EVQLVESGGGLVQPGGSLRLSCAASGFTFNTYAMNWVRQAPGKGLEWVARIRSKYNNYATYYADSVKGRFTISRDDAKNTLYLQMSSLRAEDTAVYYCVRHGNFGNSYVSWFAYWGQGTLVTVKP | anti-CD3 VH12 |
| 44 | EVQLVESGGGLVQPGGSLRLSCAASGFTFNTYAMNWVRQAPGKCLEWVARIRSKYNNYATYYADSVKGRFTISRDDAKNTLYLQMSSLRAEDTAVYYCVRHGNFGNSYVSWFAYWGQGTLVTVKP | anti-CD3 VH13 |
| 45 | EVQLVESGGGLVQPGGSLRLSCAASGFTFNTYAMNWVRQAPGKGLEWVARIRSKYNNYATYYADSVKGRFTISRDDAKNTLYLQMSSLRAEDTAVYYCVRHGNFGNSYVSWFAYWGCGTLVTVKP | anti-CD3 VH14 |

-continued

| SEQ ID NO | SEQUENCE | DESCRIPTION |
|---|---|---|
| 46 | EVQLVESGGGLVQPGGSLRLSCAASGFTFSTYAMNWVRQAPGKGLEWVAR IRSKYNNYATYYADSVKGRFTISRDDAKNTLYLQMSSLRAEDTAVYYCVRH GNFGNSYVSWFAYWGQGTLVTVSS | anti-CD3 VH15 |
| 47 | EVQLVESGGGLVQPGGSLRLSCAASGFTFNTYAMNWVRQAPGKGLEWVSR IRSKYNNYATYYADSVKGRFTISRDDAKNTLYLQMSSLRAEDTAVYYCVRH GNFGNSYVSWFAYWGQGTLVTVSS | anti-CD3 VH16 |
| 48 | EVQLVESGGGLVQPGGSLRLSCAASGFTFSTYAMNWVRQAPGKGLEWVSR IRSKYNNYATYYADSVKGRFTISRDDAKNTLYLQMSSLRAEDTAVYYCVRH GNFGNSYVSWFAYWGQGTLVTVSS | anti-CD3 VH17 |
| 49 | EVQLVESGGGLVQPGGSLRLSCAASGFTFSTYAMNWVRQAPGKCLEWVAR IRSKYNNYATYYADSVKGRFTISRDDAKNTLYLQMSSLRAEDTAVYYCVRH GNFGNSYVSWFAYWGQGTLVTVSS | anti-CD3 VH18 |
| 50 | EVQLVESGGGLVQPGGSLRLSCAASGFTFNTYAMNWVRQAPGKCLEWVSR IRSKYNNYATYYADSVKGRFTISRDDAKNTLYLQMSSLRAEDTAVYYCVRH GNFGNSYVSWFAYWGQGTLVTVSS | anti-CD3 VH19 |
| 51 | EVQLVESGGGLVQPGGSLRLSCAASGFTFSTYAMNWVRQAPGKCLEWVSRI RSKYNNYATYYADSVKGRFTISRDDAKNTLYLQMSSLRAEDTAVYYCVRH GNFGNSYVSWFAYWGQGTLVTVSS | anti-CD3 VH20 |
| 52 | EVQLVESGGGLVQPGGSLRLSCAASGFTFSTYAMNWVRQAPGKCLEWVGR IRSKYNNYATYYADSVKDRFTISRDDSKNSLYLQMNSLKTEDTAVYYCVRH GNFGNSYVSWFAYWGQGTLVTVSS | anti-CD3 VH21 |
| 53 | EVKLVESGGGLVQPGGSLRLSCAASGFTFNTYAMNWVRQAPGKCLEWVAR IRSKYNNYATYYADSVKDRFTISRDDSKSSLYLQMNNLKTEDTAMYYCVR HGNFGNSYVSWFAYWGQGTLVTVSS | anti-CD3 VH22 |
| 54 | EVKLVESGGGLVKPGRSLRLSCAASGFTFNTYAMNWVRQAPGKCLEWVAR IRSKYNNYATYYADSVKDRFTISRDDSKSILYLQMNNLKIEDTAMYYCVRH GNFGNSYVSWFAYWGQGTLVTVSS | anti-CD3 VH23 |
| 55 | EVKLVESGGGLVKPGRSLRLSCAASGFTFNTYAMNWVRQAPGKCLEWVAR IRSKYNNYATYYADSVKDRFTISRDDSKSILYLQMNSLKIEDTAMYYCVRH GNFGNSYVSWFAYWGQGTLVTVSS | anti-CD3 VH24 |
| 56 | EVKLVESGGGLVKPGRSLRLSCAASGFTFNTYAMNWVRQAPGKCLEWVAR IRSKYNNYATYYADSVKDRFTISRDDSKSILYLQMNSLKIEDTAMYYCVRH GNFGNSYVSWFAYWGQGTLVTVSS | anti-CD3 VH25 |
| 57 | EVQLLESGGGLVQPGGSLRLSCAASGFTFSTYAMNWVRQAPGKCLEWVSRI RSKYNNYATYYADSVKGRFTISRDDSKNTLYLQMNSLRAEDTAVYYCVRH GNFGNSYVSWFAYWGQGTLVTVSS | anti-CD3 VH26 |
| 58 | EVQLVESGGGLVQPGGSLRLSCAASGFTFSTYAMSWVRQAPGKCLEWVGRI RSKYNNYATYYADSVKGRFTISRDDSKNTLYLQMNSLRAEDTAVYYCVRH GNFGDSYVSWFAYWGQGTLVTVSS | anti-CD3 VH27 |
| 59 | EVQLVESGGGLVQPGGSLKLSCAASGFTFNKYAMNWVRQAPGKCLEWVA RIRSKYNNYATYYADSVKDRFTISRDDSKNTAYLQMNNLKTEDTAVYYCV RHGNFGNSYISYWAYWGQGTLVTVS | anti-CD3 VH28 |
| 60 | EVQLVESGGGLVQPGGSLRLSCAASGFTFNTYAMNWVRQAPGKCLEWVAR IRSKYNNYATYYADSVKGRFTISRDDSKNTLYLQMNSLRAEDTAVYYCVRH GNFGNSYVSWFAYWGQGTTVTVSS | anti-CD3 VH29 |
| 61 | EVQLVESGGGLVQPGGSLRLSCAASGFTFNTYAMNWVRQAPGKCLEWVAR IRSKYNNYATYYADSVKGRFTISRDDSKNTLYLQMNSLRAEDTAVYYCVRH GNFGNSYVSYFAYWGQGTTVTVSS | anti-CD3 VH30 |
| 62 | EVQLVESGGGLVQPKGSLKLSCAASGFTFNTYAMNWVRQAPGKCLEWVA RIRSKYNNYATYYADSVKDRFTISRDDSQSILYLQMNNLKTEDTAMYYCVR HGNFGNSYVSWFAYWGQGTLVTVSS | anti-CD3 VH31 |
| 63 | QAVVTQESALTTSPGETVTLTCRSSTGAVTTSNYANWVQEKPDHLFTGLIG GTNKRAPGVPARFSGSLIGDKAALTITGAQIEDEAIYFCALWYSNLWVFGG GTKLTVL | anti-CD3 VL1 |

| SEQ ID NO | SEQUENCE | DESCRIPTION |
|---|---|---|
| 64 | QAVVTQEPSLTVSPGGTVTLTCGSSTGAVTTSNYANWVQQKPGKSPRGLIG GTNKRAPGVPARFSGSLLGGKAALTISGAQPEDEADYYCALWYSNHWVFG CGTKLEIK | anti-CD3 VL2 |
| 65 | QAVVTQEPSLTVSPGGTVTLTCRSSTGAVTTSNYANWVQQKPGQAPRGLIG GTNKRAPWTPARFSGSLLGGKAALTITGAQAEDEADYYCALWYSNLWVFG GGTKLTVL | anti-CD3 VL3 |
| 66 | QAVVTQEPSFSVSPGGTVTLTCRSSTGAVTTSNYANWVQQTPGQAFRGLIG GTNKRAPGVPARFSGSLIGDKAALTITGAQADDESIYFCALWYSNLWVFGG GTKLTVL | anti-CD3 VL4 |
| 67 | QAVVTQEPSFSVSPGGTVTLTCRSSTGAVTTSNYANWVQQTPGQAFRGLIG GTNKRAPGVPARFSGSILGNKAALTITGAQADDESIYFCALWYSNLWVFGG GTKLTVL | anti-CD3 VL5 |
| 68 | QAVVTQEPSFSVSPGGTVTLTCRSSTGAVTTSNYANWVQQTPGQAFRGLIG GTNKRAPGVPARFSGSILGNKAALTITGAQADDESDYYCALWYSNLWVFG GGTKLTVL | anti-CD3 VL6 |
| 69 | QAVVTQEPSLTVSPGGTVTLTCGSSTGAVTTSNYANWVQEKPGQAFRGLIG GTNKRAPGTPARFSGSLLGGKAALTLSGAQPEDEAEYYCALWYSNLWVFG GGTKLTVL | anti-CD3 VL7 |
| 70 | QTVVTQEPSLTVSPGGTVTLTCGSSTGAVTSGNYPNWVQQKPGQAPRGLIG GTKFLAPGTPARFSGSLLGGKAALTLSGVQPEDEAEYYCVLWYSNRWVFG GGTKLTVL | anti-CD3 VL8 |
| 71 | QAVVTQEPSLTVSPGGTVTLTCGSSTGAVTTSNYANWVQQKPGQAFRGLIG GTNKRAPGVPARFSGSLLGGKAALTISGAQPEDEADYYCALWYSNHWVFG GGTKLEIK | anti-CD3 VL9 |
| 72 | QAVVTQEPSLTVSPGGTVTLTCGSSTGAVTTSNYANWVQQKPGQAFRGLIG GTNKRAPGVPARFSGSLLGGKAALTISGAQPEDEADYYCALWYSNHWVFG CGTKLEIK | anti-CD3 VL10 |
| 73 | QAVVTQEPSLTVSPGGTVTLTCGSSTGAVTTSNYANWVQQKPGQCFRGLIG GTNKRAPGVPARFSGSLLGGKAALTISGAQPEDEADYYCALWYSNHWVFG EGTKLEIK | anti-CD3 VL11 |
| 74 | QAVVTQESALTTSPGETVTLTCRSSTGAVTTSNYANWVQEKPDHLFTGLIG GTNKRAPGVPARFSGSLIGDKAALTITGAQIEDEAIYFCALWYSNLWVFGC GTKLTVL | anti-CD3 VL12 |
| 75 | QAVVTQEPSLTVSPGGTVTLTCGSSTGAVTTSNYANWVQQKPGKSPRGLIG GTNKRAPGVPARFSGSLLGGKAALTISGAQPEDEADYYCALWYSNHWVFG GGTKLEIK | anti-CD3 VL13 |
| 76 | QAVVTQEPSLTVSPGGTVTLTCRSSTGAVTTSNYANWVQQKPGQAPRGLIG GTNKRAPWTPARFSGSLLGGKAALTITGAQAEDEADYYCALWYSNLWVFG CGTKLTVL | anti-CD3 VL14 |
| 77 | QAVVTQEPSFSVSPGGTVTLTCRSSTGAVTTSNYANWVQQTPGQAFRGLIG GTNKRAPGVPARFSGSLIGDKAALTITGAQADDESIYFCALWYSNLWVFGG GTKLTVL | anti-CD3 VL15 |
| 78 | QAVVTQEPSFSVSPGGTVTLTCRSSTGAVTTSNYANWVQQTPGQAFRGLIG GTNKRAPGVPARFSGSILGNKAALTITGAQADDESIYFCALWYSNLWVFGC GTKLTVL | anti-CD3 VL16 |
| 79 | QAVVTQEPSFSVSPGGTVTLTCRSSTGAVTTSNYANWVQQTPGQAFRGLIG GTNKRAPGVPARFSGSILGNKAALTITGAQADDESDYYCALWYSNLWVFG CGTKLTVL | anti-CD3 VL17 |
| 80 | QAVVTQEPSLTVSPGGTVTLTCGSSTGAVTTSNYANWVQEKPGQAFRGLIG GTNKRAPGTPARFSGSLLGGKAALTLSGAQPEDEAEYYCALWYSNLWVFG CGTKLTVL | anti-CD3 VL18 |
| 81 | QTVVTQEPSLTVSPGGTVTLTCGSSTGAVTSGNYPNWVQQKPGQAPRGLIG GTKFLAPGTPARFSGSLLGGKAALTLSGVQPEDEAEYYCVLWYSNRWVFG CGTKLTVL | anti-CD3 VL19 |

-continued

SEQUENCE TABLE

| SEQ ID NO | SEQUENCE | DESCRIPTION |
|---|---|---|
| 82 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVMHEALHNHYTQKSLSLSPT | Knob Fc |
| 83 | DKTHTCPPCPAPELLGGPSVFLFPPKPKDTLMRSRTPEVTCVVVDVSHEDPE VKFNWYVDGVEVHNAKTKPREEQYNSTYRVVSVLTVLHQDWLNGKEYKC KVSNKALPAPIEKTISKAKGQPREPQVCTLPPSRDELTKNQVSLSCAVKGFYP SDIAVEWESNGQPENNYKTTPPVLDSDGSFFLVSKLTVDKSRWQQGNVFSC SVMHEALHNHYTQKSLSLSPT | Hole Fc |
| 84 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPCRDELTKNQVSLWCLVKGFYPSD IAVEWESNGQPENNYKTTPPVLDSDGSFFLYSKLTVDKSRWQQGNVFSCSV MHEALHNHYTQKSLSLSPT | Knob Fc |
| 85 | DKTHTCPPCPAPGGPSVFLFPPKPKDTLMRSRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNHYTQKSLSLSPT | Hole Fc |
| 86 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVMHEALHNHYTQKSLSLSPG | Knob Fc |
| 87 | DKTHTCPPCPAPELLGGPSVFLFPPKPKDTLMRSRTPEVTCVVVDVSHEDPE VKFNWYVDGVEVHNAKTKPREEQYNSTYRVVSVLTVLHQDWLNGKEYKC KVSNKALPAPIEKTISKAKGQPREPQVCTLPPSRDELTKNQVSLSCAVKGFYP SDIAVEWESNGQPENNYKTTPPVLDSDGSFFLVSKLTVDKSRWQQGNVFSC SVMHEALHNHYTQKSLSLSPG | Hole Fc |
| 88 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPCRDELTKNQVSLWCLVKGFYPSD IAVEWESNGQPENNYKTTPPVLDSDGSFFLYSKLTVDKSRWQQGNVFSCSV MHEALHNHYTQKSLSLSPG | Knob Fc |
| 89 | DKTHTCPPCPAPGGPSVFLFPPKPKDTLMRSRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNHYTQKSLSLSPG | Hole Fc |
| 90 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VMHEALHNRYTQKSLSLSPT | Hole Fc |
| 91 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNRYTQKSLSLSPT | Hole Fc |
| 92 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VMHEALHNRYTQKSLSLSPG | Hole Fc |
| 93 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNRYTQKSLSLSPG | Hole Fc |
| 94 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK | Knob Fc |

SEQUENCE TABLE

| SEQ ID NO | SEQUENCE | DESCRIPTION |
|---|---|---|
| | VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVVHEALHNHYTQKSLSLSPT | |
| 95 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVV HEALHNHYTQKSLSLSPT | Knob Fc |
| 96 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVVHEALHNHYTQKSLSLSPG | Knob Fc |
| 97 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVV HEALHNHYTQKSLSLSPG | Knob Fc |
| 98 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VVHEALHNRYTQKSLSLSPT | Hole Fc |
| 99 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIA VEWESNGQPENNYKTTPPVLDSDGSFFLVSKLTVDKSRWQQGNVFSCSVVH EALHNRYTQKSLSLSPT | Hole Fc |
| 100 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VVHEALHNRYTQKSLSLSPG | Hole Fc |
| 101 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIA VEWESNGQPENNYKTTPPVLDSDGSFFLVSKLTVDKSRWQQGNVFSCSVVH EALHNRYTQKSLSLSPG | Hole Fc |
| 102 | PGGGG | Peptide Linker |
| 103 | GGGG | Peptide Linker |
| 104 | GPAGLGLEPDGSRQARVG | Linker |
| 105 | GGSGGGGIEPDIGGSGGS | Linker |
| 106 | GGSGGGGLEADTGGSGGS | Linker |
| 107 | GSIEPDIGS | Linker |
| 108 | GSLEADTGS | Linker |
| 109 | GGSGGGGIEPDGGGSGGS | Linker |
| 110 | GGSGGGGIEPDVGGSGGS | Linker |
| 111 | GGSGGGGIEPDSGGSGGS | Linker |
| 112 | GGSGGGGIEPDTGGSGGS | Linker |
| 113 | GGGSLEPDGSGS | Linker |
| 114 | GPAGLGLEADGSRQARVG | Linker |
| 115 | GGEGGGGSGGSGGGS | Linker |

-continued

| SEQ ID NO | SEQUENCE | DESCRIPTION |
|---|---|---|
| 116 | GSSAGSEAGGSGQAGVGS | Linker |
| 117 | GGSGGGGLEAEGSGGGGS | Linker |
| 118 | GGSGGGGIEPDPGGSGGS | Linker |
| 119 | GGGGSGGGGSGGGGS | Linker |
| 120 | QLQLQESGGGLVQPGGSLRLSCAASGFTLDNYAIGWFRQAPGKEREGVSCIS SSDGSTYYADSVKGRFTISRNNAKGTVYLLMNSLKPEDTAVYYCATELVPA CTYSNGRGPLDGMDYWGKGTQVTVKP | FR alpha sdAb |
| 121 | EVQLLESGGGEVQPGGSLRLSCAASGSIFSIDATAWYRQAPGKQRELVAIITS SGSTNYPESVKGRFTISRDNAKNTVYLQMSSLRAEDTAVYYCNAITRYGGS TYDFWGQGTLVTVKP | FR alpha sdAb |
| 122 | EVQPGGSLRLSCAASETFGVVFTLGWYRQAPGKGREFVARVTGTDTVDYA ESVKGRFTISSDFARNTVYLQMNSLRAEDTAVYYCNTGAYWGQGTLVTVK P | FR alpha sdAb |
| 123 | EVQLVESGGGLVQPGGSLRLSCAASGFILDYYAIGWFRQAPGKEREGVLCID ASDDITYYADSVKGRFTISRDNAKNTVYLQMNSLKPEDTGVYYCATPIGLSS SCLLEYDYDYWGQGTLVTVKP | cMET sdAb |
| 124 | EVQLVESGGGLVQPGGSLRLSCAASGFTFSSFGMHWVRQAPGKGLEWVAY ISSDSSAIYYADTVKGRFTISRDNAKNSLYLQMNSLRDEDTAVYYCGRGREN IYYGSRLDYWGQGTTVTVSSSGGGGSGGGGSGGGGSDIQLTQSPSFLSASVG DRVTITCKASQNVDTNVAWYQQKPGKAPKALIYSASYRYSGVPSRFSGSGS GTDFTLTISSLQPEDFATYYCQQYNNYPFTFGQGTKLEIK | B7H3 scFv |
| 125 | QVQLVQSGAEVKKPGSSVKVSCKASGYAFSYSWINWVRQAPGQGLEWMG RIFPGDGDTDYNGKFKGRVTITADKSTSTAYMELSSLRSEDTAVYYCARNV FDGYWLVYWGQGTLVTVSGSGGGGSGGGGTGGGGSDIVMTQTPLSLPVTP GEPASISCRSSKSLLHSNGITYLYWYLQKPGQSPQLLIYQMSNLVSGVPDRFS GSGSGTDFTLKISRVEAEDVGVYYCAQNLELPYTFGGGTKVEIK | CD20 scFv |
| 126 | QVQLQESGPGLVKPSETLSLTCTVSGGSISSYYWSWIRQPPGKGLEWIGYVY YSGTTNYNPSLKSRVTISVDTSKNQFSLKLSSVTAADTAVYYCASIAVTGFY FDYWGQGTLVTVSSGGGGSGGGGSGGGGSEIVLTQSPGTLSLSPGERVTLSC RASQRVNNNYLAWYQQRPGQAPRLLIYGASSRATGIPDRFSGSGSGTDFTLT ISRLEPEDFAVYYCQQYDRSPLTFGGGTKLEIK | DLL3 scFv |
| 127 | EVQLVESGGGLVQPGGSLRLSCAASGFTFSSFGMHWVRQAPGKGLEWVAY ISSDSSAIYYADTVKGRFTISRDNAKNSLYLQMNSLRDEDTAVYYCGRGREN IYYGSRLDYWGQGTTVTVSSASTKGPSVFPLAPSSKSTSGGTAALGCLVKDY FPEPVTVSWNSGALTSGVHTFPAVLQSSGLYSLSSVVTVPSSSLGTQTYICNV NHKPSNTKVDKKVEPKSC | B7H3 Fd |
| 128 | DIQLTQSPSFLSASVGDRVTITCKASQNVDTNVAWYQQKPGKAPKALIYSAS YRYSGVPSRFSGSGSGTDFTLTISSLQPEDFATYYCQQYNNYPFTFGQGTKLE IKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGEC | B7H3 LC |
| 129 | EVQLVESGGGLVQPKGSLKLSCAASGFTFNTYAMNWVRQAPGKGLEWVA RIRSKSNNYATYYADSVKDRFTISRDDSQSMLYLQMNNLKTEDTAMYYCV RQWDYDVRAMNYWGQGTSVTVSSASTKGPSVFPLAPSSKSTSGGTAALGC LVKDYFPEPVTVSWNSGALTSGVHTFPAVLQSSGLYSLSSVVTVPSSSLGTQ TYICNVNHKPSNTKVDKKVEPKSC | 5T4 Fd |
| 130 | DIVMTQSHIFMSTSVGDRVSITCKASQDVDTAVAWYQQKPGQSPKLLIYWA STRLTGVPDRFTGSGSGTDFTLTISNVQSEDLADYFCQQYSSYPYTFGGGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC | 5T4 LC |
| 131 | QVQLQESGPGLVKPSQTLSLTCTVSGGSISSFNYYWSWIRHHPGKGLEWIGY IYYSGSTYSNPSLKSRVTISVDTSKNQFSLTLSSVTAADTAVYYCARGYNWN YFDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKP SNTKVDKKVEPKSC | gpNMB Fd |
| 132 | EIVMTQSPATLSVSPGERATLSCRASQSVDNNLVWYQQKPGQAPRLLIYGAS TRATGIPARFSGSGSGTEFTLTISSLQSEDFAVYYCQQYNNWPPWTFGQGTK | gpNMB LC |

SEQUENCE TABLE

| SEQ ID NO | SEQUENCE | DESCRIPTION |
|---|---|---|
| | VEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC | |
| 133 | QIQLVQSGPELKKPGETVKISCKASGYTFTNYGMNWVKQAPGKGLKWMA WINTYTGEPTYADDFKGRFAFSLETSASTASLQIINLKNEDTATYFCARIGDS SPSDYWGQGTTLTVSSSSASTKGPSVFPLAPSSKSTSGGTAALGCLVKDYFP EPVTVSWNSGALTSGVHTFPAVLQSSGLYSLSSVVTVPSSSLGTQTYICNVN HKPSNTKVDKKVEPKSC | DLL3 Fd |
| 134 | SIVMTQTPKFLLVSAGDRVTITCKASQSVSNDVVWYQQKPGQSPKLLIYYAS NRYTGVPDRFAGSGYGTDFSFTISTVQAEDLAVYFCQQDYTSPWTFGGGTK LEIRRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC | DLL3 LC |
| 135 | GGGGGS | Peptide Linker |
| 136 | IEPDI | Linker |
| 137 | LEADT | Linker |
| 138 | IEPDG | Linker |
| 139 | IEPDV | Linker |
| 140 | IEPDS | Linker |
| 141 | IEPDT | Linker |
| 142 | LEPD | Linker |
| 143 | LEAE | Linker |
| 144 | IEPDP | Linker |
| 145 | QAVVTQEPSLTVSPGGTVTLTCRSSTGAVTTSNYANWVQQKPGQAPRGLIG GTNKRAPWTPARFSGSLLGGKAALTITGAQAEDEADYYCALWYSNLWVFG GGTKLTVLGGGGSGGGGEVQLVESGGGLVQPGGSLRLSCAASGFTFSSGM HWVRQAPGKGLEWVAYISSDSSAIYYADTVKGRFTISRDNAKNSLYLQMNS LRDEDTAVYYCGRGRENIYYGSRLDYWGQGTTVTVSSGGCGGGKVAALKE KVAALKEKVAALKEKVAALKE | Second Polypeptide Chain of B7-H3 x CD3 Bispecific DART-A Diabody |
| 146 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKC KVSNKALPAPIEKTISKAKGQPREPQVYTLPPSREEMTKNQVSLSCAVKGFY PSDIAVEWESNGQPENNYKTTPPVLDSDGSFFLVSKLTVDKSRWQQGNVFS CSVMHEALHNRYTQKSLSLSPGK | Third Polypeptide Chain of B7-H3 x CD3 Bispecific DART-A Diabody |
| 147 | GGSGGGGSGGGGSGGGGS | Linker |
| 148 | TGGSGGGGIEPDIGGSGGS | Linker |
| 149 | GGGGS | Linker |
| 150 | X₁ X₂ X₃ X₄ X₅ (P4 P3 P2 P1 ↓ P1') X1 = I, L, Y, M, F, V, or A; (P4 = I, L, Y, M, F, V, or A) X2 = A, G, S, V, E, D, Q, N, or Y; (P3 = A, G, S, V, E, D, Q, N, or Y) X3 = H, P, A, V, G, S, or T; (P2 = H, P, A, V, G, S, or T) X4 = D or E; (P1 = D or E) X5 = I, L, Y, M, F, V, T, S, G or A (P1' = I, L, Y, M, F, V, T, S, G or A) | Linker consensus |
| 151 | X1 E X3 D X5 (P4 P3 P2 P1 ↓ P1') X1 = I or L; (P4 = I or L) (P3 = E) X3 = P or A; (P2 = P or A) X5 = I, V, T, S, or G (P1' = I, V, T, S, or G) | Linker consensus |
| 152 | LEPDG | Linker |
| 153 | LEADG | Linker |

-continued

| SEQ ID NO | SEQUENCE | DESCRIPTION |
|---|---|---|
| 154 | X1QARX5 (P1QAR↓(A/V))<br>X1 = any amino acid; (P1 is any amino acid)<br>X5 = A or V | Linker consensus |
| 155 | RQARX5 (RQAR(A/V))<br>X5 = A or V | Linker consensus |
| 156 | RQARV | Linker |
| 157 | X1X2 X3 X4 (P3 P2 P1 ↓ P1')<br>X1 = P, V or A; (P3 = P, V or A)<br>X2 = Q or D; (P2 = Q or D)<br>X3 = A or N; (P1 = A or N)<br>X4 = L, I or M (P1' = L, I or M) | Linker consensus |
| 158 | PX2X3X4 (P3P2 P1 ↓ P1')<br>(P3 = P)<br>X2 = Q or D; (P2 = Q or D)<br>X3 = A or N; (P1 = A or N)<br>X4 = L or I (P1' = L or I) | Linker consensus |
| 159 | GSGATNFSLLKQAGDVEENPGP | P2A |
| 160 | ATNFSLLKQAGDVEENPGP | P2A |
| 161 | QCTNYALLKLAGDVESNPGP | E2A |
| 162 | VKQTLNFDLLKLAGDVESNPGP | F2A |
| 163 | EGRGSLLTCGDVEENPGP | T2A |
| 164 | LEGGGEGRGSLLTCGDVEENPGPR | T2A |
| 165 | GGATCTGGAGCAACAAACTTCTCACTACTCAAACAAGCAGGTGACGTGG<br>AGGAGAATCCCGGACCC | P2A DNA |
| 166 | GSPAGLEADGSRQARVGS | Linker |
| 167 | EVQLVESGGGL VQPKGSLKLS CAASGFTFNT YAMNWVRQAP<br>GKGLEWVARI RSKSNNYATY YADSVKDRFT ISRDDSQSML<br>YLQMNNLKTE DTAMYXCVRQ WDYDVRAMNY WGQGTSVTVS S | anti-5T4 VH |
| 168 | DIVMTQSHIF MSTSVGDRVS ITCKASQDVD<br>TAVAWYQQKP GQSPKLLIYW ASTRLTGVPD RFTGSGSGTD FTLTISNVQS<br>EDLADYFCQQ YSSYPYTFGG GTKLEIK | anti-5T4 VL |
| 169 | DIQLTQSPSF LSASVGDRVT ITCKASQNVD TNVAWYQQKP GKAPKALIYS<br>ASYRYSGVPS RFSGSGSGTD FTLTISSLQP EDFATYYCQQ YNNYPFTFGQ<br>GTKLEIKGGG SGGGGEVQLV ESGGGLVQPG GSLRLSCAAS<br>GFTFSTYAMN<br>WVRQAPGKGL EWVGRIRSKY NNYATYYADS VKDRFTISRD<br>DSKNSLYLQM NSLKTEDTAV YYCVRHGNFG NSYVSWFAYW<br>GQGTLVTVSS GGCGGGEVAA LEKEVAALEK EVAALEKEVA<br>ALEKGGGDKT HTCPPCPAPE AAGGPSVFLF PPKPKDTLMI SRTPEVTCVV<br>VDVSHEDPEV KFNWYVDGVE VHNAKTKPRE EQYNSTYRVV<br>SVLTVLHQDW LNGKEYKCKV SNKALPAPIE KTISKAKGQP<br>REPQVYTLPP SREEMTKNQV SLWCLVKGFY PSDIAVEWES<br>NGQPENNYKT<br>TPPVLDSDGS FFLYSKLTVD KSRWQQGNVF SCSVMHEALH<br>NHYTQKSLSL<br>SPGK | First Polypeptide Chain of B7-H3 x CD3 Bispecific DART-A Diabody |
| 170 | GGGGSGGGGSGGGGS | Linker |
| 171 | GGS(GGS)n<br>wherein n is 0 to 10 | Linker |
| 172 | (GGGGS)n<br>wherein n is 1 to 4 | Linker |
| 173 | (GGGGS)n<br>wherein n is 1 to 10 | Linker |

-continued

| SEQ ID NO | SEQUENCE | DESCRIPTION |
|---|---|---|
| 174 | Gly$_x$Xaa-Gly$_y$-Xaa-Gly$_z$<br>Xaa is independently selected from A, V, L, I, M, F, W, P, G, S, T, C, Y, N, Q, K, R, H, D, or E<br>x, y, and z are each integers in the range from 1-5 | Linker |
| 175 | Gly-Gly-Gly-Xaa-Gly-Gly-Gly-Xaa-Gly-Gly-Gly<br>Xaa is independently selected from A, V, L, I, M, F, W, P, G, S, T, C, Y, N, Q, K, R, H, D, or E | Linker |
| 176 | ATTTGSSPGPT | Linker |
| 177 | GGGGG-C-GGGGG | Linker |
| 178 | (EAAAK)n<br>n = 2-20 | Linker |
| 179 | AS-(AP)n-GT<br>n = 2-20 | Linker |
| 180 | AS-(EAAAK)n-GT<br>n = 2-20 | Linker |
| 181 | (GGGGA)n<br>n = 2-20 | Linker |
| 182 | (PGGGS)n<br>n = 2-20 | Linker |
| 183 | (AGGGS)n<br>n = 2-20 | Linker |
| 184 | GGS-(EGKSSGSGSESKST)n-GGS<br>n = 2-20 | Linker |
| 185 | (SSSSG)n<br>n = 1-9 | Linker |
| 186 | SSSASASSA | Linker |
| 187 | GSPGSPG | Linker |
| 188 | QVQLQESGPG LVKPSETLSL TCTVSGGSIS SYYWSWIRQP PGKGLEWIGY VYYSGTTNYN PSLKSRVTIS VDTSKNQFSL KLSSVTAADT AVYYCASIAV TGFYFDYWGQ GTLVTVSSGG GGSGGGGSGG GGSEIVLTQS PGTLSLSPGE RVTLSCRASQ RVNNNYLAWY QQRPGQAPRL LIYGASSRAT GIPDRFSGSG SGTDFTLTIS RLEPEDFAVY YCQQYDRSPL TFGGGTKLEI K | DLL3 scFv |
| 189 | QVQLVQSGAE VKKPGSSVKV SCKASGYAFS YSWINWVRQA PGQGLEWMGR IFPGDGDTDY NGKFKGRVTI TADKSTSTAY MELSSLRSED TAVYYCARNV FDGYWLVYWG QGTLVTVSS | CD20 VH |
| 190 | DIVMTQTPLS LPVTPGEPAS ISCRSSKSLL HSNGITYLYW YLQKPGQSPQ LLIYQMSNLV SGVPDRFSGS GSGTDFTLKI SRVEAEDVGV YYCAQNLELP YTFGGGTKVE IKRTV | CD20 VL |
| 191 | QAVVTQEPSLTVSPGGTVTLTCGSSTGAVTTSNYANWVQQKPGQAFRGLIG GTNKRAPGVPARFSGSLLGGKAALTISGAQPEDEADYYCALWYSNHWVFG CGTKLTVL | anti-CD3 VL35 (CON) |
| 192 | GGGGG | linker |
| 193 | GGGGSGGGGSGGGGS | linker |
| 194 | DKTHTCPPCPAPPVAGPSVFLFPPKPKDTLMISRTPEVTCVVVDVKHEDPEV KFNWYVDGVEVHNAKTKPREEEYNSTYRVVSVLTVLHQDWLNGKEYKCK VSNKALPAPIEKTISKAKGQPREPQVYTLPPSREEMTKNQVSLTCDVSGFYPS DIAVEWESDGQPENNYKTTPPVLDSDGSFFLYSKLTVDKSRWEQGDVFSCS VMHEALHNHYTQKSLSLSPGK | Fc-Het-1 |

| SEQ ID NO | SEQUENCE | DESCRIPTION |
|---|---|---|
| 195 | DKTHTCPPCPAPPVAGPSVFLFPPKPKDTLMISRTPEVTCVVVDVKHEDPEV KFNWYVDGVEVHNAKTKPREEQYNSTYRVVSVLTVLHQDWLNGKEYKCK VSNKALPAPIEKTISKAKGQPREPQVYTLPPSREQMTKNQVKLTCLVKGFYP SDIAVEWESNGQPENNYKTTPPVLDSDGSFFLYSKLTVDKSRWQQGNVFSC SVMHEALHNHYTQKSLSLSPGK | Fc-Het-2 |
| 196 | EVQLVESGGGLVQPGGSLRLSCAASGFTFSTYAMNWVRQAPGKGLEWVGR IRSKYNNYATYYADSVKGRFTISRDDSKNTLYLQMNSLRAEDTAVYYCVRH GNFGDSYVSWFAYWGQGTLVTVSS | CD3-VH32 |
| 197 | EVQLVESGGGLVQPGGSLRLSCAASGFTFSTYAMNWVRQAPGKCLEWVGR IRSKYNNYATYYADSVKGRFTISRDDSKNTLYLQMNSLRAEDTAVYYCVRH GNFGDSYVSWFAYWGQGTLVTVSS | CD3-VH33 |
| 198 | EVQLVESGGGLVQPGGSLRLSCAASGFTFSTYAMNWVRQAPGKCLEWVAR IRSKYNNYATYYADTVKGRFTISRDDAKNTLYLQMSSLRAEDTAVYYCVR HGNFGDSYVSWFAYWGQGTLVTV | CD3-VH34 |
| 199 | QAVVTQEPSLTVSPGGTVTLTCGSSTGAVTTSNYANWVQQKPGKSPRGLIG GTNKRAPGVPARFSGSLLGGKAALTISGAQPEDEADYYCALWYSNHWVFG GGTKLTVL | CD3-VL20 |
| 200 | QAVVTQEPSLTVSPGGTVTLTCGSSTGAVTTSNYANWVQQKPGKSPRGLIG GTNKRAPGVPARFSGSLLGGKAALTISGAQPEDEADYYCALWYSNHWVFG CGTKLTVL | CD3-VL21 |
| 201 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVMHEALHNHYTQKSLSLSP | Knob Fc |
| 202 | DKTHTCPPCPAPELLGGPSVFLFPPKPKDTLMRSRTPEVTCVVVDVSHEDPE VKFNWYVDGVEVHNAKTKPREEQYNSTYRVVSVLTVLHQDWLNGKEYKC KVSNKALPAPIEKTISKAKGQPREPQVCTLPPSRDELTKNQVSLSCAVKGFYP SDIAVEWESNGQPENNYKTTPPVLDSDGSFFLVSKLTVDKSRWQQGNVFSC SVMHEALHNHYTQKSLSLSP | Hole Fc |
| 203 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPCRDELTKNQVSLWCLVKGFYPSD IAVEWESNGQPENNYKTTPPVLDSDGSFFLYSKLTVDKSRWQQGNVFSCSV MHEALHNHYTQKSLSLSP | Knob Fc |
| 204 | DKTHTCPPCPAPGGPSVFLFPPKPKDTLMRSRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNHYTQKSLSLSP | Hole Fc |
| 205 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VMHEALHNRYTQKSLSLSP | Hole Fc |
| 206 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNRYTQKSLSLSP | Hole Fc |
| 207 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVVHEALHNHYTQKSLSLSP | Knob Fc |
| 208 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVV HEALHNHYTQKSLSLSP | Knob Fc |

| SEQUENCE TABLE | | |
|---|---|---|
| SEQ ID NO | SEQUENCE | DESCRIPTION |
| 209 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VVHEALHNRYTQKSLSLSP | Hole Fc |
| 210 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIA VEWESNGQPENNYKTTPPVLDSDGSFFLVSKLTVDKSRWQQGNVFSCSVVH EALHNRYTQKSLSLSP | Hole Fc |
| 211 | GFTFNTYAMN | anti-CD3 VH CDR1 |
| 212 | RIRSKYNNYATY | anti-CD3 VH CDR2 |
| 213 | QVQLVQSGAE VKKPGSSVKV SCKASGYAFS YSWINWVRQA PGQGLEWMGR IFPGDGDTDY NGKFKGRVTI TADKSTSTAY MELSSLRSED TAVYYCARNV FDGYWLVYWG QGTLVTVSSG GGGSGGGGSG GGGSDIVMTQ TPLSLPVTPG EPASISCRSS KSLLHSNGIT YLYWYLQKPG QSPQLLIYQM SNLVSGVPDR FSGSGSGTDF TLKISRVEAE DVGVYYCAQN LELPYTFGGG TKVEIK | CD20 scFv |
| 214 | EVQLVESGGGEVQPGGSLRLSCAASGFSFSSNVMMWVRQAPGKGLEWVSTIYSSG TGTFYAESVKGRFTISRDNAKNTLYLQMSSLRPEDTAVYYCATSGPVRGWGPRSQGT LVTVKP | B7H3 sdAb B7h3 hz1A5v51 |
| 215 | EVQLVESGGGEVQPGGSLRLSCAASGSTFSSYHMSWFRQAPGKQREPVATS HHGGTTNYAGSVKGRFTISRDNAKNTVYLQMNTLRAEDTAVYYCKADHG YQGRGYWGQGTLVTVKP | sdAb B7H3 hz58E05v27 |
| 216 | EVQLVESGGGEVQPGGSLRLSCAASGFTFSSYHMSWFRQAPGKQRELVATSHHGGT TNYAGSVKGRFTISRDNAKNTVYLQMNTLRAEDTAVYYCKADHGYQGRGYWGQGT LVTVKP | sdAb B7H3 hz58E05v55 |
| 217 | EVQLVESGGGEVQPGGSLRLSCAASGFTFSSYHMSWFRQAPGKQREPVATS HHGGTTNYAGSVKGRFTISRDNAKNTVYLQMNTLRAEDTAVYYCKADHG YQGRGYWGQGTLVTVKP | sdAb B7H3 hz58E05v48 |
| 218 | EVQLVESGGGEVQPGGSLRLSCAPSERTFSTYTMGWFRQAPGKEREFVAVV NWGGGSKYYAESVKGRFTISRDNAKNTVYLQMSSLRAEDTAVYYCAAGG AYSGPYYDTRQYTYWGQGTLVTVKPGG | sdAb B7H3 hz57B04v24 |
| 219 | EVQLVESGGGEVQPGGSLRLSCAASGSIFSINAMGWYRQAPGKQRELVAGF TGDTNTIYAESVKGRFTISRDNAKNTVYLQMSSLRAEDTAVYYCAADVQLF SRDYEFYWGQGTLVTVKP | sdAb DLL3 hz10D9v7 |
| 220 | EVQLVESGGGEVQPGGSLRLSCGPSEIITSDKSMGWVRQAPGKQRNLVAGIS NVGSTNYAQSVKGRFTISRDNAKNTVYLQMSSLRAEDTAVYYCYARDFEN EYWGQGTLVTVKP | sdAb DLL3 hz8E7v16 |
| 221 | GFSFSINAMG | 41BB CDR1 |
| 222 | AIESGRNTV | 41BB CDR2 |
| 223 | LKGNRVVSPSVAY | 41BB CDR3 |
| 224 | HGNFGDSYVSWFAY | CD3-VH7, VH33 CDR3 |
| 225 | ALWYSNHWV | CD3-VL2, VL21 CDR3 |
| 226 | VLWYSNRWV | CD3-VL8 CDR3 |
| 227 | GFTFSTYAMN | CD3 VH33 CDR1 |

| SEQUENCE TABLE | | |
|---|---|---|
| SEQ ID NO | SEQUENCE | DESCRIPTION |
| 228 | RIRSKYNNYATY | CD3 VH33 CDR1 |
| 229 | GSSTGAVTTSNYAN | CD3 VL21 CDR1 |
| 230 | GTNKRAP | CD3 VL21 CDR2 |

```
                              SEQUENCE LISTING

Sequence total quantity: 230
SEQ ID NO: 1              moltype = AA  length = 218
FEATURE                   Location/Qualifiers
REGION                    1..218
                          note = IgG1 Fc
source                    1..218
                          mol_type = protein
                          organism = synthetic construct
SEQUENCE: 1
PAPELLGGPS VFLFPPKPKD TLMISRTPEV TCVVVDVSHE DPEVKFNWYV DGVEVHNAKT  60
KPREEQYNST YRVVSVLTVL HQDWLNGKEY KCKVSNKALP APIEKTISKA KGQPREPQVY 120
TLPPSRDELT KNQVSLTCLV KGFYPSDIAV EWESNGQPEN NYKTTPPVLD SDGSFFLYSK 180
LTVDKSRWQQ GNVFSCSVMH EALHNHYTQK SLSLSPGK                        218

SEQ ID NO: 2              moltype = AA  length = 215
FEATURE                   Location/Qualifiers
REGION                    1..215
                          note = xELL Fc
source                    1..215
                          mol_type = protein
                          organism = synthetic construct
SEQUENCE: 2
PAPGGPSVFL FPPKPKDTLM ISRTPEVTCV VVDVSHEDPE VKFNWYVDGV EVHNAKTKPR  60
EEQYNSTYRV VSVLTVLHQD WLNGKEYKCK VSNKALPAPI EKTISKAKGQ PREPQVYTLP 120
PSRDELTKNQ VSLTCLVKGF YPSDIAVEWE SNGQPENNYK TTPPVLDSDG SFFLYSKLTV 180
DKSRWQQGNV FSCSVMHEAL HNHYTQKSLS LSPGK                           215

SEQ ID NO: 3              moltype = AA  length = 217
FEATURE                   Location/Qualifiers
REGION                    1..217
                          note = IgG2 Fc
source                    1..217
                          mol_type = protein
                          organism = synthetic construct
SEQUENCE: 3
PAPPVAGPSV FLFPPKPKDT LMISRTPEVT CVVVDVSHED PEVQFNWYVD GVEVHNAKTK  60
PREEQFNSTF RVVSVLTVVH QDWLNGKEYK CKVSNKGLPA PIEKTISKTK GQPREPQVYT 120
LPPSREEMTK NQVSLTCLVK GFYPSDISVE WESNGQPENN YKTTPPMLDS DGSFFLYSKL 180
TVDKSRWQQG NVFSCSVMHE ALHNHYTQKS LSLSPGK                         217

SEQ ID NO: 4              moltype = AA  length = 218
FEATURE                   Location/Qualifiers
REGION                    1..218
                          note = IgG3 Fc
source                    1..218
                          mol_type = protein
                          organism = synthetic construct
SEQUENCE: 4
PAPELLGGPS VFLFPPKPKD TLMISRTPEV TCVVVDVSHE DPEVQFKWYV DGVEVHNAKT  60
KPREEQYNST FRVVSVLTVL HQDWLNGKEY KCKVSNKALP APIEKTISKT KGQPREPQVY 120
TLPPSREEMT KNQVSLTCLV KGFYPSDIAV EWESSGQPEN NYNTTPPMLD SDGSFFLYSK 180
LTVDKSRWQQ GNIFSCSVMH EALHNRFTQK SLSLSPGK                        218

SEQ ID NO: 5              moltype = AA  length = 218
FEATURE                   Location/Qualifiers
REGION                    1..218
                          note = IgG4 Fc
source                    1..218
                          mol_type = protein
```

```
                                    organism = synthetic construct
SEQUENCE: 5
PAPEFLGGPS VFLFPPKPKD TLMISRTPEV TCVVVDVSQE DPEVQFNWYV DGVEVHNAKT    60
KPREEQFNST YRVVSVLTVL HQDWLNGKEY KCKVSNKGLP SSIEKTISKA KGQPREPQVY   120
TLPPSQEEMT KNQVSLTCLV KGFYPSDIAV EWESNGQPEN NYKTTPPVLD SDGSFFLYSR   180
LTVDKSRWQE GNVFSCSVMH EALHNHYTQK SLSLSLGK                          218

SEQ ID NO: 6               moltype = AA   length = 218
FEATURE                    Location/Qualifiers
REGION                     1..218
                           note = IgG4 Fc
source                     1..218
                           mol_type = protein
                           organism = synthetic construct
SEQUENCE: 6
PAPELLGGPS VFLFPPKPKD TLMISRTPEV TCVVVDVSQE DPEVQFNWYV DGVEVHNAKT    60
KPREEQFNST YRVVSVLTVL HQDWLNGKEY KCKVSNKGLP SSIEKTISKA KGQPREPQVY   120
TLPPSQEEMT KNQVSLTCLV KGFYPSDIAV EWESNGQPEN NYKTTPPVLD SDGSFFLYSR   180
LTVDKSRWQE GNVFSCSVMH EALHNHYTQK SLSLSLGK                          218

SEQ ID NO: 7               moltype = AA   length = 14
FEATURE                    Location/Qualifiers
REGION                     1..14
                           note = Hinge
source                     1..14
                           mol_type = protein
                           organism = synthetic construct
SEQUENCE: 7
EPKSSDKTHT CPPC                                                     14

SEQ ID NO: 8               moltype = AA   length = 9
FEATURE                    Location/Qualifiers
REGION                     1..9
                           note = Hinge
source                     1..9
                           mol_type = protein
                           organism = synthetic construct
SEQUENCE: 8
DKTHTCPPC                                                            9

SEQ ID NO: 9               moltype = AA   length = 11
FEATURE                    Location/Qualifiers
REGION                     1..11
                           note = Hinge
source                     1..11
                           mol_type = protein
                           organism = synthetic construct
SEQUENCE: 9
ESKYGPPCPP C                                                        11

SEQ ID NO: 10              moltype = AA   length = 6
FEATURE                    Location/Qualifiers
REGION                     1..6
                           note = Synthetic - Linker(GGS)2
source                     1..6
                           mol_type = protein
                           organism = synthetic construct
SEQUENCE: 10
GGSGGS                                                               6

SEQ ID NO: 11              moltype = AA   length = 9
FEATURE                    Location/Qualifiers
REGION                     1..9
                           note = Synthetic - Linker (GGS)3
source                     1..9
                           mol_type = protein
                           organism = synthetic construct
SEQUENCE: 11
GGSGGSGGS                                                            9

SEQ ID NO: 12              moltype = AA   length = 12
FEATURE                    Location/Qualifiers
REGION                     1..12
                           note = Synthetic - Linker (GGS)4
source                     1..12
                           mol_type = protein
                           organism = synthetic construct
SEQUENCE: 12
GGSGGSGGSG GS                                                       12
```

```
SEQ ID NO: 13              moltype = AA   length = 15
FEATURE                    Location/Qualifiers
REGION                     1..15
                           note = Synthetic - Linker (GGS)5
source                     1..15
                           mol_type = protein
                           organism = synthetic construct
SEQUENCE: 13
GGSGGSGGSG GSGGS                                                         15

SEQ ID NO: 14              moltype = AA   length = 125
FEATURE                    Location/Qualifiers
REGION                     1..125
                           note = Synthetic - anti-CD3 VH
source                     1..125
                           mol_type = protein
                           organism = synthetic construct
SEQUENCE: 14
EVQLVESGGG LVQPKGSLKL SCAASGFTFN TYAMNWVRQA PGKGLEWVAR IRSKYNNYAT         60
YYADSVKDRF TISRDDSQSI LYLQMNNLKT EDTAMYYCVR HGNFGNSYVS WFAYWGQGTL        120
VTVSA                                                                   125

SEQ ID NO: 15              moltype = AA   length = 109
FEATURE                    Location/Qualifiers
REGION                     1..109
                           note = anti-CD3 VL
source                     1..109
                           mol_type = protein
                           organism = synthetic construct
SEQUENCE: 15
QAVVTQESAL TTSPGETVTL TCRSSTGAVT TSNYANWVQE KPDHLFTGLI GGTNKRAPGV         60
PARFSGSLIG DKAALTITGA QTEDEAIYFC ALWYSNLWVF GGGTKLTVL                   109

SEQ ID NO: 16              moltype = AA   length = 5
FEATURE                    Location/Qualifiers
REGION                     1..5
                           note = anti-CD3 VH CDR1
source                     1..5
                           mol_type = protein
                           organism = synthetic construct
SEQUENCE: 16
TYAMN                                                                     5

SEQ ID NO: 17              moltype = AA   length = 19
FEATURE                    Location/Qualifiers
REGION                     1..19
                           note = anti-CD3 VH CDR2
source                     1..19
                           mol_type = protein
                           organism = synthetic construct
SEQUENCE: 17
RIRSKYNNYA TYYADSVKD                                                     19

SEQ ID NO: 18              moltype = AA   length = 14
FEATURE                    Location/Qualifiers
REGION                     1..14
                           note = anti-CD3 VH CDR3
source                     1..14
                           mol_type = protein
                           organism = synthetic construct
SEQUENCE: 18
HGNFGNSYVS WFAY                                                          14

SEQ ID NO: 19              moltype = AA   length = 14
FEATURE                    Location/Qualifiers
REGION                     1..14
                           note = anti-CD3 VL CDR1
source                     1..14
                           mol_type = protein
                           organism = synthetic construct
SEQUENCE: 19
RSSTGAVTTS NYAN                                                          14

SEQ ID NO: 20              moltype = AA   length = 7
FEATURE                    Location/Qualifiers
REGION                     1..7
                           note = anti-CD3 VL CDR2
source                     1..7
```

```
                            mol_type = protein
                            organism = synthetic construct
SEQUENCE: 20
GTNKRAP                                                                  7

SEQ ID NO: 21               moltype = AA  length = 9
FEATURE                     Location/Qualifiers
REGION                      1..9
                            note = anti-CD3 VL CDR3
source                      1..9
                            mol_type = protein
                            organism = synthetic construct
SEQUENCE: 21
ALWYSNLWV                                                                9

SEQ ID NO: 22               moltype = AA  length = 4
FEATURE                     Location/Qualifiers
REGION                      1..4
                            note = Granzyme B substrate
source                      1..4
                            mol_type = protein
                            organism = synthetic construct
SEQUENCE: 22
LEAD                                                                     4

SEQ ID NO: 23               moltype = AA  length = 4
FEATURE                     Location/Qualifiers
REGION                      1..4
                            note = Granzyme B substrate
source                      1..4
                            mol_type = protein
                            organism = synthetic construct
SEQUENCE: 23
RQAR                                                                     4

SEQ ID NO: 24               moltype = AA  length = 4
FEATURE                     Location/Qualifiers
REGION                      1..4
                            note = MMP substrate
source                      1..4
                            mol_type = protein
                            organism = synthetic construct
SEQUENCE: 24
PAGL                                                                     4

SEQ ID NO: 25               moltype = AA  length = 19
FEATURE                     Location/Qualifiers
REGION                      1..19
                            note = Linker
source                      1..19
                            mol_type = protein
                            organism = synthetic construct
SEQUENCE: 25
TGLEADGSPA GLGRQARVG                                                    19

SEQ ID NO: 26               moltype = AA  length = 19
FEATURE                     Location/Qualifiers
REGION                      1..19
                            note = Linker
source                      1..19
                            mol_type = protein
                            organism = synthetic construct
SEQUENCE: 26
TGLEADGSRQ ARVGPAGLG                                                    19

SEQ ID NO: 27               moltype = AA  length = 19
FEATURE                     Location/Qualifiers
REGION                      1..19
                            note = Linker
source                      1..19
                            mol_type = protein
                            organism = synthetic construct
SEQUENCE: 27
TGSPAGLEAD GSRQARVGS                                                    19

SEQ ID NO: 28               moltype = AA  length = 19
FEATURE                     Location/Qualifiers
REGION                      1..19
                            note = Linker
```

```
source                      1..19
                            mol_type = protein
                            organism = synthetic construct
SEQUENCE: 28
TGPAGLGLEA DGSRQARVG                                                    19

SEQ ID NO: 29               moltype = AA  length = 19
FEATURE                     Location/Qualifiers
REGION                      1..19
                            note = Linker
source                      1..19
                            mol_type = protein
                            organism = synthetic construct
SEQUENCE: 29
TGRQARVGLE ADGSPAGLG                                                    19

SEQ ID NO: 30               moltype = AA  length = 18
FEATURE                     Location/Qualifiers
REGION                      1..18
                            note = Linker
source                      1..18
                            mol_type = protein
                            organism = synthetic construct
SEQUENCE: 30
TGSRQARVGP AGLEADGS                                                     18

SEQ ID NO: 31               moltype = AA  length = 20
FEATURE                     Location/Qualifiers
REGION                      1..20
                            note = Linker
source                      1..20
                            mol_type = protein
                            organism = synthetic construct
SEQUENCE: 31
TGPAGLGSRQ ARVGLEADGS                                                   20

SEQ ID NO: 32               moltype = AA  length = 125
FEATURE                     Location/Qualifiers
REGION                      1..125
                            note = anti-CD3 VH1
source                      1..125
                            mol_type = protein
                            organism = synthetic construct
SEQUENCE: 32
EVQLVESGGG LVQPGGSLRL SCAASGFTFS TYAMNWVRQA PGKGLEWVGR IRSKYNNYAT        60
YYADSVKDRF TISRDDSKNS LYLQMNSLKT EDTAVYYCVR HGNFGNSYVS WFAYWGQGTL       120
VTVSS                                                                  125

SEQ ID NO: 33               moltype = AA  length = 125
FEATURE                     Location/Qualifiers
REGION                      1..125
                            note = anti-CD3 VH2
source                      1..125
                            mol_type = protein
                            organism = synthetic construct
SEQUENCE: 33
EVKLVESGGG LVQPGGSLRL SCAASGFTFN TYAMNWVRQA PGKGLEWVAR IRSKYNNYAT        60
YYADSVKDRF TISRDDSKSS LYLQMNNLKT EDTAMYYCVR HGNFGNSYVS WFAYWGQGTL       120
VTVSS                                                                  125

SEQ ID NO: 34               moltype = AA  length = 125
FEATURE                     Location/Qualifiers
REGION                      1..125
                            note = anti-CD3 VH3
source                      1..125
                            mol_type = protein
                            organism = synthetic construct
SEQUENCE: 34
EVKLVESGGG LVKPGRSLRL SCAASGFTFN TYAMNWVRQA PGKGLEWVAR IRSKYNNYAT        60
YYADSVKDRF TISRDDSKSI LYLQMNNLKT EDTAMYYCVR HGNFGNSYVS WFAYWGQGTL       120
VTVSS                                                                  125

SEQ ID NO: 35               moltype = AA  length = 125
FEATURE                     Location/Qualifiers
REGION                      1..125
                            note = anti-CD3 VH4
source                      1..125
                            mol_type = protein
                            organism = synthetic construct
```

```
SEQUENCE: 35
EVKLVESGGG LVKPGRSLRL SCAASGFTFN TYAMNWVRQA PGKGLEWVAR IRSKYNNYAT    60
YYADSVKDRF TISRDDSKSI LYLQMNSLKT EDTAMYYCVR HGNFGNSYVS WFAYWGQGTL   120
VTVSS                                                              125

SEQ ID NO: 36            moltype = AA  length = 125
FEATURE                  Location/Qualifiers
REGION                   1..125
                         note = anti-CD3 VH5
source                   1..125
                         mol_type = protein
                         organism = synthetic construct
SEQUENCE: 36
EVKLVESGGG LVKPGRSLRL SCAASGFTFN TYAMNWVRQA PGKGLEWVAR IRSKYNNYAT    60
YYADSVKDRF TISRDDSKSI LYLQMNSLKT EDTAMYYCVR HGNFGNSYVS WFAYWGQGTL   120
VTVSS                                                              125

SEQ ID NO: 37            moltype = AA  length = 125
FEATURE                  Location/Qualifiers
REGION                   1..125
                         note = anti-CD3 VH6
source                   1..125
                         mol_type = protein
                         organism = synthetic construct
SEQUENCE: 37
EVQLLESGGG LVQPGGSLRL SCAASGFTFS TYAMNWVRQA PGKGLEWVSR IRSKYNNYAT    60
YYADSVKGRF TISRDDSKNT LYLQMNSLRA EDTAVYYCVR HGNFGNSYVS WFAYWGQGTL   120
VTVSS                                                              125

SEQ ID NO: 38            moltype = AA  length = 125
FEATURE                  Location/Qualifiers
REGION                   1..125
                         note = anti-CD3 VH7
source                   1..125
                         mol_type = protein
                         organism = synthetic construct
SEQUENCE: 38
EVQLVESGGG LVQPGGSLRL SCAASGFTFS TYAMSWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSS                                                              125

SEQ ID NO: 39            moltype = AA  length = 124
FEATURE                  Location/Qualifiers
REGION                   1..124
                         note = anti-CD3 VH8
source                   1..124
                         mol_type = protein
                         organism = synthetic construct
SEQUENCE: 39
EVQLVESGGG LVQPGGSLKL SCAASGFTFN KYAMNWVRQA PGKGLEWVAR IRSKYNNYAT    60
YYADSVKDRF TISRDDSKNT AYLQMNNLKT EDTAVYYCVR HGNFGNSYIS YWAYWGQGTL   120
VTVS                                                               124

SEQ ID NO: 40            moltype = AA  length = 125
FEATURE                  Location/Qualifiers
REGION                   1..125
                         note = anti-CD3 VH9
source                   1..125
                         mol_type = protein
                         organism = synthetic construct
SEQUENCE: 40
EVQLVESGGG LVQPGGSLRL SCAASGFTFN TYAMNWVRQA PGKGLEWVAR IRSKYNNYAT    60
YYADSVKGRF TISRDDSKNT LYLQMNSLRA EDTAVYYCVR HGNFGNSYVS WFAYWGQGTT   120
VTVSS                                                              125

SEQ ID NO: 41            moltype = AA  length = 125
FEATURE                  Location/Qualifiers
REGION                   1..125
                         note = anti-CD3 VH10
source                   1..125
                         mol_type = protein
                         organism = synthetic construct
SEQUENCE: 41
EVQLVESGGG LVQPGGSLRL SCAASGFTFN TYAMNWVRQA PGKGLEWVAR IRSKYNNYAT    60
YYADSVKGRF TISRDDSKNT LYLQMNSLRA EDTAVYYCVR HGNFGNSYVS YFAYWGQGTT   120
VTVSS                                                              125

SEQ ID NO: 42            moltype = AA  length = 125
FEATURE                  Location/Qualifiers
```

```
REGION                   1..125
                         note = anti-CD3 VH11
source                   1..125
                         mol_type = protein
                         organism = synthetic construct
SEQUENCE: 42
EVQLVESGGG LVQPKGSLKL SCAASGFTFN TYAMNWVRQA PGKGLEWVAR IRSKYNNYAT  60
YYADSVKDRF TISRDDSQSI LYLQMNNLKT EDTAMYYCVR HGNFGNSYVS WFAYWGQGTL 120
VTVSS                                                            125

SEQ ID NO: 43            moltype = AA  length = 125
FEATURE                  Location/Qualifiers
REGION                   1..125
                         note = anti-CD3 VH12
source                   1..125
                         mol_type = protein
                         organism = synthetic construct
SEQUENCE: 43
EVQLVESGGG LVQPGGSLRL SCAASGFTFN TYAMNWVRQA PGKGLEWVAR IRSKYNNYAT  60
YYADSVKGRF TISRDDAKNT LYLQMSSLRA EDTAVYYCVR HGNFGNSYVS WFAYWGQGTL 120
VTVKP                                                            125

SEQ ID NO: 44            moltype = AA  length = 125
FEATURE                  Location/Qualifiers
REGION                   1..125
                         note = anti-CD3 VH13
source                   1..125
                         mol_type = protein
                         organism = synthetic construct
SEQUENCE: 44
EVQLVESGGG LVQPGGSLRL SCAASGFTFN TYAMNWVRQA PGKCLEWVAR IRSKYNNYAT  60
YYADSVKGRF TISRDDAKNT LYLQMSSLRA EDTAVYYCVR HGNFGNSYVS WFAYWGQGTL 120
VTVKP                                                            125

SEQ ID NO: 45            moltype = AA  length = 125
FEATURE                  Location/Qualifiers
REGION                   1..125
                         note = anti-CD3 VH14
source                   1..125
                         mol_type = protein
                         organism = synthetic construct
SEQUENCE: 45
EVQLVESGGG LVQPGGSLRL SCAASGFTFN TYAMNWVRQA PGKGLEWVAR IRSKYNNYAT  60
YYADSVKGRF TISRDDAKNT LYLQMSSLRA EDTAVYYCVR HGNFGNSYVS WFAYWGCGTL 120
VTVKP                                                            125

SEQ ID NO: 46            moltype = AA  length = 125
FEATURE                  Location/Qualifiers
REGION                   1..125
                         note = anti-CD3 VH15
source                   1..125
                         mol_type = protein
                         organism = synthetic construct
SEQUENCE: 46
EVQLVESGGG LVQPGGSLRL SCAASGFTFS TYAMNWVRQA PGKGLEWVAR IRSKYNNYAT  60
YYADSVKGRF TISRDDAKNT LYLQMSSLRA EDTAVYYCVR HGNFGNSYVS WFAYWGQGTL 120
VTVSS                                                            125

SEQ ID NO: 47            moltype = AA  length = 125
FEATURE                  Location/Qualifiers
REGION                   1..125
                         note = anti-CD3 VH16
source                   1..125
                         mol_type = protein
                         organism = synthetic construct
SEQUENCE: 47
EVQLVESGGG LVQPGGSLRL SCAASGFTFN TYAMNWVRQA PGKGLEWVSR IRSKYNNYAT  60
YYADSVKGRF TISRDDAKNT LYLQMSSLRA EDTAVYYCVR HGNFGNSYVS WFAYWGQGTL 120
VTVSS                                                            125

SEQ ID NO: 48            moltype = AA  length = 125
FEATURE                  Location/Qualifiers
REGION                   1..125
                         note = anti-CD3 VH17
source                   1..125
                         mol_type = protein
                         organism = synthetic construct
SEQUENCE: 48
EVQLVESGGG LVQPGGSLRL SCAASGFTFS TYAMNWVRQA PGKGLEWVSR IRSKYNNYAT  60
```

```
YYADSVKGRF TISRDDAKNT LYLQMSSLRA EDTAVYYCVR HGNFGNSYVS WFAYWGQGTL    120
VTVSS                                                                125

SEQ ID NO: 49           moltype = AA  length = 125
FEATURE                 Location/Qualifiers
REGION                  1..125
                        note = anti-CD3 VH18
source                  1..125
                        mol_type = protein
                        organism = synthetic construct
SEQUENCE: 49
EVQLVESGGG LVQPGGSLRL SCAASGFTFS TYAMNWVRQA PGKCLEWVAR IRSKYNNYAT    60
YYADSVKGRF TISRDDAKNT LYLQMSSLRA EDTAVYYCVR HGNFGNSYVS WFAYWGQGTL    120
VTVSS                                                                125

SEQ ID NO: 50           moltype = AA  length = 125
FEATURE                 Location/Qualifiers
REGION                  1..125
                        note = anti-CD3 VH19
source                  1..125
                        mol_type = protein
                        organism = synthetic construct
SEQUENCE: 50
EVQLVESGGG LVQPGGSLRL SCAASGFTFN TYAMNWVRQA PGKCLEWVSR IRSKYNNYAT    60
YYADSVKGRF TISRDDAKNT LYLQMSSLRA EDTAVYYCVR HGNFGNSYVS WFAYWGQGTL    120
VTVSS                                                                125

SEQ ID NO: 51           moltype = AA  length = 125
FEATURE                 Location/Qualifiers
REGION                  1..125
                        note = anti-CD3 VH20
source                  1..125
                        mol_type = protein
                        organism = synthetic construct
SEQUENCE: 51
EVQLVESGGG LVQPGGSLRL SCAASGFTFS TYAMNWVRQA PGKCLEWVSR IRSKYNNYAT    60
YYADSVKGRF TISRDDAKNT LYLQMSSLRA EDTAVYYCVR HGNFGNSYVS WFAYWGQGTL    120
VTVSS                                                                125

SEQ ID NO: 52           moltype = AA  length = 125
FEATURE                 Location/Qualifiers
REGION                  1..125
                        note = anti-CD3 VH21
source                  1..125
                        mol_type = protein
                        organism = synthetic construct
SEQUENCE: 52
EVQLVESGGG LVQPGGSLRL SCAASGFTFS TYAMNWVRQA PGKCLEWVGR IRSKYNNYAT    60
YYADSVKDRF TISRDDSKNS LYLQMNSLKT EDTAVYYCVR HGNFGNSYVS WFAYWGQGTL    120
VTVSS                                                                125

SEQ ID NO: 53           moltype = AA  length = 125
FEATURE                 Location/Qualifiers
REGION                  1..125
                        note = anti-CD3 VH22
source                  1..125
                        mol_type = protein
                        organism = synthetic construct
SEQUENCE: 53
EVKLVESGGG LVQPGGSLRL SCAASGFTFN TYAMNWVRQA PGKCLEWVAR IRSKYNNYAT    60
YYADSVKDRF TISRDDSKSS LYLQMNNLKT EDTAMYYCVR HGNFGNSYVS WFAYWGQGTL    120
VTVSS                                                                125

SEQ ID NO: 54           moltype = AA  length = 125
FEATURE                 Location/Qualifiers
REGION                  1..125
                        note = anti-CD3 VH23
source                  1..125
                        mol_type = protein
                        organism = synthetic construct
SEQUENCE: 54
EVKLVESGGG LVKPGRSLRL SCAASGFTFN TYAMNWVRQA PGKCLEWVAR IRSKYNNYAT    60
YYADSVKDRF TISRDDSKSI LYLQMNNLKT EDTAMYYCVR HGNFGNSYVS WFAYWGQGTL    120
VTVSS                                                                125

SEQ ID NO: 55           moltype = AA  length = 125
FEATURE                 Location/Qualifiers
REGION                  1..125
                        note = anti-CD3 VH24
```

```
source                  1..125
                        mol_type = protein
                        organism = synthetic construct
SEQUENCE: 55
EVKLVESGGG LVKPGRSLRL SCAASGFTFN TYAMNWVRQA PGKCLEWVAR IRSKYNNYAT    60
YYADSVKDRF TISRDDSKSI LYLQMNSLKT EDTAMYYCVR HGNFGNSYVS WFAYWGQGTL   120
VTVSS                                                               125

SEQ ID NO: 56           moltype = AA  length = 125
FEATURE                 Location/Qualifiers
REGION                  1..125
                        note = anti-CD3 VH25
source                  1..125
                        mol_type = protein
                        organism = synthetic construct
SEQUENCE: 56
EVKLVESGGG LVKPGRSLRL SCAASGFTFN TYAMNWVRQA PGKCLEWVAR IRSKYNNYAT    60
YYADSVKDRF TISRDDSKSI LYLQMNSLKT EDTAMYYCVR HGNFGNSYVS WFAYWGQGTL   120
VTVSS                                                               125

SEQ ID NO: 57           moltype = AA  length = 125
FEATURE                 Location/Qualifiers
REGION                  1..125
                        note = anti-CD3 VH26
source                  1..125
                        mol_type = protein
                        organism = synthetic construct
SEQUENCE: 57
EVQLLESGGG LVQPGGSLRL SCAASGFTFS TYAMNWVRQA PGKCLEWVSR IRSKYNNYAT    60
YYADSVKGRF TISRDDSKNT LYLQMNSLRA EDTAVYYCVR HGNFGNSYVS WFAYWGQGTL   120
VTVSS                                                               125

SEQ ID NO: 58           moltype = AA  length = 125
FEATURE                 Location/Qualifiers
REGION                  1..125
                        note = anti-CD3 VH27
source                  1..125
                        mol_type = protein
                        organism = synthetic construct
SEQUENCE: 58
EVQLVESGGG LVQPGGSLRL SCAASGFTFS TYAMSWVRQA PGKCLEWVGR IRSKYNNYAT    60
YYADSVKGRF TISRDDSKNT LYLQMNSLRA EDTAVYYCVR HGNFGDSYVS WFAYWGQGTL   120
VTVSS                                                               125

SEQ ID NO: 59           moltype = AA  length = 124
FEATURE                 Location/Qualifiers
REGION                  1..124
                        note = anti-CD3 VH28
source                  1..124
                        mol_type = protein
                        organism = synthetic construct
SEQUENCE: 59
EVQLVESGGG LVQPGGSLKL SCAASGFTFN KYAMNWVRQA PGKCLEWVAR IRSKYNNYAT    60
YYADSVKDRF TISRDDSKNT AYLQMNNLKT EDTAVYYCVR HGNFGNSYIS YWAYWGQGTL   120
VTVS                                                                124

SEQ ID NO: 60           moltype = AA  length = 125
FEATURE                 Location/Qualifiers
REGION                  1..125
                        note = anti-CD3 VH29
source                  1..125
                        mol_type = protein
                        organism = synthetic construct
SEQUENCE: 60
EVQLVESGGG LVQPGGSLRL SCAASGFTFN TYAMNWVRQA PGKCLEWVAR IRSKYNNYAT    60
YYADSVKGRF TISRDDSKNT LYLQMNSLRA EDTAVYYCVR HGNFGNSYVS WFAYWGQGTT   120
VTVSS                                                               125

SEQ ID NO: 61           moltype = AA  length = 125
FEATURE                 Location/Qualifiers
REGION                  1..125
                        note = anti-CD3 VH30
source                  1..125
                        mol_type = protein
                        organism = synthetic construct
SEQUENCE: 61
EVQLVESGGG LVQPGGSLRL SCAASGFTFN TYAMNWVRQA PGKCLEWVAR IRSKYNNYAT    60
YYADSVKGRF TISRDDSKNT LYLQMNSLRA EDTAVYYCVR HGNFGNSYVS YFAYWGQGTT   120
VTVSS                                                               125
```

```
SEQ ID NO: 62            moltype = AA   length = 125
FEATURE                  Location/Qualifiers
REGION                   1..125
                         note = anti-CD3 VH31
source                   1..125
                         mol_type = protein
                         organism = synthetic construct
SEQUENCE: 62
EVQLVESGGG LVQPKGSLKL SCAASGFTFN TYAMNWVRQA PGKCLEWVAR IRSKYNNYAT        60
YYADSVKDRF TISRDDSQSI LYLQMNNLKT EDTAMYYCVR HGNFGNSYVS WFAYWGQGTL       120
VTVSS                                                                   125

SEQ ID NO: 63            moltype = AA   length = 109
FEATURE                  Location/Qualifiers
REGION                   1..109
                         note = anti-CD3 VL1
source                   1..109
                         mol_type = protein
                         organism = synthetic construct
SEQUENCE: 63
QAVVTQESAL TTSPGETVTL TCRSSTGAVT TSNYANWVQE KPDHLFTGLI GGTNKRAPGV        60
PARFSGSLIG DKAALTITGA QTEDEAIYFC ALWYSNLWVF GGGTKLTVL                   109

SEQ ID NO: 64            moltype = AA   length = 109
FEATURE                  Location/Qualifiers
REGION                   1..109
                         note = anti-CD3 VL2
source                   1..109
                         mol_type = protein
                         organism = synthetic construct
SEQUENCE: 64
QAVVTQEPSL TVSPGGTVTL TCGSSTGAVT TSNYANWVQQ KPGKSPRGLI GGTNKRAPGV        60
PARFSGSLLG GKAALTISGA QPEDEADYYC ALWYSNHWVF GCGTKLEIK                   109

SEQ ID NO: 65            moltype = AA   length = 109
FEATURE                  Location/Qualifiers
REGION                   1..109
                         note = anti-CD3 VL3
source                   1..109
                         mol_type = protein
                         organism = synthetic construct
SEQUENCE: 65
QAVVTQEPSL TVSPGGTVTL TCRSSTGAVT TSNYANWVQQ KPGQAPRGLI GGTNKRAPWT        60
PARFSGSLLG GKAALTITGA QAEDEADYYC ALWYSNLWVF GGGTKLTVL                   109

SEQ ID NO: 66            moltype = AA   length = 109
FEATURE                  Location/Qualifiers
REGION                   1..109
                         note = anti-CD3 VL4
source                   1..109
                         mol_type = protein
                         organism = synthetic construct
SEQUENCE: 66
QAVVTQEPSF SVSPGGTVTL TCRSSTGAVT TSNYANWVQQ TPGQAFRGLI GGTNKRAPGV        60
PARFSGSLIG DKAALTITGA QADDESIYFC ALWYSNLWVF GGGTKLTVL                   109

SEQ ID NO: 67            moltype = AA   length = 109
FEATURE                  Location/Qualifiers
REGION                   1..109
                         note = anti-CD3 VL5
source                   1..109
                         mol_type = protein
                         organism = synthetic construct
SEQUENCE: 67
QAVVTQEPSF SVSPGGTVTL TCRSSTGAVT TSNYANWVQQ TPGQAFRGLI GGTNKRAPGV        60
PARFSGSILG NKAALTITGA QADDESIYFC ALWYSNLWVF GGGTKLTVL                   109

SEQ ID NO: 68            moltype = AA   length = 109
FEATURE                  Location/Qualifiers
REGION                   1..109
                         note = anti-CD3 VL6
source                   1..109
                         mol_type = protein
                         organism = synthetic construct
SEQUENCE: 68
QAVVTQEPSF SVSPGGTVTL TCRSSTGAVT TSNYANWVQQ TPGQAFRGLI GGTNKRAPGV        60
PARFSGSILG NKAALTITGA QADDESDYYC ALWYSNLWVF GGGTKLTVL                   109
```

```
SEQ ID NO: 69              moltype = AA   length = 109
FEATURE                    Location/Qualifiers
REGION                     1..109
                           note = anti-CD3 VL7
source                     1..109
                           mol_type = protein
                           organism = synthetic construct
SEQUENCE: 69
QAVVTQEPSL TVSPGGTVTL TCGSSTGAVT TSNYANWVQE KPGQAFRGLI GGTNKRAPGT   60
PARFSGSLLG GKAALTLSGA QPEDEAEYYC ALWYSNLWVF GGGTKLTVL              109

SEQ ID NO: 70              moltype = AA   length = 109
FEATURE                    Location/Qualifiers
REGION                     1..109
                           note = anti-CD3 VL8
source                     1..109
                           mol_type = protein
                           organism = synthetic construct
SEQUENCE: 70
QTVVTQEPSL TVSPGGTVTL TCGSSTGAVT SGNYPNWVQQ KPGQAPRGLI GGTKFLAPGT   60
PARFSGSLLG GKAALTLSGV QPEDEAEYYC VLWYSNRWVF GGGTKLTVL              109

SEQ ID NO: 71              moltype = AA   length = 109
FEATURE                    Location/Qualifiers
REGION                     1..109
                           note = anti-CD3 VL9
source                     1..109
                           mol_type = protein
                           organism = synthetic construct
SEQUENCE: 71
QAVVTQEPSL TVSPGGTVTL TCGSSTGAVT TSNYANWVQQ KPGQAFRGLI GGTNKRAPGV   60
PARFSGSLLG GKAALTISGA QPEDEADYYC ALWYSNHWVF GGGTKLEIK              109

SEQ ID NO: 72              moltype = AA   length = 109
FEATURE                    Location/Qualifiers
REGION                     1..109
                           note = anti-CD3 VL10
source                     1..109
                           mol_type = protein
                           organism = synthetic construct
SEQUENCE: 72
QAVVTQEPSL TVSPGGTVTL TCGSSTGAVT TSNYANWVQQ KPGQAFRGLI GGTNKRAPGV   60
PARFSGSLLG GKAALTISGA QPEDEADYYC ALWYSNHWVF GCGTKLEIK              109

SEQ ID NO: 73              moltype = AA   length = 109
FEATURE                    Location/Qualifiers
REGION                     1..109
                           note = anti-CD3 VL11
source                     1..109
                           mol_type = protein
                           organism = synthetic construct
SEQUENCE: 73
QAVVTQEPSL TVSPGGTVTL TCGSSTGAVT TSNYANWVQQ KPGQCFRGLI GGTNKRAPGV   60
PARFSGSLLG GKAALTISGA QPEDEADYYC ALWYSNHWVF GEGTKLEIK              109

SEQ ID NO: 74              moltype = AA   length = 109
FEATURE                    Location/Qualifiers
REGION                     1..109
                           note = anti-CD3 VL12
source                     1..109
                           mol_type = protein
                           organism = synthetic construct
SEQUENCE: 74
QAVVTQESAL TTSPGETVTL TCRSSTGAVT TSNYANWVQE KPDHLFTGLI GGTNKRAPGV   60
PARFSGSLIG DKAALTITGA QTEDEAIYFC ALWYSNLWVF GCGTKLTVL              109

SEQ ID NO: 75              moltype = AA   length = 109
FEATURE                    Location/Qualifiers
REGION                     1..109
                           note = anti-CD3 VL13
source                     1..109
                           mol_type = protein
                           organism = synthetic construct
SEQUENCE: 75
QAVVTQEPSL TVSPGGTVTL TCGSSTGAVT TSNYANWVQQ KPGKSPRGLI GGTNKRAPGV   60
PARFSGSLLG GKAALTISGA QPEDEADYYC ALWYSNHWVF GGGTKLEIK              109

SEQ ID NO: 76              moltype = AA   length = 109
FEATURE                    Location/Qualifiers
```

```
REGION                  1..109
                        note = anti-CD3 VL14
source                  1..109
                        mol_type = protein
                        organism = synthetic construct
SEQUENCE: 76
QAVVTQEPSL TVSPGGTVTL TCRSSTGAVT TSNYANWVQQ KPGQAPRGLI GGTNKRAPWT    60
PARFSGSLLG GKAALTITGA QAEDEADYYC ALWYSNLWVF GCGTKLTVL               109

SEQ ID NO: 77           moltype = AA  length = 109
FEATURE                 Location/Qualifiers
REGION                  1..109
                        note = anti-CD3 VL15
source                  1..109
                        mol_type = protein
                        organism = synthetic construct
SEQUENCE: 77
QAVVTQEPSF SVSPGGTVTL TCRSSTGAVT TSNYANWVQQ TPGQAFRGLI GGTNKRAPGV    60
PARFSGSLIG DKAALTITGA QADDESIYFC ALWYSNLWVF GGGTKLTVL               109

SEQ ID NO: 78           moltype = AA  length = 109
FEATURE                 Location/Qualifiers
REGION                  1..109
                        note = anti-CD3 VL16
source                  1..109
                        mol_type = protein
                        organism = synthetic construct
SEQUENCE: 78
QAVVTQEPSF SVSPGGTVTL TCRSSTGAVT TSNYANWVQQ TPGQAFRGLI GGTNKRAPGV    60
PARFSGSILG NKAALTITGA QADDESIYFC ALWYSNLWVF GCGTKLTVL               109

SEQ ID NO: 79           moltype = AA  length = 109
FEATURE                 Location/Qualifiers
REGION                  1..109
                        note = anti-CD3 VL17
source                  1..109
                        mol_type = protein
                        organism = synthetic construct
SEQUENCE: 79
QAVVTQEPSF SVSPGGTVTL TCRSSTGAVT TSNYANWVQQ TPGQAFRGLI GGTNKRAPGV    60
PARFSGSILG NKAALTITGA QADDESDYYC ALWYSNLWVF GCGTKLTVL               109

SEQ ID NO: 80           moltype = AA  length = 109
FEATURE                 Location/Qualifiers
REGION                  1..109
                        note = anti-CD3 VL18
source                  1..109
                        mol_type = protein
                        organism = synthetic construct
SEQUENCE: 80
QAVVTQEPSL TVSPGGTVTL TCGSSTGAVT TSNYANWVQE KPGQAFRGLI GGTNKRAPGT    60
PARFSGSLLG GKAALTLSGA QPEDEAEYYC ALWYSNLWVF GCGTKLTVL               109

SEQ ID NO: 81           moltype = AA  length = 109
FEATURE                 Location/Qualifiers
REGION                  1..109
                        note = anti-CD3 VL19
source                  1..109
                        mol_type = protein
                        organism = synthetic construct
SEQUENCE: 81
QTVVTQEPSL TVSPGGTVTL TCGSSTGAVT SGNYPNWVQQ KPGQAPRGLI GGTKFLAPGT    60
PARFSGSLLG GKAALTLSGV QPEDEAEYYC VLWYSNRWVF GCGTKLTVL               109

SEQ ID NO: 82           moltype = AA  length = 226
FEATURE                 Location/Qualifiers
REGION                  1..226
                        note = Knob Fc
source                  1..226
                        mol_type = protein
                        organism = synthetic construct
SEQUENCE: 82
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPT                  226

SEQ ID NO: 83           moltype = AA  length = 226
FEATURE                 Location/Qualifiers
```

```
REGION                       1..226
                             note = Hole Fc
source                       1..226
                             mol_type = protein
                             organism = synthetic construct
SEQUENCE: 83
DKTHTCPPCP APELLGGPSV FLFPPKPKDT LMRSRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPT                  226

SEQ ID NO: 84                moltype = AA  length = 223
FEATURE                      Location/Qualifiers
REGION                       1..223
                             note = Knob Fc
source                       1..223
                             mol_type = protein
                             organism = synthetic construct
SEQUENCE: 84
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVMHEALH NHYTQKSLSL SPT                     223

SEQ ID NO: 85                moltype = AA  length = 223
FEATURE                      Location/Qualifiers
REGION                       1..223
                             note = Hole Fc
source                       1..223
                             mol_type = protein
                             organism = synthetic construct
SEQUENCE: 85
DKTHTCPPCP APGGPSVFLF PPKPKDTLMR SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVMHEALH NHYTQKSLSL SPT                     223

SEQ ID NO: 86                moltype = AA  length = 226
FEATURE                      Location/Qualifiers
REGION                       1..226
                             note = Knob Fc
source                       1..226
                             mol_type = protein
                             organism = synthetic construct
SEQUENCE: 86
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 87                moltype = AA  length = 226
FEATURE                      Location/Qualifiers
REGION                       1..226
                             note = Hole Fc
source                       1..226
                             mol_type = protein
                             organism = synthetic construct
SEQUENCE: 87
DKTHTCPPCP APELLGGPSV FLFPPKPKDT LMRSRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPG                  226

SEQ ID NO: 88                moltype = AA  length = 223
FEATURE                      Location/Qualifiers
REGION                       1..223
                             note = Knob Fc
source                       1..223
                             mol_type = protein
                             organism = synthetic construct
SEQUENCE: 88
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVMHEALH NHYTQKSLSL SPG                     223

SEQ ID NO: 89                moltype = AA  length = 223
FEATURE                      Location/Qualifiers
REGION                       1..223
```

```
                            note = Hole Fc
source                      1..223
                            mol_type = protein
                            organism = synthetic construct
SEQUENCE: 89
DKTHTCPPCP APGGPSVFLF PPKPKDTLMR SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVMHEALH NHYTQKSLSL SPG                     223

SEQ ID NO: 90               moltype = AA   length = 226
FEATURE                     Location/Qualifiers
REGION                      1..226
                            note = Hole Fc
source                      1..226
                            mol_type = protein
                            organism = synthetic construct
SEQUENCE: 90
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNRYTQKS LSLSPT                  226

SEQ ID NO: 91               moltype = AA   length = 223
FEATURE                     Location/Qualifiers
REGION                      1..223
                            note = Hole Fc
source                      1..223
                            mol_type = protein
                            organism = synthetic construct
SEQUENCE: 91
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVMHEALH NRYTQKSLSL SPT                     223

SEQ ID NO: 92               moltype = AA   length = 226
FEATURE                     Location/Qualifiers
REGION                      1..226
                            note = Hole Fc
source                      1..226
                            mol_type = protein
                            organism = synthetic construct
SEQUENCE: 92
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNRYTQKS LSLSPG                  226

SEQ ID NO: 93               moltype = AA   length = 223
FEATURE                     Location/Qualifiers
REGION                      1..223
                            note = Hole Fc
source                      1..223
                            mol_type = protein
                            organism = synthetic construct
SEQUENCE: 93
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVMHEALH NRYTQKSLSL SPG                     223

SEQ ID NO: 94               moltype = AA   length = 226
FEATURE                     Location/Qualifiers
REGION                      1..226
                            note = Knob Fc
source                      1..226
                            mol_type = protein
                            organism = synthetic construct
SEQUENCE: 94
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVVHE ALHNHYTQKS LSLSPT                  226

SEQ ID NO: 95               moltype = AA   length = 223
FEATURE                     Location/Qualifiers
REGION                      1..223
                            note = Knob Fc
```

```
source                      1..223
                            mol_type = protein
                            organism = synthetic construct
SEQUENCE: 95
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVVHEALH NHYTQKSLSL SPT                     223

SEQ ID NO: 96               moltype = AA   length = 226
FEATURE                     Location/Qualifiers
REGION                      1..226
                            note = Knob Fc
source                      1..226
                            mol_type = protein
                            organism = synthetic construct
SEQUENCE: 96
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVVHE ALHNHYTQKS LSLSPG                  226

SEQ ID NO: 97               moltype = AA   length = 223
FEATURE                     Location/Qualifiers
REGION                      1..223
                            note = Knob Fc
source                      1..223
                            mol_type = protein
                            organism = synthetic construct
SEQUENCE: 97
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP CRDELTKNQV SLWCLVKGFY PSDIAVEWES NGQPENNYKT TPPVLDSDGS   180
FFLYSKLTVD KSRWQQGNVF SCSVVHEALH NHYTQKSLSL SPG                     223

SEQ ID NO: 98               moltype = AA   length = 226
FEATURE                     Location/Qualifiers
REGION                      1..226
                            note = Hole Fc
source                      1..226
                            mol_type = protein
                            organism = synthetic construct
SEQUENCE: 98
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVVHE ALHNRYTQKS LSLSPT                  226

SEQ ID NO: 99               moltype = AA   length = 223
FEATURE                     Location/Qualifiers
REGION                      1..223
                            note = Hole Fc
source                      1..223
                            mol_type = protein
                            organism = synthetic construct
SEQUENCE: 99
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVVHEALH NRYTQKSLSL SPT                     223

SEQ ID NO: 100              moltype = AA   length = 226
FEATURE                     Location/Qualifiers
REGION                      1..226
                            note = Hole Fc
source                      1..226
                            mol_type = protein
                            organism = synthetic construct
SEQUENCE: 100
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVVHE ALHNRYTQKS LSLSPG                  226

SEQ ID NO: 101              moltype = AA   length = 223
FEATURE                     Location/Qualifiers
REGION                      1..223
                            note = Hole Fc
source                      1..223
```

```
                           mol_type = protein
                           organism = synthetic construct
SEQUENCE: 101
DKTHTCPPCP APGGPSVFLF PPKPKDTLYI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVVHEALH NRYTQKSLSL SPG                     223

SEQ ID NO: 102             moltype = AA   length = 5
FEATURE                    Location/Qualifiers
REGION                     1..5
                           note = Peptide Linker
source                     1..5
                           mol_type = protein
                           organism = synthetic construct
SEQUENCE: 102
PGGGG                                                                 5

SEQ ID NO: 103             moltype = AA   length = 4
FEATURE                    Location/Qualifiers
REGION                     1..4
                           note = Peptide Linker
source                     1..4
                           mol_type = protein
                           organism = synthetic construct
SEQUENCE: 103
GGGG                                                                  4

SEQ ID NO: 104             moltype = AA   length = 18
FEATURE                    Location/Qualifiers
REGION                     1..18
                           note = Linker
source                     1..18
                           mol_type = protein
                           organism = synthetic construct
SEQUENCE: 104
GPAGLGLEPD GSRQARVG                                                  18

SEQ ID NO: 105             moltype = AA   length = 18
FEATURE                    Location/Qualifiers
REGION                     1..18
                           note = Linker
source                     1..18
                           mol_type = protein
                           organism = synthetic construct
SEQUENCE: 105
GGSGGGGIEP DIGGSGGS                                                  18

SEQ ID NO: 106             moltype = AA   length = 18
FEATURE                    Location/Qualifiers
REGION                     1..18
                           note = Linker
source                     1..18
                           mol_type = protein
                           organism = synthetic construct
SEQUENCE: 106
GGSGGGGLEA DTGGSGGS                                                  18

SEQ ID NO: 107             moltype = AA   length = 9
FEATURE                    Location/Qualifiers
REGION                     1..9
                           note = Linker
source                     1..9
                           mol_type = protein
                           organism = synthetic construct
SEQUENCE: 107
GSIEPDIGS                                                             9

SEQ ID NO: 108             moltype = AA   length = 9
FEATURE                    Location/Qualifiers
REGION                     1..9
                           note = Linker
source                     1..9
                           mol_type = protein
                           organism = synthetic construct
SEQUENCE: 108
GSLEADTGS                                                             9

SEQ ID NO: 109             moltype = AA   length = 18
```

```
FEATURE              Location/Qualifiers
REGION               1..18
                     note = Linker
source               1..18
                     mol_type = protein
                     organism = synthetic construct
SEQUENCE: 109
GGSGGGGIEP DGGGSGGS                                                  18

SEQ ID NO: 110       moltype = AA  length = 18
FEATURE              Location/Qualifiers
REGION               1..18
                     note = Linker
source               1..18
                     mol_type = protein
                     organism = synthetic construct
SEQUENCE: 110
GGSGGGGIEP DVGGSGGS                                                  18

SEQ ID NO: 111       moltype = AA  length = 18
FEATURE              Location/Qualifiers
REGION               1..18
                     note = Linker
source               1..18
                     mol_type = protein
                     organism = synthetic construct
SEQUENCE: 111
GGSGGGGIEP DSGGSGGS                                                  18

SEQ ID NO: 112       moltype = AA  length = 18
FEATURE              Location/Qualifiers
REGION               1..18
                     note = Linker
source               1..18
                     mol_type = protein
                     organism = synthetic construct
SEQUENCE: 112
GGSGGGGIEP DTGGSGGS                                                  18

SEQ ID NO: 113       moltype = AA  length = 12
FEATURE              Location/Qualifiers
REGION               1..12
                     note = Linker
source               1..12
                     mol_type = protein
                     organism = synthetic construct
SEQUENCE: 113
GGGSLEPDGS GS                                                        12

SEQ ID NO: 114       moltype = AA  length = 18
FEATURE              Location/Qualifiers
REGION               1..18
                     note = Linker
source               1..18
                     mol_type = protein
                     organism = synthetic construct
SEQUENCE: 114
GPAGLGLEAD GSRQARVG                                                  18

SEQ ID NO: 115       moltype = AA  length = 15
FEATURE              Location/Qualifiers
REGION               1..15
                     note = Linker
source               1..15
                     mol_type = protein
                     organism = synthetic construct
SEQUENCE: 115
GGEGGGGSGG SGGGS                                                     15

SEQ ID NO: 116       moltype = AA  length = 18
FEATURE              Location/Qualifiers
REGION               1..18
                     note = Linker
source               1..18
                     mol_type = protein
                     organism = synthetic construct
SEQUENCE: 116
GSSAGSEAGG SGQAGVGS                                                  18
```

| | | |
|---|---|---|
| SEQ ID NO: 117 | moltype = AA length = 18 | |
| FEATURE | Location/Qualifiers | |
| REGION | 1..18 | |
| | note = Linker | |
| source | 1..18 | |
| | mol_type = protein | |
| | organism = synthetic construct | |
| SEQUENCE: 117 | | |
| GGSGGGGLEA EGSGGGGS | | 18 |
| | | |
| SEQ ID NO: 118 | moltype = AA length = 18 | |
| FEATURE | Location/Qualifiers | |
| REGION | 1..18 | |
| | note = Linker | |
| source | 1..18 | |
| | mol_type = protein | |
| | organism = synthetic construct | |
| SEQUENCE: 118 | | |
| GGSGGGGIEP DPGGSGGS | | 18 |
| | | |
| SEQ ID NO: 119 | moltype = AA length = 18 | |
| FEATURE | Location/Qualifiers | |
| REGION | 1..18 | |
| | note = Linker | |
| source | 1..18 | |
| | mol_type = protein | |
| | organism = synthetic construct | |
| SEQUENCE: 119 | | |
| GGGGGSGGGG GSGGGGGS | | 18 |
| | | |
| SEQ ID NO: 120 | moltype = AA length = 129 | |
| FEATURE | Location/Qualifiers | |
| REGION | 1..129 | |
| | note = FR alpha sdAb | |
| source | 1..129 | |
| | mol_type = protein | |
| | organism = synthetic construct | |
| SEQUENCE: 120 | | |
| QLQLQESGGG LVQPGGSLRL SCAASGFTLD NYAIGWFRQA PGKEREGVSC ISSSDGSTYY | | 60 |
| ADSVKGRFTI SRNNAKGTVY LLMNSLKPED TAVYYCATEL VPACTYSNGR GPLDGMDYWG | | 120 |
| KGTQVTVKP | | 129 |
| | | |
| SEQ ID NO: 121 | moltype = AA length = 119 | |
| FEATURE | Location/Qualifiers | |
| REGION | 1..119 | |
| | note = FR alpha sdAb | |
| source | 1..119 | |
| | mol_type = protein | |
| | organism = synthetic construct | |
| SEQUENCE: 121 | | |
| EVQLLESGGG EVQPGGSLRL SCAASGSIFS IDATAWYRQA PGKQRELVAI ITSSGSTNYP | | 60 |
| ESVKGRFTIS RDNAKNTVYL QMSSLRAEDT AVYYCNAITR YGGSTYDFWG QGTLVTVKP | | 119 |
| | | |
| SEQ ID NO: 122 | moltype = AA length = 101 | |
| FEATURE | Location/Qualifiers | |
| REGION | 1..101 | |
| | note = FR alpha sdAb | |
| source | 1..101 | |
| | mol_type = protein | |
| | organism = synthetic construct | |
| SEQUENCE: 122 | | |
| EVQPGGSLRL SCAASETFGV VFTLGWYRQA PGKGREFVAR VTGTDTVDYA ESVKGRFTIS | | 60 |
| SDFARNTVYL QMNSLRAEDT AVYYCNTGAY WGQGTLVTVK P | | 101 |
| | | |
| SEQ ID NO: 123 | moltype = AA length = 125 | |
| FEATURE | Location/Qualifiers | |
| REGION | 1..125 | |
| | note = cMET sdAb | |
| source | 1..125 | |
| | mol_type = protein | |
| | organism = synthetic construct | |
| SEQUENCE: 123 | | |
| EVQLVESGGG LVQPGGSLRL SCAASGFILD YYAIGWFRQA PGKEREGVLC IDASDDITYY | | 60 |
| ADSVKGRFTI SRDNAKNTVY LQMNSLKPED TGVYYCATPI GLSSSCLLEY DYDYWGQGTL | | 120 |
| VTVKP | | 125 |
| | | |
| SEQ ID NO: 124 | moltype = AA length = 245 | |
| FEATURE | Location/Qualifiers | |
| REGION | 1..245 | |

```
                        note = B7H3 scFv
source                  1..245
                        mol_type = protein
                        organism = synthetic construct
SEQUENCE: 124
EVQLVESGGG LVQPGGSLRL SCAASGFTFS SFGMHWVRQA PGKGLEWVAY ISSDSSAIYY    60
ADTVKGRFTI SRDNAKNSLY LQMNSLRDED TAVYYCGRGR ENIYYGSRLD YWGQGTTVTV   120
SSSGGGGSGG GGSGGGGSDI QLTQSPSFLS ASVGDRVTIT CKASQNVDTN VAWYQQKPGK   180
APKALIYSAS YRYSGVPSRF SGSGSGTDFT LTISSLQPED FATYYCQQYN NYPFTFGQGT   240
KLEIK                                                               245

SEQ ID NO: 125          moltype = AA  length = 247
FEATURE                 Location/Qualifiers
REGION                  1..247
                        note = CD20 scFv
source                  1..247
                        mol_type = protein
                        organism = synthetic construct
SEQUENCE: 125
QVQLVQSGAE VKKPGSSVKV SCKASGYAFS YSWINWVRQA PGQGLEWMGR IFPGDGDTDY    60
NGKFKGRVTI TADKSTSTAY MELSSLRSED TAVYYCARNV FDGYWLVYWG QGTLVTVSGS   120
GGGGSGGGGT GGGGSDIVMT QTPLSLPVTP GEPASISCRS SKSLLHSNGI TYLYWYLQKP   180
GQSPQLLIYQ MSNLVSGVPD RFSGSGSGTD FTLKISRVEA EDVGVYYCAQ NLELPYTFGG   240
GTKVEIK                                                             247

SEQ ID NO: 126          moltype = AA  length = 241
FEATURE                 Location/Qualifiers
REGION                  1..241
                        note = DLL3 scFv
source                  1..241
                        mol_type = protein
                        organism = synthetic construct
SEQUENCE: 126
QVQLQESGPG LVKPSETLSL TCTVSGGSIS SYYWSWIRQP PGKGLEWIGY VYYSGTTNYN    60
PSLKSRVTIS VDTSKNQFSL KLSSVTAADT AVYYCASIAV TGFYFDYWGQ GTLVTVSSGG   120
GGSGGGGSGG GGSEIVLTQS PGTLSLSPGE RVTLSCRASQ RVNNNYLAWY QQRPGQAPRL   180
LIYGASSRAT GIPDRFSGSG SGTDFTLTIS RLEPEDFAVY YCQQYDRSPL TFGGGTKLEI   240
K                                                                   241

SEQ ID NO: 127          moltype = AA  length = 225
FEATURE                 Location/Qualifiers
REGION                  1..225
                        note = B7H3 Fd
source                  1..225
                        mol_type = protein
                        organism = synthetic construct
SEQUENCE: 127
EVQLVESGGG LVQPGGSLRL SCAASGFTFS SFGMHWVRQA PGKGLEWVAY ISSDSSAIYY    60
ADTVKGRFTI SRDNAKNSLY LQMNSLRDED TAVYYCGRGR ENIYYGSRLD YWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSC                   225

SEQ ID NO: 128          moltype = AA  length = 214
FEATURE                 Location/Qualifiers
REGION                  1..214
                        note = B7H3 LC
source                  1..214
                        mol_type = protein
                        organism = synthetic construct
SEQUENCE: 128
DIQLTQSPSF LSASVGDRVT ITCKASQNVD TNVAWYQQKP GKAPKALIYS ASYRYSGVPS    60
RFSGSGSGTD FTLTISSLQP EDFATYYCQQ YNNYPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 129          moltype = AA  length = 225
FEATURE                 Location/Qualifiers
REGION                  1..225
                        note = 5T4 Fd
source                  1..225
                        mol_type = protein
                        organism = synthetic construct
SEQUENCE: 129
EVQLVESGGG LVQPKGSLKL SCAASGFTFN TYAMNWVRQA PGKGLEWVAR IRSKSNNYAT    60
YYADSVKDRF TISRDDSQSM LYLQMNNLKT EDTAMYYCVR QWDYDVRAMN YWGQGTSVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSC                   225

SEQ ID NO: 130          moltype = AA  length = 214
```

```
FEATURE                     Location/Qualifiers
REGION                      1..214
                            note = 5T4 LC
source                      1..214
                            mol_type = protein
                            organism = synthetic construct
SEQUENCE: 130
DIVMTQSHIF MSTSVGDRVS ITCKASQDVD TAVAWYQQKP GQSPKLLIYW ASTRLTGVPD   60
RFTGSGSGTD FTLTISNVQS EDLADYFCQQ YSSYPYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 131              moltype = AA  length = 222
FEATURE                     Location/Qualifiers
REGION                      1..222
                            note = gpNMB Fd
source                      1..222
                            mol_type = protein
                            organism = synthetic construct
SEQUENCE: 131
QVQLQESGPG LVKPSQTLSL TCTVSGGSIS SFNYYWSWIR HHPGKGLEWI GYIYYSGSTY   60
SNPSLKSRVT ISVDTSKNQF SLTLSSVTAA DTAVYYCARG YNWNYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SC                     222

SEQ ID NO: 132              moltype = AA  length = 215
FEATURE                     Location/Qualifiers
REGION                      1..215
                            note = gpNMB LC
source                      1..215
                            mol_type = protein
                            organism = synthetic construct
SEQUENCE: 132
EIVMTQSPAT LSVSPGERAT LSCRASQSVD NNLVWYQQKP GQAPRLLIYG ASTRATGIPA   60
RFSGSGSGTE FTLTISSLQS EDFAVYYCQQ YNNWPPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 133              moltype = AA  length = 223
FEATURE                     Location/Qualifiers
REGION                      1..223
                            note = DLL3 Fd
source                      1..223
                            mol_type = protein
                            organism = synthetic construct
SEQUENCE: 133
QIQLVQSGPE LKKPGETVKI SCKASGYTFT NYGMNWVKQA PGKGLKWMAW INTYTGEPTY   60
ADDFKGRFAF SLETSASTAS LQIINLKNED TATYFCARIG DSSPSDYWGQ GTTLTVSSSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSC                    223

SEQ ID NO: 134              moltype = AA  length = 214
FEATURE                     Location/Qualifiers
REGION                      1..214
                            note = DLL3 LC
source                      1..214
                            mol_type = protein
                            organism = synthetic construct
SEQUENCE: 134
SIVMTQTPKF LLVSAGDRVT ITCKASQSVS NDVVWYQQKP GQSPKLLIYY ASNRYTGVPD   60
RFAGSGYGTD FSFTISTVQA EDLAVYFCQQ DYTSPWTFGG GTKLEIRRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 135              moltype = AA  length = 6
FEATURE                     Location/Qualifiers
REGION                      1..6
                            note = Peptide linker
source                      1..6
                            mol_type = protein
                            organism = synthetic construct
SEQUENCE: 135
GGGGGS                                                               6

SEQ ID NO: 136              moltype = AA  length = 5
FEATURE                     Location/Qualifiers
REGION                      1..5
                            note = Linker
source                      1..5
```

```
                         mol_type = protein
                         organism = synthetic construct
SEQUENCE: 136
IEPDI                                                                5

SEQ ID NO: 137           moltype = AA  length = 5
FEATURE                  Location/Qualifiers
REGION                   1..5
                         note = Linker
source                   1..5
                         mol_type = protein
                         organism = synthetic construct
SEQUENCE: 137
LEADT                                                                5

SEQ ID NO: 138           moltype = AA  length = 5
FEATURE                  Location/Qualifiers
REGION                   1..5
                         note = Linker
source                   1..5
                         mol_type = protein
                         organism = synthetic construct
SEQUENCE: 138
IEPDG                                                                5

SEQ ID NO: 139           moltype = AA  length = 5
FEATURE                  Location/Qualifiers
REGION                   1..5
                         note = Linker
source                   1..5
                         mol_type = protein
                         organism = synthetic construct
SEQUENCE: 139
IEPDV                                                                5

SEQ ID NO: 140           moltype = AA  length = 5
FEATURE                  Location/Qualifiers
REGION                   1..5
                         note = Linker
source                   1..5
                         mol_type = protein
                         organism = synthetic construct
SEQUENCE: 140
IEPDS                                                                5

SEQ ID NO: 141           moltype = AA  length = 5
FEATURE                  Location/Qualifiers
REGION                   1..5
                         note = Linker
source                   1..5
                         mol_type = protein
                         organism = synthetic construct
SEQUENCE: 141
IEPDT                                                                5

SEQ ID NO: 142           moltype = AA  length = 4
FEATURE                  Location/Qualifiers
REGION                   1..4
                         note = Linker
source                   1..4
                         mol_type = protein
                         organism = synthetic construct
SEQUENCE: 142
LEPD                                                                 4

SEQ ID NO: 143           moltype = AA  length = 4
FEATURE                  Location/Qualifiers
REGION                   1..4
                         note = Linker
source                   1..4
                         mol_type = protein
                         organism = synthetic construct
SEQUENCE: 143
LEAE                                                                 4

SEQ ID NO: 144           moltype = AA  length = 5
FEATURE                  Location/Qualifiers
REGION                   1..5
                         note = Linker
```

```
source                  1..5
                        mol_type = protein
                        organism = synthetic construct
SEQUENCE: 144
IEPDP                                                                       5

SEQ ID NO: 145          moltype = AA  length = 274
FEATURE                 Location/Qualifiers
REGION                  1..274
                        note = Second Polypeptide Chain of B7-H3 x CD3 Bispecific
                         DART-A Diabody
source                  1..274
                        mol_type = protein
                        organism = synthetic construct
SEQUENCE: 145
QAVVTQEPSL TVSPGGTVTL TCRSSTGAVT TSNYANWVQQ KPGQAPRGLI GGTNKRAPWT  60
PARFSGSLLG GKAALTITGA QAEDEADYYC ALWYSNLWVF GGGTKLTVLG GGGSGGGGEV  120
QLVESGGGLV QPGGSLRLSC AASGFTFSSF GMHWVRQAPG KGLEWVAYIS SDSSAIYYAD  180
TVKGRFTISR DNAKNSLYLQ MNSLRDEDTA VYYCGRGREN IYYGSRLDYW GQGTTVTVSS  240
GGCGGGKVAA LKEKVAALKE KVAALKEKVA ALKE                              274

SEQ ID NO: 146          moltype = AA  length = 227
FEATURE                 Location/Qualifiers
REGION                  1..227
                        note = Third Polypeptide Chain of B7-H3 x CD3 Bispecific
                         DART-A Diabody
source                  1..227
                        mol_type = protein
                        organism = synthetic construct
SEQUENCE: 146
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLSCAVK GFYPSDIAVE WESNGQPENN YKTTPPVLDS  180
DGSFFLVSKL TVDKSRWQQG NVFSCSVMHE ALHNRYTQKS LSLSPGK                227

SEQ ID NO: 147          moltype = AA  length = 18
FEATURE                 Location/Qualifiers
REGION                  1..18
                        note = Linker
source                  1..18
                        mol_type = protein
                        organism = synthetic construct
SEQUENCE: 147
GGSGGGGSGG GGSGGGGS                                                         18

SEQ ID NO: 148          moltype = AA  length = 19
FEATURE                 Location/Qualifiers
REGION                  1..19
                        note = Linker
source                  1..19
                        mol_type = protein
                        organism = synthetic construct
SEQUENCE: 148
TGGSGGGGIE PDIGGSGGS                                                        19

SEQ ID NO: 149          moltype = AA  length = 5
FEATURE                 Location/Qualifiers
REGION                  1..5
                        note = Linker
source                  1..5
                        mol_type = protein
                        organism = synthetic construct
SEQUENCE: 149
GGGGS                                                                       5

SEQ ID NO: 150          moltype =   length =
SEQUENCE: 150
000

SEQ ID NO: 151          moltype =   length =
SEQUENCE: 151
000

SEQ ID NO: 152          moltype = AA  length = 5
FEATURE                 Location/Qualifiers
REGION                  1..5
                        note = Linker
source                  1..5
                        mol_type = protein
```

```
                               organism = synthetic construct
SEQUENCE: 152
LEPDG                                                                     5

SEQ ID NO: 153          moltype = AA   length = 5
FEATURE                 Location/Qualifiers
REGION                  1..5
                        note = Linker
source                  1..5
                        mol_type = protein
                        organism = synthetic construct
SEQUENCE: 153
LEADG                                                                     5

SEQ ID NO: 154          moltype =    length =
SEQUENCE: 154
000

SEQ ID NO: 155          moltype = AA   length = 5
FEATURE                 Location/Qualifiers
REGION                  1..5
                        note = Linker consensus
VARIANT                 5
                        note = X5 = A or V
source                  1..5
                        mol_type = protein
                        organism = synthetic construct
SEQUENCE: 155
RQARX                                                                     5

SEQ ID NO: 156          moltype = AA   length = 5
FEATURE                 Location/Qualifiers
REGION                  1..5
                        note = Linker
source                  1..5
                        mol_type = protein
                        organism = synthetic construct
SEQUENCE: 156
RQARV                                                                     5

SEQ ID NO: 157          moltype =    length =
SEQUENCE: 157
000

SEQ ID NO: 158          moltype =    length =
SEQUENCE: 158
000

SEQ ID NO: 159          moltype = AA   length = 22
FEATURE                 Location/Qualifiers
REGION                  1..22
                        note = P2A
source                  1..22
                        mol_type = protein
                        organism = synthetic construct
SEQUENCE: 159
GSGATNFSLL KQAGDVEENP GP                                                 22

SEQ ID NO: 160          moltype = AA   length = 19
FEATURE                 Location/Qualifiers
REGION                  1..19
                        note = P2A
source                  1..19
                        mol_type = protein
                        organism = synthetic construct
SEQUENCE: 160
ATNFSLLKQA GDVEENPGP                                                     19

SEQ ID NO: 161          moltype = AA   length = 20
FEATURE                 Location/Qualifiers
REGION                  1..20
                        note = E2A
source                  1..20
                        mol_type = protein
                        organism = synthetic construct
SEQUENCE: 161
QCTNYALLKL AGDVESNPGP                                                    20

SEQ ID NO: 162          moltype = AA   length = 22
```

```
FEATURE                 Location/Qualifiers
REGION                  1..22
                        note = F2A
source                  1..22
                        mol_type = protein
                        organism = synthetic construct
SEQUENCE: 162
VKQTLNFDLL KLAGDVESNP GP                                            22

SEQ ID NO: 163          moltype = AA  length = 18
FEATURE                 Location/Qualifiers
REGION                  1..18
                        note = T2A
source                  1..18
                        mol_type = protein
                        organism = synthetic construct
SEQUENCE: 163
EGRGSLLTCG DVEENPGP                                                 18

SEQ ID NO: 164          moltype = AA  length = 24
FEATURE                 Location/Qualifiers
REGION                  1..24
                        note = T2A
source                  1..24
                        mol_type = protein
                        organism = synthetic construct
SEQUENCE: 164
LEGGGEGRGS LLTCGDVEEN PGPR                                          24

SEQ ID NO: 165          moltype = DNA  length = 66
FEATURE                 Location/Qualifiers
misc_feature            1..66
                        note = P2A
source                  1..66
                        mol_type = other DNA
                        organism = synthetic construct
SEQUENCE: 165
ggatctggag caacaaactt ctcactactc aaacaagcag gtgacgtgga ggagaatccc   60
ggaccc                                                              66

SEQ ID NO: 166          moltype = AA  length = 18
FEATURE                 Location/Qualifiers
REGION                  1..18
                        note = Linker
source                  1..18
                        mol_type = protein
                        organism = synthetic construct
SEQUENCE: 166
GSPAGLEADG SRQARVGS                                                 18

SEQ ID NO: 167          moltype = AA  length = 122
FEATURE                 Location/Qualifiers
REGION                  1..122
                        note = MISC_FEATURE - anti-5T4 VH
SITE                    97
                        note = misc_feature - Xaa can be any naturally occurring
                         amino acid
source                  1..122
                        mol_type = protein
                        organism = Mus musculus
SEQUENCE: 167
EVQLVESGGG LVQPKGSLKL SCAASGFTFN TYAMNWVRQA PGKGLEWVAR IRSKSNNYAT   60
YYADSVKDRF TISRDDSQSM LYLQMNNLKT EDTAMYXCVR QWDYDVRAMN YWGQGTSVTV  120
SS                                                                 122

SEQ ID NO: 168          moltype = AA  length = 107
FEATURE                 Location/Qualifiers
REGION                  1..107
                        note = MISC_FEATURE - anti-5T4 VL
source                  1..107
                        mol_type = protein
                        organism = Mus musculus
SEQUENCE: 168
DIVMTQSHIF MSTSVGDRVS ITCKASQDVD TAVAWYQQKP GQSPKLLIYW ASTRLTGVPD   60
RFTGSGSGTD FTLTISNVQS EDLADYFCQQ YSSYPYTFGG GTKLEIK                107

SEQ ID NO: 169          moltype = AA  length = 504
FEATURE                 Location/Qualifiers
REGION                  1..504
```

```
                        note = First Polypeptide Chain of B7-H3 x CD3 Bispecific
                        DART-A Diabody
source                  1..504
                        mol_type = protein
                        organism = synthetic construct
SEQUENCE: 169
DIQLTQSPSF LSASVGDRVT ITCKASQNVD TNVAWYQQKP GKAPKALIYS ASYRYSGVPS    60
RFSGSGSGTD FTLTISSLQP EDFATYYCQQ YNNYPFTFGQ GTKLEIKGGG SGGGGEVQLV   120
ESGGGLVQPG GSLRLSCAAS GFTFSTYAMN WVRQAPGKGL EWVGRIRSKY NNYATYYADS   180
VKDRFTISRD DSKNSLYLQM NSLKTEDTAV YYCVRHGNFG NSYVSWFAYW GQGTLVTVSS   240
GGCGGGEVAA LEKEVAALEK EVAALEKEVA ALEKGGGDKT HTCPPCPAPE AAGGPSVFLF   300
PPKPKDTLMI SRTPEVTCVV VDVSHEDPEV KFNWYVDGVE VHNAKTKPRE EQYNSTYRVV   360
SVLTVLHQDW LNGKEYKCKV SNKALPAPIE KTISKAKGQP REPQVYTLPP SREEMTKNQV   420
SLWCLVKGFY PSDIAVEWES NGQPENNYKT TPPVLDSDGS FFLYSKLTVD KSRWQQGNVF   480
SCSVMHEALH NHYTQKSLSL SPGK                                         504

SEQ ID NO: 170          moltype = AA length = 15
FEATURE                 Location/Qualifiers
REGION                  1..15
                        note = Linker
source                  1..15
                        mol_type = protein
                        organism = synthetic construct
SEQUENCE: 170
GGGGSGGGGS GGGGS                                                    15

SEQ ID NO: 171          moltype = AA length = 6
FEATURE                 Location/Qualifiers
REGION                  1..6
                        note = Linker
REPEAT                  4..6
                        note = repeated 0 to 10 times
source                  1..6
                        mol_type = protein
                        organism = synthetic construct
SEQUENCE: 171
GGSGGS                                                               6

SEQ ID NO: 172          moltype = AA length = 6
FEATURE                 Location/Qualifiers
REGION                  1..6
                        note = Linker
REPEAT                  1..6
                        note = repeated 1 to 4 times
source                  1..6
                        mol_type = protein
                        organism = synthetic construct
SEQUENCE: 172
GGGGGS                                                               6

SEQ ID NO: 173          moltype = AA length = 5
FEATURE                 Location/Qualifiers
REGION                  1..5
                        note = Linker
REPEAT                  1..5
                        note = Repeated 1 to 10 times
REPEAT                  1..5
                        note = Repeated 1 to 5 times
source                  1..5
                        mol_type = protein
                        organism = synthetic construct
SEQUENCE: 173
GGGGS                                                                5

SEQ ID NO: 174          moltype =   length =
SEQUENCE: 174
000

SEQ ID NO: 175          moltype = AA length = 11
FEATURE                 Location/Qualifiers
REGION                  1..11
                        note = Linker
VARIANT                 4
                        note = X4 = A, V, L, I, M,F, W, P, G, S, T, C, Y, N,Q, K,
                        R, H, D, or E
VARIANT                 8
                        note = X8 = A, V, L, I, M,F, W, P, G, S, T, C, Y, N,Q, K,
                        R, H, D, or E
source                  1..11
```

```
                         mol_type = protein
                         organism = synthetic construct
SEQUENCE: 175
GGGXGGGXGG G                                                              11

SEQ ID NO: 176           moltype = AA  length = 11
FEATURE                  Location/Qualifiers
REGION                   1..11
                         note = Linker
source                   1..11
                         mol_type = protein
                         organism = synthetic construct
SEQUENCE: 176
ATTTGSSPGP T                                                              11

SEQ ID NO: 177           moltype = AA  length = 11
FEATURE                  Location/Qualifiers
REGION                   1..11
                         note = Linker
source                   1..11
                         mol_type = protein
                         organism = synthetic construct
SEQUENCE: 177
GGGGGCGGGG G                                                              11

SEQ ID NO: 178           moltype = AA  length = 5
FEATURE                  Location/Qualifiers
REGION                   1..5
                         note = Linker
REPEAT                   1..5
                         note = Repeated 2 to 20 times
source                   1..5
                         mol_type = protein
                         organism = synthetic construct
SEQUENCE: 178
EAAAK                                                                      5

SEQ ID NO: 179           moltype = AA  length = 6
FEATURE                  Location/Qualifiers
REGION                   1..6
                         note = Linker
REPEAT                   3..4
                         note = Repeated 2 to 20 times
source                   1..6
                         mol_type = protein
                         organism = synthetic construct
SEQUENCE: 179
ASAPGT                                                                     6

SEQ ID NO: 180           moltype = AA  length = 9
FEATURE                  Location/Qualifiers
REGION                   1..9
                         note = Linker
REPEAT                   3..7
                         note = Repeated 2 to 20 times
source                   1..9
                         mol_type = protein
                         organism = synthetic construct
SEQUENCE: 180
ASEAAAKGT                                                                  9

SEQ ID NO: 181           moltype = AA  length = 5
FEATURE                  Location/Qualifiers
REGION                   1..5
                         note = Linker
REPEAT                   1..5
                         note = Repeated 2 to 20 times
source                   1..5
                         mol_type = protein
                         organism = synthetic construct
SEQUENCE: 181
GGGGA                                                                      5

SEQ ID NO: 182           moltype = AA  length = 5
FEATURE                  Location/Qualifiers
REGION                   1..5
                         note = Linker
REPEAT                   1..5
                         note = Repeated 2 to 20 times
```

```
source                  1..5
                        mol_type = protein
                        organism = synthetic construct
SEQUENCE: 182
PGGGS                                                                     5

SEQ ID NO: 183          moltype = AA   length = 5
FEATURE                 Location/Qualifiers
REGION                  1..5
                        note = Linker
REPEAT                  1..5
                        note = Repeated 2 to 20 times
source                  1..5
                        mol_type = protein
                        organism = synthetic construct
SEQUENCE: 183
AGGGS                                                                     5

SEQ ID NO: 184          moltype = AA   length = 20
FEATURE                 Location/Qualifiers
REGION                  1..20
                        note = Linker
REPEAT                  4..17
                        note = Repeated 2 to 20 times
source                  1..20
                        mol_type = protein
                        organism = synthetic construct
SEQUENCE: 184
GGSEGKSSGS GSESKSTGGS                                                    20

SEQ ID NO: 185          moltype = AA   length = 5
FEATURE                 Location/Qualifiers
REGION                  1..5
                        note = Linker
REPEAT                  1..5
                        note = Repeated 1 to 9 times
source                  1..5
                        mol_type = protein
                        organism = synthetic construct
SEQUENCE: 185
SSSSG                                                                     5

SEQ ID NO: 186          moltype = AA   length = 9
FEATURE                 Location/Qualifiers
REGION                  1..9
                        note = Linker
source                  1..9
                        mol_type = protein
                        organism = synthetic construct
SEQUENCE: 186
SSSASASSA                                                                 9

SEQ ID NO: 187          moltype = AA   length = 7
FEATURE                 Location/Qualifiers
REGION                  1..7
                        note = Linker
source                  1..7
                        mol_type = protein
                        organism = synthetic construct
SEQUENCE: 187
GSPGSPG                                                                   7

SEQ ID NO: 188          moltype = AA   length = 241
FEATURE                 Location/Qualifiers
REGION                  1..241
                        note = DLL3 scFv
source                  1..241
                        mol_type = protein
                        organism = synthetic construct
SEQUENCE: 188
QVQLQESGPG LVKPSETLSL TCTVSGGSIS SYYWSWIRQP PGKGLEWIGY VYYSGTTNYN        60
PSLKSRVTIS VDTSKNQFSL KLSSVTAADT AVYYCASIAV TGFYFDYWGQ GTLVTVSSGG       120
GGSGGGGSGG GGSEIVLTQS PGTLSLSPGE RVTLSCRASQ RVNNNYLAWY QQRPGQAPRL       180
LIYGASSRAT GIPDRFSGSG SGTDFTLTIS RLEPEDFAVY YCQQYDRSPL TFGGGTKLEI       240
K                                                                       241

SEQ ID NO: 189          moltype = AA   length = 119
FEATURE                 Location/Qualifiers
REGION                  1..119
```

```
                        note = CD20 VH
source                  1..119
                        mol_type = protein
                        organism = synthetic construct
SEQUENCE: 189
QVQLVQSGAE VKKPGSSVKV SCKASGYAFS YSWINWVRQA PGQGLEWMGR IFPGDGTDY    60
NGKFKGRVTI TADKSTSTAY MELSSLRSED TAVYYCARNV FDGYWLVYWG QGTLVTVSS   119

SEQ ID NO: 190          moltype = AA   length = 115
FEATURE                 Location/Qualifiers
REGION                  1..115
                        note = CD20 VL
source                  1..115
                        mol_type = protein
                        organism = synthetic construct
SEQUENCE: 190
DIVMTQTPLS LPVTPGEPAS ISCRSSKSLL HSNGITYLYW YLQKPGQSPQ LLIYQMSNLV   60
SGVPDRFSGS GSGTDFTLKI SRVEAEDVGV YYCAQNLELP YTFGGGTKVE IKRTV       115

SEQ ID NO: 191          moltype = AA   length = 109
FEATURE                 Location/Qualifiers
REGION                  1..109
                        note = anti-CD3 VL35 (CON)
source                  1..109
                        mol_type = protein
                        organism = synthetic construct
SEQUENCE: 191
QAVVTQEPSL TVSPGGTVTL TCGSSTGAVT TSNYANWVQQ KPGQAFRGLI GGTNKRAPGV   60
PARFSGSLLG GKAALTISGA QPEDEADYYC ALWYSNHWVF GCGTKLTVL              109

SEQ ID NO: 192          moltype = AA   length = 5
FEATURE                 Location/Qualifiers
REGION                  1..5
                        note = linker
source                  1..5
                        mol_type = protein
                        organism = synthetic construct
SEQUENCE: 192
GGGGG                                                                5

SEQ ID NO: 193          moltype = AA   length = 15
FEATURE                 Location/Qualifiers
REGION                  1..15
                        note = linker
source                  1..15
                        mol_type = protein
                        organism = synthetic construct
SEQUENCE: 193
GGGGSGGGGS GGGGS                                                    15

SEQ ID NO: 194          moltype = AA   length = 226
FEATURE                 Location/Qualifiers
REGION                  1..226
                        note = Fc-Het-1
source                  1..226
                        mol_type = protein
                        organism = synthetic construct
SEQUENCE: 194
DKTHTCPPCP APPVAGPSVF LFPPKPKDTL MISRTPEVTC VVVDVKHEDP EVKFNWYVDG   60
VEVHNAKTKP REEEYNSTYR VVSVLTVLHQ DWLNGKEYKC KVSNKALPAP IEKTISKAKG  120
QPREPQVYTL PPSREEMTKN QVSLTCDVSG FYPSDIAVEW ESDGQPENNY KTTPPVLDSD  180
GSFFLYSKLT VDKSRWEQGD VFSCSVMHEA LHNHYTQKSL SLSPGK                 226

SEQ ID NO: 195          moltype = AA   length = 226
FEATURE                 Location/Qualifiers
REGION                  1..226
                        note = Fc-Het-2
source                  1..226
                        mol_type = protein
                        organism = synthetic construct
SEQUENCE: 195
DKTHTCPPCP APPVAGPSVF LFPPKPKDTL MISRTPEVTC VVVDVKHEDP EVKFNWYVDG   60
VEVHNAKTKP REEQYNSTYR VVSVLTVLHQ DWLNGKEYKC KVSNKALPAP IEKTISKAKG  120
QPREPQVYTL PPSREQMTKN QVKLTCLVKG FYPSDIAVEW ESNGQPENNY KTTPPVLDSD  180
GSFFLYSKLT VDKSRWQQGN VFSCSVMHEA LHNHYTQKSL SLSPGK                 226

SEQ ID NO: 196          moltype = AA   length = 125
FEATURE                 Location/Qualifiers
REGION                  1..125
```

```
                        note = CD3-VH32
source                  1..125
                        mol_type = protein
                        organism = synthetic construct
SEQUENCE: 196
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSS                                                               125

SEQ ID NO: 197          moltype = AA   length = 125
FEATURE                 Location/Qualifiers
REGION                  1..125
                        note = CD3-VH33
source                  1..125
                        mol_type = protein
                        organism = synthetic construct
SEQUENCE: 197
EVQLVESGGG LVQPGGSLRL SCAASGFTFS TYAMNWVRQA PGKCLEWVGR IRSKYNNYAT    60
YYADSVKGRF TISRDDSKNT LYLQMNSLRA EDTAVYYCVR HGNFGDSYVS WFAYWGQGTL   120
VTVSS                                                               125

SEQ ID NO: 198          moltype = AA   length = 123
FEATURE                 Location/Qualifiers
REGION                  1..123
                        note = CD3-VH34
source                  1..123
                        mol_type = protein
                        organism = synthetic construct
SEQUENCE: 198
EVQLVESGGG LVQPGGSLRL SCAASGFTFS TYAMNWVRQA PGKCLEWVAR IRSKYNNYAT    60
YYADTVKGRF TISRDDAKNT LYLQMSSLRA EDTAVYYCVR HGNFGDSYVS WFAYWGQGTL   120
VTV                                                                 123

SEQ ID NO: 199          moltype = AA   length = 109
FEATURE                 Location/Qualifiers
REGION                  1..109
                        note = CD3-VL20
source                  1..109
                        mol_type = protein
                        organism = synthetic construct
SEQUENCE: 199
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GGGTKLTVL               109

SEQ ID NO: 200          moltype = AA   length = 109
FEATURE                 Location/Qualifiers
REGION                  1..109
                        note = CD3-VL21
source                  1..109
                        mol_type = protein
                        organism = synthetic construct
SEQUENCE: 200
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GCGTKLTVL               109

SEQ ID NO: 201          moltype = AA   length = 225
FEATURE                 Location/Qualifiers
REGION                  1..225
                        note = Knob Fc
source                  1..225
                        mol_type = protein
                        organism = synthetic construct
SEQUENCE: 201
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSP                   225

SEQ ID NO: 202          moltype = AA   length = 225
FEATURE                 Location/Qualifiers
REGION                  1..225
                        note = Hole Fc
source                  1..225
                        mol_type = protein
                        organism = synthetic construct
SEQUENCE: 202
DKTHTCPPCP APELLGGPSV FLFPPKPKDT LMRSRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
```

```
DGSFFLVSKL TVDKSRWQQG NVFSCSVMHE ALHNHYTQKS LSLSP            225

SEQ ID NO: 203          moltype = AA  length = 222
FEATURE                 Location/Qualifiers
REGION                  1..222
                        note = Knob Fc
source                  1..222
                        mol_type = protein
                        organism = synthetic construct
SEQUENCE: 203
DKTHTCPPCP APGGPSVFLF PPKPKDTLMI SRTPEVTCVV VDVSHEDPEV KFNWYVDGVE  60
VHNAKTKPRE EQYNSTYRVV SVLTVLHQDW LNGKEYKCKV SNKALPAPIE KTISKAKGQP 120
REPQVYTLPP CRDELTKNQV SLWCLVKGFY PSDIAVEWES NGQPENNYKT TPPVLDSDGS 180
FFLYSKLTVD KSRWQQGNVF SCSVMHEALH NHYTQKSLSL SP                    222

SEQ ID NO: 204          moltype = AA  length = 222
FEATURE                 Location/Qualifiers
REGION                  1..222
                        note = Hole Fc
source                  1..222
                        mol_type = protein
                        organism = synthetic construct
SEQUENCE: 204
DKTHTCPPCP APGGPSVFLF PPKPKDTLMR SRTPEVTCVV VDVSHEDPEV KFNWYVDGVE  60
VHNAKTKPRE EQYNSTYRVV SVLTVLHQDW LNGKEYKCKV SNKALPAPIE KTISKAKGQP 120
REPQVCTLPP SRDELTKNQV SLSCAVKGFY PSDIAVEWES NGQPENNYKT TPPVLDSDGS 180
FFLVSKLTVD KSRWQQGNVF SCSVMHEALH NHYTQKSLSL SP                    222

SEQ ID NO: 205          moltype = AA  length = 225
FEATURE                 Location/Qualifiers
REGION                  1..225
                        note = Hole Fc
source                  1..225
                        mol_type = protein
                        organism = synthetic construct
SEQUENCE: 205
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVCT LPPSRDELTK NQVSLSCAVK GFYPSDIAVE WESNGQPENN YKTTPPVLDS 180
DGSFFLVSKL TVDKSRWQQG NVFSCSVMHE ALHNRYTQKS LSLSP                 225

SEQ ID NO: 206          moltype = AA  length = 222
FEATURE                 Location/Qualifiers
REGION                  1..222
                        note = Hole Fc
source                  1..222
                        mol_type = protein
                        organism = synthetic construct
SEQUENCE: 206
DKTHTCPPCP APGGPSVFLF PPKPKDTLMI SRTPEVTCVV VDVSHEDPEV KFNWYVDGVE  60
VHNAKTKPRE EQYNSTYRVV SVLTVLHQDW LNGKEYKCKV SNKALPAPIE KTISKAKGQP 120
REPQVCTLPP SRDELTKNQV SLSCAVKGFY PSDIAVEWES NGQPENNYKT TPPVLDSDGS 180
FFLVSKLTVD KSRWQQGNVF SCSVMHEALH NRYTQKSLSL SP                    222

SEQ ID NO: 207          moltype = AA  length = 225
FEATURE                 Location/Qualifiers
REGION                  1..225
                        note = Knob Fc
source                  1..225
                        mol_type = protein
                        organism = synthetic construct
SEQUENCE: 207
DKTHTCPPCP APELLGGPSV FLFPPKPKDT LYISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPCRDELTK NQVSLWCLVK GFYPSDIAVE WESNGQPENN YKTTPPVLDS 180
DGSFFLYSKL TVDKSRWQQG NVFSCSVVHE ALHNHYTQKS LSLSP                 225

SEQ ID NO: 208          moltype = AA  length = 222
FEATURE                 Location/Qualifiers
REGION                  1..222
                        note = Knob Fc
source                  1..222
                        mol_type = protein
                        organism = synthetic construct
SEQUENCE: 208
DKTHTCPPCP APGGPSVFLF PPKPKDTLYI SRTPEVTCVV VDVSHEDPEV KFNWYVDGVE  60
VHNAKTKPRE EQYNSTYRVV SVLTVLHQDW LNGKEYKCKV SNKALPAPIE KTISKAKGQP 120
REPQVYTLPP CRDELTKNQV SLWCLVKGFY PSDIAVEWES NGQPENNYKT TPPVLDSDGS 180
FFLYSKLTVD KSRWQQGNVF SCSVVHEALH NHYTQKSLSL SP                    222
```

```
SEQ ID NO: 209          moltype = AA   length = 225
FEATURE                 Location/Qualifiers
REGION                  1..225
                        note = Hole Fc
source                  1..225
                        mol_type = protein
                        organism = synthetic construct
SEQUENCE: 209
DKTHTCPPCP APELLGGPSV FLFPPKPKDT LYISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVVHE ALHNRYTQKS LSLSP                   225

SEQ ID NO: 210          moltype = AA   length = 222
FEATURE                 Location/Qualifiers
REGION                  1..222
                        note = Hole Fc
source                  1..222
                        mol_type = protein
                        organism = synthetic construct
SEQUENCE: 210
DKTHTCPPCP APGGPSVFLF PPKPKDTLYI SRTPEVTCVV VDSHEDPEV KFNWYVDGVE     60
VHNAKTKPRE EQYNSTYRVV SVLTVLHQDW LNGKEYKCKV SNKALPAPIE KTISKAKGQP   120
REPQVCTLPP SRDELTKNQV SLSCAVKGFY PSDIAVEWES NGQPENNYKT TPPVLDSDGS   180
FFLVSKLTVD KSRWQQGNVF SCSVVHEALH NRYTQKSLSL SP                      222

SEQ ID NO: 211          moltype = AA   length = 10
FEATURE                 Location/Qualifiers
REGION                  1..10
                        note = anti-CD3 VH CDR1
source                  1..10
                        mol_type = protein
                        organism = synthetic construct
SEQUENCE: 211
GFTFNTYAMN                                                           10

SEQ ID NO: 212          moltype = AA   length = 12
FEATURE                 Location/Qualifiers
REGION                  1..12
                        note = anti-CD3 VH CDR2
source                  1..12
                        mol_type = protein
                        organism = synthetic construct
SEQUENCE: 212
RIRSKYNNYA TY                                                        12

SEQ ID NO: 213          moltype = AA   length = 246
FEATURE                 Location/Qualifiers
REGION                  1..246
                        note = CD20 scFv
source                  1..246
                        mol_type = protein
                        organism = synthetic construct
SEQUENCE: 213
QVQLVQSGAE VKKPGSSVKV SCKASGYAFS YSWINWVRQA PGQGLEWMGR IFPGDGDTDY    60
NGKFKGRVTI TADKSTSTAY MELSSLRSED TAVYYCARNV FDGYWLVYWG QGTLVTVSSG   120
GGGSGGGGS GGGSDIVMTQ TPLSLPVTPG EPASISCRSS KSLLHSNGIT YLYWYLQKPG   180
QSPQLLIYQM SNLVSGVPDR FSGSGSGTDF TLKISRVEAE DVGVYYCAQN LELPYTFGGG   240
TKVEIK                                                              246

SEQ ID NO: 214          moltype = AA   length = 118
FEATURE                 Location/Qualifiers
REGION                  1..118
                        note = B7H3 sdAb B7h3 hz1A5v51
source                  1..118
                        mol_type = protein
                        organism = synthetic construct
SEQUENCE: 214
EVQLVESGGG EVQPGGSLRL SCAASGFSFS SNVMMWVRQA PGKGLEWVST IYSSGTGTFY    60
AESVKGRFTI SRDNAKNTLY LQMSSLRPED TAVYYCATSG PVRGWGPRSQ GTLVTVKP     118

SEQ ID NO: 215          moltype = AA   length = 117
FEATURE                 Location/Qualifiers
REGION                  1..117
                        note = sdAb B7H3 hz58E05v27
source                  1..117
                        mol_type = protein
                        organism = synthetic construct
```

```
SEQUENCE: 215
EVQLVESGGG EVQPGGSLRL SCAASGSTFS SYHMSWFRQA PGKQREPVAT SHHGGTTNYA    60
GSVKGRFTIS RDNAKNTVYL QMNTLRAEDT AVYYCKADHG YQGRGYWGQG TLVTVKP     117

SEQ ID NO: 216          moltype = AA   length = 117
FEATURE                 Location/Qualifiers
REGION                  1..117
                        note = sdAb B7H3 hz58E05v55
source                  1..117
                        mol_type = protein
                        organism = synthetic construct
SEQUENCE: 216
EVQLVESGGG EVQPGGSLRL SCAASGFTFS SYHMSWFRQA PGKQRELVAT SHHGGTTNYA    60
GSVKGRFTIS RDNAKNTVYL QMNTLRAEDT AVYYCKADHG YQGRGYWGQG TLVTVKP     117

SEQ ID NO: 217          moltype = AA   length = 117
FEATURE                 Location/Qualifiers
REGION                  1..117
                        note = sdAb B7H3 hz58E05v48
source                  1..117
                        mol_type = protein
                        organism = synthetic construct
SEQUENCE: 217
EVQLVESGGG EVQPGGSLRL SCAASGFTFS SYHMSWFRQA PGKQREPVAT SHHGGTTNYA    60
GSVKGRFTIS RDNAKNTVYL QMNTLRAEDT AVYYCKADHG YQGRGYWGQG TLVTVKP     117

SEQ ID NO: 218          moltype = AA   length = 127
FEATURE                 Location/Qualifiers
REGION                  1..127
                        note = sdAb B7H3 hz57B04v24
source                  1..127
                        mol_type = protein
                        organism = synthetic construct
SEQUENCE: 218
EVQLVESGGG EVQPGGSLRL SCAPSERTFS TYTMGWFRQA PGKEREFVAV VNWGGGSKYY    60
AESVKGRFTI SRDNAKNTVY LQMSSLRAED TAVYYCAAGG AYSGPYYDTR QYTYWGQGTL   120
VTVKPGG                                                             127

SEQ ID NO: 219          moltype = AA   length = 120
FEATURE                 Location/Qualifiers
REGION                  1..120
                        note = sdAb DLL3 hz10D9v7
source                  1..120
                        mol_type = protein
                        organism = synthetic construct
SEQUENCE: 219
EVQLVESGGG EVQPGGSLRL SCAASGSIFS INAMGWYRQA PGKQRELVAG FTGDTNTIYA    60
ESVKGRFTIS RDNAKNTVYL QMSSLRAEDT AVYYCAADVQ LFSRDYEFYW GQGTLVTVKP   120

SEQ ID NO: 220          moltype = AA   length = 115
FEATURE                 Location/Qualifiers
REGION                  1..115
                        note = sdAb DLL3 hz8E7v16
source                  1..115
                        mol_type = protein
                        organism = synthetic construct
SEQUENCE: 220
EVQLVESGGG EVQPGGSLRL SCGPSEIITS DKSMGWVRQA PGKQRNLVAG ISNVGSTNYA    60
QSVKGRFTIS RDNAKNTVYL QMSSLRAEDT AVYYCYARDF ENEYWGQGTL VTVKP       115

SEQ ID NO: 221          moltype = AA   length = 10
FEATURE                 Location/Qualifiers
REGION                  1..10
                        note = 41BB CDR1
source                  1..10
                        mol_type = protein
                        organism = synthetic construct
SEQUENCE: 221
GFSFSINAMG                                                           10

SEQ ID NO: 222          moltype = AA   length = 9
FEATURE                 Location/Qualifiers
REGION                  1..9
                        note = 41BB CDR2
source                  1..9
                        mol_type = protein
                        organism = synthetic construct
SEQUENCE: 222
AIESGRNTV                                                             9
```

```
SEQ ID NO: 223          moltype = AA  length = 13
FEATURE                 Location/Qualifiers
REGION                  1..13
                        note = 41BB CDR3
source                  1..13
                        mol_type = protein
                        organism = synthetic construct
SEQUENCE: 223
LKGNRVVSPS VAY                                                        13

SEQ ID NO: 224          moltype = AA  length = 14
FEATURE                 Location/Qualifiers
REGION                  1..14
                        note = CD3-VH7, VH33 CDR3
source                  1..14
                        mol_type = protein
                        organism = synthetic construct
SEQUENCE: 224
HGNFGDSYVS WFAY                                                       14

SEQ ID NO: 225          moltype = AA  length = 9
FEATURE                 Location/Qualifiers
REGION                  1..9
                        note = CD3-VL2, VL21 CDR3
source                  1..9
                        mol_type = protein
                        organism = synthetic construct
SEQUENCE: 225
ALWYSNHWV                                                              9

SEQ ID NO: 226          moltype = AA  length = 9
FEATURE                 Location/Qualifiers
REGION                  1..9
                        note = CD3-VL8 CDR3
source                  1..9
                        mol_type = protein
                        organism = synthetic construct
SEQUENCE: 226
VLWYSNRWV                                                              9

SEQ ID NO: 227          moltype = AA  length = 10
FEATURE                 Location/Qualifiers
REGION                  1..10
                        note = CD3 VH33 CDR1
source                  1..10
                        mol_type = protein
                        organism = synthetic construct
SEQUENCE: 227
GFTFSTYAMN                                                            10

SEQ ID NO: 228          moltype = AA  length = 12
FEATURE                 Location/Qualifiers
REGION                  1..12
                        note = CD3 VH33 CDR2
source                  1..12
                        mol_type = protein
                        organism = synthetic construct
SEQUENCE: 228
RIRSKYNNYA TY                                                         12

SEQ ID NO: 229          moltype = AA  length = 14
FEATURE                 Location/Qualifiers
REGION                  1..14
                        note = CD3 VL21 CDR1
source                  1..14
                        mol_type = protein
                        organism = synthetic construct
SEQUENCE: 229
GSSTGAVTTS NYAN                                                       14
```

-continued

```
SEQ ID NO: 230        moltype = AA  length = 7
FEATURE               Location/Qualifiers
REGION                1..7
                      note = CD3 VL21 CDR2
source                1..7
                      mol_type = protein
                      organism = synthetic construct
SEQUENCE: 230
GTNKRAP                                                              7
```

What is claimed is:

1. A multispecific polypeptide construct, the multispecific polypeptide construct comprising a first component comprising an immunoglobulin Fc region and a second component comprising a CD3-binding region, wherein:
the CD3 binding region is an anti-CD3 disulphide-stabilized Fv antibody fragment (dsFv) comprising a variable heavy chain region (VH) and a variable light chain region (VL);
the Fc region is a heterodimeric Fc comprising a first Fc polypeptide and a second Fc polypeptide and the VH and VL of the anti-CD3 antibody or antigen binding fragment are linked to opposite polypeptides of the heterodimeric Fc;
the first and second components are coupled by a non-cleavable linker, wherein the Fc region is linked to the N-terminus of the CD3-binding region;
the first component comprises at least one antigen binding domain that bind a tumor associated antigen (TAA), wherein the at least one antigen binding domain is linked to the N-terminus of the Fc region and wherein the at least one antigen binding domain is an sdAb.

2. The multispecific polypeptide construct of claim 1, wherein the at least one antigen binding domain is a first antigen binding domain and a second antigen binding domain, wherein each of the at least one antigen binding domain of the first component is linked amino-terminal to the Fc region.

3. The multispecific polypeptide construct of claim 1, wherein the CD3-binding region binds CD3.

4. The multispecific polypeptide construct of claim 1, wherein each of the Fc polypeptides of the heterodimeric Fc independently comprise at least one amino acid modification.

5. The multispecific polypeptide construct of claim 4, wherein the at least one modification is selected from a steric modification(s), a knob-into-hole modification(s), a charge mutation(s) to increase electrostatic complementarity of the polypeptides, a modification(s) to alter the isoelectric point, or combinations thereof.

6. The multispecific polypeptide construct of claim 1, wherein the non-cleavable linker is a polypeptide linker.

7. The multispecific polypeptide construct of claim 1, wherein the non-cleavable linker is a polypeptide that is 3 to 18 amino acids in length.

8. The multispecific polypeptide construct of claim 1, wherein the non-cleavable linker comprises (GGS) n, wherein n is 1 to 10;
(GGGGS)n (SEQ ID NO: 173), wherein n is 1 to 10; or
(GGGGGS)n (SEQ ID NO:172), wherein n is 1 to 4.

9. The multispecific polypeptide construct of claim 1, wherein the non-cleavable linker is or comprises an amino acid sequence selected from the group consisting of GGS; GGGGS (SEQ ID NO: 149); GGGGGS (SEQ ID NO: 135); (GGS) 2 (SEQ ID NO: 10); GGSGGSGGS (SEQ ID NO: 11); GGSGGSGGSGGS (SEQ ID NO: 12); GGSGGSGGSGGSGGS (SEQ ID NO: 13); GGGGSGGGGSGGGGS (SEQ ID NO: 119); GGSGGGGSGGGGSGGGGS (SEQ ID NO: 147); and GGGGSGGGGSGGGGS (SEQ ID NO: 170).

10. The multispecific polypeptide construct of claim 1, wherein the multispecific polypeptide construct comprises at least (i) a first polypeptide comprising the first Fc polypeptide of the heterodimeric Fc region, the linker and the VH domain of the anti-CD3 antibody or antigen binding fragment thereof; and (ii) a second polypeptide comprising the second Fc polypeptide of the heterodimeric Fc region, the linker and the VL domain of the anti-CD3 antibody or antigen binding fragment thereof, wherein one or both of the first and second polypeptide comprise the at least one antigen-binding domain that binds to a tumor associated antigen (TAA).

11. The multispecific polypeptide construct of claim 10, wherein the VH of the anti-CD3 antibody or antigen-binding fragment is on the same polypeptide as the at least one antigen-binding domain that binds to a tumor associated antigen (TAA).

12. The multispecific polypeptide construct of claim 10, wherein the polypeptide comprising the VL of the anti-CD3 antibody or antigen-binding fragment does not contain the at least one antigen-binding domain that binds to a tumor associated antigen (TAA).

13. The multispecific polypeptide construct of claim 10, wherein only one of the first and second polypeptide comprises the at least one antigen-binding domain that binds a TAA.

14. The multispecific polypeptide construct of claim 1, wherein the multispecific polypeptide construct comprises:
at least a first antigen binding domain and a second antigen binding domain, wherein the first antigen binding domain and second antigen binding domain bind to the same TAA;
at least a first antigen binding domain and a second antigen binding domain wherein the first antigen binding domain and the second antigen binding domain binds different epitopes of the same TAA;
at least a first antigen binding domain and a second antigen binding domain wherein the first antigen binding domain and the second antigen binding domain bind the same epitope of the same TAA; or
at least a first antigen binding domain and a second antigen binding domain wherein the first antigen binding domain and the second antigen binding domain bind a different TAA.

15. The multispecific polypeptide construct of claim 1, wherein:
the anti-CD3 antibody or antigen-binding fragment thereof comprises a VH CDR1 comprising the amino acid sequence GFTFNTYAMN (SEQ ID NO: 211); a VH CDR2 comprising the amino acid sequence RIR- SKYNNYATY (SEQ ID NO: 212); a VH CDR3 comprising the amino acid sequence HGNFGNSYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21).

16. The multispecific polypeptide of claim 1, wherein: the anti-CD3 antibody or antigen-binding fragment comprises a VH CDR1 sequence that includes at least the amino acid sequence GFTFNTYAMN (SEQ ID NO: 211); a VH CDR2 sequence that includes at least the amino acid sequence RIRSKYNNYATY (SEQ ID NO: 212); a VH CDR3 sequence that includes at least the amino acid sequence HGNFGNSYVSWFAY (SEQ ID NO: 18), a VL CDR1 sequence that includes at least the amino acid sequence GSSTGAVTTSNYAN (SEQ ID NO: 229); a VL CDR2 sequence that includes at least the amino acid sequence GTNKRAP (SEQ ID NO: 230); and a VL CDR3 sequence that includes at least the amino acid sequence ALWYSNHWV (SEQ ID NO: 225).

17. The multispecific polypeptide construct of claim 16, wherein the anti-CD3 dsFv comprises:
a VH having the amino acid sequence of any of SEQ ID NOS: 44, 50, 53-56, and 60-62 or a sequence that exhibits at least 90%, sequence identity to any of SEQ ID NOS: 44, 50, 53-56, and 60-62; and
a VL having the amino acid sequence of any of SEQ ID NOS: 64, 72, 80, 81, 191, and 200 or a sequence that exhibits at least 90% sequence identity to any of SEQ ID NOS: 64, 72, 80, 81, 191, and 200.

18. The multispecific polypeptide construct of claim 16, wherein the anti-CD3 dsFv comprises a VH having a sequence that exhibits at least 90% sequence identity to SEQ ID NO: 44; and a VL having a sequence that exhibits at least 90% sequence identity SEQ ID NO: 72.

19. The multispecific polypeptide construct of claim 1, wherein the anti-CD3 dsFv comprises the amino acid sequence of SEQ ID NO: 44 and the amino acid sequence of SEQ ID NO: 72.

20. The multispecific polypeptide construct of claim 1, wherein the multispecific polypeptide construct is conjugated to an agent selected from the group consisting of the following: a therapeutic agent, an antineoplastic agent, a toxin or fragment thereof, a detectable moiety, and a diagnostic agent.

21. A pharmaceutical composition comprising the multispecific polypeptide construct of claim 1 and a pharmaceutically acceptable carrier.

* * * * *